United States Patent
Ryan et al.

(10) Patent No.: US 6,399,349 B1
(45) Date of Patent: *Jun. 4, 2002

(54) HUMAN AMINOPEPTIDASE P GENE

(75) Inventors: James W. Ryan, 3047 Lake Forest Dr., Augusta, GA (US) 30909-3027; Terry Joe Curtis Sprinkle, Evans, GA (US)

(73) Assignee: James W. Ryan, Augusta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,053

(22) Filed: Sep. 2, 1998

Related U.S. Application Data

(60) Provisional application No. 60/057,854, filed on Sep. 2, 1997.

(51) Int. Cl.[7] .................. C12N 15/57; C12N 15/79; C12N 9/64; C12Q 1/68
(52) U.S. Cl. .................. 435/226; 435/69.1; 435/252.3; 435/320.1; 435/471; 435/6; 536/23.2
(58) Field of Search .................. 435/226, 69.1, 435/6, 252.3, 320.1; 536/23.2

(56) References Cited

U.S. PATENT DOCUMENTS

| | | | | |
|---|---|---|---|---|
| 5,234,811 A | * | 8/1993 | Beutler et al. ............ | 435/6 |
| 5,645,995 A | * | 7/1997 | Kieback ................... | 435/6 |
| 5,648,478 A | * | 7/1997 | Henderson ............... | 536/24.1 |
| 5,688,927 A | * | 11/1997 | Godiska et al. ......... | 530/388.23 |
| 5,739,407 A | * | 4/1998 | Bergstrom et al. ..... | 800/2 |
| 5,830,649 A | * | 11/1998 | Bergsma et al. ......... | 435/6 |
| 5,872,237 A | * | 2/1999 | Feder et al. ............. | 536/23.5 |

FOREIGN PATENT DOCUMENTS

| | | | |
|---|---|---|---|
| WO | WO 95/17205 | * | 6/1995 |
| WO | WO 95/33480 | * | 12/1995 |
| WO | WO 96/12033 | * | 4/1996 |
| WO | WO 97/27284 | * | 7/1997 |

OTHER PUBLICATIONS

GenBank/NCBI Accession No. Z73496, 1996, "Human chromosome X DNA segment of 43,902 nucleotides comprising EST's and STS's associated with Lowe oculocerebrorenal syndrome", Mistry, S., Sanger Centre, Cambridgeshire, U.K.*

GenBank/NCBI Accession No. W91937, 1997, "Soares human fetal liver–spleen 1NFLS–S1, a primer-generated cDNA clone, IMAGE:41514, of 616 nucleotides", Hillier, L., et al., Washington University, School of Medicine.*

GenBank/NCBI Accession No. U85196, 1997, "Human chromosomal DNA segment of 111,597 nucleotides comprising a region of the human alpha/delta T–cell receptor locus", Boysen, C., University of Washington Molecular Biotechnology.*

GenBank/NCBI Accession No. L30268, 1994, "Human sequence tagged site [STS] UT8111, a chromosomal microsatellite marker of 199 nucleotides", Gerken, S.C., et al., University of Utah, Department of Human Genetics.*

(List continued on next page.)

*Primary Examiner*—Ponnathapu Achutamurthy
*Assistant Examiner*—William W. Moore
(74) *Attorney, Agent, or Firm*—Cheryl H. Agris

(57) ABSTRACT

Disclosed are the human aminopeptidase P cDNA and genomic DNA. Also disclosed is the human aminopeptidase P protein and antibodies reactive with human aminopeptidase P. These molecules, and derivatives of these molecules, are useful for assay for detecting aminopeptidase polymorphisms, protein variants, and activity, and identifying compounds that inhibit expression of aminopeptidase genes and activity of aminopeptidase protein.

18 Claims, 1 Drawing Sheet

OTHER PUBLICATIONS

GenBank/NCBI Accession No. H73550, 1995, "Soares human fetal liver–spleen 1NFLS, a primer–generated cDNA clone, IMAGE:214429, of 422 nucleotides", Hillier, L., et al., Washington University School of Medicine.*

GenBank/NCBI Accession No. G28201, 1996, "Human sequence tagged site [STS] SHGC–3409, a primer–generated chromosomal of 92 nucleotides", Myers, R.M., et al., Stanford University School of Medicine, Department of Genetics.*

GenBank/NCBI Accession No. W78093, 1996, "Soares human fetal heart NbHH19W, a primer–generated cDNA clone, IMAGE:346730, of 437 nucleotides", Hillier, L., et al., Washington University School of Medicine.*

Aebersold, R., "Internal amino sequence analysis of proteins after in situ protease digestion on nitrocellulose", *A Practical Guide to Protein and Peptide Purification for Microsequencing,* pp 71–90 (1989).

Aitken, Geisow, et al., "Peptide preparation and characterization", *Protein Sequencing: A Practical Approach,* pp. 43–68 (1989).

Altshul, S.F., et al., "Basic local alignment search tool", *J. Mol. Biol.* 215:403–410 (1990).

Aonuma, et al, "Studies on heart. XX. Further effects of bovine ventricle protein (BVP) and antiarrythmic peptide (AAP) on myocardial cells in culture", *Chem. Pharm. Bull.* 28:3340–3346 (1980).

Aonuma, et al., "Studies on heart, XXIV. Inhibitory effect of antiarrhythmic peptide (AAP) on experimental thromboses", *Chem. Pharm. Bull.* 32:219–227 (1984).

Aonuma, et al., "Studies on heart. XXIII. Distribution of [1–$^{14}$C] acetamidino–antiarrhythmic peptide ($^{14}$C–AAP) in mice[20]", *Chem. Pharm. Bull.* 31:612–619 (1983).

Aonuma, et al., "Studies on heart. XIX. Isolation of an atrial peptide that improves the rhythmicity of cultured myocardial cell clusters", *Chem. Pharm. Bull.* 28:3322–3339 (1980).

Aonuma, et al., "Studies on heart. XXI. Amino acid sequence of antiarrythmic peptide (AAP) isolated from atria", *J. Pharmacol. Dyn.* 5:40–48 (1982).

Aonuma, et al., "Studies on heart. XXII. Inhibitory effect of an atrial peptide (AAP) on several drug–induced arrythmias in vivo", *Yakugaku Zasshi* 103:662–666 (1983).

Aroor, A.R., et al., "Phosphorylation of the rabbit reticulocyte guanine nucleotide exchange factor in vivo. Identification of putative casein kinase II phosphorylation sites", *Biochemistry* 3:350–3357 (1993).

Aviv, H. and Leder, P., "Purification of biologically active globin messenger RNA by chromatography on oligothymidylic acid–cellulose", *Proc. Natl. Acad. Sci.* 69:1408–1412 (1972).

Baker, et al., "Kinin Metabolism in the Perfused Ventilated rat Lung. I. Bradykinin Metabolism in a System Modeling the Normal, Uninjured Lung," *Circulatory Shock* 33: 37–47 (1991).

Bazan, et al., "Sequence and structure comparisons suggest that methionine aminopeptidase, prelates, aminopeptidase P, and cretinize share a common fold", *Proc. Natl. Acad. Sc. USA,* 91:2473–2477 (1994).

Bechhofer, D.H., "A method for sequencing polymerase chain reaction products can be used to sequence *Bacillus Subtlis* miniprep plasmid DNA", *BioTechniques* 10:17–20 (1991).

Berger, J., et al., "COOH–terminal requirements for the correct processing of phosphotidylinositol–glycan anchored membrane protein", *J. Biol. Chem.* 263:10016–10021 (1998).

Blau, et al., "Peptiduria presumably caused by aminopeptidase–P deficiency. A new inborn error of metabolism", *J. Inher. Metab. Dis.* 11:240–242, (1988).

Blaukat, A., et al., "Ligand–induced phosphorylation/dephosphorylation of the endogenous bradykinin B2 receptor from human fibroblasts", *J. Biol. Chem.* 271:32366–32374 (1996).

Bleiweis, A.S., et al., "Cloning and inactivation of the gene responsible for a major surface antigen on streptococcus mutants", *Arch Oral Biol.* 35:15S–23S (1990).

Bodenmuller, H. and Schaller, H.C., "Conserved amino acid sequence of a neuropeptide, the head activator, from coelenterates to humans", *Nature* 293:579–580 (1981).

Bonner, et al., "Hemodynamic effects of bradykinin on systemic and pulmonary circulation in healthy and hypertensive humans", *J. Cardiovas. Pharmacol.* 15:S46–S56 (1990).

Boothroyd, J.C., et al., "Variant surface glycoproteins of *trypanosoma brucci* are synthesized with cleavable hydrophobic sequences at the carboxy and amino termini", *Nucleic Acids Res.* 9:4735–4743 (1981).

Butler, et al., "Cloning and characterization of an aminopeptidase P–encoding gene from *Streptococcus lividans"*, *Gene,* 123:115–119 (1993).

Caldwell, et al., "Angiotensin converting enzyme: Vascular endothelial localization", *Science* 191:1050–1051 (1976).

Campbell, B.J., et al., "β–lactamase activity of purified and partially characterized human renal dipeptidase", *J. Biol. Chem.* 259:14586–14590 (1984).

Casey, J. and Davidson N., "Rates of formation and thermal stabilities of RNA: DNA and DNA: DNA duplexes at high concentrations of formamide", *Nucleic Acids Res.* 4:1539–1552 (1997).

Chang, W.J. et al., "Purification and characterization of smooth muscle cell caveolae", *J. Cell Biol.* 126:127–138 (1994).

Chen, "Species Variation in pulmonary Endothelial Aminopeptidase P Activity," *J. Pharmacol. Exp. Ther.* 259(3):1301–1307 (1991).

Chomczynski, P. and Succhi, N., "Single–step method of RNA isolation by acid guanidinium thiocyanate–phenol–chloroform extraction", *Anal. Biochem.* 162:156–159 (1987).

Chun, M., et al., "Signal transduction of a G protein–coupled receptor in caveolae: colocalization of endothelin and its receptor with caveolin", *Proc. Natl. Acad. Sci. USA* 91:11728–117323 (1994).

Cleveland, D.W., et al., "Peptide mapping by limited proteolysis in sodium dodecyl sulfate and analysis by gel electrophoresis", *J. Biol. Chem.* 252:1102–1106 (1977).

Davies, A. and Morgan, B.P., "Expression of glyosylphosphatidylinositol–linked complement–inhibiting protein CD59 antigen in insect cells using a baculovirus vector", *Biochem. J.* 295:889–896 (1993).

Dayhoff, M.O., et al., "Establishing Homologies in Protein Sequences", *Methods Enzymol.* 91:524–545 (1983).

Dehm, et al., "The cleavage of prolyl peptides by kidney peptidases", *Eur. J. Biochem.* 17:372–377 (1970).

Dehm, et al., "The cleavage of prolyl peptides by kidney peptidases", *Eur. J. Biochem.* 17:364–371 (1970).

Denslow, et al., "Guinea Pig Membrane–bound Aminopeptidase P is a Member of the Proline Peptidase Family" *Biochem. Biophys res. Commun.* 205(3):1790–1795 (1994).

Dorer, F.E., et al., "Kinetic properties of pulmonary angiotensin converting enzyme. Hydrolysis of hippurglycylglycine", *Biochem. Biophys. Acta* 429:220–228 (1976).

Dos Santos, et al., "Processing and metabolism of peptide–YY: pivotal roles of dipeptidylpeptidase–IV, aminopeptidase P. and endopeptidase–24.11", *Endocrinology* 134:2088–2094 (1994).

Elder, J. and Alexander, S., "Endo–β–B–N–acerylglucosaminidase F: Endoglycosidase from *flavobacterium meningosepticum* cleaves both high–mannose and complex glycoproteins", *Proc. Nat. Acad. Sci. USA* 79:4540–4544 (1982).

Endo, F. and Matsuda, L., "Molecular bases of prolidase (peptidase D) deficiency", *Mol. Biol. & Med.* 8:117–127 (1991).

Endo, F., Tanoue, et al., "Primary structure and gene localization of human prolidase", *J. Biol. Chem.,* 264:4476–4481 (1989).

Erickson, A.H. and Blobel, G., "Early events in the biosynthesis of the lysosomal enzyme cathespin D", *J. Biol Chem.,* 254:11771–11774 (1979).

Ersahin, et al., "Inhibition of Both Aminopeptidase P and Angiotensin–Converting Enzyme Prevents Bradykinin Degradation in the Rat Coronary Circulation," *J. Cardiovasc. Pharmacol.* 30: 96–101 (1997).

Ferguson, M.A.J., et al., "Glycosyl–phosphatidylinositol moiety that anchors trypanosoma brucei variant surface glycoprotein to the membrane", *Science* 239:753–759 (1988).

Feurle, G.E., et al., "The neuropeptide head activator stimulates amylase release from rat pancreas in vitro", *Neurosci. Lett.* 38:287–289 (1983).

Fleminger, et al., "Fluorogenic Substrates for Bacterial Aminopeptidase P and Its Analogs Detected in Human Serum and Calf Lung," *Int. J. Biochem* 125: 609–615 (1982).

Flinta, C., et al ., "Sequence determinants of cytosolic N–terminal protein processing", *Eur. J. Biochem.* 154:193–196 (1986).

Fujimoto, T., "Calcium pump of the plasma membrane is localized in caveolae", *J. Cell. Biol.* 120:1147–1157 (1993).

Fujimoto, T., et al., "Inositoll.4,5–triphosphate receptor–like proteins in plasmalemmal caveolae is linked to actin filaments", *J. Cell Sci.* 108:7–15 (1995).

Fujimoto, T., et al., "Localization of inositol 1, 1, 5–triphosphate receptor–like protein in plasmalemmal caveolae", *J. Cell. Biol.* 119:1507–1513 (1992).

Garcia–Cardena, et al., "Targeting of nitric oxide synthase to endothelial cell caveolae via palmitoylation: implication for nitric oxide signaling", *Proc. Natl. Acad. Sci. USA* 93:6448–6453 (1996).

Gavras, et al., "Antihypertensive effect of the oral angiotensin converting–enzyme inhibitor SQ 14225 in man", *N. Eng. J. Med.* 298–8647–8650 (1991).

Gordon, J.I., et al.,. "Protein N–myristoylation", *J. Biol. Chem.* 266:8647–8650 (1991).

Grafe, et al., "Effect of angiotensin–converting–enzyme inhibition on bradykinin metabolism by vascular endothelial cells", *Am. J. Physiol.* 264:H1493–H1497 (1993).

Hall, R.L. and Moyer, R.W., "Identification, cloning, and sequencing of a fragment of *Amsacta moorei* entomopoxvirus DNA containing the spheroidin gene and three vaccinia virus–related open reading frames", *J. Virol.* 65:6516–6527 (1991).

Harbeck, et al., "Aminopeptidase P from rat brain—Purification and action on bioactive peptides", *Eur. J. Biochem.* 198:451–458 (1991).

Hedner, et al, "Angio–oedema in relation to treatment with angiotensin converting enzyme inhibitors", *BMJ* 304–941–946 (1992).

Heltianu, C., et al., "A method for selective radiolabeling of lung endothelium plasmalemmal vesicles, in situ", *Eur. J. Cell Biol.* 64:61–70 (1994).

Hendriks, et al., "Aminopeptidase P and dipeptidyl peptidase IV activity inhuman leukocytes and in stimulated lymphocytes", *Clin. Chim. Acta* 196:87–96 (1991).

Henikoff, S. and Henikoff, J.G., "Automated assembly of protein blocks for database searching", *Nucleic Acids Res.* 19:6565–6572 (1991).

Herman, K., et al., "High performance liquid chromatography for the separation of angiotensin and its metabolites in human plasma and sweat", J. Chromatog., *Science* 28:524–528 (1990).

Hjelmeland, L.M., "Solubilization of native–membrane proteins", *Meth. in Enzym.* 192:253, 264 (1990).

Ho, S.N., et al., "Site–directed mutagenesis by overlap extension using the polymerase chain reaction", *Gene* 77:51–59 (1989).

Holtzman, B.J., et al., "Aminopeptidase, P activity in rat organs and human serum", *Anal. Biochem.* 162:476–484 (1987).

Homans, S.W., et al., "Complete structure of the glycosyl phosphatidylinositol membrane anchor of rat brain thy–1 glycoprotein", *Nature* 333:269–272 (1988).

Hooper, et al., "Inhibition by converting enzyme inhibitors of pig kidney aminopeptidase P", *Hypertension* 19:281–285 (1992).

Hooper, et al., "Characterization of antibodies to the glycosyl phosphatidylinositol membrane anchors of mammalian proteins", *Biochem.* 273:301–306 (1991).

Hooper, et al., "Ectoenzymes of the kidney microvillar membrane", *FEBS Lett.* 229:340–344 (1988).

Hooper, et al., "Ectoenzymes of the kidney molecular membrane", *Biochem. J.* 250:865–869 (1988).

Hooper, et al., "Purification and characterization of pig kidney aminopeptidase P", *Biochem J.* 267:509–515 (1990).

Hopp, et al., "Prediction of protein antigenic determinants from amino acid sequences", *Proc. Natl. Acad. Sci. USA* 78:3824–3828 (1981).

Hyde, R.J., et al., "Molecular cloning and expression in COS–1 cells of pig kidney aminopeptidase P", *Biochem. J.* 319:197–200 (1996).

Ishida, et al., "Role of angiotensin converting enzyme and other peptidases in in vivo metabolism of kinins", *Hypertension* 14:322–327 (1989).

Jacobs, K.A., et al., "The thermal stability of oligonucleotide duplexes is sequence independent in tetraaklyammonium salt solutions: Application to identifying recombinant DNA clones", *Nucleic Acids Res.* 16:4637–4650 (1988).

Jentoft, N., and Dearborn, D.G., "Labeling of proteins by reductive methylation using sodium cyanoborohydride", *J. Biol. Chem.* 254:4359–4365 (1979).

Karp, D.R., et al., "Genetic variation in glycosylation of the fourth component of murine complement", *J. Biol. Chem.* 257:7330–7335 (1982).

Kitamura, S., et al., "Effect of combined inhibition of angiotensin–converting enzyme and aminopeptidase P on hemodynamic response in severe hypertension", *Hypertension* 26:P18 (1995).

Kitamura, S., et al., "Potentiation by aminopeptidase P of blood pressure response to bradykinin", *Br. J. Pharmacol.* 114:6–7 (1995).

Kittel, et al., "Ecto–ATPases and 5'–nucleotidases in the caveolae of smooth muscle. Enzyme–histochemical evidence may indicate a role for caveolae in neurotransmission", *Cell Biol. Internatl.* 18:875–879 (1994).

Kohama, et al., "Determination of immunoreactive antiarrhythmic peptide (Ap) in rats", *J. Pharmacobio–Dyn.* 8:1024–1031 (1985).

Kozak, M., "Compilation and analysis of sequences upstream from the translational start site in eukaryotic mRNAs", *Nucleic Acids Res.* 12:857–872 (1984).

Krepela, E., et al., "Dipeptidyl peptidase IV in Mammalian lungs", *Lung* 163:33–54 (1985).

Krishna, R.G., et al., "N–terminal sequences analysis of an alpha–acetylated proteins after unblocking with N–acylaminoacyl–peptide hydrolase", *Anal. Biochem.* 199:45–50 (1991).

Landon, M., "Cleavage of Aspartyl–Prolyl Bonds", *Methods in Enzymology*, (eds. C.H.W. Hirs, S.N. Timasheff), vol. XLVII, Part E, pp. 145–149.

Lasch, et al., "Enzymic properties of intestinal aminopeptidase P: a new continuous assay," *FEB* 227(2): 171–174 (1988).

Laskey, R.E., et al., "Calcium entry–dependent oscillations of cytoplasmic calcium concentration in cultured endothelial cell monolayers", *Proc. Natl. Acad. Sci. USA* 89:1690–1694 (1992).

Laskey, R.E., et al., "Membrane potential and NA(+)–K + pump activity modulate resting and bradykinin–stimulated changes in cytosolic free calcium in cultured endothelial cells from bovine atria", *J. Biol. Chem.* 265:2613–2619 (1990).

Legendre, N. and Matsidaira, P. "Direct protein microsequencing from immobilon–P transfer membranes", *BioTechniques* 6:154–159 (1988).

Li, S., et al., "Evidence for a regulated interaction between heterotrimeric G proteins and caveolin", *J. Biol. Chem.* 270:15693–15701 (1995).

Li, S., et al., "Expression and characterization of recombinant caveolin", *J. Biol. Chem.* 771:568–573 (1996).

Li, S., et al., "Phosphorylation of caveolin by src tyrosine kinases. The alpha isoform of caveolin is selectively phosphorylated by v–Src in vivo", *J. Biol. Chem.* 271:3863–3868 (1996).

Li, S., et al., Baculovirus–based expression of mammalian caveolin in Sf21 insect cells, *J. Biol. Chem.* 271:28647–28654 (1996).

Lim, J.N. and Turner, A.J., "Chemical modification of porcine kidney aminopeptidase P indicates the involvement of two critical histidine residues", *FEBS Letters* 381:188–190 (1996).

Lin, J. N. and Brandts, J.F., "Evidence suggesting that some proteolytic enzymes may cleave only the trans form of the peptide bond", *Biochemistry* 18:43–47 (1979).

Lisanti, M.P., et al "Characterization of caveolin–rich membrane domains isolated from an endothelial–rich source: Implications for human disease", *J. Cell Biol.* 126:11–126 (1994).

Liu, P., et al., "Localization of platelet–derived growth factor stimulated phosphorlyation cascade to caveolae", *J. Biol. Chem.* 271:10299–10303 (1996).

Liu, S.M., et al.,"Microtubules are involved in transport of macromolecules by vesicles in cultured bovine aortic endothelial cells", *J. Cell Physiol.* 156:311–316 (1993).

Low, et al., "Factors affecting the ability of glycosyl–phosphatidylinositol specific phospholipase D to degrade the membrane anchors of cell surface proteins", *Biochem. J.* 279:483–493 (1991).

Low, M.G. and Saltiel, A.B., "Structural and functional roles of glycosyl–phosphatidylinositol in membranes", *Science* 239:268–275 (1988).

Low, M.G., "Glycosyl–phosphatidylinositol: a versatile anchor for cell–surface proteins", *The FASEB J.* 3:1600–1608 (1989).

Mann, "Disulfide Bonds and Free SH–Group in Pig Kidney Aminopeptidase P," *Biol. Chem* 377:857–858 (1996).

Mastick, C.C., et al., "Insulin stimulates the tyrosine phosphorylation of caveolin", *J. Cell Biol.* 129:1523–1533 (1995).

Mayor, S. and Maxfield, F.R., "Insolubility and redistribution of GPI anchored proteins at the cell surface after detergent treatment", *Mol. Biol. Cell* 6:929–944 (1995).

Mayor, S., et al., Sequestration of GPI anchored proteins in caveolae triggered by cross–linking, et al., *Science* 264:1948–1951 (1994).

Mentlein, R., et al., "Proline–specific proteases in cultivated neuronal and grid cells", *Brain Research* 527:159–162 (1990).

Mock, W.L. and Green, P.C., "Mechanism and inhibition of prolidase", *J. Biol. Chem.* 265:19606–19610 (1990).

Moldovan, N.I., et al., "Ultrastructural evidence of differential solubility in Triton X–100 of endothelial vesicles and plasma membrane", *Experimental Cell Research* 219:309–313 (1995).

Montan, et al., "Randomized controlled trial of atendol and pindolol in human pregnancy effects on fetal haemodynamics," *BMJ* 304: 946–949 (1992).

Neven, L., et al., "Association of 70 kDa heat shock cognate proteins and acclimation to cold", *Plant Physiology* 99:1362–1369 (1992).

Nordwig, et al., "Breakdown of protein: Cleavage of peptides of the x–Pro Y type by kidney peptidases," *Biochim. Biophys. Acta* 166: 293–295 (1968).

Orawski and Simmons, "Purification and properties of membrane–bound aminopeptidase P from rat lung", *Biochemistry* 343:11227–11236 (1995).

Orawski, A.T. and Simmons, W.H., "aminopeptidases P: Purification of a Membrane–Bound Brandykinase from Rat Lung," in *Recent Progress in Kinins*, Birkhauser Verlag Basel: (1992) pp. 414–421.

Parton, R.G., et al., "Regulated internalization of a caveolae", *J. Cell Biol.* 127:1199–1215 (1994).

Pellacani, et al., "Plasma kinins increase after angiotensin–converting enzyme inhibition in human subjects," *Clin Sci* 87: 567–574 (1994).

Persson B., et al., "Structures of N–terminally acetylated proteins", *Eur. J. Biochem.* 152:523–527 (1985).

Pesquero, et al., "Bradykinin metabolism pathway in the rat pulmonary circulation," *J. Hypertension* 10: 1471–1478 (1992).

Prechel, M.M., et al., "Effect of a new aminopeptidase P inhibitor, apstatin, on bradykinin degradation in the rat lung", *J. Pharm. Exper. Ther.* 275:1136–1142 (1995).

Predescu, D., et al., "Transcytosis in the continuous endothelium of the myocardial microvasculature is inhibited by N–ethylmaleimide", *Proc. Natl. Acad. Sci. USA* 91:3014–3018 (1994).

Rasmussen, S., et al., "Blood bradykinin concentration remains unchanged during captopril treatment", *Agents Actions* 9:592–597 (1982).

Robbi, M. and Beaufay, H., "The COOH terminus of several liver carboxylesterases targets these enzymes to the lumen of the endoplasmic reticulum", *J. Biol. Chem.* 266: 20498–20503 (1991).

Roberts, W.L., et al., "Structural characterization of the glycoinositol phospholipid membrane anchor of human erythrocyte acetylcholinesterase by fast atom bombardment mass spectrometry", *J. Biol. Chem.* 263:18776–18784 (1988).

Robinson, L.J. and Michael, T., "Mutagenesis of palmitoylation sites in endothelial nitric oxide synthase identifies a novel motif for dual acylation and subcellular targeting", *Proc. Natl. Acad. Sci. USA* 91:11776–11780 (1995).

Roblero, "Assay of Kinins by their Effects on Blood Pressure," *Res. Comm Chem. Path. Pharmacol.* 6(1): 207–212 (1973).

Roblero, J., et al., "A simple bioassay for rat glandular kallikrein", *Adv. Exp. Med. Biol.* 156a:437–443 (1983).

Rosenberry, T.L., et al., "The glycoinositol phospholipid anchor of human erythrocyte acetylcholinesterase", In *Biological Mass Spectrometry,* (A.L. Burlingame and J.A. McCloskey, eds.) pp. 455–475, Elsevier Science Publishers, Amsterdam (1988).

Rusko, J., et al., "Calcium–activated potassium channels in native endothelial cells from rabbit aorta: conductance, $Ca^{2+}$ sensitivity and block", *J. Physiol.* 455: 601–621 (1992).

Rusu, I. and Yaron, A., et al., "Aminopeptidase P from human leukocytes", *Eur. J. Biochem.* 210:93–100 (1992).

Ryan, et al., "Characterization of Rat pulmonary Vascular Aminopeptidase P in Vivo: Role in the Inactivation of Bradykinin," *J. Pharmacol. Exp. Therapeutics* 269(3): 941–947 (1994).

Ryan, et al., "Immunoaffinity Purifications of Aminopeptidase P from Guinea Pig Lungs, Kidney and Serum," *Biochem. Biophys. Res. Commun.* 205(3): 1796–1802 (1994).

Ryan, et al., "Purification and characterization of guinea pig serum aminoacylproline hydrolase (aminopeptidase P)", *Biochim. Biophys. Acta* 1119: 140–147 (1992).

Ryan, J.W., et al., "A radiochemical assay for aminopeptidase N.", *Analyt. Biochem.* 210: 27–33 (1993).

Ryan, J.W., et al., "Estimation of rate constants for reactions of pulmonary microvascular angiotensin converting enzyme with an inhibitor and a substrate in vivo", *J. Pharmacol. Exptl. Ther.* 270:260–268 (1994).

Sanger, F., et al., "DNA sequencing with chain–terminating inhibitors", *Proc. Natl. Acad. Sci.* 74:5463–5467 (1977).

Sargiacomo, M., et al., "Signal transducing molecules and glycosylphosphatidylinositol–linked proteins form a caveolin–rich insoluble complex in MDCK cells", *J. Cell Biol.* 122:789–807 (1993).

Schagger, H. and von Jagow, G., "Tricine–sodium dodecyl sulfate–polyacrylamide gel electrophoresis for the separation of proteins in the range from 1 to 100 kDa", *Anal. Biochem.* 166:368–379 (1987).

Schaller, et al., "Enzyme–linked immunosorbent assay for the neuropeptide ;head activator,"*Eur. J. Biochem.* 138: 365–371 (1984).

Schnitzer, J.E., et al., "Caveolae from luminal plasmalemma of rat lung endothelium: Microdomains enriched in caveolin, $Ca^{2+}$–ATPase, and inositol triphosphate receptor", *Proc. Natl. Acad. Sci. USA* 92:1759–1763 (1995).

Schnitzer, J.E., et al., "Endothelial caveolae have the molecular transport machinery for vesicle budding, docking, and fusion including VAMP, NSF, SNAP annexins, and GTPases", *J. Biol. Chem.* 270:14399–14404 (1995).

Schnitzer, J.E., et al., "Separation of caveolae from associated microdomains of GPI–anchored proteins", *Science,* 269:1435–1439 (1995).

Shimamoto, K. and IImura, O., "Measurement of circulating kinins, their changes by inhibition of kininase II and their possible blood pressure lowering effect", *Agents Actions* 22: 297–307 (1987).

Simionescu, M., et al., "Differentiated microdomains on the luminal surface of capillary endothelium: distribution of lectin receptors", *J. Cell Biol.* 94:406–413, (1982).

Simionescu, N., et al., "Rings of membrane sterols surround the openings of vesicles and fenestrae, in capillary endothelium", *J. Cell Biol.* 97:1592–1600 (1983).

Simmons, et al., "Membrane–bound aminopeptidase P from bovine lung", *J. Biol. Chem.* 267:4897–4903 (1992).

Smits, et al., "Interaction of ANP and bradykinin during endopeptidase 24.11 inhibition: renal effects", *Am. J. Physiol.* 258: F1417–1424 (1990).

Song, et al., "Co–purification and direct interaction of ras with caveolin, an integral membrane protein of caveolae microdomains", *J. Biol. Chem.* 271:9690–9697 (1996).

Stahl, et al., "The urokinase–type plasminogen activator receptor, a GPI–linked protein, is localized in caveolae", *J. Cell Biol.* 129:335–344 (1995).

Sturrock, et al., "Assignment of free and disulfide–bonded cysteine residues in testis angiotensin–converting enzyme: functional implications", *Biochemistry* 35:9560–9566 (1996).

Suggs, et al., "User of synthetic oligonucleotides as hybridization probes: Isolation of cloned cDNA sequences for human B2microglobulin", *Proc. Natl. Acad. Sci.* 78:6613–6617 (1981).

Tanoue, A., et al., "Structural organization of the gene for human prolidase (peptidase D) and demonstration of a partial gene deletion in a patient with prolidase deficiency", *J. Biol. Chem.* 265:11306–11311 (1990).

Tanoue, et al., "Molecular defect in siblings with prolidase deficiency and absence or presence of clinical symptoms",*J. Clin. Invest.* 87:1171–1176 (1991).

Tsunasawa, et al., "Microsequence analysis of N–terminally blocked proteins", *J. Prot. Chem.* 11:382–383 (1992).

Udenfriend, et al., "Prediction of a $\omega$ Site in Nascent Precursor of Glycosylphosphatidylinositol Protein," *Meth. Enzymol.* 150: 571–582 (1995).

Vallee, et al., "Zind coordination, function, and structure of zinc enzymes and other proteins", *Biochemistry* 29:5647–5659 (1990).

Vanhoof, et al., "Kininase activity in human platelets: Cleavage of the $Arg^1$–$Pro^2$ bond of bradykinin by aminopeptidase P", *Biochem. Pharmacol.* 44:479–487 (1992).

Vanhoof, et al., "Localization and characterization of aminopeptidase P in bovine adrenal medulla", *Neurochem. Int.* 21:203–208 (1992).

Venema, R.C., et al., "Role of the enzyme calmodulin–binding domain in membrane association in phospholipid inhibition of endothelial nitric oxide synthase", *J. Biol. Chem.* 270: 14705–14711 (1995).

Venema, R.C., et al., "Identification, characterization, and comparison of the calmodulin–binding domains of the endothelial and inducible nitric oxide synthase", *J. Biol. Chem.* 271:1–6 (1996).

Venema, R.C., et al ., "Organization of the bovine gene encoding the endothelial nitric oxide synthase", *Biochim. Biophys. Acta* 1218:413–420 (1994).

Vergas Romero, et al., "Purification and amino acid sequence of aminopeptidase P from pig kidney", *Eur. J. Biochem.* 229:262–269 (1995).

von Heijne, "Patterns of Amino Acids near Signal–Sequence Cleavage Sites," *Eur. J. Biochem.* 133:17–21 (1983).

Wallace, R.B., , et al., "The use of synthetic oligonucleotides as hybridization probes, II. Hybridization of oligonucleotides of mixed sequence to rabbit β–globin DNA", *Nucleic Acids Res.* 9:879–894 (1981).

Walter, R., et al., "Proline specific endo– and exopeptidases", *Mol. Cell. Biochem.* 30:111–127 (1980).

Wold, F., "In vivo chemical modification of proteins (Post–translational modification)", *Ann. Rev. Biochem.* 50:783–814 (1981).

Wood, W.I., et al., "Base composition independent hybridization in tetramethylammonium chloride: A method for oligonucleotide screening of highly complex gene libraries", *Proc. Natl. Acad. Sci.* 82:1585–1588 (1985).

Yaron, A. and Naider, F., "Proline–dependent structural and biological properties of peptides and proteins", *Crit. Rev. Biochem. Mol. Biol.* 28:31–81 (1993).

Yaron, et al., "Aminopeptidase–P", *Biochem. Biophys. Res. Comm.* 32:658–663 (1968).

Yoshimoto, et al., "Sequencing and high expression of aminopeptidase P gene from *E. coli* HB 101", *J. Biochem.* 105:412–416 (1989).

Yoshimoto, et al., "Substrate Specificity of Aminopeptidase P from *Escherichia coli:* Comparison with Membrane–Bound Forms from Rat and Bovine Lung," *Arc. Biochem. Biophys.* 311(1):28–34 (1994).

Yoshimoto, et al., "A Novel Assay Method for Aminopeptidase P and Partial Purification of To Types of the Enzyme in *Escherichia coli,"* *Agric. Biol. Chem.* 52(8): 1957–1963 (1988).

Yuen, et al., "Microanalysis of SDS–PAGE electroblotted proteins", *BioTechniques* 7:74–82 (1989).

Zamze, S.E., et al., "Characterization of the cross–reacting determinant (CRD) of the glycosyl–phosphatidylinositol membrane anchor of *trypanosoma brucei* variant surface glycoprotein", *Eur. J. Biochem.* 176:527–534 (1988).

Venema et al., 1997, "Cloning and tisue distribution of human membrane–bound aminopeptidase P." Biochimica et Biophysica Acta 1354:45–58.

Ju et al., 1997, "Aminopeptidase P in human tissues: Northern blot analysis." FASEB J. 11:A504.

Sidorowicz et al., 1984, "Kinin cleavage by human erythrocytes." Am. J. Hematol. 17:383–392.

\* cited by examiner

```
human  MARAHWGCCPWLVLLCACAWGHTKPLDLGGQ--DVRNCSTNPPYLPVTVV   48
       || | |||| |||||| |||||||| | |    | |||||||| ||||||| |
pig    MAQACWGCYPWLVLICACAWGHPKSLN---QREDVRNCSTSPPYLPVTAV   47 human  NTTMSLTALRQQMQTQNLSAYIIPGTDAHMNEYIGQHDERRAWITGFTGS   98
       ||| ||||| || |||||||||| |||||| ||| | ||||||||| ||
pig    NTTAQLTALREQMLTQNLSAYIIPDTDAHMSEYIGECDQRRAWITGFIGS   97 human  AGTAVVTMKKAAVWTDSRYWTQAERQMDCNWELHKEVGTTPIVTWLLTEI  148
       || |||| |   ||||||||||||||||||||||||||||  |  ||||||||
pig    AGIAVVTERKAALWTDSRYWTQAERQMDCNWELHKEVSTGHIVTWLLTEI  147 human  PAGGRVGFDPFLLSIDTWESYDLALQGSNRQLVSITTNLVDLVWGSERPP  198
       | |||||||||| | ||||| ||| ||   ||| ||||||||||||||||
pig    PVGGRVGFDPFLFSIDSWESYDVALQDADRELVSITVNLVDLVWGSERPP  197 human  VPNQPIYALQEAFTGSTWQEKVSGVRSQMQKHQKVPTAVLLSALEETAWL  248
       ||||||||||||||||||||||||| ||||||||  ||||||||||| |||||||
pig    LPNAPIYALQEAFAGSTWQEKVSNIRSQMQKHHERPTAVLLSALDETAWL  247 human  FNLRASDIPYNPFFYSYTLLTDSSIRLFANKSRFSSETLSYLNSSCTGPM  298
       |||| ||||||||||||||||||||||||||||||||||| ||||||| |
pig    FNLRSSDIPYNPFFYSYTLLTDSSIRLFANKSRFSSETLQYLNSSCNSSM  297 human  CVQIEDYSQVRDSIQAY-SLGDVRIWIGTSYTMYGIYEMIPREKLVTDTY  347
       ||| ||||| ||||||| | |||| ||||| | ||| || |  ||| | |
pig    CVQLEDYSQIRDSIQAYTS-GDVKIWIGTRYTSYGLYEVIPKEKLVEDDY  346 human  SPVMMTKAVKNSKEQALLKASHVRDAVAVIRYLVWLEKNVPKGTVDEFSG  397
       ||||| ||||||| |||||||||||||||||||| ||||||| ||||||||
pig    SPVMITKAVKNSREQALLKASHVRDAVAVIRYLAWLEKNVPTGTVDEFSG  396 human  AEIVDKFRGEEQFSSGPSFETISASGLNAALAHYSPTKELNRKLSSDEMY  447
       |  | |||||| | ||||||||||||||||||||||||||| |||||||||
pig    AKRVEEFRGEEEFFSGPSFETISASGLNAALAHYSPTKELHRKLSSDEMY  446 human  LLDSGGQYWDGTTDITRTVHWGTPSAFQKEAYTRVLIGNIDLSRLIFPAA  497
       ||||||||||||||||||||||||||||||||||||||||||||||||| ||||
pig    LLDSGGQYWDGTTDITRTVHWGTPSAFQKEAYTRVLIGNIDLSRLVFPAA  496 human  TSGRMVEAFARRALWDAGLNYGHTGHGIGNFLCVHEWPVGFQSNNIAMA  547
       |||| |||||||| |||| |||||||||||||||||||||||||  || ||
pig    TSGRVVEAFARKALWDVGLNYGHTGHGIGNFLCVHEWPVGFQYGNIPMA  546 human  KGMFTSIEPGYYKDGEFGIRLEDVALVVEAKTKYPGE-LPDLVVSFVPYD  596
       |||||||||||| |||||||||||||||||||||||||| | |||||||||
pig    EGMFTSIEPGYYQDGEFGIRLEDVALVVEAKTKYPGTYLTFEVVSLVPYD  596 human  RNLIDVSLLSPEHLQYLNRYYQTIREKVGPELQRRQLLEEFEWLQQHTEP  646
       | |||||||||| |||||||||| |||||||||||| ||||  ||| ||||
pig    RKLIDVSLLSPEQLQYLNRYYQAIREKVGPELQRRGLLEELSWLQRHTEP  646 human  LAARA-PDTASWASVLV-VSTLAILGWSV..............        673
       | ||| |  | ||  || |||||||||
pig    LSARAAPTT-SLGS-LMTVSALAILGWSV..............        673
```

FIG. 1

HUMAN AMINOPEPTIDASE P GENE

CROSS REFERENCE TO RELATED APPLICATION

This application claims benefit of U.S. Provisional Application Ser. No. 60/057,854, filed Sep. 2, 1997.

BACKGROUND OF THE INVENTION

Evidence of an aminoacylproline hydrolase was first encountered in studies of the metabolism of bradykinin (BK). It was found that BK (Arg-Pro-Pro-Gly-Phe-Ser-Pro-Phe-Arg) is inactivated virtually quantitatively during a single passage through the rat pulmonary vascular bed (1,2). BK is degraded through 5–8 half-lifes during the 2–3 sec required for a single transit from the right to the left side of the heart (31). If, as appears to be the case, the overall metabolism occurs within the pulmonary capillary bed (mean transit time of about 0.2 sec), the half-life of BK within the capillary bed is on the order of 0.03 sec. From these data, it was postulated that the relevant kininase enzymes are situated on, or near, the luminal surface of pulmonary endothelium so as to have access to intravascular substrates (1,2,4). In time, it was shown that angiotensin converting enzyme (ACE) plays a central role in the inactivation of BK and is, in fact, disposed on the luminal surface of pulmonary microvascular endothelium (5,6). ACE was found to account for one of the hydrolytic reactions (cleavage of the $Pro^7$-$Phe^8$ bond) observed in the earliest studies (2).

The original data indicated that a peculiar aminopeptidase also participated in the degradation of BK (1,2). The result caused some concern and confusion in that none of the aminopeptidases then known was capable of hydrolyzing an imido bond ($Arg^1$-$Pro^2$). Shortly thereafter, an aminoacylproline hydrolase was isolated from an extract of *E. coli* and was shown to be capable of hydrolyzing polyproline and the $Arg^1$-$Pro^2$ bond of BK (204,205). The bacterial enzyme was named aminopeptidase P, a name now used for aminoacylproline hydrolases obtained from any animal or plant source.

Shortly after the discovery of *E. coli* AmP, it was found that pig kidney extracts contained a particulate-associated AmP activity and that the AmP-like substance was not solubilized by detergents (78). The AmP-like material, believed to have been solubilized in a butanol/aqueous solvent system, behaved like a complex mixture of substances on chromatography. As a further complication, pig kidney AmP did not hydrolyze polyproline, the substrate used to assay *E. coli* AmP. A weakly reactive synthetic substrate was prepared, Gly-Pro-Hyp, and AmP activity was measured in terms of the rate of formation of free glycine in a two-step assay protocol (78).

Membrane-associated AmP remained effectively inaccessible to conventional chemical and biochemical analysis until the early 1990's. The difficulties of AmP catalytic assay was solved by preparing the synthetic substrate Arg-Pro-Pro-[$^3$H]benzylamide (APPBz-$^3$H) (20 Ci/mmol), a substrate related to the N-terminal tripeptide of bradykinin (21,22). APPBz-$^3$H proved to be highly reactive with AmP and could, by virtue of its high specific radioactivity, be used under conditions of first order enzyme kinetics. However, the problem of the inefficient solubilization of particulate-associated AmP was not solved, and a search for soluble forms of AmP was therefore conducted. Guinea pig serum was found to be an enormously rich source of AmP (21,22) and was used as the starting material to obtain apparently homogeneous AmP in two isoforms, Mr 89,000 and 81,500 (22).

Independently, Hooper et al (111) solved the problem of solubilizing pig kidney AmP. They found that AmP is bound to membranes via a glycosyl phosphatidylinositol (GPI) lipid anchor and can be solubilized efficiently using phosphatidylinositol-specific phospholipase C (PI-PLC). Subsequently, Simmons et al (180) and Ryan, et al. (32) showed that rat and bovine lung and guinea pig lung and kidney forms of AmP are solubilized by PI-PLC. Human kidney AmP is also solubilized by PI-PLC. Once thus solubilized, AmP no longer behaves anomalously on conventional chromatography matrices.

Aminopeptidase P (AmP; EC 3.4.11.9) is the only known human enzyme capable of hydrolyzing a N-terminal imido bond, a bond common to many collagen degradation products and some neuropeptides, cytokines and vasoactive peptides (14,16,21,22,31,98,111,146,147,152,165,192,205). AmP occurs in cell membrane-bound and intracellular soluble forms and is not uniformly distributed among tissues nor among cell-types of a given tissue (21,39,165,205), which implies that physiologic roles of AmP are determined by anatomic disposition (a determinant of reaction conditions and access to substrates) as well as by catalytic selectivity.

It is therefore an object of the present invention to help define both molecular and anatomic determinants of AmP functions.

SUMMARY OF THE INVENTION

The genomic DNA and full-length cDNA sequence of human kidney AmP has been determined. The deduced amino acid sequence indicates that AmP is a member of the recently-recognized "pita bread-fold" protein family, a family of very little sequence homology but of high similarity in three-dimensional structure (59). Within the "pita bread-fold" family, there is a subdivision called the "proline peptidase" family, with which human kidney AmP shares at least five short blocks of amino acid sequences of fair to high homology (although overall homologies are low). These blocks are known to contain the amino acid residues that compose the catalytic site of *E. coli* methionine aminopeptidase, a metallo-peptidase whose structure has been determined by x-ray crystallography (59). Based on these comparisons, it is postulated that human kidney AmP amino acid residue H430 serves as the proton shuttle, and D450, D461, H520, E555 and E569 (see SEQ ID NO:2) are the catalytic metal ligands. This can be tested by preparing the site-specific mutants H430F, D450N, D461N, H520F, E555Q and E569Q. In addition, each of five potential N-glycosylation sites and each of five C residues can be mutated to examine for indirect effects of glycosyl groups and disulfide bonds on catalytic activity, solubility and protein stability. In addition, one can determine the chromosome location of AmP.

Using the sequence and immunocytochemistry at the level of electron microscopy (EM), one can define, in major organs, the cellular and subcellular sites of AmP, and, using subcellular fractions, dispositions of AmP in terms of anatomically proximate receptors and cell signaling molecules (the bradykinin B2 receptor, eNOS and guanylate cyclase) whose activities may directly or indirectly be affected by AmP activities.

This will help characterize structure-function relationships of human AmP at three levels; 1. molecular structure/catalytic activity, 2. cellular and subcellular distributions that determine orientations (and access to substrates) of the catalytic site, and 3. disposition in respect to "nearest-neighbor" effector and cell signaling molecules.

In addition to providing conceptual advances in understanding of AmP functions, this work provides tools (antibodies and oligonucleotide probes) useful for clinical studies of AmP deficiency states.

Use of the cDNA, genomic DNA, or a combination, for protein expression has commercial implications. The inferred amino acid sequence can be used as a starting point for defining higher structure and function. Through protein expression, crystals can be prepared for determination of higher structure. Reverse transcriptase-polymerase chain reactions was used to obtain four overlapping fragments of AmP cDNA. The intact full-length cDNA can be obtained by ligation. The first (nt 1–474) and second (359–734) fragments are digested with XmnI (nt 365) and then ligated. The product (1–734) and the third fragment (634–1702) are digested with SacI (nt 652) and ligated to yield 1–1702; which, with the fourth fragment (1588–3428), are digested with ScaI (nt 1625) and ligated to yield 1–3428. DNA encoding human AmP can also be produced by direct synthesis of appropriate oligonucleotides based on the disclosed amino acid and nucleotide sequences. For large scale protein expression, the full-length DNA is transferred into the expression vector pVL1393 and used with co-transfectant, Baculogold, in the baculovirus/Sf9 insect cell system. This system has the capacity to produce recombinant AmP in the amounts needed for x-ray crystallography. Knowledge of cellular and subcellular sites of AmP will be predictive of the consequences of specific peptidase deficiency or inhibition. Membrane-bound forms appear to be disposed as ectoenzymes, which can be verified by EM immunocytochemistry. Soluble AmP is believed to be disposed in as yet unknown intracellular sites. Actual dispositions can be determined as a means of defining functional roles of AmP: AmP disposed in the endoplasmic reticulum of, for example, lymphocytes is expected to have functions and reaction conditions different from ectoenzyme forms disposed on renal proximal tubule and small intestine brush border epithelia and different yet again from AmP disposed on the luminal surface of vascular endothelium.

Oligonucleotide probes and primers can be used to identity patients with homozygous or heterozygous AmP deficiencies. Primers can be used to examine for faulty AmP mRNA. Two pediatric patients with apparent homozygous deficiencies have been identified, at least one of which was mentally-retarded, epileptic and microcephalic. Early gene therapy could moderate any central nervous system injuries attributable to the lack of AmP, if administered early enough. Prenatal diagnosis of an AmP deficiency state would help decision making by parents and health care providers.

As a member of the so-called "pita bread-fold" protein family, human AmP has a recognizable putative proton shuttle and five putative metal ligands. With molecular modelling, and expressed protein, one can design inhibitors of AmP. Since AmP inactivates the blood pressure-lowering oligopeptide bradykinin, inhibitors of AmP could be useful as antihypertensive agents. Bradykinin is reported to be antimitogenic and antiatherogenic. Thus, inhibition of AmP (and concomitant preservation of bradykinin) should be useful in preventing or limiting arterial stenosis or restenosis and development of atherosclerosis. By similar means, the structure of AmP can be used to design synthetic substrate, which in turn can be used to develop diagnostic assays based on AmP catalytic activity. These substrates and others will be of value, along with recombinant AmP, for screening of drugs designed to inhibit AmP.

Since AmP is a protease capable of hydrolyzing N-terminal imido bonds it should be useful in degrading industrial protein feedstocks to free amino acids, and in breaking down wastes that have significant protein content, especially proline-rich collagenous protein wastes (wastes that are otherwise resistant to degradation by better-known enzymes such as trypsin and chymotrypsin). In so-called intestinal malabsorption syndromes, patients are sometimes given encapsulated digestive enzymes to improve breakdown of foodstuffs. AmP should be a beneficial additive to the mix of encapsulated enzymes to facilitate breakdown of proline-rich peptides.

Human AmP cDNA and genomic DNA can be used for designing antisense oligonucleotides, which may, in turn, be useful in patients having a surplus of AmP that, for example, contributes to arterial stenosis or restenosis or that contributes to development of atherosclerosis. By analogy with uses of AmP inhibitors, some downward modulation of AmP activity via use of antisense nucleotides might provide antihypertenstive effects.

There are now some highly reliable computer programs that can identify peptide sequences within the primary structure of a protein that are likely to be immunogenic. Such programs can be used to identify immunogenic sequences within the inferred human AmP structure. Thus, knowledge of the nucleotide sequence of human AmP cDNA and genomic DNA can lead to the design of synthetic "epitopes" and preparation of highly specific polyclonal and monoclonal antibodies. Antibodies are useful in the development of immunoassays having diagnostic uses. Alternatively, recombinant expression of AmP protein clearly provides an appropriate antigen for preparing specific antibodies to AmP.

Human AmP cDNA and genomic DNA can be used to develop transgenic animal models and can be used, under low stringency conditions, to clone AmP cDNAs and genomic DNAs of other animal species. By the latter means, knockout animal models can be prepared and provided commercially to other investigators. The AmP cDNA and genomic DNA can also be used to prepare stable transformants that can be provided commercially to other investigators. With knowledge of the AmP DNA sequence and its coding for putative critical amino acid residues of the catalytic site, mutants can be prepared to modulate catalytic activity. Similarly, unglycosylated, truncated forms of AmP can be expressed that are catalytically active but more amenable than wild-type AmP to crystallization. Such forms should be highly useful to drug design firms.

The DNA of a functionally related enzyme, angiotensin converting enzyme (ACE), is known to be polymorphic, and one form is associated with high levels of serum ACE. Human AmP cDNA and genomic DNA can be used to examine for polymorphisms, which, if found, can be further studied for functional impacts.

BRIEF DESCRIPTION OF THE DRAWINGS

FIG. 1 is a comparison of the amino acid sequence of human aminopeptidase P to porcine amino peptidase P.

DETAILED DESCRIPTION OF THE INVENTION

History of Isolation and Physiological Roles of AmP

Using guinea pig serum AmP as immunogen, mouse polyclonal and then monoclonal antibodies, which were found to bind guinea pig and rat lung and kidney forms of AmP at high affinity, were prepared. One of the monoclonal antibodies, HL510, also binds human AmP (32). The anti-AmP preparations have proved to have many uses and have been particularly helpful in immunoaffinity chromatography. Immunoaffinity chromatography has substantially simplified the task of purifying AmP and yields apparently pure AmP in the mole quantities needed for structure studies. HL510 has also been used for light microscopy immunocytochemistry. In guinea pigs, spleen, kidney, liver, lungs and small intestine are particularly rich sources of catalytically-active immunoreactive AmP.

Extensive amino acid sequencing using guinea pig lung and kidney forms of AmP were performed. Protein and cDNA databases were searched. It was found that guinea pig AmP contains at least three of six blocks of highly conserved sequences characteristic of a recently recognized group of proteins called the proline peptidase family. The match of primary structures appears to have functional significance in that all family members (e.g. human proline dipeptidase) are, like mammalian AmP, capable of hydrolyzing imido (as opposed to amido) bonds. The conserved blocks provided a simple guide for cloning AmP cDNA because one could then specify, in terms of block placements (e.g. block C within the middle of AmP and block F near the C-terminus), pairs of primers that would yield large or small stretches of cDNA.

Recently, pig kidney cortex AmP has been sequenced almost completely (Edman degradation and some mass spectroscopy) (196). In addition, AmP and the entire proline peptidase family have been postulated to be members of a larger protein family ("pita bread-fold" family) not characterized by common functions but by highly similar 3-dimensional structures. Using these new findings and our data, human kidney AmP cDNA was clone. Unexpectedly, the primers prepared originally to correspond with guinea pig lung AmP sequences worked as well with human kidney mRNA.

In addition, the database searches made evident that AmP has a clinical relevance greater than previously supposed. A Medline search of the biochemistry of human proline dipeptidase (PDP) raised several apparently relevant issues. For example, PDP deficiencies are well-documented and appear to be caused by several different gene defects, including single base mutations and inappropriate splicing (83,84,187, 188). Both protein-positive and protein-negative PDP deficiency states have been described. It is therefore believed that the genetics of PDP deficiencies will provide a guide for searches for AmP deficiencies. It was also found that AmP deficiencies have been reported and can have clinical expressions like those seen in PDP deficiencies. Blau et al (62) found two boys of consanguineous parents who excreted in urine a mixture of proline-containing oligopeptides, including Gly-Pro, a dipeptide excretory product characteristic of PDP deficiency. However, the boys excreted in greater amounts (up to 30 mg/day) a tetrapeptide, Gly-Pro-Hyp-Gly, not seen in urines of normal subjects nor patients with PDP deficiencies. It was determined that the excreted tetrapeptide has a sequence identical to the N-terminal tetrapeptide of a putative hormone called antiarrhythmic peptide (AAP) (Gly-Pro-Hyp-Gly-Ala-Gly) (51–56). In the characterization of guinea pig serum AmP (21,22), it has been found that AmP binds AAP at high affinity in vitro. Gly-Pro-Hyp-Gly is among the commonest tetrapeptide sequences of collagen, and its excretion in urine of an AmP-deficient patient may reflect failure in late stage collagen metabolism and amino acid conservation.

In addition, Blau et al (62) found that an intestinal biopsy sample obtained from one patient contained saccharase and PDP activities within the normal range but did not contain AmP catalytic activity (less than 2% of the normal mean).

Both of the patients were mentally-retarded. One, in addition, had microencephaly and epilepsy. Mental retardation is also a characteristic of PDP deficiency (84,187,188). It may be relevant to both deficiency states that AmP and PDP occur in rat cerebral cortex, largely in association with astrocytes (98,147,148). It may also be relevant that astrocytes appear to 'guide' vasculogenesis in retina (30) and perhaps in other parts of the central nervous system. AmP-related mental retardation may result in part from deficient vasculogenesis in early development of the central nervous system.

In rat lungs, AmP and ACE together account for all of the bradykinin-inactivating activity. This result initially appeared to be inconsistent with the fact that five of the eight peptide bonds of BK are hydrolyzed during passage through the rat pulmonary vascular bed (1,2,14). However, biologically-inert metabolic fragments of BK are not, a priori, invulnerable to proteolytic attack. Indeed, one pulmonary endothelial peptidase, dipeptidyl peptidase IV (DP IV), cannot hydrolyze BK (124,199) but can rapidly degrade the BK fragments formed by AmP (e.g. des-Arg$^1$-BK) to release Pro-Pro. Pro-Pro is a BK metabolite. It thus appears that three of the five hydrolytic reactions occur after BK has been inactivated by AmP and/or ACE. Recently, Simmons and colleagues (120) have confirmed these findings and have shown that combined inhibition of ACE and AmP has profound blood pressure lowering effects in renin-related hypertension (119).

There are large interspecific differences in distributions of AmP. AmP occurs in abundance in guinea pig and rat kidneys and lungs but is virtually absent from rabbit and cat kidneys and lungs (16). In fact, human tissues were found to have AmP in relatively high abundance (Table 1). By Northern blot analysis, human kidney, liver, small intestine, heart, lung, colon and placenta are particularly enriched in AmP mRNA (47).

TABLE 1

Relative abundance of aminopeptidase P mRNA in various human tissues

| Tissue | Relative intensity |
| --- | --- |
| Kidney | 100 |
| Lung | 32 |
| Heart | 42 |
| Placenta | 16 |
| Liver | 55 |
| Small Intestine | 55 |
| Colon | 21 |

This information can be used to a) relate molecular structure to AmP catalytic activity, b) define its cellular and subcellular dispositions so as to clarify orientations of the catalytic site, and c) define the anatomic relationships of AmP to functionally-related "nearest-neighbor" effector and cell signaling molecules.

The underlying hypothesis is that roles of AmP in systemic biochemistry are likely to be determined by reaction conditions, access to substrates and responses of "nearest neighbors" (all set by anatomical relationships) as well as by catalytic selectivity. Thus, AmP disposed near cell matrix may be well-positioned to participate in secondary, tertiary or higher stages of collagen metabolism, AmP disposed on intestinal brush border epithelium likely functions as a specialized digestive enzyme, AmP disposed on renal proximal tubule epithelium plausibly participates in conservation of proline, AmP in neuronal tissues may process neuropeptides, and AmP disposed on vascular endothelium processes circulating peptide hormones such as bradykinin (31,34,39,181). It has been suggested that soluble forms of AmP disposed in platelets and lymphocytes may act to modulate effects of cytokines and peptides that mediate acute inflammation (165,191,192,205).

As noted above, two pediatric patients with AmP deficiencies have been identified, both mentally-retarded (62). Whether mental retardation can be attributed to AmP deficiency is not yet clear, but the possibility should be testable in that the cloned human AmP cDNA provides a guide for preparing AmP knockout mice. Similarly, there is a basis for blocking AmP expression in rats by use of antisense AmP oligonucleotides. Rat AmP cDNA can be cloned using human AmP cDNA, or fragments, as a probe.

Both AmP-deficient patients excreted oligopeptides having N-terminal Xaa-Pro-residues, and these peptides (most notably Gly-Pro-Hyp-Gly) may most directly reflect the AmP deficiency state. AmP should degrade the latter peptide to form Gly plus Pro-Hyp-Gly. The latter is a substrate for DAP IV, and the expected dipeptide, Pro-Hyp, is a substrate for proline dipeptidase (PDP). Normally, human renal proximal tubule contains AmP, DAP IV and PDP in abundance (110), and the three enzymes may constitute a cascade of reactions important for amino acid conservation.

Homozygous AmP deficiencies are probably rare. Partial AmP deficiencies may be relatively common, a possibility that has been suggested vis a vis a side effect of angiotensin converting enzyme (ACE) inhibitor therapy (31): ACE inhibitors are widely-used for the treatment of hypertension and congestive heart failure (93). Most patients experience few, if any, side effects. However, a small percentage of patients develop urticaria and angioedema (99), problems that can also occur when bradykinin is infused i.v. in relatively high doses (66). It appears that AmP is normally the last defense against the entry of BK into the systemic arterial blood of patients treated with ACE inhibitors (31). Clearly, patients with a relative or complete AmP deficiency could be at exceptional risk if treated with an ACE inhibitor. When angioedema affects tissues of the upper airway, thereby obstructing air flow, death can occur within minutes. Therefore, even though angioedema is an uncommon side effect of ACE inhibitors, it would be worthwhile to determine its molecular basis. If an AmP deficiency underlies ACE inhibitor-induced angioedema, a pretreatment test for the deficiency could spare some patients from life-threatening ACE inhibitor-induced angioedema.

Using the AmP catalytic assay described herein and the knowledge that human plasma, platelets, lymphocytes and urine (all being readily accessible biopsy tissues) normally contain AmP catalytic activity (21,106,165,191,205), untreated hypertensive patients can be screened now for AmP deficiencies. Antibodies to human AmP and genetic probes can be produced. Thus, AmP deficiency states, protein-positive and protein-negative, and their bases at the molecular level can all be determined.

Molecular Structure and Function

Purification of Aminopeptidase P.

Three groups independently purified aminopeptidase P (AmP) to apparent homogeneity. As noted above, guinea pig serum is a rich source of soluble AmP, which can be purified to obtain two isoforms. Mr 89,000 and 81,500 (22). On concanavalin-Sepharose chromatography, both isoforms were found to behave as a mixture of biantennary and high mannose glycoproteins (70%/30%). Turner and colleagues (111) purified pig kidney cortex AmP, after converting the amphipathic into the hydrophilic form with phosphatidylinositol-specific phospholipase C (PI-PLC), to obtain an apparent single isoform, Mr 95,000, that was converted by treatment with N-glycosidase F into two isoforms. Mr 71,500 and 68,000. Simmons and Orawski (180) purified bovine lung AmP, solubilized with PI-PLC, which on SDS-PAGE migrated at Mr 95,000. All three purifications were laborious and required seven or more steps. The Turner protocol employed nine steps and provided apparently pure AmP in a 1% yield (111). Guinea pig, pig and bovine forms of AmP all behaved as if N-blocked on Edman degradation.

To obtain a simpler means of purifying AmP, two mice were immunized with the biantennary form of guinea pig serum AmP. Both mice produced high titer anti-AmP, which, on Western blotting, proved to be reactive with both AmP isoforms, Mr 89,000 and 81,500. The spleen of one mouse was used to produce hybridomas, twelve of which produced anti-AmP, all of the $IgG_1$ isotype. A hybridoma that produced anti-AmP with anticatalytic effects on reaction with guinea pig serum, rat kidney and human serum AmPs, was selected. After double cloning, ascites monoclonal antibodies, known hereinafter as HL510, was produced.

HL510 was used to prepare an immunoaffinity matrix (antibody bound to protein A-Sepharose and then crosslinked with a bifunctional active ester). The immunoaffinity matrix enabled isolated of homogeneous guinea pig AmP in the quantities needed for amino acid sequencing and was used to purify hydrophilic (post-PI-PLC treatment) forms of kidney and lung AmP as well as serum AmP. A 4 ml column of the matrix was used repeatedly to obtain a total of about 20 nmol of apparently pure AmP.

Others tried to purify soluble "cytosolic" forms of AmP. Harbeck and Mentlein (98) obtained highly-purified rat brain AmP, which behaved on molecular sieving (Mr 143,000) as if a dimer of the Mr 71,000 monomer found on SDS-PAGE under reducing conditions. Whether brain AmP is an unglycosylated alternative gene product related to gpi-anchored AmP is not yet clear. The profile of rat brain AmP in terms of selectivity of substrate hydrolysis and responses to inhibitors and other affectors is similar to those of kidney, lung and serum AmPs, and alternative splicing of the primary transcript may account for the apparent absence of gpi-anchoring. However, it has been reported that some strains of *E. coli* contain two AmP products and two separate genes (206), which may also be the case for human AmPs.

Soluble forms of AmP have also been purified from human platelets (191) and leukocytes (165). Both AmPs migrate on SDS-PAGE at Mr 71,000. On molecular sieving, platelet AmP behaves as a cilel (Mr 223,000) and leukocyte AmP behaves as a dimer (Mr 140.000). No direct studies have been performed to clarify glycosylation, but human platelet AmP was not retained by a mixed concanavalin A/wheat germ lectin chromatography matrix.

Sequencing

Guinea pig AmP behaved on Edman degradation as if N-blocked. LysC digests of both kidney and lung AmP were therefore prepared, and the peptide products separated on Tris-tricine gels (79,172). Partial digestion conditions were used to generate relatively large fragments. Separated peptides were blotted to a Problott membrane (ABI), and three lung and four kidney AmP fragments were selected for sequencing. Where overlaps occurred (80 amino acid residues), lung and kidney AmPs were found to be identical in structure.

The "BLAST" network (49,50) was used to look for possible similarities to known proteins. The search picked up a tentative match with human proline dipeptidase (PDP). A second search using the "BLOCKS" program (102)

revealed that guinea pig AmP contains at least three of six highly conserved blocks of amino acid sequences that define a newly-recognized protein family called the proline peptidase family. Further details on how guinea pig kidney and lung AmPs line up with sequences of known members of the proline peptidase family (of which PDP is a member) were obtained using the program "IALIGN" (77). Through the foregoing analysis, it was evident that guinea pig kidney and lung AmPs contained all of proline peptidase blocks C,E and F.

The six conserved blocks in human prolidase (blocks A–F) are arranged alphabetically from the N-terminus. By comparison with human PDP, the order of sequenced fragments of guinea pig kidney and lung AmP was deduced. Importantly, the expected length of protein between the fragments could be estimated, keeping in mind that the number of residues between conserved regions in AmP are not the same as found for other members of the family (blocks E and F are fused in AmP but are separated by more than 20 amino acid residues in PDP) (83,84). This information reduced the number of PCR primers that one would need to test and provided clues for analyzing PCR data. Knowledge of the placement of blocks of conserved sequences also provided clear directions for the use of nested primers.

The proline peptidase group is a small family of related proteins including *E. coli* aminopeptidase P II, *E. coli* proline dipeptidase and human proline dipeptidase (PDP; prolidase). All three of these proteins are classified as manganese metalloenzymes, primarily because they are stimulated by $Mn^{2+}$. In this regard, mammalian AmP is also stimulated by $Mn^{2+}$ in its reaction with some, but not all, substrates (22, 31, 32, 111, 152, 180). Zinc, 0.2 mole, was reported to be present per *E. coli* AmP subunit as detected by atomic absorption spectrophotometry (206), and pig kidney AmP is reported to contain about 1 mole of Zn per mole of enzyme (108). Finding a match of guinea pig lung AmP with human PDP was intriguing because of their similarity in substrate selectivity. Proline dipeptidase cleaves imide bonds of dipeptides in which proline is C-terminal, whereas AmP acts as an aminoacylproline hydrolase (22,29,32,83,188).

Matthews and colleagues solved the three-dimensional structure of *E. coli* methionine aminopeptidase (AMPM) by x-ray crystallography (59). They began a database search for sequence-relatives and found 12 other proteins with small blocks of fair sequence similarity. One sequence-relative was found to be *P. putida* creatinase (CREA), another protein whose three-dimensional structure is known. Although the primary sequence homology between AMPM and CREA is low. Matthews and coworkers found that each protein possessed a C-terminal domain disposed in a "pita bread" fold. 218 $C^{\alpha}$ atoms of each protein are superimposable to within 2.5 Å. Further examination of the primary sequences of other sequence-relatives of AMPM (including AmPs of *E. coli*, *S. lividans* and *M. tuberculosis*) revealed, in each case, $\alpha\alpha\beta\beta\beta$ sequences characteristic of "pita bread" folds. Of no less importance, binding sites for the catalytic divalent metal of AMPM were well-characterized and were known to be disposed on either side of a two-β-sheet cleft common to AMPM and CREA. Based on the homologous tertiary structural blocks of the AMPM "pita bread" family and their similarities to at least four of the conserved blocks of the proline peptidase family in combination with the sequence data, one could predict part of the tertiary structure of guinea pig AmP and identify at least four of the metal-binding amino acid residues of the catalytic site; all without knowing the complete amino acid sequence. Block C clearly is within a β-sheet of the catalytic crevice and contains two divalent metal ligands (later identified in human kidney AmP as D450 and D451; see below), and blocks E and F are clearly part of an apposing β-sheet and contain two more metal ligands (E555 and E569 in human AmP).

Dr. Wolfram Schäfer of the Max-Planck-Institut für Biochemie sequenced most of pig kidney AmP by Edman degradation and some mass spectrometry (196). Within the limits of the sequence data, guinea pig and pig AmP sequences are 93% identical and 98% highly homologous.

The data on human AmP, with those of Matthews and colleagues (59) and Schäfer and colleagues, makes evident that mammalian AmPs contain the six conserved blocks characteristic of the proline peptidase family and that all known members of the proline peptidase family in fact compose a subgroup of the AMPM/CREA family of proteins characterized (not by their functions but) by their "pita bread" tertiary conformations. Blocks A and B of proline peptidases are parts of exterior α-helices and blocks C, D, E and F are parts of the two apposing β-sheets that contain the catalytic site. With the primary sequence of human kidney AmP (see SEQ ID NO:2), the catalytic metal binding sites could be assigned: block C, D450 and D461; block D, H520; block E. E555; and block F, E569. A putative proton shuttle, H430, could also be postulated. Each of the putative divalent metal-binding ligands and the putative proton shuttle is a reasonable target for preparing site-specific mutants.

Human Kidney AmP cDNA.

There are large interspecific differences in AmP abundance and distributions among organs (16,21). Using human kidney and lung poly A RNAs in reverse transcriptase polymerase chain reaction (RT-PCR) studies with degenerate guinea pig primers, five cDNA fragments whose nucleotide sequences enabled preparation of nondegenerate primers for human AmP cDNA were obtained.

A sense primer based on QMDCNW (now known to be residues 124–129 of human AmP) was used with a reverse primer based on FQKEAY (residues 474–479) to obtain a 1068 bp fragment. Fragments from three separate PCR reactions were subcloned (TA Cloning Kit, Invitrogen) and sequenced. All three independent PCR products were found to have identical sequences, ruling out PCR nucleotide-incorporation errors. The remaining 5' and 3' nucleotide sequences were obtained by RACE methods. 5'-RACE was performed using both human kidney and lung poly A RNAs. PCR products were subcloned and sequenced. Kidney and lung cDNA sequences were identical for the N-terminal open reading frame plus 264 bases of the 5'-untranslated region. 3'-RACE was performed to obtain the C-terminal portion of AmP coding sequence plus a 1145 base 3'-untranslated region. Two independent reactions gave identical sequence results.

Composite cDNA and Amino Acid Sequences.

The composite cDNA sequence is shown in SEQ ID NO:1. The DNA sequence has an open reading frame of 2019 nucleotides. The deduced amino acid sequence (SEQ ID NO:2) comprises 673 residues with a calculated molecular weight of 75,490. Comparison of the human AmP amino acid sequence to that of the pig (reported by Turner, 113) shows evolutionary divergence with only 83% amino acid sequence identity between the two species (FIG. 1). Five of six potential N-glycosylation sites found in the pig sequence at residues 34, 48, 64, 277, 290, and 294 are conserved in the human sequence at residues 35. 49, 65, 278, and 291. Five of six cysteine residues that are potentially involved in disulfide bond formation are also conserved. These are located in the human sequence at positions 36, 127, 294, 299, and 531. By comparison of the human AmP amino acid sequence with that of *E. coli* methionine aminopeptidase (59), it is postulated that, for human AmP, H430 is the proton shuttle and D450, D461, H520, E555 and E569 are the catalytic metal ligands. Site-specific mutants can be used to test this and to determine placements of disulfide bonds. Potential N-glycosylation sites can be mutated to examine for effects on AmP solubility and stability.

Because AmP is a GPI-anchored protein, it is expected that the mature protein can be derived from a nascent form containing N- and C-terminal signal peptides that are removed during processing in the endoplasmic reticulum. Based on the weight-matrix method of von Heijne, analysis of the pig sequence (113) suggests that the N-terminal cleavage site is either Lys-24 or His-22. The most important sequence positions in the von Heijne method are those at -1 and -3. If Lys-24 represents the true cleavage site this would put Pro at the -1 position in the pig sequence which is unusual in eukaryotic signal sequences. Lys-24 and His-22 are both conserved in the human sequence as are the -1 and -3 positions relative to His-22 (FIG. 1). The -3 position relative to Lys-24 is also conserved. The −1 position, however, contains a Thr residue rather than a Pro which is more commonly found in this position in eukaryotic signal sequences. Based on the cleavage prediction criteria developed by Udenfriend and Kodukula (61), Ala-649 has been predicted to be the C-terminal ω-residue in the pig enzyme with Arg and Ala in the important ω+1 and ω+2 positions, respectively (113). Identical ω, ω+1, and ω+2 residues are found in the human AmP enzyme (FIG. 1). The exact anchorage site can be examined by mutation and by Edman degradation and mass-spectrometry of C-terminal peptides produced by GluC digestion.

Genomic DNA Sequence of Human AmP.

A search of GenBank using the human AmP cDNA sequence revealed a sequence, dJ753P9 (an unfinished human chromosome X genomic sequence from the Sanger Center group of the Human Genome project), containing human AmP sequences. A comparison of this clone with the AmP cDNA sequence revealed segments of the genomic sequence that were in the wrong orientation or relative position, or which were spurious. These errors would not have been readily apparent without comparison to the cDNA sequence. Using the cDNA sequence as a guide, the jumbled dJ753P9 sequence was rearranged to arrive at the genomic sequence of human AmP, including introns. A second sequence, dJ454M7 (a genomic sequence containing the oculocerebrorenal syndrome gene also from the Sanger Center group of the Human Genome project), overlapped the dJ753P9 sequence in the upstream region. 110,000 nucleotides of the dJ454M7 sequence was combined with the rearranged dJ753P9 sequence to arrive at the disclosed human AmP genomic sequence. The sequence data of sequences dJ753P9 and dJ454M7 were produced by the X Chromosome Sequencing Group at the Sanger Centre and can be obtained from ftp://ftp.sanger.ac.uk/pub/dJ753P9 and ftp://ftp.sanger.ac.uk/pub/dJ454M7, respectively.

The assembled genomic sequence is shown in SEQ ID NOs:3, 4, 5, 6, and 7. SEQ ID NO:3 shows the first 50,000 nucleotides of the AmP genomic DNA (nucleotides 1 to 50,000). SEQ ID NO:4 shows the next 50,000 nucleotides of the AmP genomic DNA (nucleotides 50,001 to 100,000). SEQ ID NO:5 shows the next 44,453 nucleotides of the AmP genomic DNA (nucleotides 100,001 to 144,453). SEQ ID NO:6 shows the next 45,546 nucleotides of the AmP genomic DNA (nucleotides 144,454 to 189,999). SEQ ID NO:7 shows the last 16,955 nucleotides of the AmP genomic DNA (nucleotides 190,000 to 206,954). SEQ ID NOs:3, 4, and 5 represent sequences upstream of the AmP coding region. SEQ ID NO:6 represents the AmP coding region (including introns) and some downstream sequences. SEQ ID NO:7 represents sequences downstream of the AmP coding region. The location of introns in the AmP genomic DNA is shown in Table 2. The position refers to the nucleotide positions in SEQ ID NO:6.

TABLE 2

Location of introns in the AmP genomic DNA

| Intron | Position (in SEQ ID NO:6) |
|---|---|
| 1 | 49–2893 |
| 2 | 2969–4749 |
| 3 | 4861–5990 |
| 4 | 6054–7023 |
| 5 | 7129–7382 |
| 6 | 7470–8394 |
| 7 | 8542–11255 |
| 8 | 11361–12535 |
| 9 | 12614–12936 |
| 10 | 13135–13947 |
| 11 | 14038–15260 |
| 12 | 15372–16083 |
| 13 | 16159–17270 |
| 14 | 17346–19969 |
| 15 | 20030–21300 |
| 16 | 21370–21959 |
| 17 | 22068–22796 |
| 18 | 22854–23481 |
| 19 | 23560–28390 |
| 20 | 28415–28418 |
| 21 | 28482–29079 |

The coding region in the exonic sequences contain a total of 2019 nucleotides, in perfect agreement with the coding region of human AmP cDNA. The cDNA sequence (SEQ ID NO:1) contains 264 nucleotides of 5' untranslated region, which starts at nucleotide 144,190 in the genomic sequence (nucleotide 44,190 of SEQ ID NO:5). The 3' untranslated region starts at nucleotide 173,725 in the genomic sequence (nucleotide 29,272 of SEQ ID NO:6). Regulatory sequences are present in the sequences upstream and downstream of the AmP coding sequence. The locations in AmP genomic DNA of restriction sites for rare-cutting restriction enzymes are shown in Table 3. The position refers to the nucleotide positions of the entire genomic sequence (1 to 206,954).

TABLE 3

Locations in AmP genomic DNA of restriction sites

| Enzyme | Position | Recognition sequence |
|---|---|---|
| I-CeuI | | |
| I-DmoI | | |
| I-PpoI | | |
| I-SceI | | |
| PI-PspI | | |
| PI-SceI | | |
| PI-TliI | | |
| SfiI | 28417 | GGCCCTCCTGGCC |
| SfiI | 35327 | GGCCTGGAAGGCC |
| SfiI | 59892 | GGCCGCCGCGGCC |
| SfiI | 123855 | GGCCTGAGAGGCC |
| SfiI | 127512 | GGCCAAGGTGGCC |
| SfiI | 147456 | GGCCCTTGTGGCC |
| SfiI | 163911 | GGCCTCAATGGCC |
| SfiI | 173654 | GGCCGCCAGGGCC |

TABLE 3-continued

Locations in AmP genomic DNA of restriction sites

| Enzyme | Position | Recognition sequence |
|---|---|---|
| SfiI | 174720 | GGCCAAATTGGCC |
| SfiI | 191056 | GGCCCCATCGGCC |
| SfiI | 199214 | GGCCACAGAGGCC |
| XcmI | 805 | CCAAGCCCTCCATGG |
| XcmI | 3268 | CCAGACCCCTGCTGG |
| XcmI | 9208 | CCACTGAAGGCTTGG |
| XcmI | 11273 | CCAGATGTGTGGTGG |
| XcmI | 13446 | CCAGTCTAACTATGG |
| XcmI | 20139 | CCATGCCCCTCCTGG |
| XcmI | 22210 | CCAGGTGAGAGGTGG |
| XcmI | 24186 | CCAGATCTCTCCTGG |
| XcmI | 30663 | CCAAAAGCAATCCTGG |
| XcmI | 33277 | CCAGCCCGGCCATGG |
| XcmI | 34994 | CCAGGCAATGGCTGG |
| XcmI | 38816 | CCAGTGGTCTTCTGG |
| XcmI | 41331 | CCATGTCTCAATTGG |
| XcmI | 43990 | CCATTGTGGCTATGG |
| XcmI | 44005 | CCATGCCTAGTCTGG |
| XcmI | 51655 | CCAAGGAATGGCTGG |
| XcmI | 54873 | CCAGGAGGGGGGTGG |
| XcmI | 55199 | CCAAGACAAGCCTGG |
| XcmI | 56459 | CCAGCCGGGCCCTGG |
| XcmI | 57685 | CCAAGGACAAAGTGG |
| XcmI | 59638 | CCAGCCGCCCCATGG |
| XcmI | 62439 | CCAATCCTTGATTGG |
| XcmI | 63335 | CCATAACAGCTATGG |
| XcmI | 64615 | CCACGTCTCTTGTGG |
| XcmI | 68860 | CCAGTTCCGTTATGG |
| XcmI | 69175 | CCACAAACTTCGTGG |
| XcmI | 71843 | CCACTGGTTTGGTGG |
| XcmI | 74250 | CCACTTTTTGATTGG |
| XcmI | 82876 | CCAGTATCTCAGTGG |
| XcmI | 84993 | CCATGCCTGATCTGG |
| XcmI | 85463 | CCAGGGGAGAAATGG |
| XcmI | 91933 | CCAGGGTTGGTGTGG |
| XcmI | 93853 | CCAATCACAGGGTGG |
| XcmI | 101230 | CCATCATTTTCTTGG |
| XcmI | 101577 | CCACCAACTGGGTGG |
| XcmI | 102163 | CCAAGAAGCACCTGG |
| XcmI | 104088 | CCACAAGGCTCTTGG |
| XcmI | 105177 | CCATAGACTGGGTGG |
| XcmI | 106153 | CCAGCCCCACTATGG |
| XcmI | 106482 | CCAGGGGCTTGTTGG |
| XcmI | 106541 | CCAGTGGAGGCCTGG |
| XcmI | 106612 | CCAGTGCAAGAGTGG |
| XcmI | 107121 | CCAAGGATGAGATGG |
| XcmI | 110156 | CCAGCTCAGCCTTGG |
| XcmI | 110232 | CCAACTGACCAGTGG |
| XcmI | 112312 | CCATCTGTCTGCTGG |
| XcmI | 120228 | CCAAGCACAGGATGG |
| XcmI | 121774 | CCATTGGCCACTTGG |
| XcmI | 124227 | CCATCCTCTCCCTGG |
| XcmI | 129232 | CCAATTCTTTCTTGG |
| XcmI | 130760 | CCATATGTCCCCTGG |
| XcmI | 131995 | CCAAGCCACATCTGG |
| XcmI | 132931 | CCAGCCAGCAATTGG |
| XcmI | 132981 | CCAGCACCGACTTGG |
| XcmI | 133432 | CCAGAGAGGGGCTGG |
| XcmI | 133986 | CCACCCCATCTATGG |
| XcmI | 135217 | CCAATGAGAACATGG |
| XcmI | 156250 | CCAGGGACCCACTGG |
| XcmI | 158121 | CCAGAGTGCTGGTGG |
| XcmI | 158928 | CCAAATTATTCCTGG |
| XcmI | 159043 | CCAATTCCTAACTGG |
| XcmI | 159777 | CCAAAGGCACAGTGG |
| XcmI | 165124 | CCACATCGCCTCTGG |
| XcmI | 166087 | CCACAGCAATTATGG |
| XcmI | 167088 | CCAGAGCCAATCTGG |
| XcmI | 169063 | CCATAAACAACATGG |
| XcmI | 173427 | CCATCTGGACTATGG |
| XcmI | 174118 | CCAAGGGTGCCATGG |
| XcmI | 178624 | CCAGGCCGGGCATGG |
| XcmI | 178990 | CCAAGGCCTTCCTGG |
| XcmI | 182319 | CCAGCAAGGACCTGG |

TABLE 3-continued

Locations in AmP genomic DNA of restriction sites

| Enzyme | Position | Recognition sequence |
|---|---|---|
| XcmI | 182870 | CCAAAGGCCCGATGG |
| XcmI | 183061 | CCAAAGAATGTATGG |
| XcmI | 184682 | CCATAGTGACAATGG |
| XcmI | 185891 | CCACTTTGGCCATGG |
| XcmI | 185967 | CCAACCTGGAGATGG |
| XcmI | 185992 | CCATTCCAGTCTTGG |
| XcmI | 186440 | CCAGGTGCCCTATGG |
| XcmI | 188286 | CCACTTTCTCCATGG |
| XcmI | 193275 | CCAGCTCCCCCGTGG |
| XcmI | 195033 | CCACTGAGGCAGTGG |
| XcmI | 199546 | CCAAACTGACCATGG |
| XcmI | 204870 | CCAACTTGACTGTGG |

Tissue Distribution Determined by Northern blots.

The expression of membrane-bound AmP mRNA in human tissues was examined by Northern hybridization analysis of poly (A)$^+$ RNA (Clontech) using the 1068 bp human AmP cDNA fragment. A single 3.5 kb message was detected in human kidney, lung, heart, placenta, liver, small intestine, and colon. No transcript was detected in Northern analysis of poly (A)$^+$ RNA from human brain, skeletal muscle, pancreas, spleen, thymus, prostate, testis, ovary, and peripheral blood leukocytes. Possibly AmP RNA is in low abundance in the latter tissues, which can be determined by RT-PCR studies. The relationships between membrane-bound and soluble forms of AmP are unknown, but it may be relevant that heart poly A RNA gave a strong signal on Northern blotting. According to Simmons and collaborators (152), heart contains AmP in a soluble form.

Anatomic Determinants of Function.

Because AmP is not uniformly distributed among tissues and is apparently disposed as an ectoenzyme on some cell-types and as an intracellular enzyme in other cell-types, its roles in systemic biochemistry must be determined in part by its cellular and subcellular dispositions, distributions that restrict access to substrates and set reaction conditions.

Reactions of AmP in vivo.

To gain further insight into functions of AmP in systemic biochemistry, studies were conducted to determine the physiologically-relevant question: Is BK in central venous blood hydrolyzed by pulmonary endothelial AmP in vivo? The immediate metabolic fate of the AmP synthetic substrate Arg-Pro-Pro-[$^3$H]benzylamide (APPBz-$^3$H) (20 Ci/mmol) during a single transit from the right heart to the left was examined. Effects of increasing quantities of carrier APPBz and alternative AmP substrates such as bradykinin (BK) and des-Arg$^9$-BK (31) were then measured. It was found that tracer doses of APPBz-$^3$H are extensively hydrolyzed (mean hydrolysis of about 55% during a 2–3 sec mean transit time) and that the metabolic process is saturable (carrier APPBz injected at 42 nmol/kg b.w. reduced fractional hydrolysis of coinjected APPBz-$^3$H by half). Using isolated rat lungs perfused with Krebs-Henseleit solution containing albumin, 4 g %, it was found that APPBz-$^3$H is still extensively hydrolyzed, a result to be expected it AmP is largely disposed on the pulmonary vascular surface (5,6,12,14,31, 167). It was also found that carrier APPBz at 2 $\mu$mol/kg completely inhibited hydrolysis of coinjected tracer substrate and can thus be used as a short-acting AmP inhibitor. As implied by the saturable characteristics of APPBz-$^3$H hydrolysis, alternative substrates for AmP should, in saturating doses, also inhibit APPBz-$^3$H hydrolysis. In fact, BK proved to be an alternative substrate of even higher affinity than carrier APPBz: coinjected BK, at 13 nmol/kg, reduced APPBz-$^3$H hydrolysis by half. Des-Arg$^9$-BK was an alternative substrate of lesser affinity; $ED_{50}$ of 107 nmol/kg. Des-Arg$^1$-BK is apparently not a substrate for AmP but binds to the catalytic site nonetheless (21,22,31); thus, des-Arg$^1$-BK coinjected with APPBz-$^3$H was expected to reduce hydrolysis of the tracer, an expectation met experimentally ($ED_{50}$ of 30 nmol/kg).

Potentiation of Effects of Bradykinin (BK).

If BK inhibits hydrolysis of APPBz-$^3$H, BK hydrolysis by AmP should be inhibited by APPBz; a possibility tested as follows: Log dose-response curves were constructed by measuring the mean systemic arterial blood pressure effects of BK injected into the superior vena cava (i.v.) or the root of the aorta (i.a.). As shown previously (1,2,161), BK is extensively degraded during passage through the rat pulmonary vascular bed. Thus, the i.v. dose of BK required to reduce arterial blood pressure by, say, 25 mm Hg is 40 or more times the i.a. dose of BK required to exert equivalent effects. To the extent that pulmonary AmP contributes to BK inactivation, saturation of AmP with an inhibitor or alternative substrate should, in effect, potentiate blood pressure effects of i.v. BK. It was found that either of carrier APPBz or des-Arg$^9$-BK potentiated blood pressure effects of i.v. BK by up to 4-fold. Effects of i.a. BK were also potentiated, a result that suggests that AmP is disposed on both pulmonary and extra-pulmonary vascular surfaces. From the relationship $PF=2^n$, where PF is "potentiating factor" and n is the number of biological half-lifes, it can be computed that a 4-fold potentiation of i.v. BK effects on blood pressure effects bespeaks the ability of pulmonary AmP to degrade BK through two half-lifes in a time interval of less than three sec (mean pulmonary transit time). Thus, AmP alone can degrade BK by 75%.

Pulmonary angiotensin converting enzyme (ACE) is a major contributor to BK inactivation (119,120,167). Inhibition of ACE potentiates blood pressure effects of i.v. BK by 40- to 200-fold. The four-fold potentiation of i.v. BK effects achieved by inhibition of AmP is less spectacular but, as discussed below, important nonetheless. To clarify relative contributions of ACE and AmP to the metabolic fate of BK administered i.v., blood pressure effects of i.v. BK under control conditions and then after administration of a long-acting ACE inhibitor, RAC-X-65, were compared. After ACE inhibition, BK was injected (i.v. and i.a.) alone or BK co-mixed with APPBz at a dose capable of saturating AmP (2 μmol/kg). ACE inhibition shifted both i.v. and i.a. log dose-response curves leftward. The i.v. curves were most affected but still lay to the right of the i.a. curves by a factor of about four. Inhibition of both ACE and AmP caused the i.v. and i.a. BK log dose-response curves to become superimposable. The latter result appears to mean that, in rat lungs, ACE and AmP account entirely for the pulmonary metabolism of BK. When both AmP and ACE are inhibited, effects of i.v. BK are potentiated by up to 800-fold. In one experiment of this series, 2.5 ng of i.v. BK (about 2 pmol) reduced systemic arterial blood pressure by 20 mm Hg; a finding that gives new emphasis to the importance of pulmonary AmP and ACE in preventing the entry of BK into the systemic circulation under physiologic conditions.

Clinical Implications.

Precisely how BK is inactivated in humans is a matter of clinical importance. BK is an edematogenic compound capable of inducing urticaria when administered i.v., and has been postulated to play a role in induction of angioedema (99). Human lungs contain ACE, which is distributed so as to have access to circulating substrates such as BK and angiotensin I (66). However, there are now several million patients under treatment with ACE inhibitors and who therefore lack the ability to inactivate BK via the ACE pathway. Available data suggest that BK does not normally accumulate to any great extent in the blood of patients treated with ACE inhibitors (157,177), which in turn suggests that there is a backup, or supplemental, system for BK inactivation. Whether AmP accounts (or accounts for a significant fraction) for BK inactivation in patients treated with ACE inhibitors is not yet known, but the possibility is worthy of consideration in terms of adverse effects of ACE inhibitors. An infrequent, but potentially fatal, adverse effect of ACE inhibition is angioedema, a complication that may be due to the lack in some patients of a non-ACE BK-inactivating system, possibly AmP. It is likely that some subjects lack AmP. Blau et al. (62) have reported that an intestinal biopsy sample from a 15-year-old male contained normal saccharase activity but no measurable AmP activity (less than 2% of the mean of control values). Plausibly, subjects lacking AmP activity are at risk for ACE inhibitor-induced angioedema. By analogy, a relative lack of AmP could be associated with other, more frequent, ACE inhibitor-related side effects such as cough and pemphigus-like skin eruptions (31,99).

Immunocytochemistry.

Functions of AmP are likely to be determined in part by its anatomic dispositions which are evident by immunocytochemistry performed at the level of light microscopy. A description of these studies follows.

Antibody Specificity.

HL510 and the polyclonal anti-AmP have been used in the immunocytochemistry studies described below. Although the epitope bound by HL510 is not yet known, all data support its specificity. HL510 binds to guinea pig plasma, lung and kidney AmP isoforms and works well for immunoprecipitations, western blots and immunocytochemical studies. HL510 binds rat forms of AmP; thus, parallel studies of the disposition of AmP in guinea pig and rat tissues were conducted. HL510 has anticatalytic effects on human plasma AmP and has proved to be useful for purifying human lung AmP. HL510 reacts specifically with human pulmonary artery, lung microvascular and aortic endothelial cells as evidenced by indirect immunofluorence and immunoprecipitation studies. HL510 immunoaffinity matrix binds the two isoforms (Mr 89,000 and 76,000) of PI-PLC solubilized guinea pig kidney AmP quantitatively. Prolidase, a proline peptidase family relative of MW 56,000 (83), is not bound by the immunoaffinity matrix nor by HL510 alone as evidenced by the fact that the two kidney AmP isoforms were obtained in homogeneous forms on immunoaffinity chromatography (32) and the fact that a Mr 56,000 protein has not been found in AmP preparations collected by immunoprecipitation. Cross-reacting contaminants having Mr's like those of the AmP isoforms can also be ruled out. Eight peptides produced by LysC digestions of immunoaffinity-purified guinea pig lung and kidney AmPs have been sequenced. Each of the eight peptides sequenced as if pure (no secondary sequence signals). All of the sequences aligned with high similarity with the pig kidney AmP sequence. These results, then, are consistent with the conclusion that HL510 is specific for AmP.

Light Microscopy.

Based on the early studies of pulmonary angiotensin converting enzyme (ACE) (5,6), glutaraldehyde fixatives were used, and the light microscopy studies using frozen sections and sections of tissues were fixed in picric acid/paraformaldehyde. The latter fixative is adequate for electron microscope (EM) immunocytochemistry at moderately high resolution (5,6). Thus, the data should be directly applicable to EM immunocytochemical studies. In addition, Vector ABC kit reagents were used throughout (second antibody bridged via a biotin:avidin complex to horseradish peroxidase), and these too can be used for some EM studies.

As shown in micrographs, the entire alveolar-capillary unit of guinea pig lung appears to react with anti-AmP. This is a picture essentially identical to that obtained in light microscope immunocytochemistry studies of pulmonary ACE (69), a target known to be disposed almost exclusively on the luminal surface of pulmonary endothelial cells (5,6). Resolution at the EM level will therefore be required to determine precise cellular and subcellular dispositions of AmP. It is very likely relevant, however, that the AmP immunoreactivity of the arteriole shown in the left upper quadrant of a crograph is restricted to the endothelial layer. Initially, it was believed that AmP would co-localize with ACE, given the facts that 1) ACE is disposed on endothelium and 2) both enzymes have access to peptide substrates injected i.v. (31,167). Results obtained thus far are consistent with localization of AmP on endothelium. AmP immunoreactivity in association with some airway epithelial cells and mononuclear leukocytes, cell-types that are not reactive with anti-ACE, has been found. To distinguish similarities and differences in the cellular dispositions of AmP and ACE, EM studies are planned in which tissue is examined using both mouse anti-AmP and rabbit anti-ACE. AmP, unlike ACE, is believed to participate in the metabolism of collagen fragments formed by collagenase (205), thus whether AmP is disposed in, or near, intercellular matrix can be determined.

Micrographs show that AmP immunoreactivity is also disposed on guinea pig renal proximal tubule, jejunum enterocytes and villus vascular cores and in association with microvessels of the endocrine and exocrine pancreas. The kidney micrograph illustrates that cells of the glomerulus, including glomerular endothelium, lack AmP immunoreactivity. Previous studies of ACE were similar: glomerular endothelium was unique among endothelia studied in that it failed to react with anti-ACE (69). Endothelium of small arteries of the renal cortex react with anti-AmP, but by far the greatest AmP immunoreactivity is that of the proximal tubules.

Immunocytochemistry studies of rat tissues were, with one exception (see below), consistent with the studies of guinea pig tissues. Pulmonary alveolar-capillary units were heavily stained, as were airway epithelial cells. Similarly, small intestine enterocytes and kidney proximal tubules were heavily stained, and glomerular cells were apparently free of AmP immunoreactivity. However, rat spleen contained few, if any, sites of AmP immunoreactivity, whereas the red pulp of guinea pig spleen (and microvessels of red and white pulp) were heavily stained. In guinea pig spleen red pulp, cells on sinusoid walls were heavily stained, as were mononuclear leukocytes. Some human lymphocytes contain a 71,000 Mr AmP in soluble form (165), as do rat cerebral astrocytes (147). The results indicate that some guinea pig leukocytes possess AmP immunoreactivity. If the guinea pig leukocyte AmP immunoreactivity represents the soluble 71,000 Mr isoform, one can purify it using the immunoaffinity columns now on hand. Guinea pig and rat tissue homogenates were assessed for AmP catalytic activity (21,22). Rat kidney, lung and jejunum contained AmP at the highest specific activities. For guinea pig, the highest specific activities were found in homogenates of spleen, kidney, liver, and jejunum. The immunocytochemistry results are in accord with the biochemical surveys.

Immunofluorescence photographs show the reaction of HL510 with human pulmonary microvascular endothelial cells in culture. Ref. 34 contains an immunofluorescence micrograph of the reaction of HL510 with human aorta endothelial cells. Antibodies to AmP can be prepared by using as immunogens unique peptide sequences of human AmP predicted to be antigenic (EGCG program). Further to favor precise localizations, antibodies labeled with colloidal gold particles can be used. As a gpi-anchored enzyme, membrane-bound AmP is expected to be localized in caveolae (137,184). Indeed, the distribution of immunofluorescent spots in micrographs is typical of antigens situated in caveolae (90,91).

AmP and its Nearest-neighbors.

Increasingly, it appears that cell membrane receptor/cell signaling reaction cascades depend in part on close anatomic proximity of all or many of the relevant reactants. Extensive biochemical data have revealed close associations between receptors, signaling molecules and caveolins (74,89,92,130, 138,160,173,175,183). Complementary morphologic data are lacking. Specifically, subcellular dispositions of endothelial AmP in respect to effectors and signaling molecules whose functions may directly or indirectly be influenced by AmP catalytic activity can be determined. AmP in respect to the bradykinin (BK) B2 receptor, eNOS and guanylate cyclase can be determined.

As a gpi-anchored enzyme, it is anticipated that AmP is disposed within endothelial caveolae (3,4,11,74,90,137, 173). Some have reported that localization of gpi-anchored proteins within caveolae is an artifact attributable to crosslinking of antigen: antibody complexes by second antibodies (143,145). However, cytochemical techniques without crosslinking agents have shown that endothelial 5'-nucleotidase, now known to be gpi-anchored, is disposed almost exclusively within caveolae (3,4). Further, coupled functions of cell membrane receptors with cell signaling proteins known to be disposed on the cytoplasmic aspect of caveolae argue in favor of anatomic proximity (9–11,63,89, 127,128,164).

Given the high likelihood that AmP functions in part as a BK inactivating enzyme (31) and that BK in near-physiologic concentrations (~10 pM) exerts effects on endothelial cells (e.g. mobilization of arachidonate and synthesis of Tx $A_2$ and $PGI_2$) (7–11), endothelial cells have been used in culture to examine morphologically for functionally-significant anatomic proximities of AmP with the BK B2 receptor and well-characterized BK-activated signaling molecules known to be associated with caveolae (90,91,131,173). A two antigen immunocytochemistry approach can be used. This should reveal aspects of AmP functions that are dependent not only on subcellular disposition but also on functionally-related proximate proteins.

AmP in Human Pulmonary Microvascular Endothelial Cells.

Cultures were fixed with 4% formaldehyde, permeabilized with 0.2% Triton X-100 in BSA/PBS, incubated with primary antibody (1:100 dilution) (monoclonal anti-GP-AmP, overnight at 4° C.) followed by secondary antibody (FITC-labeled goat anti-mouse IgG, 1 hour at 22° C.) and then analyzed and photographed using a Biorad confocal microscope.

Transient Expression of AmP in COS-1 Cells.

The full length 3.5 kb cDNA encoding human kidney AmP can be inserted into the expression vector pBKCMV as described for pig kidney AmP cDNA (113). The orientation of the insert can be verified by a directional PCR reaction, and the correct construct can be used to transfect COS-1 cells. About 2E+06 cells are plated in 150 cm² culture flasks and allowed to proliferate for 24 h at 37° C. (113). Cells are then washed with OptI-Mem and transfected (5 μg of DNA/flask) using lipofectAmine. After 2 h at 37° C., Dulbecco's modified Eagle's medium containing 10% FCS is added. Twenty four h later, the medium is replaced with fresh, and the cells will be incubated at 37° C. for another 24 h.

Parallel control cultures, transfected with vector lacking the AmP cDNA insert, can be processed similarly. A small portion of control and test cells are harvested and examined by indirect immunofluorescence using our monoclonal anti-AmP HL510 as the primary antibody. A second portion of each of the control and test cells are washed free of culture medium and then resuspended in 50 mM Hepes/NaOH buffer, pH 7.4, containing 0.15 M NaCl (assay buffer). The AmP substrate Arg-Pro-Pro-[$^3$H]benzylamide (21) is added to the cell suspension to a final concentration of 20 nM (1 μCi/ml). The cell/substrate reaction mixture is incubated at 37° C., and aliquots is collected at timed intervals for measurement of the rate of formation of the expected product. Pro-Pro-[$^3$H]benzylamide (21,22). AmP activity can be computed to yield the first order rate constant, Vmax/Km. COS-1 control cells (transfected with vector lacking the AmP cDNA insert) do not express AmP (113); thus we expect to be able to detect even low levels of expression of human kidney AmP.

The bulk of the COS-1 cells can be worked up to prepare cell membranes. The cells, in assay buffer containing 10 μg/ml of each of pepstatin, leupeptin and aprotinin, are homogenized, and the homogenate is subjected to differential centrifugation (32,110,111). The cell membrane-enriched fraction is assayed for AmP catalytic activity (see above), and then solubilized with 60 mM octyl glucoside (76). Half of the resulting mixture is treated with phosphatidylinositol-specific phospholipase C (recombinant PI-PLC from B. thuringiensis) before phase separation with Triton X-114, and the remaining half is directly phase separated. If, as expected, the expressed AmP possesses a glycosyl phosphatidylinositol (gpi) lipid anchor, PI-PLC treatment should convert the amphipathic form (partitioned into the Triton phase) into the hydrophilic form. Both amphipathic and hydrophilic forms are subjected to SDS/PAGE under reducing conditions (10% gel). The proteins will be transferred on to Immobilon P for western blot analysis using anti-AmP HL510. Expressed monomeric AmP is expected to have an Mr near 90,000 (22,32,111,152, 180).

Overexpression of AmP.

The baculovirus/Sf9 insect cell system, a system known to be capable of expressing biologically functional, glycosylated gpi-anchored proteins, will be used to obtain human kidney AmP in milligram quantities. Recombinant human cluster of differentiation antigen CD59 has been thus obtained in milligram quantities, with not less than 98% of the product bearing the gpi anchor, as judged by Triton X-114 phase partitioning before and after treatment with PI-PLC (76). Approximately half of CD59 was anchored to the cell membrane, and the remainder was secreted into culture medium. The secreted CD59 was in amphipathic form and could be converted by PI-PLC into the hydrophilic form. CD59 was produced in three isoforms, all with the expected N-terminal amino acid sequence and all bearing a gpi anchor. Apparently, the glycosylation process was overwhelmed by high protein expression such that the two smaller isoforms were inefficiently glycosylated. The ability of Sf9 cells to N-glycosylate recombinant proteins at expected sites is well-recognized; however, the glycosyl groups are generally of the high mannose type (76). The efficiency of glycosylation improves with increasing time of culture, thus it may be useful to analyze samples, and harvest and replace if indicated, culture medium daily so as to collect separately secreted AmP isoforms that differ in terms of numbers and possibly types of glycosyl groups. As for glycosyl groups, the types of anchors attached to recombinant proteins are characteristic of Sf9 cells and can differ in structure from gpi anchors attached by, e.g., human kidney proximal tubule epithelial cells (76). Nonetheless, Sf9 cell-produced proteins have the expected full-length peptide, correctly folded and crosslinked by disulfide bonds. Recombinant enzymes thus produced are typically fully active (76,194,195).

Overexpression of Wild-type Human AmP.

The cDNA sequence encoding human AmP can be subcloned into the polyhedrin-based plasmid transfer vector pVL1393 (Pharmingen). Recombinant transfer vector can then be cotransfected with Baculogold (Pharmingen) viral DNA into Sf9 insect cells (2×10$^6$ cells in monolayer). Six days after cotransfection, the cells can be harvested and expression of AmP examined by assay of catalytic activity, immunofluorescence and western blotting. Conditioned medium containing recombinant virus is used to reinfect Sf9 cells through 2–3 rounds of amplification to obtain a high titer virus stock (1E+08 virus particles/ml). Optimal conditions of multiplicity of infection and length of infection can be defined. Maximal expression is typically obtained after 3–4 days of infection, at which time conditioned medium can be harvested and worked up in parallel with the Sf9 cells for their contents of recombinant human AmP. Samples of conditioned medium can be collected at timed intervals before final harvest in order to monitor efficiency of glycosylation. N-glycosylation of AmP early in culture is expected to be relatively inefficient and may provide useful insights if multiple isoforms are obtained at final harvest. Triton X-114 phase extractions can be performed to examine for the efficiency of gpi-anchor attachments. As for recombinant human CD59, it is expected that conditioned medium will contain substantial quantities of recombinant AmP in its amphipathic form (76).

Purification of wild-type human AmP can be based primarily on the immunoaffinity procedure that we have described previously (32). However, two early group separation procedures may simplify purification and improve yields. In the first step, amphipathic protein is selected for by Triton X-114 phase separation. The Triton phase is collected, diluted and then treated with PI-PLC. In a second step, the PI-PLC-formed hydrophilic protein, expected to be N-glycosylated with high mannose side functions (76), is isolated on concanavalin A-Sepharose. AmP is eluted. The immunoaffinity purification step can then be performed using relatively low protein loads. The goal is to obtain at least 20 nmol (about 2 mg) of pure AmP per 150 cm² culture flask. The high titer virus stock produced as described above can be used to scale up production of recombinant AmP as needed. All of the following studies of wild-type AmP can be performed using less than 50 nmol of the pure protein.

Characterization of Wild-type AmP.

Kinetics.

Using Arg-Pro-Pro-[$^3$H]benzylamide as substrate, kcat, Km and kcat/Km can be measured as described in the studies of guinea pig serum AmP (22). Pure recombinant wild-type human AmP is expected to have a second order rate constant, kcat/Km, on the order of 1.8E+08 $M^{-1}$ $min^{-1}$ (22). In addition, kinetics of the reaction of AmP with bradykinin, Arg-Pro-Pro and Gly-Pro-Hyp can be characterized (22,111, 180). pH optimum and pH stability studies can be performed using Mes, Hepes and phosphate buffers. Recombinant AmP can be examined for expected responses to effectors such as $Mn^{2+}$, EDTA, o-phenanthroline, p-hydroxymercuribenzoate, and dithiothreitol (22,111,113, 152,180). Recombinant AmP can also be tested for thermal stability (152,180), not only for comparison against naturally-occurring AmP, but also to set a baseline for characterizing potentially unstable mutants that lack disulfide bonds, glycosylation sites or metal ligands.

Chemical Properties.

Incorrect estimations of the molar extinction coefficient of angiotensin converting enzyme (ACE) caused confusion for more than a decade, especially in terms of determination of the number of atoms of zinc per molecule of ACE and the specific activity of the pure enzyme (see 27 and its references). To avoid such confusion for AmP, UV spectra (210–340 nm) can be developed using three concentrations of wild-type AmP (optical densities of about 0.2, 0.5 and 1.0 at 280 nm). To enable accurate computation of AmP concentrations, a sample of each AmP preparation thus tested can be submitted to quantitative amino acid analysis. Special focus can be placed on histidine which is expected to be recovered in a mole ratio (His/AmP) of 12. When the molar extinction coefficient is established, it can be used to calibrate protein assay results obtainable by conventional Lowry, BCA and dye-binding methodologies.

Recombinant AmP (1 nmol in a 1 mm light path cell) can also be characterized by circular dichroism. Spectra can be recorded at 13° C. using a AVIV-60DS spectropolarimeter, and, with buffer baseline corrections, relative percentages of α-helix, β-sheet, β-turn and random coil structures can be estimated using AVIV software. The major purpose of these studies is to establish a basis for detecting variations in higher structure of unstable or catalytically-inactive mutants.

Recombinant AmP can be analyzed by MALDI-TOF mass spectrometry to weigh the parent molecule and any dimer or trimer forms, and examine for characteristic fragmentation patterns that may later be useful for analyzing mutants (36,196). O-glycosidase can be used to rule in or out the presence of O-linked carbohydrate (196). The following text assumes that AmP does not contain O-linked carbohydrate, and the approach will require adjustments along obvious lines if the assumption is incorrect. At present, O-glycosylation seems unlikely in that exhaustive treatment of pig AmP (PI-PLC solubilized) with N-glycosidase F yields a peptide of Mr 71,000, essentially as expected for a 626 residue peptide plus a gpi-anchor remnant (196).

Human kidney AmP contains a single Asp-Pro bond (D157-P158) (see SEQ ID NO:2) that is expected to hydrolyze spontaneously under the acid conditions required to form CNBr or BNPS skatole fragments (75,126). Since its spontaneous hydrolysis could complicate early efforts to interpret peptide fragment fingerprints, hydrolysis of AmP at D157-P158 should be attempted before beginning conventional fingerprinting. As described below, several analytical advantages accrue if the D—P bond can be hydrolyzed efficiently.

Recombinant AmP, 0.1 nmol initially, is dissolved in 1 ml of 7M guanidinium chloride in 10% acetic acid adjusted to pH 2.5 with pyridine (126). The mixture is incubated at 37° C. for up to 96 h. At timed intervals, samples are examined by mass spectrometry and N-sequenced; the latter to monitor the rate of appearance of the new N-terminus, PFLL (residues 158–161). For the following, it is assumed for convenient discussion that K24 (probably acylated) is the first residue of mature AmP and that A649 is the last. Elsewhere, these assumptions can be tested. The expected two pieces (N-piece, residues 24–157; and C-piece, residues 158–649) should be readily separated on Sephadex G-50. If reduction is required for separation of the N- and C-pieces, this will be evidence for the presence of a disulfide bond. The N-piece contains three potential N-glycosylation sites, N35, N49 and N65, and two Cys residues. C36 and C127. The N-piece is expected to have an N-α acyl modification (22,111,180). If, in fact, the N-piece is resistant to Edman degradation, it can be digested with AspN to obtain a 43 amino acid (a.a.) residue peptide which contains C36 and potential glycosylation sites N35, N49 and N65. If , as predicted, K24 is the N-terminal residue of mature AmP, an acylated (possibly diacylated) tripeptide is expected, and its mass should reveal the identity of the acyl-function (125, 154,189). If one or more of its glycosylation sites is glycosylated, the 43 residue peptide can be separated from the remainder of the AspN digest using con A-Sepharose (see above). If C36 and C127 are linked by a disulfide, reduction of the high mannose fraction eluted from con A-Sepharose should yield a second peptide (residues 114–157), which can be identified by mass spectrometry. Mass spectrometry of the 43 a.a. residue peptide should also suggest, in terms of actual mass versus expected mass, whether one, two or all three of the potential N-glycosylation sites are glycosylated in fact. Edman degradation should make clear whether N35 and/or N49 are glycosylated. Given its distance from the AspN-generated N-terminus, N65 can be made more effectively accessible to Edman sequencing by cleavage of the M61-Q62 bond with CNBr (41,48,49,75). The expected peptide, Q62-T74, can be weighed by mass spectrometry to determine whether N65 is or is not glycosylated (36). As is needed to isolate peptides of special interest (e.g. the AspN-generated N-terminal acyl-tripeptide) that cannot be collected on con A-Sepharose, reverse phase HPLC (Brownlee, aquapore 300) with a morpholine phosphate buffer, pH 6.5, as the mobile phase can be used (103). This system provides high resolution under conditions unlikely to damage the expected gpi-tail piece and unlikely to hydrolyze peptide bonds artifactually.

Analysis of the potential N-glycosylation sites, and possible disulfide bonds, of the acid hydrolysis-produced C-piece (P158-A625) can proceed similarly. Exhaustive digestion with GluC is expected to yield two peptides containing potential N-glycosylation sites: a 41 a.a. residue peptide containing N278 (peptide T245-E285) and an 18 residue peptide (T286-E303) containing N291 and two Cys residues, C294 and C299. If glycosylated, both peptides should be susceptible to isolation from the GluC digest on con A-Sepharose. Since high mannose glycosyl groups are expected from a baculovirus/Sf9 expression system, failure of one or both peptides to bind to con A-Sepharose is presumptive evidence of the absence of an N-glycosyl sidechain (26). If both T245-E285 and T286-E303 are isolated on con A-Sepharose, mass spectrometry can be used to verify that each of N278 and N291 is glycosylated. Edman degradation of T286-E303 may reveal whether C294 and C299 are, or are not, linked by a disulfide bond.

GluC digestion of the C-piece (P158-A649) is expected to generate a relatively small C-terminal peptide, the last residue of which, in native AmP, is attached, via ethanolamine, to the gpi anchor (86,139–141,144,159,162). If GluC can hydrolyze an E—P bond, the C-terminal peptide is expected to be PLAA. If not, the GluC-generated C-terminal peptide is expected to be W639-A649. It should be possible to collect either peptide by immunoprecipitation. The PI-PLC-generated hydrophilic form of AmP is known to possess a C-terminal common recognition determinant (CRD) (29,32,111,113,180). PI-PLC cleaves the phosphodiester bond between inositol and the diacylglycerol, forming a 1,2-cyclic phosphate ring on the inositol residue. The cyclic inositol phosphate is highly immunogenic, and antibodies prepared against any PI-PLC-solubilized protein cross-react with this epitope (the cross-reacting determinant, CRD) (86,139,140,208). We have one such antiserum (prepared against trypanosome variant surface glycoprotein) and have shown that it recognizes the CRD of PI-PLC-solubilized guinea pig kidney AmP and with an AmP peptide generated by LysC digestion (29,32).

With the anti-CRD, one can isolate the C-terminal peptide of AmP (expected to be PLAA-CRD or W639-A649-CRD) from the above-described GluC digest by immunoprecipitation and then recover the free peptide-CRD by elution using buffer containing 1 mM 1,2-cyclic inositol phosphate (available from Sigma). By N-sequencing the recovered peptide to its ethanolamine moiety, one can establish unequivocally the exact gpi anchor attachment site. There is a caveat: the CRD is acid labile (86,140) and may be damaged during the procedure used to hydrolyze the D157-P158 bond (see above). If in fact the AmP-CRD is destroyed, AmP (not previously exposed to strong acid) can be digested, in a separate experiment, with GluC and then isolate the CRD-bearing peptide as described above.

Focus on Cysteine Residues.

The foregoing chemical analysis will make it clear which of the potential N-glycosylation sites of wild-type recombinant AmP are in fact glycosylated. As also noted, some clues may be gained on the presence and dispositions of disulfide bonds. However, unequivocal assignments of Cys residues taken up in disulfide bonding will require an independent approach, such as the following.

Native recombinant AmP, 1 nmol, in 50 mM Hepes/NaOH buffer, pH 8.3 (21,22), can be reacted with 1,000 nmol of (1-$^{14}$C)iodoacetamide, ~3 Ci/mol, at 25° C. for 1 h. Excess $^{14}$C-iodoacetamide is removed by centrifugal ultrafiltration (10K NMWL) with washing. Specific radioactivity can be measured by liquid scintillation counting to estimate the number of alkylated C residues. The $^{14}$C-labeled protein product can then be acid-treated to hydrolyze the D157-P158 bond (see above) and recover the N- and C-pieces (respectively, K24-D157 and P158-A649). The N- and C-pieces (with or without a reducing agent) are separated, and their specific radioactivities measured. Following procedures described above, the N-piece can be digested with AspN to yield the 43 residue peptide that contains C36 and a 44 residue peptide that contains C127. The former peptide, expected to be glycosylated, is separated from the latter on con A-Sepharose column chromatography. Each of the separated peptides can be assayed for its $^{14}$C-content. If the N-piece is itself not labeled with $^{14}$C, AspN digestion and subsequent studies will not be necessary.

If the C-piece of alkylated AmP is labeled with $^{14}$C, the focus should be on GluC-digest peptides containing residues C294 and C299 (peptide T286-E303) and C531 (peptide A505-E534). T286-E303, if glycosylated at N291, should be easily separated on con A-Sepharose from A505-E534. If not, the 18 residue peptide should be readily separated from the 30 residue peptide by reverse phase HPLC. The separated peptides can be assayed for their contents of $^{14}$C. Near-neighbor C residue pairs are often linked by disulfide bonds (185). If this is true for C294 and C299, peptide T286-E303 may be unlabeled. For reasons described below, C531 will be labeled with $^{14}$C.

A parallel experiment can be conducted in which native AmP saturated with bradykinin (BK) (50 μM; Ki 1.1 μM (22,113)), is reacted with $^{14}$C-iodoacetamide as above. AmP is not a thiol protease and is not inhibited by iodoacetamide nor N-ethylmaleimide. However, it is partially (~70%) inhibited by p-hydroxy-mercuribenzoate, even with the latter at low concentration (~10 nM) (21,22,111,180). Given that C531 is situated more or less in the middle of the putative catalytic metal ligands, D450, D461, H520, E555 and E569, it is highly plausible that p-hydroxymercuribenzoate binds to C531 and sterically hinders substrate binding and/or interferes with appropriate ligation of catalytic metal to the peptide backbone. By saturating AmP with its high affinity substrate BK, alkylation of C531 by $^{14}$C-iodoacetamide should be prevented or strongly inhibited.

A third experiment can be performed in which native AmP is reacted with $^{14}$C-iodoacetamide as in the first experiment. After 1 h at 25° C., excess $^{14}$C-iodoacetamide is removed and then the $^{14}$C-labeled AmP is denatured and reduced (185). The reduced peptide is treated with vinylpyridine. The subsequent work up can proceed as in the first experiment to obtain AspN peptides of the N-piece and GluC peptides of the C-piece (pieces produced by acid hydrolysis of D157-P158). The relevant peptides can then be N-sequenced to determine which C residues were alkylated with iodoacetamide and which, after reduction, were covalently-bound to vinylpyridine.

Further studies to clarify dispositions of disulfides will depend on results obtained to this point. For example, if C531 is accessible to $^{14}$C-iodoacetamide and C36, C127, C294, and C299 are modified only after reduction by vinylpyridine, the obvious possibilities for two disulfide bonds can be examined. One can analyse existing date to discern among the six possibilities (C36→C127, C36→C294, C36→C299, C127→C294, C127→C299, and C294→C299). For example, in experiments 1 and 2 after hydrolysis of the D127—P158 bond, was it necessary to add a reducing agent to separate the N-piece from the C-piece? If the N-piece and C-piece were separable without reduction, the disulfides are most likely to link C36→C127 and C294→C299. If more than one Cys is in reduced form, there cannot be fewer than three reduced Cys residues, in which case there cannot be more than one disulfide bond. In the latter scenario, the two disulfide-linked Cys residues can be identified as their vinylpyridine derivatives. Sturrock et al (185) have recently detailed a MALDI-TOF mass spectrometry approach for locating disulfide bonds which we plan to use if our simpler plans yield equivocal results. Dr. Nancy D. Denslow has recently developed a procedure in which a target protein is hydrolyzed by reacting reduced Cys residues with DTNB (36).

If C36 immediately follows an N-glycosylation site, N35, and may, if in reduced form, be sterically-hindered and inaccessible to $^{14}$C-iodoacetamide, this anomalous behavior can be clarified, if encountered, by reacting AmP with N-glycanase before treatment with $^{14}$C-iodoacetamide. Similarly, one can examine for sterically-hindered reduced Cys residues by titrating native and denatured AmP with Ellman's reagent (185).

Mutant Forms of AmP.

The baculovirus/Sf9 expression system can also be used to produce mutant forms of AmP. The mutants are selected to help clarify catalytic function in terms of roles of the putative protein shuttle, H430, and putative catalytic metal ligands, D450, D461, H520, E555 and E569. In addition, one can examine roles played by glycosyl groups and disulfides in AmP function. Initially, site-specific mutations will be introduced into the wild-type human AmP cDNA sequence by the PCR-based splicing-by-overlap-extension technique described by Ho et al (105). Incorporation of the desired mutations can be confirmed by directional PCR. Mutant proteins will then be expressed in the baculovirus/ Sf9 insect cell system under the conditions established for expression of the wild-type enzyme. The cells themselves will be examined by catalytic assay and immunofluorescence. Mutant proteins will be purified and analyzed as described above for wild-type AmP. All mutants will be characterized by mass spectrometry, UV spectrometry, circular dichroism, quantitative amino acid analysis and fingerprinting of peptide fragments (mass spectrometry and SDS-PAGE with and without a reducing agent). Catalytically-active mutants will be characterized to measure kcat, Km and kcat/Km using Arg-Pro-Pro-[$^3$H] benzylamide, bradykinin and Gly-Pro-Hyp as substrates (22,113,180). Temperature and pH stabilities will be defined (180).

The first mutant to be prepared is one in which the putative proton shuttle, H430, is replaced with F. If H430 is in fact the proton shuttle, the F430 mutant is expected to be essentially inactive. Pig kidney AmP is completely inactivated by diethylpyrocarbonate in a concentration that derivatizes two H residues per molecule of AmP (134). Activity is restored by treatment of the derivatized AmP with hydroxylamine. It is plausible that H430 is accessible to diethylpyrocarbonate.

The second mutant to be prepared is that in which the putative catalytic metal ligand H520 (also likely to be accessible to diethylpyrocarbonate) is replaced with F. One will then proceed to obtain mutants for each of the remaining putative four metal ligands as follows: D450→N, D461→N, E555Q, and E569→Q. One will thereafter focus on obtaining mutants lacking potential N-glycosylation sites. Five mutants will be prepared: N35→Q, N49→Q, N65→Q, N278→Q and N291→Q. Our objective here is to determine whether glycosyl groups indirectly support catalytic activity, perhaps in terms of maintaining structure, stability and solubility. Should the glycosyl groups effect catalytic function little or not at all, it may be feasible in a future grant period to obtain a catalytically-active "deglycosylated" AmP amenable to x-ray crystallography analysis.

To obtain complementary data on roles of Cys residues and disulfide bonds, one will prepare five C→S mutants (C36, C127, C294, C299 and C531). Characterization of these mutants should reveal roles of disulfide bonds in maintaining higher structure. In addition, the C531→S mutant may help clarify the anomalous partial inhibition of wild-type AmP by p-hydroxymercuribenzoate (pHMB): The S531 mutant is expected to be catalytically-active and resistant to inhibition by pHMB.

One plans to use both site-specific mutation and deletion mutation to characterize the C-terminus of AmP. For example, A648 and A649 (the postulated gpi anchor attachment residue) will be replaced with R residues or simply deleted. These studies may also be guided by results of a parallel study. In the latter study, one plans to compare membrane-bound AmP with apparently soluble forms of AmP. AmPs in astrocytes, platelets, heart, adrenal medulla and lymphocytes appear to be soluble enzymes of cytosol (98,101,106,147,148,152,165,191,192). Conceivably, soluble AmP is the product of a different gene. However, it is also conceivable that alternative processing occurs such that, e.g., kidney and heart AmPs differ in their C-terminal sequences. To test the latter possibility, one will prepare sense primers to, with the antisense APT primer of the 3'RACE system, obtain the nucleotide sequence(s) of soluble AmP cDNA from human kidney AmP cDNA nucleotide 2070 to the poly A tail. For these purposes, one have prepared poly A RNA's of human heart, adrenal gland and brain. It may be relevant that residues 643–646 (HTEP) closely resemble a known cell retention sequence signal (HTEL) that directs some liver carboxylesterases to storage in the endoplasmic reticulum (158).

Cellular and Subcellular Dispositions of Human Aminopeptidase P.

To a large degree, the functions of AmP in integrative biology are likely to be determined by its anatomical dispositions. Like other exopeptidases, AmP is selective, but not specific, in terms of substrate hydrolysis. In these terms, anatomical distribution can be understood to restrict access of AmP to those substrates available in the cellular or extracellular compartment in which the catalytic site is disposed. Thus, AmP disposed on small intestine brush border epithelium could plausibly function as a digestive enzyme that facilitates breakdown of collagenous foodstuffs, whereas AmP disposed on renal proximal tubule epithelium may function to process filtered peptides so as to conserve amino acids and modulate effects of some peptide hormones. Thus, the first objective is to determine by immunocytochemistry at the level of electron microscopy anatomical dispositions of AmP and orientation of its catalytic site.

From another perspective, anatomical disposition of a given protein can be a determinant of secondary or tertiary reactions conducted by "near-neighbor" molecules, a concept well-recognized in terms of receptors and coupled signaling proteins. Given that AmP is probably disposed in part in specialized cell membrane domains (e.g. in endothelial caveolae) believed to play key roles in cell signaling (74,92,121,131,136,137,173–175), the second objective is to help define morphologically "near-neighbors" of AmP whose functions may reasonably be influenced by reactions catalyzed by AmP.

Preparation of Antibodies.

Monoclonal antibody HL510, prepared against guinea pig serum AmP (22,32), is reactive with human AmP and has been used in immunofluorescence studies to localize AmP on human endothelial cells (34). In the short term, one will continue to use HL510 for immunocytochemistry; however, one will in parallel prepare antibodies against specific peptide sequences in human kidney AmP that are predicted to be highly antigenic. For the latter search, one used the EGCG program (Wellcome Trust Genome) to identify antigenic sequences (112). The goal is to obtain at least one high affinity antiserum to a known epitope that does not occur in other proteins of the "pita bread" family of proteins (59).

AmP peptide E285-W323, which contains one potential N-glycosylation site and two C residues that may be disulfide-linked, will be the first tested. The 39-amino acid residue peptide will be synthesized by the University of Florida peptide synthesis facility. The free peptide and the peptide coupled to polylysine will be used as immunogens. The monoclonal antibody facility will immunize five mice with each immunogen. Antibody titers will be measured by ELISA. Typically, one of a group of five mice is superior in terms of antibody response (titer and affinity) and provides a basis for choosing which mouse to use for preparing hybridomas.

Antibody isotype will be determined, and octyl glucoside-treated homogenate of human kidney cortex (from the National Disease Research Interchange/Human Biological Data Interchange, NDRI) will be used for SDS-PAGE and western blotting. The homogenate will also be used for protein A-Sepharose immunoprecipitation of AmP. Part of the immunoprecipitate will be denatured and subjected to SDS-PAGE to examine for the expected Mr 90,000 protein. The remainder will be packed into a small column and then washed with 0.1 M ethanolamine to separate native AmP from antibody (113). The eluted protein will be examined for AmP catalytic activity using Arg-Pro-Pro-[$^3$H]benzylamide as substrate (21). The goal is to obtain a specific antibody capable of binding human AmP at an affinity sufficiently high to enable immunocytochemistry studies and immunoaffinity purifications of native AmP from a range of human tissue sources. The immediate work plan focuses largely on determining cellular and subcellular dispositions of AmP. Longer term, the antibodies to AmP will be useful for other purposes such as epidemiologic surveys for AmP deficiency states (62). The first immunogen, E285-W323, contains a tyrosine residue and could therefore be readily labeled with $^{125}$I for development of a competitive radioimmunoassay for AmP. If the first peptide immunogen fails to yield an antibody capable of immunoprecipitating native human AmP, one will prepare alternative antigenic sequences; in order of predicted high scores: T38-T51, P582-R597 and (if needed) L568-K578.

For the reasons stated above, one prefers to use relatively small antigenic, unique peptide sequences for preparing anti-AmP. If necessary, however, one will use recombinant wild-type human kidney AmP to prepare a large peptide antigen. The N-terminal third of AmP is unique in comparison with sequences of other members of the "pita bread" protein family (59). Thus, it should be possible to prepare a specific anti-AmP by using as immunogen the N-piece of AmP formed by acid hydrolysis of the D157–P158 bond. When anti-human AmP becomes available, one will prepare an immunoaffinity chromatography matrix (32) to obtain pure native AmP from kidney and other tissues. Native human kidney AmP will be compared with recombinant wild-type AmP.

Antibodies will be purified on DE-52 cellulose (5,6). As necessary, specific anti-AmP will be immunoabsorbed on antigen covalently bound on Sepharose or the original peptide synthesis resin and then eluted with 0.1 M ethanolamine (32,113). Initially, one will use second antibody conjugates for immunocytochemical studies. However, it has been argued that crosslinking of primary antibodies by second antibodies may cause cell membrane antigens to move into caveolae (143,145,153). If the subcellular localization AmP appears to be influenced by second antibody, one will conjugate AmP directly. In our previous studies of the subcellular distribution of angiotensin converting enzyme (ACE), one developed means of conjugating anti-ACE to octapeptide microperoxidase via a bifunctional active ester (6). The same labeling procedure will be used for anti-AmP.

Cellular and Subcellular Dispositions of AmP.

Immunocytochemistry studies at the level of light microscopy were described above. A major objective now is to define the dispositions of human AmP at the cellular and subcellular levels. The need for high resolution studies can be illustrated as follows: Light micrographs of lung tissue indicate that anti-AmP is captured at sites throughout the alveolar-capillary unit and on endothelium of small arteries and veins. The high resolution of electron microscopy is required to define the actual cellular and subcellular disposition(s) of AmP.

In addition to the need to distinguish which of the cell-types of the alveolar capillary unit possess AmP, there are two other questions raised by our light microscopy studies. Unlike pulmonary ACE, which is disposed on endothelium, one has detected AmP immunoreactivity in association with airway epithelial cells and mononuclear leukocytes. Thus, EM studies are needed to identify the host epithelial cells and leukocytes and to determine whether AmP is disposed on or within the cells. Anticipating that glutaraldehyde-based fixatives may mask AmP epitopes (as was the case for ACE; 5), one conducted all of the light microscopy immunocytochemical studies using fresh tissues (frozen sections) and tissues fixed in picric acid/paraformaldehyde; a fixative adequate for moderately high resolution electron microscopy (5,6). Further one showed that the apparent dispositions of AmP epitopes were not changed by fixation, and one showed that mouse monoclonal anti-AmP (HL510) was not inferior to mouse polyclonal anti-AmP for our immunocytochemical purposes. One can therefore proceed from light microscopy studies directly to EM immunocytochemistry of human tissues using picric acid/paraformaldehyde-fixed tissues reacted with monoclonal anti-AmP HL510 (IgG$_1$ isotype). Antibodies to human AmP antigenic amino acid sequences (see above) will be prepared for final studies. Initially, one will use second antibody conjugates as markers (conjugates of rabbit anti-mouse IgG$_1$ and, separately, goat anti-mouse IgG$_1$). The second antibodies will be labeled with colloidal gold (5 or 20 nm) (Goldmark), and reacted tissues will then be prepared for EM as one have described elsewhere (5,6). Alternatively, primary antibodies labeled with 5 or 20 nm colloidal gold can be used. Negative controls will include omission of anti-AmP and substitution of the specific antibody with mouse IgG$_1$ anti-theophylline (the latter irrelevant antibody to examine for Fc receptors). Anti-AmP previously saturated with AmP will also be used. Positive controls will include use, as the first antibody, monoclonal mouse anti-ACE (an IgM) and polyclonal rabbit anti-fibronectin (30).

The positive control studies will provide a basis for comparison of the disposition(s) of AmP with a marker known to occur on the luminal surface of endothelium (ACE) and with a marker known to be disposed in large part in the extracellular matrix (fibronectin). AmP is believed to be disposed in part on the endothelial surface (31,34,39,44, 46). In addition, AmP is believed to be among the enzymes that degrade collagen fragments produced by collagenase (165,204,205); thus, some AmP may be disposed near collagen matrix. To label AmP and fibronectin in the same experiment, one will use two differently conjugated second antibodies; e.g., rabbit anti-mouse IgG$_1$-5 nm colloidal gold for AmP and goat anti-rabbit IgG-20 nm colloidal gold (Zymed) for fibronectin. In addition to the monoclonal anti-ACE noted above, one have a polyclonal rabbit anti-ACE that will be used similarly for the co-localizations of AmP and ACE.

Our mouse anti-guinea pig AmP binds human AmP (32), but at relatively low affinity. The polyclonal mouse anti-human AmP is expected to have a much higher affinity, and one or more of the monoclonal antibodies may as well. Immunocytochemical localizations of AmP will use human tissues (from NDRI); kidney, small intestine, liver, heart, lymphocytes, platelets, bone marrow and lungs fresh-fixed in picric acid/paraformaldehyde. Similarly, Clonetics also supplies human renal proximal tubule epithelial cells and endothelial cells from aorta, pulmonary artery and lung microvasculature, all of which one will use for comparison studies.

Cells in culture provide special opportunities for EM immunocytochemistry. As shown previously, cells in monolayer culture can be examined in cross section and as whole cell mounts (10). For example, one showed using cross sections that calmodulin is disposed in endothelial caveolae. By high voltage EM of permeabilized whole endothelial cells viewed on face, calmodulin was found disposed in tracts of caveolae, along microfilming and in cleavage furrows of dividing cells. Thus, using renal proximal tubule epithelial and vascular endothelial cells in culture, one can localize AmP bound to cell membrane and/or disposed in intracellular compartments. If, in fact, soluble forms of AmP are reactive with our anti-human kidney AmP, one should be able to localize AmP within lymphocytes and platelets permeabilized after fixation.

Membrane-bound Forms of AmP.

Human kidney cortex will be the first tissue to be examined. Our light microscopy studies indicate that the vast preponderance of renal AmP is associated with renal proximal tubule epithelium, with lesser amounts being distributed on all endothelia except for glomerular endothelium (39). At present, relatively little is known of the subcellular distribution of gpi-anchored proteins on specialized epithelia, thus our findings on the disposition(s) of AmP may be instructive in terms of other gpi-anchored proteins, such as membrane dipeptidase (109,110). For reasons presented above, one expects that most renal AmP will be shown to be an ectoenzyme with its catalytic site oriented to the luminal space. Fixed tissue will also be permeabilized with 1% Triton X-100 to facilitate detection of AmP in intracellular sites (10). Proximal tubule epithelial cells in culture will be examined similarly and tested in addition for AmP catalytic activity. Intact and permeabilized fixed cells will be examined in cross section and en face. Endothelial-associated AmP is expected to be disposed as an ectoenzyme and, as a gpi-anchored protein, may be disposed largely in caveolae (121,171,175).

AmP appears by light microscopy (39) to be disposed on brush border epithelium and endothelium of the villus vascular core of the small intestine. Lung tissue will be examined next, as described above. Separately, fixed cultures of endothelial cells from aorta, pulmonary artery and lung microvasculature (all from Clonetics) will be examined, intact and permeabilized.

Soluble Forms of AmP.

It is not yet known whether the soluble forms of AmP that are found in lymphocytes, platelets, neuronal tissues and adrenal medulla (98,147,165,191,192) are alternative products of the same gene that encodes membrane-bound forms. To gain insight into the question, one will attempt immunoprecipitation of these soluble AmPs using antibodies to human kidney AmP (see above). Clearly, if the immunoprecipitations are successful, one will have a basis for proceeding to immunocytochemical localization using the target tissues fixed add permeabilized. As a further step, one will examine poly A RNAs of lymphocytes and adrenal medulla by RT-PCR using nested primers designed from kidney AmP cDNA. The sense and antisense primers will be selected to cover sequence from just upstream of the putative proton shuttle (H430) to a downstream site just 3' to the last putative metal ligand (E569). The PCR product, if obtained, will be sequenced. If, in fact, lymphocyte and adrenal medulla AmPs are encoded over their putative "pita bread" domains as is kidney AmP, one will (as described above) examine by 3'RACE RT-PCR for alternative C-terminal sequences that may direct soluble AmPs to intracellular sites.

Simmons has reported that human heart AmP is soluble (152), and this may be true for liver AmP as well. However, the possibility is not ruled out that heart and liver contain an abundance of phospholipase C or D that, during the homogenization process, converts amphipathic AmP into a hydrophilic form. Immunocytochemistry studies should help resolve this question. Even if soluble and normally stored in intracellular sites, human heart and liver AmP must have a strong structural resemblance to kidney AmP: On Northern blotting using human kidney AmP cDNA that encodes the kidney AmP sequence R123-A478, heart and liver poly A RNAs were found to be highly reactive (47). Further, each had a single message of the size, 3.5kb, of the kidney AmP RNA. If heart and liver AmPs are, in intact tissue, disposed intracellularly, it should be a straightforward matter to identify a C-terminal sequence signal that directs cell retention.

Membrane-bound AmP and its Nearest Neighbors.

Reactions at the cell surface can set off a cascade of secondary, tertiary and higher reactions that are determined in part by the physical proximity and fit of downstream protein reactants. Receptor activation and subsequent cell signaling is perhaps the clearest example (63,74,130,137, 142), especially for receptors with seven transmembrane domains with intracellular peptide loops, one or more of which can be phosphorylated and dephosphorylated (63). There is an abundant and growing literature describing close chemical and biochemical associations between ligand-bound receptors, signaling molecules and caveolins (e.g. see 92,130,131,137,138,160,171,173,175,183). An objective in this subproject is to develop morphologic means of documenting close anatomical associations of functionally-related molecules.

Increasingly, it appears that reactions involving cell surface gpi-anchored proteins can also set off a cascade of events. Gpi-anchored T-cell receptor is coupled to Src-family kinases (142). An insulin-dependent gpi-anchor hydrolysis has been described and leads to generation of inositol phosphoglycan (IPG) second messengers (142). Purified IPGs alone can mimic insulin activities. Through the same, or a parallel pathway, insulin stimulates a tyrosine phosphorylation of caveolin (142).

Previously, it was shown that bradykinin (BK), in concentrations as low as 10 pM, causes endothelial cells to mobilize arachidonate, some of which is converted into thromboxane $A_2$ (8–11). Des-$Arg^1$-BK, the product formed by AmP, is the only lower homolog of BK, in a near-comparable concentration, capable of mobilizing endothelial arachidonate. Possibly of relevance, des-$Arg^1$-BK has as great an affinity for AmP as BK itself. It is a tenable speculation that a BK-dependent gpi-anchor hydrolysis exists, a gpi-anchor at issue is that of AmP, and part or all of the arachidonate mobilized comes from the diacylglycerol formed by gpi-anchor hydrolysis. In these terms, BK may exert some of its effects via AmP.

It is now widely believed that most of the biological effects of BK are initiated by activation of the B2 receptor and are mediated through calmodulin-dependent eNOS and guanylate cyclase (see 63 and its references). If, as expected, endothelial AmP is largely restricted to caveolae, it is well-positioned for at least indirect linkage with eNOS and guanylate cyclase, which appear to be largely disposed on the cytoplasmic aspect of caveolae (92,131). Endothelial cells respond to BK as if they have B2 receptors; however the subcellular dispositions of B2 receptors have, to our knowledge, never been defined at the level of electron microscopy.

If, in fact, binding of BK to the B2 receptor activates eNOS and guanylate cyclase (as opposed to binding of BK to an alternative effector), the B2 receptor is likely in very close physical proximity. Our immediate objective here is to develop a novel perspective on how BK exerts effects on endothelium by helping to define nearest-neighbors of AmP and the B2 receptors. Such data as are available indicate that the B2 receptor is situated on or within a cell membrane microdomain, perhaps in caveolae, that can be rapidly taken up by endocytosis (63).

It is proposed to use endothelial cell plasma membrane/caveolae fractions prepared as described previously (3,4,8, 11). In brief, post-confluent endothelial cells in culture (which contain caveolae in large numbers (7,8,10,11)) will be harvested with a rubber spatula, homogenized, and then centrifuged to remove nuclei and cell debris. The supernatant will then be reacted with 5'-adenosine monophosphate (5'-AMP) in the presence of lead nitrate. Caveolar 5'-AMPase, a gpi-anchored protein, hydrolyzes 5'-AMP to form adenosine and Pi, Pi is precipitated as lead phosphate within caveolae and thereby greatly increases the density of the plasma membrane/caveolae fraction. The latter fraction is then easily separated from soluble proteins and other membrane systems by low g-force (~100×g) centrifugation of the reaction mixture through a relatively dense sucrose cushion (4). Remarkably, about 65% of the 5'-AMPase remains active, and angiotensin converting enzyme (3,4) and AmP activities (unpublished) are readily measured.

The resulting endothelial cell membrane/caveolae "ghosts" provide a number of advantages for our present purposes. Firstly, antigenic sites on both the extracellular and cytoplasmic aspects of the cell membrane are accessible to added antibodies. Secondly, the fraction contains both "unspecialized" cell membrane and attached caveolae. Should, contrary to expectations, the B2 receptor be disposed at sites outside of caveolae, one will find these sites. Thirdly, when of interest, the plasma membrane/caveolae fraction can be treated with Triton X-100 to form its Triton-soluble and Triton-insoluble subfractions (150,175). AmP and 5'-AMPase are expected to be enriched in the Triton-insoluble particulate.

One can use a rabbit anti-human B2 receptor that binds to a cytoplasmic epitope of the B2 receptor, C361-Q395 (63). One or more of the serines of C361-Q395 is phosphorylated when the B2 receptor of human foreskin fibroblasts is reacted with BK (63). With our mouse anti-AmP and rabbit anti-B2 receptor preparations, one can localize the target antigens on human endothelial cell (Clonetics) plasma membrane/caveolae fractions using anti-mouse IgG conjugated to 5 nm colloidal gold and anti-rabbit IgG conjugated to 20 nm colloidal gold. If second antibody places gold particles too distant for assigning antigen sites, we will label primary antibodies (6).

By the same approach, one can define the subcellular dispositions of AmP and the B2 receptor in respect to dispositions of eNOS and guanylate cyclase (using commercially-available anti-eNOS and anti-guanylate cyclase). Our aim is to develop and document a morphologic approach to complement biochemical data already in hand on the apparently tight physical association of signal transduction molecules believed to be disposed in association with caveolae (e.g. see 89,90,92,130,131,160,173). In addition, our approach should also help clarify anatomic associations between proteins disposed on the extracellular aspect of the plasma membrane with functionally-linked counterparts disposed on the cytoplasmic aspect.

Success in this subproject can be exploited by us and others in terms of relating morphologically a host of other proteins of interest, including (but not limited to) the caveolins, $Ca^{2+}$-ATPase, the $IP_3$ receptor, adenosine and prostaglandin transporters and heterotrimeric G proteins (90,130,132,137,173,184).

Alternative Splicing.

Complementary DNA clones encoding human membrane-bound AmP were isolated by reverse transcription-polymerase chain reaction (RT-PCR) of human kidney and lung poly(A)+ RNA. Northern hybridization analysis and RT-PCR suggests that the soluble and membrane-bound forms of human AmP are products of two distinct mRNAs which may be produced through alternative splicing, have different C-terminal sequences. Intronic sequences involved in such alternative splicing can be included in human AmP constructs to allow production of both forms of human AmP. In such constructs, it is preferred that sequences from only the specific introns involved in the alternative splicing be used. Such a construct is thus a cDNA/genomic hybrid construct, containing both cDNA and genomic DNA. The cDNA portion of such a construct lacks intronic sequences which are present in corresponding genomic sequences.

Construction of Transgenic Animals.

Animal Sources.

Animals suitable for transgenic experiments can be obtained from standard commercial sources such as Charles River (Wilmington, Mass.), Taconic (Germantown, N.Y.), and Harlan Sprague Dawley (Indianapolis, Ind.). Many strains are suitable, but Swiss Webster (Taconic) female mice are preferred for embryo retrieval and transfer. B6D2F$_1$ (Taconic) males can be used for mating and vasectomized Swiss Webster studs can be used to stimulate pseudopregnancy. Vasectomized mice and rats can be obtained from the supplier.

Microinjection Procedures.

The procedures for manipulation of the rodent embryo and for microinjection of DNA are described in detail in Hogan et al., Manipulating the Mouse Embryo (Cold Spring Harbor Laboratory, Cold Spring Harbor, N.Y., 1986), the teachings of which are incorporated herein.

Transgenic Mice.

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two cell stage.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

Transgenic Rats.

The procedure for generating transgenic rats is similar to that of mice (Hammer et al., *Cell* 63:1099–112 (1990)). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus' cells surrounding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg. ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10 to 12 embryos are transferred into each rat oviduct through the infundibulum. The incision is then closed with sutures, and the foster mothers are housed singly.

Embryonic Stem (ES) Cell Methods.

Introduction of DNA into ES Cells.

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and Embryonic Stem Cells, A Practical Approach*, ed. E. J. Robertson, (IRL Press 1987), the teachings of which are incorporated herein. Selection of the desired clone of transgene-containing ES cells can be accomplished through one of several means. For random gene integration, an AmP clone is co-precipitated with a gene encoding neomycin resistance. Transfection is carried out by one of several methods described in detail in Lovell-Badge, in *Teratocarcinomas and Embryonic Stem Cells, A Practical Approach*, ed. E. J. Robertson. (IRL Press 1987), or in Potter et al., *Proc. Natl. Acad. Sci. USA* 81:7161 (1984). Lipofection can be performed using reagents such as provided in commercially available kits, for example DOTAP (Boehringer-Mannheim) or lipofectin (BRL). Calcium phosphate/DNA precipitation, lipofection, direct injection, and electroporation are the preferred methods. In these procedures, $0.5 \times 10^6$ ES cells are plated into tissue culture dishes and transfected with a mixture of the linearized AmP clone and 1 mg of pSV2neo DNA (Southern and Berg, *J. Mol. Appl. Gen.* 1:327–341 (1982)) precipitated in the presence of 50 mg lipofectin (BRL) in a final volume of 100 μl. The cells are fed with selection medium containing 10% fetal bovine serum in DMEM supplemented with G418 (between 200 and 500 μg/ml). Colonies of cells resistant to G418 are isolated using cloning rings and expanded. DNA is extracted from drug resistant clones and Southern blots using an AmP cDNA probe can be used to identify those clones carrying the AmP sequences. PCR detection methods may also used to identify the clones of interest.

DNA molecules introduced into ES cells can also be integrated into the chromosome through the process of homologous recombination, described by Capecchi (1989). Direct injection results in a high efficiency of integration. Desired clones can be identified through PCR of DNA prepared from pools of injected ES cells. Positive cells within the pools can be identified by PCR subsequent to cell cloning (Zimmer and Gruss, *Nature* 338:150–153 (1989). DNA introduction by electroporation is less efficient and requires a selection step. Methods for positive selection of the recombination event (for example, neo resistance) and dual positive-negative selection (for example, neo resistance and gancyclovir resistance) and the subsequent identification of the desired clones by PCR have been described by Joyner et al., *Nature* 338:153–156 (1989), and Capecchi (1989), the teachings of which are incorporated herein.

Embryo Recovery and ES Cell Injection.

Naturally cycling or superovulated female mice mated with males can be used to harvest embryos for the implantation of ES cells. It is desirable to use the C57BL/6 strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10 to 20 ES cells are injected into blastocysts using a glass microneedle with an internal diameter of approximately 20 μm.

Transfer of Embryos to Pseudopregnant Females.

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 gauge needle through which the blastocysts are transferred. After the transfer, the ovary and uterus are pushed back into the body and the incision is closed by two sutures. This procedure is repeated on the opposite side if additional transfers are to be made.

Identification, Characterization, and Utilization of Transgenic Mice and Rats.

Transgenic rodents can be identified by analyzing their DNA. For this purpose, tail samples (1 to 2 cm) can be removed from three week old animals. DNA from these or other samples can then be prepared and analyzed by Southern blot, PCR, or slot blot to detect transgenic founder ($F_0$,) animals and their progeny ($F_1$ and $F_2$).

Disclosed is an isolated nucleic acid molecule encoding the amino acid sequence shown in SEQ ID NO:2, or a fragment of at least six amino acids of the amino acid sequence shown in SEQ ID NO:2. Preferably the nucleic acid molecule includes expression sequences, at least one intron, or both. Preferred forms of the nucleic acid molecule are SEQ ID NO:1, SEQ ID NO:6, and nucleotides 1 to 29,271 of SEQ ID NO:6. Also disclosed are fragments of SEQ ID NO:1, or fragments of the collective sequence represented by SEQ ID NO:3, SEQ ID NO:4, SEQ ID NO:5, SEQ ID NO:6, and SEQ ID NO:7 (the genomic sequence). It is preferred that the fragments contain at least 10 nucleotides, at least 15 nucleotides, at least 18 nucleotide, or at least 20 nucleotides. Also disclosed are aminopeptidase P regulatory sequences present SEQ ID NOs:3, 4, 5, 6, and 7. A preferred regulatory sequence is a fragment of SEQ ID NO:5 that promotes transcription of a nucleic acid segment operatively linked to the fragment.

Also disclosed are proteins having the amino acid sequence shown in SEQ ID NO:2 or a variant amino acid sequence where one or more amino acids shown in SEQ ID NO:2 are replaced with a conservative substitute amino acid. A preferred form of the protein has from one to ten amino acids shown in SEQ ID NO:2 are replaced with a conservative substitute amino acid. Also disclosed are proteins including a portion of the amino acid sequence shown in SEQ ID NO:2 such that the protein is soluble in aqueous solution (also referred to as soluble aminopeptidase P). A protein having the amino acid sequence shown in SEQ ID NO:2 or a variant amino acid sequence, where the protein has aminopeptidase activity. Also disclosed are peptides including a fragment of at least six amino acids of the amino acid sequence shown in SEQ ID NO:2. Also disclosed are antibodies reactive with the disclosed proteins or peptides.

Also disclosed is a method of detecting aminopeptidase P mutants performed by comparing all or a part of a nucleotide sequence encoding aminopeptidase P with the corresponding nucleotide sequence of SEQ ID NO:1, or the collective nucleotide sequence represented by SEQ ID NO:3, SEQ ID NO:4, SEQ ID NO:5, SEQ ID NO:6, and SEQ ID NO:7. Also disclosed is a method of identifying a compound that inhibits aminopeptidase P by bringing into contact cells and a compound to be tested, measuring the level of aminopeptidase P activity in the cells, and comparing the measured level of activity with the level of activity in cells not brought into contact with the compound to be tested. Also disclosed is a method of identifying a compound that inhibits aminopeptidase P expression by bringing into contact cells expressing aminopeptidase and a compound to be tested, measuring the level of aminopeptidase P expression in the cells, and comparing the measured level of expression with the level of expression in cells not brought into contact with the compound to be tested.

Publications

1. Ryan, et al. Biochem J., 110:795–797. 1968.
2. Ryan, et al.: Inactivation of bradykinin in rat lung. In Vol. 8, *Adv. Exp. Med. Biol.* (eds. N. Back, F. Sicuteri and M. Rocha e Silva), Plenum Press, N.Y., pp. 263–271, 1970.
3. Ryan, et al. Trans. Ass. Am. Physcns., 84:297–306, 1971.
4. Ryan, et al. Biochim. Biophys. Acta, 249:177–180, 1971.
5. Ryan, et al. Biochem. J., 146:497–499, 1975.
6. Ryan,et al. Tissue & Cell, 8:111–124, 1976.
7. Ryan, et al. Trans. Assoc. Amer. Physcns., 91:343–350, 1978.
8. Ryan, et al. Adv. Exp. Med. Biol., 120A:375–391, 1979.
9. Crutchley, et al. Adv. Exp. Med. Biol., 156A:527–532, 1983.
10. Ryan, et al. Adv. Exp. Med. Biol., 156A:671–679, 1983.
11. Ryan, et al. Adv. Exp. Med. Biol., 156B:767–774, 1983.
12. Ryan, J. W.: The metabolism of angiotensin I and bradykining by endothelial cells. In *The Biology of Endothelial Cells*, (E. Jaffe. ed.), Martinus Nijhoff, The Netherlands, pp 317–329, 1984.
13. Lanclos, et al. Biochim. Biophys. Acta, 1008:109–112, 1989.
14. Ryan, Am. J. Physiol. (Lung Cell. Mol. Physiol. 1), 257:L53–L60, 1989.
15. Agrawal, et al. J. Biol. Chem., 265:11849–11853, 1990.
16. Chen, et al. J. Pharmacol. Exptl. Ther., 259:1301–1307, 1991.
17. Lanclos, et al. Blood, 77:2488–2496, 1991.
18. Caldwell, et al. Microvasc. Res., 42:229–244, 1991.
19. Caldwell, et al. Invest. Ophthalmol. Vis. Science, 33:1610–1619, 1992.
20. Öner, C et al. Blood, 79:813–819, 1992.
21. Ryan, et al. Biochim. Biophys. Acta, 1119:133–139, 1992.
22. Ryan, et al. Biochim. Biophys. Acta, 1119:140–147, 1992.
23. Sprinkle, et al. Genomics, 13:877–880, 1992.
24. Tho, et al. Amer. J. Obstet. Gynecol., 167:1794–1802, 1992.
25. Layman, et al. Adolesc. Pediatr. Gynecol., 6:214–219, 1993.
26. Ripka, et al. Biochem. Biophys. Res. Commun., 196:503–508, 1993.
27. Ryan, et al. Biochem. Biophys. Res. Commun., 196:509–514, 1993.
28. Sprinkle, et al. Genomics, 16:542–545, 1993.
29. Denslow, et al. Biochem. Biophys. Res. Comm., 205: 1790–1795. 1994.
30. Jiang, et al. J. Cell Science, 107:2499–2508, 1994.
31. Ryan, et al. J. Pharmacol. Exptl. Ther., 269:941–947, 1994.
32. Ryan, et al. Biochem. Biophys. Res. Commun., 205:1796–1802, 1994.
33. Morgan, et al. Amer. J. Hematology, 51:12–18, 1996.
34. Ryan, et al. Immunopharmacology, 32:149–152, 1996.
35. Papapetropoulos, et al. Circulation Research, 79:512–523, 1996.
36. Denslow, N. D. and Nguyen, H. P. "Specific Cleavage of Blotted Proteins at Cysteine Residues after Cyanylation: Analysis of Products by MALDI-TOF". In *Techniques in Protein Chemistry VII* (D. Marshak, Ed), Academic Press, San Diego, pp. 241–248, 1996.
37. Layman, L., Lanclos, K. D., Tho, S. P. T., Sweet, C. R. and McDonough, P. G.: Polymerase chain reaction amplification of gonadotropin-releasing hormone gene sequences in idiopathic hypogonadotropic hypogonadism. (In press), 1997.
38. Denslow, N. D., Nguyen, H. P., Parten, B. and Ryan, J. W.: "Novel means of identifying C-terminal peptide fragments of glycosyl phosphoinositol (GPI)-anchored proteins," Fifth Symposium of the Protein Society, Baltimore, Md., 1991.
39. Revann, et al. Aminopeptidase P is disposed on guinea pig vascular endothelium and some epithelia. FASEB Journal 5:A1579, 1991 (Abstr. 7014).
40. Ryan, et al. FASEB Journal 5:A1579, 1991 (Abstr. 7015).
41. Denslow, N. D., Nguyen, H. and Parten, B.: In-gel cleavage strategies for sequencing internal regions of proteins separated by SDS-PAGE. Sixth Symposium of the Protein Society, San Diego, Calif., 1992.
42. Denslow, N. D., Parten, B., Tran, N., Barry, P. and Pluskal, M.: Microsequencing proteins bound to immobilon-CD membranes: A novel method for difficult proteins. 9th International Conference on Methods in Protein Sequence Analysis, Otsu, Japan, Sep. 20–24, 1992.
43. Ryan, et al. FASEB Journal 6:A990, 1992 (Abstr. 312).
44. Antonov. et al. FASEB Journal 7:A795, 1993 (Abstr. 4593).
45. Denslow, et al. FASEB Journal 7:A477, 1993 (Abstr. 2766).

46. J. W Ryan, A. Papapetropoulos, A. Antonov, R. Virmani, F. D. Kolodgie, D. H. Munn, N. Masczin, R. G. Gerrity & J. D. Catravas.: Aminopeptidase P is disposed on human endothelial cells: KININ 95, Denver 1995.
47. Ju, H., Venema, R. C., Zou, R., Venema, V. J. and Ryan, J. W.: Aminopeptidase P in human tissues: Northern blot analysis. FASEB Journal, 1997, in press.
48. Aebersold, R., "Internal amino sequence analysis of proteins after in situ protease digestion on nitrocellulose", *A Practical Guide to Protein and Peptide Purification for Microsequencing*, pp 71–90 (1989).
49. Aitken, et al., "Peptide preparation and characterization", *Protein Sequencing. A Practical Approach*, pp. 43–68 (1989).
50. Altschul, et al., *J. Mol. Biol.* 215:403–410 (1990).
51. Aonuma, et al., *J. Pharmacol. Dyn.* 5:40–48 (1982).
52. Aonuma, et al. *Chem. Pharm. Bull.* 28:3322–3339 (1980).
53. Aonuma, et al., *Yakugaku Zasshi* 103:662–666 (1983).
54. Aonuma, et al, *Chem. Pharm. Bull.* 28:3340–3346 (1980).
55. Aonuma, et al. *Chem. Pharm Bull.* 31:612–619 (1983).
56. Aonuma, et al. *Chem. Pharm. Bull.* 32:219–227 (1984).
57. Aroor, et al. *Biochemistry* 3:350–3357 (1993).
58. Aviv. and Leder *Proc. Natl. Acad. Sci.* 69:1408–1412 (1972).
59. Basin et al. *Proc. Natl. Acad. Sc. USA*, 91:2473–2477 (1994).
60. Bechhofe *BioTechniques* 10: 17–20 (1991).
61. Berger, et al. *J. Biol. Chem.* 263:10016–10021 (1998).
62. Blau, et al. *J. Inher. Metab. Dis.* 11:240–242, (1988).
63. Blaukat, et al. *J. Biol. Chem.* 271:32366–32374 (1996).
64. Bleiweis, et al. *Archs. Oral Biol.* 35:15S–23S (1990).
65. Bodenmuller and Schaller *Nature* 293:579–580 (1981).
66. Bonner, et al. *J. Cardiovas. Pharmacol.* 15:S46–S56 (1990).
67. Boothroyd et al. *Nucleic Acids Res.* 9:4735–4743 (1981).
68. Butler, et al. *Gene* 123:115–119 (1993).
69. Caldwell, et al. *Science* 191:1050–1051 (1976).
70. Campbell et al. *J. Biol. Chem.* 259:14586–14590 (1984).
71. Casey et al. *Nucleic Acids Res.* 4:1539–1552 (1997).
72. Chang et al. *J. Cell Biol.* 126:127–138 (1994).
73. Chomazynski et al. *Anal. Biochem.* 162:156–159 (1987).
74. Chun, et al. *Proc. Natl. Acad. Sci. USA* 91:11728–11732 (1994).
75. Cleveland, et al. *J. Biol. Chem.* 252:1102–1106 (1977).
76. Davies et al. *Biochem. J.* 295:889–896 (1993).
77. Dayhoff, et al. *Methods Ensymol.* 91:524–545 (1983).
78. Dehm et al. *Eur. J. Biochem.* 17:364–371 (1970).
79. Denslow, N. D., et al., "In-gel cleavage strategies for sequencing internal regions of proteins separated by SDS-PAGE", *Sixth Symposium of the Protein Society*, San Diego, Calif. (1992).
80. Denslow, N. D., et al., "A membrane for electroblotting peptides after enzymatic digestion in gel slices", *Protein Analysis Renaissance, Applied Biosystems* (1993).
81. Dorer, et al. *Biochem. Biophys. Acta* 429:220–228 (1976)
82. Elder et al. *Proc. Nat. Acad. Sci. USA* 79:4540–4544 (1982).
83. Endo, et al. *J. Biol. Chem.*, 264:4476–4481 (1989).
84. Endo et al. *Mol. Biol. & Med.* 8:117–127 (1991).
85. Erickson, et al. *J. Biol Chem.*, 254:11771–11774 (1979).
86. Ferguson, et al. *Sience* 239:753–759 (1988).
87. Feurle, et al. *Neurosci. Lett.* 38:287–289 (1983).
88. Flinta, et al. *Eur. J. Biochem.* 154:193–196 (1986).
89. Fujimoto, et al. *J. Cell Sci.* 108:7–15 (1995).
90. Fujimoto, et al. *J. Cell Biol.* 119:1507–1513 (1992).
91. Fujimoto, et al. *J. Cell. Biol.* 120:1147–1157.(1993).
92. Garcia-Cardena, et al. *Proc. Natl. Acad. Sci. USA* 93:6448–6453 (1996).
93. Gavras, et al. *N. Eng. J. Med.* 298–8647–8650 (1991).
94. Gordon, et al. *J. Biol. Chem.* 266:8647–8650 (1991).
95. Grafe, et al. *Am. J. Physiol.* 264:H1493–H1497 (1993).
96. Gruenwald, S. and Heitz, J., "Baculovirus Expression Vector System", *Procedures and Methods Manual, Second Edition, In Pharmingen*, pp. 5–73 (1993).
97. Hall, et al. *J. Virol.* 65:6516–6527 (1991).
98. Harbeck et al. *Eur. J. Biochem.* 198:451–458 (1991).
99. Hedner, et al. *BMJ* 304–941–946 (1992).
100. Heltianu, et al. *Eur. J. Cell Biol.* 64:61–70 (1994).
101. Hendriks, et al. *Clin. Chim. Acta* 196:87–96 (1991).
102. Henikoff et al. *Nucleic Acids Res.* 19:6565–6572 (1991).
103. Herman, et al. J. Chromatog., *Sience* 28:524–528 (1990).
104. Hjelmeland, Meth. in *Enzym.* 192:253, 264 (1990).
105. Ho, et al. *Gene* 77:51–59 (1989).
106. Holtzman, et al. *Anal. Biochem.* 162:476–484 (1987).
107. Homans, et al. *Nature* 333:269–272 (1988).
108. Hooper, et al. *Hypertension* 19:281–285 (1992).
109. Hooper, et al. *Biochem.* 273:301–306 (1991).
110. Hooper, et al., *FEBS Lett.* 229:340–344 (1988).
111. Hooper, et al. *Biochem J.* 267:509–515 (1990).
112. Hopp, et al. *Proc. Natl. Acad. Sci. USA* 78:3824–3828 (1981).
113. Hyde, et al. *Biochem. J.* 319:197–200 (1996).
114. Ishida, et al. *Hypertension* 14:322–327 (1989).
115. Jacobs, et al. *Nucleic Acids Res.* 16:4637–4650 (1988).
116. Jentoft, et al. *J. Biol. Chem.* 254:4359–4365 (1979).
117. Karp, et al. *J. Biol. Chem.* 257:7330–7335 (1982).
118. Khandjian, et al. *BioTechnology* 5:165 (1987).
119. Kitamura, et al. *Hypertension* 26:P18 (1995).
120. Kitamura, et al. *Br. J. Pharmacol.* 114:6–7 (1995).
121. Kittel et al. *Cell Biol. Internatl.* 18:875–879 (1994).
122. Kohama, et al. *J. Pharmacobio-Dyn.* 8:1024–1031 (1985).
123. Kozak, et al., *Nucleic. Acids Res.* 12:857–872 (1984).
124. Krepela, et al. *Lung* 163:33–54 (1985).
125. Krishna, et al. *Anal. Biochem.* 199:45–50 (1991).
126. Landon, M., "Cleavage at Aspartyl-Prolyl Bonds", *Methods in Enzymology*, (eds. C. H. W. Hirs, S. N. Timasheff), Vol. XLVII, Part E, pp. 145–149.
127. Laskey, et al. *J. Biol. Chem.* 265:2613–2619 (1990).
128. Laskey, et al. *Prac. Natl. Acad. Sci. USA* 89:1690–1694 (1992).
129. LaScothe, et al. *BioTechniques* 6:154–159 (1988).
130. Li, et al. *J. Biol. Chem.* 271:3863–3868 (1996).
131. Li, et al. *J. Biol. Chem.* 270:15693–15701 (1995).
132. Li, et al. *J. Biol. Chem.* 271:28647–28654 (1996).
133. Li, S., et al., "*J. Biol Chem.* 771:568–573 (1996).
134. Lin *FEBS Letters* 381:188–190 (1996).
135. Lin et al. *Biochemistry* 18:43–47 (1979).
136. Lisanti et al. *J. Cell Biol.* 126:11–126 (1994).
137. Liu et al. *J. Biol. Chem.* 271:10299–10303 (1996).
138. Liu, et al. *J. Cell Physiol.* 156:311–316 (1993).
139. Low et al. *Sience* 239:268–275 (1988).
140. Low, et al. *FASEB J.* 3:1600–1608 (1989).
141. Low, et al. *Biochem. J.* 279:483–493 (1991).
142. Mastick, et al. *J. Cell Biol.* 129:1523–1533 (1995).
143. Mayor et al., *Mol. Biol. Cell* 6:929–944 (1995).
144. Mayor, S. and Menon, A. K., "Structural analysis of the glycosylinositol phospholipid anchors of membrane proteins", In Methods: *A Composition to Methods in Enzymol.* 1:297–305 (1990).

145. Mayor, et al. *Sience* 264:1948–1951 (1994).
146. Medeiros, et al. *Endocrinology* 134:2088–2094 (1994).
147. Mentlein, et al. *Brain Research* 527:159–162 (1990).
148. Mentlein, et al. *Peptides* 17:709–720 (1996).
149. Mock, et al. *J. Biol. Chem.* 265:19606–19610 (1990).
150. Moldovan, et al. *Experimental Cell Research* 219:309–313 (1995).
151. Neven, et al. *Plant Physiology* 99:1362–1369 (1992).
152. Orawski, et al. *Biochemistry* 34:11227–11236 (1995).
153. Parton, et al., *J. Cell Biol.* 127:1199–1215 (1994).
154. Persson et al. *Eur. J. Biochem.* 152:523–527 (1985).
155. Prechel, et al., *J. Pharm. Exper. Ther.* 275:1136–1142 (1995).
156. Predescu, et al. *Proc. Natl. Acad. Sci. USA* 91:3014–3018 (1994).
157. Rasmussen, et al. *Agents Actions* 9:592–597 (1982).
158. Robbi, et al. *J. Biol. Chem.* 266: 20498–20503 (1991).
159. Roberts, et al. *J. Biol. Chem.* 263:18776–18784 (1988).
160. Robinson, et al. *Proc. Natl. Acad. Sci. USA* 92:11776–11780 (1995).
161. Roblero, et al. *Adv. Exp. Med. Biol.* 156a:437–443 (1983).
162. Rosenberry, et al. *In Biological Mass Spectrometry*, (A. L. Burlingame and J. A. McCloskey, eds.) pp. 455–475, Elsevier Sience Publishers, Amsterdam (1988).
163. Ruano, et al. "PCR: The first few cycles", *In Amplifications*, (Perkin Elmer Cetus) (1991).
164. Rusko, et al, *J. Physiol.* 455: 601–621 (1992).
165. Rusu, et al. *Eur. J. Biochem.* 210:93–100 (1992).
166. Ryan, et al. *Analyt. Biochem.* 210: 27–33 (1993).
167. Ryan, et al. *J. Pharmacol. Exptl. Ther.* 270:260–268 (1994).
168. Rychlik, W., "Oligo 4.0—Primer analysis software" (1991).
169. Sambrook, J., et al., "Molecular cloning, a laboratory manual", Cold Spring Harbor Laboratory Press, Cold Spring Harbor.
170. Sanger, et al. *Proc. Natl. Acad. Sci.* 74: 5463–5467 (1977).
171. Sargiacomo, et al., *J. Cell Biol.* 122:789–807 (1993).
172. Schagger, et al. *Anal. Biochem.* 166:368–379 (1987).
173. Schnitzer, et al. *Proc. Natl. Acad. Sci. USA* 92:1759–1763 (1995).
174. Schnitzer, et al. *J. Biol. Chem.* 270:14399–14404 (1995).
175. Schnitzer, et al. *Sience*, 269:1435–1439 (1995).
176. Shaul, et al. *J. Bio. Chem.* 271: 6518–6522 (1996).
177. Shimamoto, et al. *Agents Actions* 22: 297–307 (1987).
178. Simionescu, et al. *J. Cell Biol.* 94:406–413, (1982).
179. Simionescu, et al. *J. Cell Biol.* 97:1592–1600 (1983).
180. Simmons, et al. *J. Biol. Chem.* 267:4897–4903 (1992).
181. Simmons, et al. *Kinin'95*, Denver, Sept. 9–15 (1995).
182. Smits, et al. *Am. J. Physiol.* 258: F1417–1424 (1990).
183. Song, etal. *J. Biol. Chem.* 271:9690–9697 (1996).
184. Stahl et al. *J. Cell Biol.* 129:335–344 (1995).
185. Sturrock, et al. *Biochemistry* 35:9560–9566 (1996).
186. Suggs, et al. *Proc. Natl. Acad. Sci.* 78:6613–6617 (1981).
187. Tanoue, et al. *J. Clin. Invest.* 87:1171–1176 (1991).
188. Tanoue, et al. *J. Biol. Chem.* 265:11306–11311 (1990).
189. Tsunasawa et al. *J. Prot. Chem.* 11:382–383 (1992).
190. Vallee et al. *Biochemistry* 29:5647–5659 (1990).
191. Vanhoof et al. *Biochem. Pharmacol.* 44:479–487 (1992).
192. Vanhoof et al. *Neurochem. Int.* 21:203–208 (1992).
193. Venema et al. *Biochim. Biophys. Acta* 1218:413–420 (1994).
194. Venema, et al. *J. Biol. Chem.* 271:1–6 (1996).
195. Venema, et al. *J. Biol. Chem.* 270:14705–14711 (1995).
196. Vergas Romero, et al., *Eur. J. Biochem.* 229:262–269 (1995).
197. Vrati, S., et al., "Alkaline northern blots: Transfer of RNA from agarose gels to zeta-probe membrane in dilute NaOH", *In Molecular Biology Reports*, (Bio-Rad Laboratories), I(3):I(1987).
198. Wallace et al. *Nucleic Acids Res.* 9:879–894 (1981).
199. Walter et al. *Mol. Cell. Biochem.* 30:111–127 (1980).
200. Wilson, K. J. and Yuan, P. M., "Protein and peptide purification", *In Protein Sequencing: A Practical Approach*, (Findlay J. B. C. and Geisow, M. J., eds.), IRL Press, New York, pp. 1–41 (1989).
201. Wold, F., *Ann. Rev. Biochem.* 50:783–814 (1981).
202. Wood, et al. *Proc. Natl. Acad. Sci.* 82:1585–1588 (1985).
203. Wu, S., Gupta, et al., "Peptide chain initiation factor, $p^{67}$ characteristics gene cloning and possible therapeutic uses", *In Down Strand Processing in Biotechnology*, R. N. Mukherjee (ed.), Tat McGraw Hill, India (1992).
204. Yaron et al., *Biochem. Biophys. Res. Comm.* 32:658–663 (1968).
205. Yaron et al. *Crit. Rev. Biochem. Mol. Biol.* 28:31–81 (1993).
206. Yoshimoto, et al. *J. Biochem.* 105:412–416 (1989).
207. Yuen, et al. *BioTechniques* 7:74–82 (1989).
208. Zamze, et al. *Eur. J. Biochem.* 176:527–534 (1988).

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule comprising a nucleic acid sequence encoding a wild-type human aminopeptidase P which is (i) a member of "pita bread-fold" protein family; (ii) has metal ligand binding sites at Asp450, Asp461, His520, Glu555 and Glu569, (iii) contains five N-glycosylation sites; (iv) contains five cysteine residues and (v) comprises the amino acid sequence 235–583 of SEQ ID NO:2.

2. The isolated nucleic acid molecule of claim 1, wherein said wild-type human aminopeptidase P further comprises an amino acid sequence 24–583 of SEQ ID NO:2.

3. The isolated nucleic acid molecule of claim 1, wherein said human aminopeptidase P further comprises an N-terminal amino acid sequence from 1–583 of SEQ ID NO:2 and a C-terminal amino acid sequence from 643–660 of SEQ ID NO:2.

4. The isolated nucleic acid molecule of claim 1 wherein said nucleic acid molecule comprises a cDNA molecule.

5. The isolated nucleic acid molecule of claim 4, wherein said cDNA further comprises nucleotides 1–1702 of SEQ ID NO:1.

6. The isolated nucleic acid molecule of claim 1, wherein said nucleic acid molecule comprises a genomic DNA molecule.

7. The isolated nucleic acid molecule of claim 6, wherein said genomic nucleic acid molecule further comprises at least 20 introns and noncoding regions depicted in SEQ ID NO:3, SEQ ID NO:4, SEQ ID NO:5, from nucleotides 29727–45546 of SEQ ID NO:6 and SEQ ID NO:7.

8. The isolated nucleic acid molecule of claim 6, wherein said genomic nucleic acid molecule further comprises 11 SfiI sites and 50 XcmI sites.

9. A vector comprising the nucleic acid molecule of claim 1.

10. A host cell comprising the vector of claim 9.

11. An insolated nucleic acid molecule comprising a nucleic acid sequence encoding a variant of wild-type human aminopeptidase P, wherein said wild-type aminopeptidase P is (a) a member of "pita bread-fold" protein family; (b) has metal ligand binding sites at Asp450, Asp461, His520, Glu555 and Glu569, (c) contains five N-glycosylation sites; (d) contains five cysteine residues and (e) comprises the amino acid sequence 235–583 of SEQ ID NO:2, wherein said variant has altered properties as compared to said wild-type human aminopeptidase P, and wherein said variant comprises a substitution at an amino acid residue selected from the group consisting of N35, C36, N49, N65, C127, N278, N291, C294, C299, H430, D450, D461, H520F, C531S, E555Q and E569.

12. The nucleic acid molecule of claim 11, wherein said variant of human aminopeptidase P is selected from the group consisting of N35Q, C36S, N49Q, N65Q, C127S, N278Q, N291Q, C294S, C299S, H430F, D450N, D461 N, H520F, C531S, E555Q and E569Q.

13. A vector comprising the nucleic acid molecule of claim 11.

14. A host cell comprising the vector of claim 13.

15. A method for producing a human aminopeptidase P which is (i) a member of "pita bread-fold" protein family; (ii) has metal ligand binding sites at Asp450, Asp462, His520, Glu555 and Glu569, (iii) contains five N-glycosylation sites; (iv) contains five cysteine residues and (v) comprises the amino acid sequence 235–583 of SEQ ID NO:2, said method comprising (a) culturing the host cell of claim 10, under conditions that provide for the expression of said human aminopeptidase P and (b) recovering said expressed human aminopeptidase P.

16. A method for producing a variant of wild-type human aninopeptidase P, wherein said wild-type aninopeptidase P is (i) a member of "pita bread-fold" protein family; (ii) has metal ligand binding sites at Asp450, Asp461, His520, Glu555 and Glu569, (iii) contains five N-glycosylation sites; (iv) contains five cysteine residues and (v) comprises the amino acid sequence 235–583 of SEQ ID NO:2, wherein said variant has altered properties as compared to said wild-type human aminopeptidase P, and wherein said variant comprises a substitution at an amino acid residue selected from the group consisting of N35, C36, N49, N65, C127, N278, N291, C294, C299, H430, D450, D461, H520, C53 1, ESSS, and E569 (a) culturing the host cell of claim 14 under conditions that provide for the expression of said variant human aminopeptidase P and (b) recovering said expressed variant human aminopeptidase P.

17. A method of identifying patients with an aminopeptidase P deficiency comprising:

(a) determining the presence or absence of a mutation in the nucleic acid molecule of claim 1 and (b) diagnosing a pathological condition or a susceptibility to a pathological condition based on the presence or absence of said mutation.

18. A method for preventing, treating or ameliorating a medical condition, comprising administering to a subject an amount of the nucleic acid molecule of claim 1 effective to prevent, treat or ameliorate said medical condition.

* * * * *

SEQUENCE LISTING

<160> NUMBER OF SEQ ID NOS: 7

<210> SEQ ID NO 1
<211> LENGTH: 3428
<212> TYPE: DNA
<213> ORGANISM: Homo sapiens
<220> FEATURE:
<221> NAME/KEY: CDS
<222> LOCATION: (265)..(2283)

<400> SEQUENCE: 1

```
cacctatcc tacactacta ggaacttgca cagtccgcct cgggcagccc aaagctcctc    60
tgcccaccct ggctcccaaa accctccaaa acaaaagacc agaaaagcac tctccaccca   120
gcagccaaac gcctccttct tgacgccagc ccccaccctg tgtctgctcg agcccaggaa   180
aggcctgaag gaacaggccg gggaaggagc cctccctctc tcccttgtcc ctccatccac   240
ccagcgccgg catctggaga ccct atg gcc cgg gct cac tgg ggc tgc tgc      291
                          Met Ala Arg Ala His Trp Gly Cys Cys
                           1               5 ccc tgg ctg gtc ctc ctc tgt gct tgt gcc tgg ggc cac aca aag cca     339
Pro Trp Leu Val Leu Leu Cys Ala Cys Ala Trp Gly His Thr Lys Pro
 10              15                  20                  25 ctg gac ctt gga ggg cag gat gtg aga aat tgt tcc acc aac ccc cct     387
Leu Asp Leu Gly Gly Gln Asp Val Arg Asn Cys Ser Thr Asn Pro Pro
                 30                  35                  40 tac ctt cca gtt act gtg gtc aat acc aca atg tca ctc aca gcc ctc     435
Tyr Leu Pro Val Thr Val Val Asn Thr Thr Met Ser Leu Thr Ala Leu
             45                  50                  55 cgc cag cag atg cag acc cag aat ctc tca gcc tac atc atc cca ggc     483
Arg Gln Gln Met Gln Thr Gln Asn Leu Ser Ala Tyr Ile Ile Pro Gly
         60                  65                  70 aca gat gct cac atg aac gag tac atc ggc caa cat gac gag agg cgt     531
Thr Asp Ala His Met Asn Glu Tyr Ile Gly Gln His Asp Glu Arg Arg
     75                  80                  85 gcg tgg att aca ggc ttt aca ggg tct gca gga act gca gtg gtg act     579
Ala Trp Ile Thr Gly Phe Thr Gly Ser Ala Gly Thr Ala Val Val Thr
 90                  95                 100                 105 atg aag aaa gca gct gtc tgg acc gac agt cgc tac tgg act cag gct     627
Met Lys Lys Ala Ala Val Trp Thr Asp Ser Arg Tyr Trp Thr Gln Ala
                110                 115                 120 gag cgg caa atg gac tgt aat tgg gag ctc cat aag gaa gtt ggc acc     675
Glu Arg Gln Met Asp Cys Asn Trp Glu Leu His Lys Glu Val Gly Thr
            125                 130                 135 act cct att gtc acc tgg ctc ctc acc gag att ccc gct gga ggg cgt     723
Thr Pro Ile Val Thr Trp Leu Leu Thr Glu Ile Pro Ala Gly Gly Arg
        140                 145                 150 gtg ggt ttt gac ccc ttc ctc ttg tcc att gac acc tgg gag agt tat     771
Val Gly Phe Asp Pro Phe Leu Leu Ser Ile Asp Thr Trp Glu Ser Tyr
    155                 160                 165 gat ctg gcc ctc caa ggc tct aac aga cag ctg gtg tcc atc aca acc     819
Asp Leu Ala Leu Gln Gly Ser Asn Arg Gln Leu Val Ser Ile Thr Thr
170                 175                 180                 185 aat ctt gtg gac ctg gta tgg gga tca gag agg cca ccg gtt cca aat     867
Asn Leu Val Asp Leu Val Trp Gly Ser Glu Arg Pro Pro Val Pro Asn
                190                 195                 200 caa ccc att tat gcc ctg cag gag gca ttc aca ggg agc act tgg cag     915
Gln Pro Ile Tyr Ala Leu Gln Glu Ala Phe Thr Gly Ser Thr Trp Gln
            205                 210                 215 gag aaa gta tct ggc gtc cga agc cag atg cag aag cat caa aag gtc     963
Glu Lys Val Ser Gly Val Arg Ser Gln Met Gln Lys His Gln Lys Val
        220                 225                 230 ccg act gcc gtc ctt ctg tcg gcg ctt gag gag acg gcc tgg ctc ttc    1011
Pro Thr Ala Val Leu Leu Ser Ala Leu Glu Glu Thr Ala Trp Leu Phe
    235                 240                 245 aac ctt cga gcc agt gac atc ccc tat aac ccc ttc ttc tat tcc tac    1059
Asn Leu Arg Ala Ser Asp Ile Pro Tyr Asn Pro Phe Phe Tyr Ser Tyr
250                 255                 260                 265 acg ctg ctc aca gac tct tct att agg ttg ttt gca aac aag agt cgc    1107
Thr Leu Leu Thr Asp Ser Ser Ile Arg Leu Phe Ala Asn Lys Ser Arg
```

```
                   270                 275                 280
ttt agc tcc gaa acc ttg agc tat ctg aac tcc agt tgc aca ggc ccc     1155
Phe Ser Ser Glu Thr Leu Ser Tyr Leu Asn Ser Ser Cys Thr Gly Pro
            285                 290                 295 atg tgt gtg caa atc gag gat tac agc caa gtt cgt gac agc atc cag     1203
Met Cys Val Gln Ile Glu Asp Tyr Ser Gln Val Arg Asp Ser Ile Gln
            300                 305                 310 gcc tac tca ttg gga gat gtg agg atc tgg att ggg acc agc tat acc     1251
Ala Tyr Ser Leu Gly Asp Val Arg Ile Trp Ile Gly Thr Ser Tyr Thr
            315                 320                 325 atg tat ggg atc tat gaa atg ata cca agg gag aaa ctc gtg aca gac     1299
Met Tyr Gly Ile Tyr Glu Met Ile Pro Arg Glu Lys Leu Val Thr Asp
330                 335                 340                 345 acc tac tcc cca gtg atg atg acc aag gca gtg aag aac agc aag gag     1347
Thr Tyr Ser Pro Val Met Met Thr Lys Ala Val Lys Asn Ser Lys Glu
                350                 355                 360 cag gcc ctc ctc aag gcc agc cac gtg cgg gac gct gtg gct gtg atc     1395
Gln Ala Leu Leu Lys Ala Ser His Val Arg Asp Ala Val Ala Val Ile
            365                 370                 375 cgg tac ttg gtc tgg ctg gag aag aac gtg ccc aaa ggc aca gtg gat     1443
Arg Tyr Leu Val Trp Leu Glu Lys Asn Val Pro Lys Gly Thr Val Asp
            380                 385                 390 gag ttt tcg ggg gca gag atc gtg gac aag ttc cga gga gaa gaa cag     1491
Glu Phe Ser Gly Ala Glu Ile Val Asp Lys Phe Arg Gly Glu Glu Gln
            395                 400                 405 ttc tcc tcc gga ccc agt ttt gaa acc atc tct gct agt ggt ttg aat     1539
Phe Ser Ser Gly Pro Ser Phe Glu Thr Ile Ser Ala Ser Gly Leu Asn
410                 415                 420                 425 gct gcc ctg gcc cac tac agc ccg acc aag gag ctg aac cgc aag ctg     1587
Ala Ala Leu Ala His Tyr Ser Pro Thr Lys Glu Leu Asn Arg Lys Leu
                430                 435                 440 tcc tca gat gag atg tac ctg ctg gac tct ggg ggg cag tac tgg gac     1635
Ser Ser Asp Glu Met Tyr Leu Leu Asp Ser Gly Gly Gln Tyr Trp Asp
            445                 450                 455 ggg acc aca gac atc acc aga aca gtc cac tgg ggc acc ccc tct gcc     1683
Gly Thr Thr Asp Ile Thr Arg Thr Val His Trp Gly Thr Pro Ser Ala
            460                 465                 470 ttt cag aag gag gca tat acc cgt gtg ctg ata gga aat att gac ctg     1731
Phe Gln Lys Glu Ala Tyr Thr Arg Val Leu Ile Gly Asn Ile Asp Leu
            475                 480                 485 tcc agg ctc atc ttt ccc gct gct aca tca ggg cga atg gtg gag gcc     1779
Ser Arg Leu Ile Phe Pro Ala Ala Thr Ser Gly Arg Met Val Glu Ala
490                 495                 500                 505 ttt gcc cgc aga gcc ttg tgg gat gct ggt ctc aat tat ggt cat ggg     1827
Phe Ala Arg Arg Ala Leu Trp Asp Ala Gly Leu Asn Tyr Gly His Gly
                510                 515                 520 aca ggc cac ggc att ggc aac ttc ctg tgt gtg cat gag tgg cca gtg     1875
Thr Gly His Gly Ile Gly Asn Phe Leu Cys Val His Glu Trp Pro Val
            525                 530                 535 gga ttc cag tcc aac aac atc gct atg gcc aag ggc atg ttc act tcc     1923
Gly Phe Gln Ser Asn Asn Ile Ala Met Ala Lys Gly Met Phe Thr Ser
            540                 545                 550 att gaa cct ggt tac tat aag gat gga gaa ttt ggg atc cgt ctc gaa     1971
Ile Glu Pro Gly Tyr Tyr Lys Asp Gly Glu Phe Gly Ile Arg Leu Glu
            555                 560                 565 gat gtg gct ctc gtg gta gaa gca aag acc aag tac cca ggg gag cta     2019
Asp Val Ala Leu Val Val Glu Ala Lys Thr Lys Tyr Pro Gly Glu Leu
570                 575                 580                 585 cct gac ctt gtg gta tca ttt gtg ccc tat gac cgg aac ctc atc gat     2067
```

```
            Pro Asp Leu Val Val Ser Phe Val Pro Tyr Asp Arg Asn Leu Ile Asp
                        590                 595                 600 gtc agc ctg ctg tct ccc gag cat ctc cag tac ctg aat cgc tac tac       2115
Val Ser Leu Leu Ser Pro Glu His Leu Gln Tyr Leu Asn Arg Tyr Tyr
            605                 610                 615 cag acc atc cgg gag aag gtg ggt cca gag ctg cag agg cgc cag cta       2163
Gln Thr Ile Arg Glu Lys Val Gly Pro Glu Leu Gln Arg Arg Gln Leu
        620                 625                 630 cta gag gag ttc gag tgg ctt caa cag cac aca gag ccc ctg gcc gcc       2211
Leu Glu Glu Phe Glu Trp Leu Gln Gln His Thr Glu Pro Leu Ala Ala
    635                 640                 645 agg gcc cca gac acc gcc tcc tgg gcc tct gtg tta gtg gtc tcc acc       2259
Arg Ala Pro Asp Thr Ala Ser Trp Ala Ser Val Leu Val Val Ser Thr
650                 655                 660                 665 ctt gcc atc ctt ggc tgg agt gtc tagaggctcc agactctcct gttaaccctc      2313
Leu Ala Ile Leu Gly Trp Ser Val
                670
```
catctagatg gggggctccc ttgcttagct cccctcaccc tgcactgaac ataccccaag    2373 agccctgct ggcccattgc ctagaaacct ttgcattcat cctccttctc caagacctat    2433
ggagaaggtc ccaggcccca ggaaacacag ggcttcttgg ccccagatgg cacctccctg    2493 cacccgggg ttgtatacca caccctgggc ccctaatccc aggccccgaa ataggaaagc    2553
cagctagtct cttctcttct gtgatctcag taggcctaac ctataaccta acacagactg    2613
ctacagctgc tcccctcccg ccaaacaaag ccccaagaaa acaatgcccc taccacccaa    2673
gggtgccatg gtcccgggaa acccaacct gtcaccgcgt gttgggcgta accagaactg    2733 ttcccccca ccagggctta aaaatcgccc cacttttta accatcgtcc attaccacc    2793 tggtgggcat agccagagct gttcgaaccc agccagggat gaaaaatcaa ccccccgacat    2853 ggaacccatg attcctaaac ccggggtagg ttccatgcca agtaacagca gagggagtta    2913
agccatagga atttggctgt ggagtaagag ggaatgcggt gaggcagtgt ggaatatgac    2973
cctaccagag gttggagaac aaacttgggc agccggaacc cgtcactatt ttagattcct    3033
ggcattcgag gagccctttg aactttccaa agtgcagcca cagctacaat gctgttaaat    3093
cctcccacat ttcttggatg ccccttcacc ttgtgtggac agtgtctggt ttccccattt    3153
tacagacagg aaaactgagc ttcagacagg gggtgggctt tgcctaagga cacacaaatt    3213
tggttgggag ttgatggggc cagatgagcc agcattccag ctgtttcacc cttcagcaac    3273
atgcagagtc cctgagccca cctcccagcc ctctcctcat tctctgaacc cactgtggtg    3333
agaagaattt gctccggcca aattggccgt tagccacctg ggtccacatc ctgctaagac    3393
gtttaaaaca gcctaacaaa gacacttgcc tgtgg    3428

<210> SEQ ID NO 2
<211> LENGTH: 673
<212> TYPE: PRT
<213> ORGANISM: Homo sapiens

<400> SEQUENCE: 2

Met Ala Arg Ala His Trp Gly Cys Cys Pro Trp Leu Val Leu Leu Cys
 1               5                  10                  15

Ala Cys Ala Trp Gly His Thr Lys Pro Leu Asp Leu Gly Gly Gln Asp
                20                  25                  30

Val Arg Asn Cys Ser Thr Asn Pro Pro Tyr Leu Pro Val Thr Val Val
            35                  40                  45

Asn Thr Thr Met Ser Leu Thr Ala Leu Arg Gln Gln Met Gln Thr Gln

```
              50                  55                  60
Asn Leu Ser Ala Tyr Ile Ile Pro Gly Thr Asp Ala His Met Asn Glu
 65                  70                  75                  80

Tyr Ile Gly Gln His Asp Glu Arg Arg Ala Trp Ile Thr Gly Phe Thr
                 85                  90                  95

Gly Ser Ala Gly Thr Ala Val Val Thr Met Lys Lys Ala Ala Val Trp
            100                 105                 110

Thr Asp Ser Arg Tyr Trp Thr Gln Ala Glu Arg Gln Met Asp Cys Asn
            115                 120                 125

Trp Glu Leu His Lys Glu Val Gly Thr Thr Pro Ile Val Thr Trp Leu
130                 135                 140

Leu Thr Glu Ile Pro Ala Gly Gly Arg Val Gly Phe Asp Pro Phe Leu
145                 150                 155                 160

Leu Ser Ile Asp Thr Trp Glu Ser Tyr Asp Leu Ala Leu Gln Gly Ser
                165                 170                 175

Asn Arg Gln Leu Val Ser Ile Thr Thr Asn Leu Val Asp Leu Val Trp
            180                 185                 190

Gly Ser Glu Arg Pro Pro Val Pro Asn Gln Pro Ile Tyr Ala Leu Gln
            195                 200                 205

Glu Ala Phe Thr Gly Ser Thr Trp Gln Glu Lys Val Ser Gly Val Arg
            210                 215                 220

Ser Gln Met Gln Lys His Gln Lys Val Pro Thr Ala Val Leu Leu Ser
225                 230                 235                 240

Ala Leu Glu Glu Thr Ala Trp Leu Phe Asn Leu Arg Ala Ser Asp Ile
                245                 250                 255

Pro Tyr Asn Pro Phe Phe Tyr Ser Tyr Thr Leu Leu Thr Asp Ser Ser
            260                 265                 270

Ile Arg Leu Phe Ala Asn Lys Ser Arg Phe Ser Ser Glu Thr Leu Ser
            275                 280                 285

Tyr Leu Asn Ser Ser Cys Thr Gly Pro Met Cys Val Gln Ile Glu Asp
            290                 295                 300

Tyr Ser Gln Val Arg Asp Ser Ile Gln Ala Tyr Ser Leu Gly Asp Val
305                 310                 315                 320

Arg Ile Trp Ile Gly Thr Ser Tyr Thr Met Tyr Gly Ile Tyr Glu Met
                325                 330                 335

Ile Pro Arg Glu Lys Leu Val Thr Asp Thr Tyr Ser Pro Val Met Met
            340                 345                 350

Thr Lys Ala Val Lys Asn Ser Lys Glu Gln Ala Leu Leu Lys Ala Ser
            355                 360                 365

His Val Arg Asp Ala Val Ala Val Ile Arg Tyr Leu Val Trp Leu Glu
            370                 375                 380

Lys Asn Val Pro Lys Gly Thr Val Asp Glu Phe Ser Gly Ala Glu Ile
385                 390                 395                 400

Val Asp Lys Phe Arg Gly Glu Gln Phe Ser Ser Gly Pro Ser Phe
                405                 410                 415

Glu Thr Ile Ser Ala Ser Gly Leu Asn Ala Ala Leu Ala His Tyr Ser
            420                 425                 430

Pro Thr Lys Glu Leu Asn Arg Lys Leu Ser Ser Asp Glu Met Tyr Leu
            435                 440                 445

Leu Asp Ser Gly Gly Gln Tyr Trp Asp Gly Thr Thr Asp Ile Thr Arg
            450                 455                 460

Thr Val His Trp Gly Thr Pro Ser Ala Phe Gln Lys Glu Ala Tyr Thr
465                 470                 475                 480
```

```
Arg Val Leu Ile Gly Asn Ile Asp Leu Ser Arg Leu Ile Phe Pro Ala
                485                 490                 495
Ala Thr Ser Gly Arg Met Val Glu Ala Phe Ala Arg Arg Ala Leu Trp
            500                 505                 510
Asp Ala Gly Leu Asn Tyr Gly His Gly Thr Gly His Gly Ile Gly Asn
            515                 520                 525
Phe Leu Cys Val His Glu Trp Pro Val Gly Phe Gln Ser Asn Asn Ile
        530                 535                 540
Ala Met Ala Lys Gly Met Phe Thr Ser Ile Glu Pro Gly Tyr Tyr Lys
545                 550                 555                 560
Asp Gly Glu Phe Gly Ile Arg Leu Glu Asp Val Ala Leu Val Val Glu
                565                 570                 575
Ala Lys Thr Lys Tyr Pro Gly Glu Leu Pro Asp Leu Val Val Ser Phe
            580                 585                 590
Val Pro Tyr Asp Arg Asn Leu Ile Asp Val Ser Leu Leu Ser Pro Glu
                595                 600                 605
His Leu Gln Tyr Leu Asn Arg Tyr Tyr Gln Thr Ile Arg Glu Lys Val
        610                 615                 620
Gly Pro Glu Leu Gln Arg Arg Gln Leu Leu Glu Glu Phe Glu Trp Leu
625                 630                 635                 640
Gln Gln His Thr Glu Pro Leu Ala Ala Arg Ala Pro Asp Thr Ala Ser
                645                 650                 655
Trp Ala Ser Val Leu Val Val Ser Thr Leu Ala Ile Leu Gly Trp Ser
            660                 665                 670
Val

<210> SEQ ID NO 3
<211> LENGTH: 50000
<212> TYPE: DNA
<213> ORGANISM: Homo sapiens

<400> SEQUENCE: 3
gattcctagg ctccagaaat tctgagtcag ttggtctgag aggaggcaca ggagtctgca      60
ttctaaatca ggacccaaga gcattttgat gcaggaccac actttgagaa taccacccta     120
aaggatctga cctctgccta ccataaccct tcctcacccc tgccaatata ctctgatact     180
gtccttttac tcctcccagt gagctgaact cttt ccagcc tcagggcctt tgcatgtgct     240
gtttacccag aaaactcctt cctctctctt tcttgcctca gtccccatct ttgctgtgcc     300
taaccctaag tcacccgccc tgtcccattg actctctgcc ctcattcctg ggcttcctgg     360
tatagcatgc tggctgactg cccctgggct tgccatgtac tcttccacaa tcttcctctt     420
cctctcttga tgacctcacg tacctgctcc acggggcctg gggaggcagg aagctatagt     480
ggttcttcac ataggctcta atgaccagac tgcctgagtt caaatcccag ctctgccact     540
tctagatgtg tgaccctgat caaaagttaa ttgacgtctc tgtgccttgg tttccatgtc     600
ttttctctcc agctttattg ggtataattg agaagacaaa ttgtacgtat tgaaggtgtt     660
tccacatctt aaaagtaatg atagcacctt tcctcatagt atcatcatga ggatgagatc     720
agatactaca tttccaggcc ttggaacagt gcctggtgcc taagtgctaa ataaatggca     780
gctagtgcaa ttattcccaa gccctccatg ggcctccagg cccagaaccc gcttctgctg     840
cccttcagct cccagcaagt gactgtaccc tttactttgt gaaaatgtca aaacagcctt     900
gccccctgca catcaaaatg tcttcagctt aacctcatcc ctcccccttt ccatctgtct     960
```

-continued

```
gagaataagc ggtcctcctc gccaagacca gctcttccac ctgcactttt gagcccttct    1020
cctccaccct ctctggactt ttccccatca accatcactc ctcctcctac atctcagtat    1080
gggttattca cttgacaagt atttgttgag tggctcctgt gcgccctgtg ctgttcaagg    1140
tgctggggat ctagaattaa accagacaag gttgccgctc tcatggtgcc ttcatcaaga    1200
gggcagggca gggatgaggg tggacagaca tgcaaattaa cagtacccaa ggtcactaca    1260
gatcctgaca agtactgtgg agagtatcaa acggggatgc actcgagggt acagcggggg    1320
gccttggtca ggaaaagttt atttgaggag gtgatgtttt agctgagact taaacctcag    1380
gaagccaaga caccgtatct tgatttgaat accccccaaaa agagccacac gtgcaagatc    1440
tggcaaaaga cattctgagc aaaggaaaag agaaatgcaa aggccctaag gcagcaaaac    1500
agctggctgt gctcagggga cagccaggca gaactctgtg agggacagga cttgctggac    1560
aactgatgag caggaacgtg atcacagagg gcctgaggaa ccccaggcag gagcttgcat    1620
ttcattcgac accacaggga gccatggctg gctttactca gggaagtgac gtgatgtgac    1680
ttctgtatgc tccttctcct aaccttagga agagtaataa ctaataactc tagctgtcat    1740
ttatcccaga tactaataca tttaacatca cttttgcctt tacgatagcc tgataaagta    1800
ctacattatc ccacttttttt ttttttttttt taagacggag tctagctctg tcacccaggc    1860
tggagtgcgg tagcataatc tcggctcact gcaacctcca cctcccgtgt tcaagctatt    1920
ctcctgcctc agcctcccga gtagctggga ttacaggcac gtgccaccac gcctggctaa    1980
gttttgtatt tttagtagtg acagggtttc accatcttgg ccaggctggt ctgaaactcc    2040
tgacctcgtg atccaccccgc cttggcctcc caaagtgctg ggattacagg tgtgagccac    2100
catgcccggc cattagccca cttttatagg tgagaaaact gaggctcaga gagacagcat    2160
aacttggtac tcggctagtg gctgaccaga aaatgacttc tgagcccaaa atttgtgctc    2220
ttaaacacag ccattgtctc cccagctgga gtgggcatga aggtgagggt gcttcttaaa    2280
acccctatcc cttctagcta catcccaaga tttcatgtca gctagattgc ctgctggcag    2340
gtcaaattca acttctcttt gaccttgacc agcttctcct ggcatcctcc tctctcccat    2400
cacccaggcc taagcttttg gttattttttg gcccctgccc cactttctaa tcagttacca    2460
attgcaattc aacaaatatt tatccagcac ctgccaagtg caggctacca tgcagggttc    2520
tgaaggaaac caaaatgggt gagactggtc gttacaagac aagacagaca taatattttt    2580
gtttgttttg tttatttga cacggagtct cactctgttg cccaggctgg agtgcagtgg    2640
cgcgatcttg gctcactgca acctgcacct cctgtgttca gcgattctc ctgtctcagc    2700 ctccctagta gctgggacta caggcgcgtg ccaccacacc cagctaattt atttgtattt    2760 ttattttttag tagagacggg ctttcaccat gttggccagg ctggtcttga actcctgatc    2820
tcaggtgatc agcctgcctt ggcctcccaa agtgttggga ttacaggtgt gagccactgc    2880
acctggccaa tatttttttta aagaaggaa aaaaggaaa gatggatgaa agaagggcag    2940
gaaggaagaa aagagggagg aagatgagaa aaagggaaga agcaagaaa gaagaaggag    3000 ggaggaagga aggacctcca cggaaaaggg gccgagatca gctcaaccgc agtctctagc    3060
tggcccctcc tttccactgc gcatttccca gcccctccaa ctcctgcccc accccccac    3120 caataaaatt caaacactca ttgcctcatg taaggagtta aatcgcctga tgtatttaac    3180
tcctttctaa ctaatttctc agttgccagt ttctctccct gtacacatca ctgcactgtt    3240
ttgatgtctc tcccctattc cagacccctg ctggccccc agcccacttg ccacagaagt    3300
tccaatcctt ctgcctggca tgcaaagctc tccttagtct cttccaccca cctctcaggc    3360
```

-continued

```
tgagtctccc actcgacctt ctcatgccgt tcccttccct aaactcatgc gcactctctg     3420
ctttggctcg gtggtctgta ccagccacct ggaaccctcc agcccccacc tctccacctg     3480
cccaaacccc atcaaaccca aatgtcacct cttccaggaa gccttttccc acaaccctg      3540 cccaccaccc ccctccccg aactcctaga acctgccctc tgtaccacta ttttaacaca     3600
ctacatacca aaggatgttg ttgccccttt gggactggaa gcttcaggag agtgggaacc     3660
aagctgggcg tattttagtt tccccacaat gccttgcaga gagtaagtgt tcaatgatgt     3720
ttggctaata aataaagatt gtctgttaaa gcataagtgt atccaataag tgttcctgaa     3780
atgtatatac atttaattat tcattctgag ctctattaac tttagaggag ttcatgtggt     3840 aggggggac ttactgaatt atattaatgt aatccaagaa gataatagtt tttagcaacc      3900
acacagtact gttatttct attgttttgt aggcaacaaa atcagccttg ttaaatttgc      3960
tttttaaaat tgattctcaa agtttattaa aaaattagaa ctagaactac catatggttc     4020
agcaatccca cttctagaga tatatccaaa agaattgaaa gcagggtctc aaagctatat     4080
ttgcacaccc atgttcctag cagcattatt cacaatagcc aaaagatgga agcaccccaa     4140
atgtccatgg atagaaaaac aaaatgtgtt agttctctac atacaatgga atatgattca     4200
gccttaaaaa ggaaggaatt ctgacacatg ctgctacatg gatcaacctt gaggacatta     4260
tgctaaacga aataagccag tcccaaaaag cactgtatga ttctacttct atgaggtccc     4320
tagaatagtc aaatccatag agaaaagaag catggtgtta ccaggggctg gggattgggg     4380
aaatgggcag ttgtttgatg ggtatacagt ttcagctttg caagatgaaa atgttctgga     4440
gattcattgc atagcaatgt gaatactcct aacactattg aactctacac ttaaatatgg     4500
ctaagatgat caatttttatg ttttgtgctt ttttttttt tttgagtcta gctctgccac     4560
ccaggctgga gtgcagtggc gcgatcttgg ctcactacaa cctccgcctc ccaggttcaa     4620
gcgattctcc tgcctcagcc tcccgagtag ctgggattac aggcacccgc caccatgccc     4680
agctaatttt tgtatttta gtagagacag gatttcactg tgttggccag gctggtctca     4740
aactcctgac ctcgtgatct gccctcagcc tcccaaagtg ctgggattac aagcatgagc     4800
caccgtgcct ggcccctgtt ttgtgctttt taccatgatt aacatttttt ttttatctta     4860
agtgattttc caaaggcaag tctgatcaca tcaccctct ctgggtccca gaattcttac      4920
ctggacccac aagccttggc ttgtctgctt gtcatggact caagcctcct cccacatcct     4980
gccatccccc attctttcag atgagatgag gcacattcac ggtggtatgg ccgtagaccc     5040
atcccccatt ttttcagact ggacttctgt ccttgtctgc tccttgctcc ctctcaccac     5100
agagccaact cctcccaagg cctcagtctc tgcgaaaaca cactttctc tgaggagctt      5160 tccctggcca cctcctagcc taggctgtaa catgtccttg tgacacgctc tccttgcacc     5220
ctttcctctc cttcactttg taattacaca tttattattt gatcaaggtc actctctccc     5280
accagctcag gaacgctgct gaggcagaga ccacatcttt tcctcccctt actatcatat     5340
ctccagcagc tagcctgatg cctggcatcc agtaatcttc atcattgatt attccagtgt     5400
tggcaaaggc aaggaaaaac aagcccgcct gctgcttgga caagagtaaa taagtgtcac     5460
ctttctaaaa gcaatgtggc aacatgcatt aagagcctgg aagcattcac actcgtaatt     5520
tcacttctag gaaatcaccc tagaggagcg caatggcgta agtccacccc tgttcatctc     5580
aacatactca ttagcacaaa aaacaaagca atttacataa ccttcatcac cagaagaagg     5640
gtaaacacat tgtagatgtt tatggatata ttatggcgcc ttttcaaata atgttttga     5700
```

-continued

```
ggaattgtga tgtggaaaaa tgttaggata taacatgagg tggaaaaggc agcatataag     5760
taggtatgta cctaatgttc ctaaatttaa aatatcagat ataaagataa tacataggca     5820
caaaaatagt ggaagtccat tctccaaact gttaatagca gtcaccccta gagggtggca     5880
tcatgggcag tcgtggcttc agaatgtcta cataggaggg tttagaaacc atcgaaaggt     5940
aggctagggg attcgtcttg aagctgcaag atggcctttg cttagcaagc agggttttgc     6000
cttacactgc atctatattc agagtcacta tggggtgct gatggagatt aggataaagc      6060
ccccaagcca ctctctggag ccaatctcaa ttttttttt tttttactct tatttatatg      6120
tctggttttc taaatgctct acaatgaaga tgtatgactt ttataatcag aaaaagatta     6180
aggaaaacat tatttcatga agaaaggca cttctgtgtg ttgggatgaa tgaacacagt      6240
gtcctgctca agcacatagg cggctggaca gggccttgcc agcacagtcg ctcaccgcag     6300
ctccctcaca tcacaagcct gccctctccc tcgcacccgc aggcatctgt cctccagctg     6360
ctgacacagc tgggcagcaa aggtcccatc ttgactgtgc acctcggagg cagcaccgtg     6420
gagcatggag ttctaaggca tgtccacggg ccaagcacac ttgtaaaggc catttgacaa     6480
caatgggcta taccctcta cctctaacgg tggccctggc tttgaagagc aaggatcgtt      6540
ttctgattgt agctgtggcc actagatggc agaggagaat gacggtttcc agttgtataa     6600
taaaattggt atttaaagct gcagttactt ttcttatttc atgatcattt ctattttggg     6660
aaattcggtt gacttttctc cttacagtct cttacttatg gccttaaaag tccacaaaaa     6720
caaaaacttt ttttttcag aactaggtta aagtatcta aagttcatgg aagtttcagc       6780
actcttcatt gaacacaggt agaattaaat cacattttcc tctcttgcct ctttcactgt     6840
ccatcaatgt ttcaagttat tttgaaagtg tcaacaatgg ttgggaggtg atctcactgc     6900
tgaaaggtaa tgacttcgat cttctctgga gaggggtcag ctgggaagga acgatggaat    6960
caatcgaggc agttggagag gcggggagaa acacagttgt gacctgggaa gaaacagact    7020
aatccctggc cagaagatgg cacagcaaag tggagaggaa ggagaccaaa agggaatggg    7080
gcttgttaca ggttcagttg tatccccca aaatcgatat gttgaagtcc taatccccag     7140
tacctgtgaa tgtgacctta tttggaaata gactcgtcac agatataatt agttaagtaa     7200
gatgaggtta tactggagt agggtgggcc ctaatctaat ataactggtt tccttataaa     7260
aaagggaaat ttggacagag acacacacac agggagaaca ctgtgtaaag gcaaaggcag    7320
ggatcagggt gatgcatctc taagccaaag aatgccaaaa attgccagca aaccatcaga    7380
agctcaggat gggcatgaga cagattctct ttcacagccc tcagaaggaa ccaaccctgc    7440
tgacctcgat ttcacactct ggcctccaga tctgtgagac aacatgtttc taagcctccc    7500
actgtggtac tttgttactg cagccctggg aaactaatac aaggattttg gagccatgga    7560
atagtggtaa aatcgtaata gaatttcttc actcacttct aggactgttg gacctgatac    7620
gtgggggtga tggctgaagg atagaagttt cctcctctac cattctatca tcccctccac    7680
aatcacattt ctcatttctt ttctttttt tttttttctc tctttttttt tttttgagac    7740
agaatttcgc tcctgttgcc caggctggag tgcagtggcg cgatctcggc tcactgcaac    7800
ctctgcctcc caggttcaag tgattctcct gcctcagcct cccttagtagc tgggattaca    7860 ggcacatgcc accacgcccg actaattttt catattttta gtagagacag ggtttcacca    7920
tgttggtcag ctggtctcga actcctgacg tcaggtgatc cacccacctc ggcttcccaa    7980
agtgctgaga ttacaggtat gagccacatt tcttgaacga gttgtctcca cttgttgtcc    8040
ccactttctt acctccactc ccccctcaac cctttctagc ccattcctct gacatgattc    8100
```

-continued

```
tcaccaaggt caccagcaac ctccatgctg ccaaaaccaa aggtcgtttc tcagtcctca    8160
cctaacccaa cctctcagca gcattccacc ccttcttcag gaacactccc ttcaccgggg    8220
tgcaggaact ccacactctt cccagagttc ctgctgcctc accaaccact ccatctccat    8280
ctccattgca ggctcctcta ctttcttggc cccgccacta gatgatgcca tgtgctgagg    8340
tttaggcttg ggtcacttct cttcttactc tatactctct ctctcgctcc ataaacccca    8400
ctcactcctc tgtctgcagc tgtctccaaa ctctatctga agcagtctgt tgctgccacc    8460
atacacttca gacttgttta cagtggcatt acatcctatt caggtttaca tcctttttt    8520 tttttttttt tttttgagac agagtctcga tctgtcaccc aggctggagt gcagctgcat    8580
gatctcagct cactgcaacc tccacctccc gggttcaagc gattcccctg cctcagcctc    8640
ccgagtagct gggattacag gcgtgcgcca ccacgcttgg ctaattttg tatttttaat    8700 agagatgggg tttcaccatg ttggtcaggc tggtctcgaa ctcctgacct tgtgatctgc    8760
ccgtcttggc ctcccaaagt gctgggatta caggcgtgag ccactgcgcc tggccaacca    8820
tgctcatttg tttatatatt gtctatactt gctttgggc tgcaacagca gagttgagtg    8880
gttgctacag agactgtatg gtctgcagag tctaaaatac ttactatctg acctttaca    8940 gaaagtttgc caaactttga tctagaccaa gcttgtccaa ccagtggccc gtgggctgca    9000
tgcgacccag gacagctttg caggcagccc aacacaaatt cataaaattt cttaaaacat    9060
tatgagatgt ttttgtgatt tgattttttc tttcttttt tttctttagc ttttcagcta    9120
tcgttagtgt attttatgtg tggcccaggg aagccaaaag attggacagc cctgatctac    9180
actgtggtct cagccttcac cactgaaggc ttggggtccc ttaacatagt cagacagcca    9240
gatgggaagg gctccctggc agaacctccc acggcctgcg cactgggaag aatgcgaagt    9300
ggggtggagc cacataagtt cctgtcattt gcagccggga ggcgccaggc ccctcctctt    9360
cctgggtgga acctgagatt cagcaagcgg agacaactct ttcaagaaat gtggctcacg    9420
gccgtgatcc cagcactttg ggaggctgag gcgggtggat cacctgaggt caggagttcg    9480
agaccagact ggccaacatg gtgaaacccc gtctctacta aaatacaaa aaattagccg    9540 ggcgtggtgg cgtgcacctg taatccagct actcctcagg ggatatagta aagactaatg    9600
accaaaactc gagagaaagg aggggcttg ccattcctag ggcatggctc accatctgct    9660
gccagaggac attggaagtc aaagggaggc accagcagtg ggtcagtgac agcttcagcc    9720
tctgcactac atcctgaggt gtccccagtc ctcatagcac atgcctgcag tctgaagaca    9780
agagagggag ctgagtttcc tgagccaggc tcctgttcag tcaccccaga ccagcttcaa    9840
gctctggccc acaaagtcat ctggggtctg ttgtctctc agctcccctc cttgggacat    9900
ggatcctcac ctcttgccat acacaggctc cagtgtggaa gggatacagg atggggcatt    9960
tgggggttct ttctgactgg ctgtgacccc agagagggag gtgtcatgct ggagagttgg    10020
acagccaccc tctatggcga ccagccctac cacccggcct ggaaacatgc ccactgtggg    10080
gaacccaatt gtgagattcc cctctgcctc accccagttt ctgggcgga gatgtccaca    10140 ggcaagtgtg ggcgggtcct ctggcacatt aagctttatc tgtaggctgg tacctatgaa    10200
atctggaagg ctgggatttt cggaatctct gacccattca acctggagca tcttgctgag    10260
tcccaccaag aatggagacc tcagggccta gttgtttgat ttgcgaaatg tcatttttagg    10320 ccacctcctt accagcgggt ccactgcaca aatgtcttgc tcagatcctt aagagctgag    10380
gagtgccaac agcactcctg acggatgggt ggccagcagc agaggcagga gccctgtgcc    10440
```

```
ctgccagggg agaatcagga atgaaaagct ttcccagtgc tggctgggcg cggtggttta    10500
cgcctgtaat cccagcactt tgggaggccg agctgggtgg attatgaggt caggagatca    10560
agaccatcct ggctaacatg gtgaaacgct gtctctacta aaatacaaa aaattacctg     10620
ggcgtggtgg cacgcgccta tagtcccagc tagttgggag gctgaggcag aagaatcgct    10680
tgaacccagg aggcaaaggt tgcagtgagc ccagatcgtg ccactgcact ccagcctggg    10740
tgacagagcg agactctgtc taaaacaaac aaacaaacaa aaacaactt tcccagtgct     10800
tacaaatcca tcttccatct cacctcggcc tgcagtgtgc tgtgtgacca ctaagaggca    10860
ctgtgaggtc acaagaagct tggagaagcg cggccaccat ttcagtccca gcctccggga    10920
agtgagaaaa ccctagggaa aaggtgcagg attctgggac tctttgggac atccctccct    10980
ggcagaaagg atctattcta gtcagcagtg gggacctggg ctgggcacct catgctggcc    11040
gttgcgaagg gtggtgcaaa gaggaaaaga acagagacct aaaggggccc taattcatcc    11100
caggcaccgg ccactggcag atgactggcc caaacaagcc cggagggcca cactgcagaa    11160
ccaagcagga ggcggagccg agcagggaag gcgggaccct ggaggacgtc ttggctcctg    11220
gcttcgcggg ttctttggga tgttttagga aggactcttg acctccagat gtgtggtggt    11280
tggaggtatg ggatgcagtg gaggacccaa cacggaacaa acgggagact gggtgttgtt    11340
ttgacacctc cctttcatgt tctcacgtcc atgtcatcgc caagttcttt catttctacc    11400
tcctgaatat ccctggaatt tttcccctttt gacccaaatc tgctccctcc accccttgtct   11460
aagccaccat catctctcct tgatgtctcc aagatacggt tgccgcataa aatacaggac    11520
acccagttaa atttgaattt cacataaaca cagaataatt tttagtacat cttgtacaat    11580
acttgggatg tacttatact aaaaaaccat tgtctattat ctgaaattcc catttaactg    11640
ggtatccggg gtttggtttt gtttcactct tttgttttgt ttctaaatct ggcaactcga    11700
ccaagagttt tccagcccct gtgcctcttc aaggctttct ctacagagca gccagaatga    11760
acatacagaa attcaaatct acccaggtca ctgccttgct taaaaccctg accacctccc    11820
agctctcaac tccatcttcc actgtttccc taagcccaca gcatgccccc agcaaaccaa    11880
atacactgtt gcctcttaaa tgtgccccac atccttctac acactcccat ccctgtccag    11940
ccacctaaag aattcaaaca tggttatcaa actcaactac caccccttt tgtcaggctc     12000
ttccagacat gtcgcctgcc tcccccaagc caagcacgcc ctctttgcac tgtatagtag    12060
cctttttgtag agcacttgtt tagctgtatc taaatgattt gtttaggtgt ctgacttccc    12120
ccactagact gtgtcctcct tcaaggaagg ggcccagtgt tattcatctt tgcaaccaca    12180
gtgcacagca cagtgcgtgg cccagagtgg ggcattcaat gaaggaagga agaaggaag     12240
gaagtaagga aggaaggaag gaaggaagga aggaaggaag gaaggaagga aggaaggaag    12300
gaaaattcgt gattccaaat ctgaagccta gatgggccac tggaagtgac tgcaatgaca    12360
gtacaggaca ccaggggca gaataacctc agttttcttt aagggagagg ggcgtggtac     12420
agaaagccga cttcttggct ctgggcttcc ttctccagtt ccaaagagaa gagttttatt    12480
gttttgtttt gttttttaaat cacggaaaca taaaacaaga atggaccta agagaccatg     12540
ggaaccagtc ctctgctttt tcgtagttaa aaaattcttt gcatttccac ttaactatct    12600
gttttcaggt ggtgaaaaac atcctttggt ttgttacaga caaatcacag agaggttaga    12660
ggacttgctc caaattaccc agcaagtgag cagtacaagg aggcctggag cccagtgttc    12720
tgcagacatg atcccatttc atcctcactg cagccccatg agcgaggcac tattgttgtc    12780
ttacaggtgg ggaacataga gaggttgtca tctgactgga tcacaccgtg gtagagcagg    12840
```

```
gagttggatg aatgcaggca ggtctccaat cttcctttct agtgtccctg cctctcttac   12900
actctcaaat ctttgcttgg ctcttttttt tttttttttt tttgacagag tctcactctg   12960
tcgcccaggc tggagtgcag tggcgccatc tcggctcact gcaaactctg cctcccgggt   13020
tcaagtgatt ctcctgcctc agcctcccta tagctggga ctacaggcgc gtgccaccac    13080
acccagctaa ttgcttggct tttttggggg ggttgggggg tgggtgctaa ccccagatcc   13140
ctacatcctc agcactcaag cccagaacgt cttcatggga ctgacagctt ctgtgaatcc   13200
cgtggggaac cactgggcat cgacccaggc cctgtgacag ctacaaatag gtaagacaaa   13260
tgagggtatc tgggatgcag actctaggga ggcattcctt caagggcagg ggtatgcctg   13320
agagtgagcc cctcctgaca ctgtgtgccc cagggtcctc acttgcctcc ctctaacctt   13380
ggccctgggt gcagtatttg aacagaaacc ctgttctcct ttcctccaac tgctaggcca   13440
gtctaactat ggagaggtct caaggaggca ggagccactt gagctctttg aggaaggtga   13500
gatggatggc aagtgaccac cagagactgt gttccgccct gtataactgc ttcattgtag   13560
agcctcaact caatagggta caaacacaca atgcttttct ctttccacag tcatgaacca   13620
tcttggcagg gttctggagg cttccccact tcagagttcc ctgacatggg agaagctatt   13680
tggccactac ttcttccaac caacccaatc cctacccaca cctatgcaca cctgtccc    13740 cagcagtatc tacaaagacc tttgttgttg aggtcccctt gccctgaagc cagtcctctt   13800
gaacaggaca aggtaagaca actcaaatgt gtgaccttttg gaggtgtccc tctgacctga   13860
ggaaagcgca catggctggc tacaccactg ccgcctctgc tctttgccct ctctccactc   13920
ccctttagtt gttctcatag gctcagggca gagtcacaag gctgccaccc aagcagatgt   13980
ccaaccagga atgagataac atgtcccact tcacagcctg accccctatg ccgtcccaat   14040
cttgatggca ttctcttgga acccctcact tggccacaac actgggccaa agtctcctga   14100
tcatcccagt ggtgccccac cactactttc tgcttatcta gacggggtgg gagcagtaga  14160
acctgtttgc taagctctta ataagccctg aaggaagcat tggtccccta tcattggaag   14220
ttccttggca cttctttctt ggaactagtc ctcagctttg ggcccttgtt gccagttctc   14280
aggtctatag aagtcccact cacatcctgt tgaatgtcaa ttgcataatt ttgtatccct   14340
gtgttccaac tcctgaggac tggagggaaa atgagtgtcc cctcttcacc tcagctattt   14400
tacattggat ggaaatgggg catagagtac caaggtgcca agaatggagg aaaggataag   14460
ctgggagcca ttctcaagta aaagggacct tggagtagtg gaaagagtaa ctcattgtca   14520
ctcactggat gcatgccttg tgcaagtcac ggaactccct gagattcagt ttcttcatct   14580
gtaaactgca gataacacaa atgtcccagg aatgtagtaa agattagatg agatcatgta   14640
tgtagaagcc ttatataaac tgtaaagcac tgatcaaagg agtgaagcta attattaatt   14700
agttttaaag aagccatccc taccatcaaa gatcttgcag ggattgggta gcaattcata   14760
agagattatg acagagggct gagctgtggg aggcagtaga gagcagttgt taagagcagg   14820
gaccttggtt tctagctctg gcacatccta gctgtgtgac tttgaataag tcactgcccc   14880
tctctgaacc tcagtttcct cagatgtaaa gtaaggatga taacacctcc ctcaggacct   14940
gggaggatcg gatgaaatgg tacacaagaa gaatgagcta gcacagggct taatacatag   15000
tggtgcccaa taaatgttgg ctgtagctag ggttattaag agatcagcag ccattacaaa   15060
gggaaggagg ggtcagggaa aatctcctat gggagattag gcttgaattt ggccttgaaa   15120
acaggagaca aatttggaat gtcagaaaaa gttgcatata agtaagtctt gccaagcact   15180
```

-continued

```
gggggaacaa aaaagtaagg ccccaaagtt tacttccatc ctctctccta gatggtctga    15240
aaagatggtc atgcaggtgg cctggcccaa gaggggcatg ccagtgagaa gccataggga    15300
aactgacata gtgacatggc cctcctactc ctgctgaaat tcaaacctct tcacaggcag    15360
tcgagggaga actctgggcc aagctgtgcg gtctacctcc tactttgtga cccagggtgg    15420
ccctgaggcc ctgggcctgt ccctctagcc ctcccctgat aaatcagtcc ctaacatgtg    15480
cctcttggtt gtcagtggat aaatgcatga ctccttccag ggaactggtg tgcatttcag    15540
tgggggcttt ctagaaacaa taccttacct cccagagttt cccaagagca gctggagctc    15600
ttgtttcttt acttgaaacc tcagtggatt cctccagcag tttaaatctt catcgtttgc    15660
tgaatcccag gacccaggaa gcacagtttg cacctgtctt aatacccagg actcactggg    15720
gccaccttca gccttggaga caagatgggc cagagggaga acagctggtg gcccacatct    15780
gcttttgctt ttgtttggac aaagatgatg tgccatgtcc ttttctctgt cactgtgcat    15840
tggtcagaat atgtggagtt atgctgcaat aacacagaaa ccctgaaatc tcaggggttt    15900
aacacaagaa aggcttattt ctggttctca caaaagtcta gtgcaggttg gatgacacgt    15960
agtaaggcca acctgaaaca tgtggcctcc tagaactcca cagcaggggg aaagacagat    16020
ggagaagtaa atagtcttag tcagcatggg ctgtcataac aaactagcat agactgggta    16080
gcttaaagaa gaggaattca tttctcacag ttccacagct ggaaagccca cagtcaagac    16140
actggcagat tcagtgtcag gtaagggcac tctttctggc ttgcagatgg ctgacttctc    16200
gctgtgtctt cccatggctg agagagagct agctctctgg tatctcctct tacgaaggca    16260
ctaatcctat tggatcaggg ccccatactc atttaaccttt aattacttcc taacaccaaa    16320
tacagccaca ctggcggtct agtgtttcaa tatatggata agggggacac aattcagccc    16380
ataacagcac accaactctt aactgtcttg gcccagaaat gatgcacatt aagttcactg    16440
actctcttgg tcagaattag tcacgtggcc caagcttaat tgcaagaaag gctgagaaat    16500 gtagggagc aaatatttgc tgagcgcaat ctgtgccaca cactgtcttc taggctgagc    16560
cttgaggaag aaggaaagtc tcgaaagtca gaacagtggc tcggatgtaa agtgtaagga    16620
aacacacacc tgggactgtc tgccaggcag gttcaaggaa ccaagaccag gaacctggtt    16680
ctgaatagaa ttcttggggg aagagggggg aggaggggaac ttgtccctgt gtttggtata    16740
tttcgaggtt tactatgtct tctgcccagg atgtgaacac aaatccttca tcacagatat    16800
atcaatagac actcaggaaa ttcagatgaa ttaggcagag atcagagttt ttattctgtt    16860
tttaaaaatc aacatattga atgtttcccc caaaactacg tgttttattt tatttattta    16920
tttattttga gacagagtct cactctgtca cccaggctgg agcacagtgg cgcaatctcg    16980
gctcactgca agctccgcct cccgggttca cgccattctc ctgcctcagc ctctcaagta    17040
gctgggacta caggcgcccg ccaccatgcc ctgctaattt tatgtatttt tagtagagac    17100
ggggtttcac cgtgttagcc aggatggtct caatctcctg accttgtgat ccgcccgcct    17160
cagcatccca aaatgctggg attacaggcg tgagccactg tgcccggcca acgtgttttt    17220
tttttttttt aacaatcatt ttccactaca tagcaatagg aagagggtta acacaattat    17280
gtcaaatagg aatcttcagg agcgagcttt agtgaataga taagcctgat atgcaagcag    17340
cacagccatg gttgatttct aacttgctgg tgggtctgtt tttttaaaca gaagatcctg    17400
ggttcctttg gtgggtactg ggaggcagtg tatcaaaccc actgtctcat agcccaaccg    17460
ctatatgaac tagttcaaag cttgaattgg tgaagtccaa aaaagagaag ctttgctttt    17520
ccaacatgtt cagaactgtg atgggaaaat ggttgactaa gtgccacatc tttcctctgc    17580
```

```
tcgaatagaa tgtagatcat tgagccatgt gtagtgacaa ggtgtttttg ggaaaggtct   17640
caatgctatg aattgttatt gtgctcatga ccctcccttca agatggcgta aacgccctgg   17700
catgatcagc ccacacctgc ctctttaacc ttatctctct gcctaatccc atagggacac   17760
cagcctccat tctggtccaa gaggcccaa gtcctttgct gccctggggc ttttgtgctg    17820
gctgttctct ctgcctggaa tgttcttcct ccagattttt gtgggctgct tccttttcat   17880
ctttcaggct cagctcaaaa gccactagct catagaggtc tgacaaccca tataaagtca   17940
aagtatctcc cctggtaccc cagaaacaca tatactgttt gtcatcaccc agtttatttc   18000
tttgttaata aatatcacag tcatcccta tcttgttcat caattactta cttctgaatg     18060
tcttcggaga aatttcttag ggctgagcct actagactgt gagtttccca agggaaaata   18120
gggactgagg tctctatagc ctttgtctcc tgcaaggtag ggaagaggca gtgatgactc   18180
atgtttaaga atacttgagt tctggctggg catggtggct catgcctgta atcccagcac   18240
tttgggaggc cgaggcaggt ggattgcttg aggtcaggag ttcaagacca gcctggccaa   18300
cacggtgaaa tcttgtctct actaaaaata caaaaattag ccaggcatgg tggcgggcgc   18360
ctgtaatccc agctacatgg gaggctgagg caggagaatt gcttgaacct ggaaggcaga   18420
ggttgcagtg agccaagatc ataccactgc aatccagcct gggtggcaga gcaagactcc   18480
atctcaaaaa aagaaatac ttgagtccta aagtagtagt agagttatca aattcccagg     18540
tgaaagacac tcctgaggtt tcattgagca cctactgtgt ataagtttag catccactat   18600
gttctagggc tctaggctgg catggtcctt gcctgcctcc atggaacttg cagttccaat   18660
ggaaaaagca taaatcaagc aattactact tttaattatc atcatttaat aataatgtac   18720
tgatagtagt agcaatggct aactcatatt atgcttatgt gttttgtgct gggcacaggg   18780
aggggggtta tagatcctct ctgaagacac acagtgtcca gcacaaaaca agacaaataa   18840
taagagacat ttatatagtg cttattatgt accatgcatt gttccaaaca ctttgcatct   18900
attaactcat ttaattctca cagtggccct atgaggtagg taccattatt attcctagtt    18960
ttacagatga ggacattgag gctcagagag gtcaaacagg ttgctcaagg ccacacagcc   19020
agtgagggtg aaatgagcta ttattagtca ctacctggga attcccctgt ttttgttgtg   19080
gttgttgttg atctgggttg cttaggaagt gctacatcaa ttcctacagc attttagatc   19140
ctgtctgctg atagttgtgg taaacaaaca ataccctatt agatgctgct gattttctc    19200 attgattttg tatatgattt aatagttttg aatctcagtc agaagtgaag attacctgtc   19260
agacactatg ctcactacct gggtgacagg atcatttgta caccaaacct gagtggcatg   19320
tgatttaccc atgtaacaaa cctgcacatg tactcccgaa cctaaaataa aagttgagag   19380 gaaaacaag aaaaaaaaag agagtgaaga tttcaaaaag tcatcttggc agggaagtca   19440
tgttgacaag aattttcttt gttctatgtt aggatctcgc gctacccagt ttaatgaatt   19500
ctatgtagaa atgttcccaa acaccgtgtg cttccctcaa ggaatggctg aaaatgcagt   19560
agaatgtaaa tatcatcatg ttttgtagac tgctcacaaa tcatcgaaat cagtgaattc   19620
attccagcaa attcttcttg agctccaact atgtggaagc tacaattctt ggtactggga   19680
ttacagcagt gatcaaaaca gcctaaagcc ccctgctttc atggtacata tgatataata   19740
gagcgagaca gaaataaag aaaatgaata agtaaaaatt gtcatttgat gataaatgct    19800
attagagaaa cataaagcat agaagggggaa tagggagagt gggggttggg tgcaacttta   19860 aataggggtga ccagggcagg actcactgag gaagtaactc atgagcaaag ctctgaaggg   19920
```

```
agtgagggca tttccagtag tccagcttga ggccctagta tatgtgagac ctgaggcatt   19980
ggcctggctt gccctagatg ttcctcttct ttttgagcct gcttgtgttt gtcggctatt   20040
gggtgaggct tggcacaagc agttgggccc aagggcaccc actcatccct cctgggcttg   20100
gaaagctgct gtgctgaaat gaccccaccc ccatgcccct cctggggaca ggggacagtc   20160
aaagagccac tagaggctcc caaaactctc aaaggggcaa accctctccc cagaacctta   20220
tcagtttcct ggtgcaggca ctgctgagga cctcagctgt tgtctgtcct tctgggtttc   20280
tatgtttagt gtgaaggcag ccctggcaca ggccttcctt ccccttccaa tccgcaacag   20340
cctgtgctct gcattgcagc gtcacttccc tgctggaggt tgcaatgttt gcaccaaaaa   20400
gatggctttc aaagcccaag gtgtgtgtgc gggggagggg tatgtgcac acacacaatg    20460 gaagggggc tgtatctcag accctcacat tcatggatt catatgtctt ttgctctgag     20520
cataaggcta ttgaagtcac agtcatggat tcctgttctt tcgtttattc aacattacag   20580 catgggtta ccagcctgac tactagcatc acattgactt gaccttgaat attagcccaa    20640
ccatctgctt gccatacgac cttagacaag ctacctgtaa cctctctgag tgttattctc   20700
atctgtaaaa tgggactcaa atgcagtacc ttccttgtaa ggttgtcaag attaaatgag   20760
atcatctttg aaaggcattc agcaccatgc ctggcacaca gtaggtgtct cataaatgac   20820
agctgctatt actattaatt agccagggct tactgcacac ccattgtgtg ccaggcacag   20880
tgctaggtgc tggcagagtt agcaagagga actcaaagat gagtgagaca aggcccagct   20940
tggctccatt cctcacccac atgtggctgc cccaagcag tcacctcatc caaggaggcct   21000 tgcagctgag tgtgcaagca cctgggcccct ggcgtgggac ccagtggggt tcaggccagg   21060
gagtgtcacc agatgggtgc aacacccata cccttaccct cacaaatgcc ccccgcccca   21120
cgctgccaga atgtcacctg agtgctgagt gccgggcctg ccccacaggg cattgggacg   21180
gagggctcag caccaaggca aggagctgct ctgtgggctg gtctgacac agtggagatc    21240 tgggtcagcg ttttctgag tgaattcttt ttttttttttt tttgagtcgg agtctccccc   21300
tgttacccag gctggagtgc agtggtgcca tcttggctca ctgaagcctc tgcctcctgg   21360
gttcaagcta ttctcctgcc tcagccttcc gtgttcaagc gattctcctg cctcagcctc   21420
ccgagtagct gggattacag gcatgtgcca ccacgcccgg ttaattttg tattttagt     21480 agagacaggg tttcgccatg ttggccaggc tggtcttgaa ctcctgacct caggtgatct   21540
gctggcctcg gcctcccaaa gtgctgggat tacaggcatg agccacggtg cccagccttg   21600
ggtcagtgtt cttctgttta ccctcttcag tgtctcagcg gttggcaagg catcatcact   21660
ctctaccttt tcttgggaag tggattcccc tccctgtcag agactcttcc tattattttg   21720
gggccccttt ctctttcaca ctcattcaca cactccccaa tctatgtcct cagtcactac   21780
tagccttagt ggtcagtgga tccccatggc gaagggaag ctcattggat catagcaata    21840
tagctcactc gcccacaggg cgtggcccac tggaagaaga ggagaggaca ggacaggact   21900
tggcctctgc cttgcctgat ggattgtgtt atctcatgca ggagggagtg gggaaaccca   21960
tgtggcattc gatacacagc ccagtgctaa actatgcagt ctgagctcta tgctgtctaa   22020
gaagagggca aggcagtga gggccatagc aaggaaggga gacttgagct gaatctcaaa    22080
ggagaagaag gattgggatg gggtggcaga ctccaacctg gtccaggggg atgtgctca    22140 gctgtctgat ggctggaagc agagaccccat gtgccatgag gagtgaagat gtccattagg   22200
cccaggtgag aggtggagca tgcgaagtgg gggtcagggc tggggggaga agaaaggcat   22260
agaggaacca ttggccagaa ggttgcagag gccatagggg tagcctttt cctccaactc    22320
```

```
ccattctatt ctcttttag cctttatttt ccgcaccatt cccctcctct actctctttc  22380
cctttttgg ggtctctttg tcaccctcct ccctttttc tgagtctcag ttattttatc   22440
tgcaagataa atgtgctcat cctggaagct ggtgatgttg cctctcctgc ttttcattcc  22500
aattctgaga tctcattcag caagaactgc tgtcttaggg ctgctctccc aggactgggc  22560
cctgttggct cctgtggata tacatccacc agcagaaaag cctgagggtc caggccttgg  22620
gatctgtgcc actgcttgct gggggttgcg ggacaagcct gttttgcttc tcactcaggc  22680
tgaagacagg tgaggatgcc aagtccagaa attgctttgc ttccagcatc aaatggcttc  22740
ctctcagcag cacagtccct ttaagatggc gggggcggg gaagctagaa gaagaccttt   22800
gatgttgttc aactgagaaa tccatcaggt gggaacaagc ccggaaatgc cagagtgaag  22860
ggctccgtgg ttggctgcat tggtgggtct actgcctgga ctttgttttc tgatggtaaa  22920
cgttccctga cataaacaca ggcagagcag ggaataacaa cattcagtcc ccaaacaaac  22980
aaaacaggaa tgggacctgt cttgcacggg gaatggctct tgttgcaatg atatagctca  23040
agaggccttc actgtggaat ttcctgcctt gagcatgatg aattttccat tcttgtcctc  23100
gaatgaacag tcgccataga gcttagtggc tggcctgtga agctcagcaa ggccctctgg  23160
gaaatgggca gcttcgcctt ggctgagcct ggtcagaggg gcatgcctac ctttccttga  23220
atcagttgct actgtacgcc ttaaagtgcc atgagaacca tcatcctcaa atgcttaaag  23280
actgagctta aagccatctt cctttctac ctcatcttta ttattattat tattattat   23340
gttattatta ttattttgag acagagtttc attccatcac ccaggctgga gtgcagtggt  23400
gtgatcttgg ctcactgcaa cctctgcttc ccaagttcaa gtgattctcc tgcctctgcc  23460
tcccgagtag ctgggattac aggcatgctc caccacgcct ggctaatttt tgtaatttga  23520
gtagagatgg ggtttcatca tgtttccagg ctggtctcaa actcctgatc tcaagggatc  23580
cactcacctc aacctcccaa aatgctggga ttacaggtgt cagccaccgc accacctatt  23640
tcctacccca tcttatttga ctcccttca tgcaccagac actccagcca tatcagatgc   23700
atacccgctt tccacgagta ggccatttc ttgcattcct gactttgctt attctattcc   23760
tattgcttgg accactctgc ccacatcccc atttctgccc atccaagagg cagtatgcac  23820
agtggtgatg agcatggaat ctgtctaggt ttgattctgg gctccattgc ttaccatcca  23880
tgtggccttg ggcaagtcat ttaacctctc tgtgtttcta tttccatgtc tgttaaaagg  23940
gtgtgataat ggcacttact ttataggatt gtggtaagac ctaagtgagt tactatttgc  24000
aaggcactta gaagagtatg tggtacatag taagcattct gccaagcatt aggaattaat  24060
attgaaatcc taccctcttt caaggttcag ctcaaatgcc acctccccag tgaatctctc  24120
ctgatccacc ccagtggaaa tgttctctcc ctcctctaac tttccatagc cttttaacca  24180
gatctctcct ggggagctac atgcctggta tcataacaat gtatgcacat gtatctgcta  24240
cccgagggtt gggactcttc cataacttcc aaagggcctt acacccagta gttgctcaac  24300
agatcctggg agaaggattg aatggagttg aaaggtgat aacacgaccc aggaggagag   24360
cacagctgct tgttaagcct ggctggcctc cccaccagaa agtgagggac ttgactcttc  24420
gccagcgagt tatgtgtgtc acagttggta ctggctcata tagatctgtc actcctccct  24480
tatcaggcct tcctggtgag cactggcaag gcttgggca aagtcaacag ggaacacagt   24540
gaagggatat gccaagcagc aatgttgtcc cctgatggta accatgaggc atcctggacc  24600
agatctgggc tgctttatgc ccacctgaat cccaggattc tggctctaca gtagagccag  24660
```

-continued

```
atcaatcttg aactaagagc caaagcctac acattccctt ccctcaaaat gcaacccgct    24720
ggtccccttc tcatatgact tacccagttg ctgctgaact tgggcctcca gatgctgccc    24780
gcttgctttc ccttctttcc ttcctggcca aagattctag acatagccag cactgccttg    24840
agtcagatcc atcatccatt gaggcaggac tcagcacccc cacatacctt taactactct    24900
attatctgat ttctgttctt tgctggtgct acttcttgct gaaatgactt ctctgtgtgc    24960
tgcaagtgac catgactttt ttgtatacat catagcacat agcatggagg tagatgttgg    25020 cttgcctgt agtagaagct tccttaattc tttttggttg aatcaagggt tgggagatgg     25080
gaaataaagc tatagtcatt ctggttatat ttttcttaac ttttacgatt ttgatcatgc    25140
gagtggatct ctgagtcatc agggccctct atgcccttg agatctaaat gacattgctt     25200 tgagcccct tctacccctg tgccatgaac agtgcaagtc aagacccag cccaagatat      25260 ttttgaattt ctaagtgagt tactatttgc aaggcactta aagagtatc tggtacatag     25320 taagcactct gccaagcatt aggaattaat attgaaatcc ttgaatgaac agttgcctta   25380
gagcttagtg tttggccagt gaagctcagc aaggccctct gggaaatggg cagcattgtc   25440
tgggctgggt ctggtcagag gggcatggct actttttctt gatccaggcc tggggtgagt  25500
gttgctactg cacccttaa agtgctgtga gacccattgt cctccagtgc ttaaagactg    25560
agcttgaagt caccttcctt tcccactct aagccacctt cccttagagt ggaagaagag   25620
ggaagagtta tatcctcatg gccttcttac cacccacgtt ctgcagctct gagcttggtc   25680
tctgctttca cactgttgac caaagcacca gacctagacc ctttctcagt tcccaccaag   25740
aaaatgtgag tagtggaatc tactaaagat cttttggtggg atgaaatcct gggaggtgga  25800
tgtggtcacc tcacacagtg gacagccttc ccacacctct ctggctcctc tgtcccctt    25860 tctccctgct cctctctttc cctccagggt ttccgaagtt gctccaaatt cttcccctgc   25920 ccctgaggc cttggcacct ataaagggta ttaaatcagg gatgggtatc actttctact   25980
cttcagagct tatctaagta ttttttacca acataggtag tcttgccctg tgcattctgg  26040
tgccagccct taagcaatat atgagcaagg cccttcctgt ctctggacct tagtttcatg   26100
atctgtaaaa tggactggaa tcactagacc agccctgtcc aatagataat aatgcaatat  26160
gtaattttaa attttctagt agccacattg aaaaaaataa actgaagaac ttagttattt  26220
ttatccttta gagtagccac ggggaagcca ctgaggaatt tttaaacagt gttattgaga  26280
tacaatttac atataataag gtgttcatat ctaaagtgta caatttgaca cgtttcgata  26340
tatgtagacc tccctgaaac catcaccaca atcaagaggg tgaaccacat gcaacattcc  26400
cggaagattc ctcgtgtccc tttgtaatta tgtatattta atagtatatt tttaatttaa  26460
tttggtatat ccaaaatatt atcatttta catgtaatca atataaaata ttagtgagat   26520
cttttacatt ctttttttt tttcatagaa agtcttcaga ttccattgtg tgttttaccc   26580
ttggagaaca ttctgttttg tggtagccac gtttcaagtg ctccatagcc acatgtggct  26640
catggtgacg gttctggaca gcaaggtcca tgtgatctgt aagcaccttt ccctctctca   26700
tgttgaaggc ctccatgtgt ctatatttcc tgacgtgtgt tcttatcatt gattactact  26760
gctgttgctg ctgtgtgcac agcccaggag gtggccttgc tgcctgccat ctggtgggga  26820
cccatagtcc ccaccacccc acctcggctg gggcaattgc aggaaaacca cttgttggaa   26880
accctcttat accatcgaat tccagagtag gctctggatg gggccatctc tgttaacaac   26940
agagttgagg tagatcaatt gtaaggtgtg ttactaataa aaagtatcaa agtttgcaaa   27000
gaagtgactt tgcatcataa aagaggttag attcaagatt attcttatta caaataaggg   27060
```

```
aggcgttatc cctagaataa agtcactttc cctctgaccc atattcttaa atgggagaac   27120 aaaggggggca gaggatgcta ttgcttctat gctgggaacc ttagcctgtc ttccctgtgc   27180
taaaatcttg agcgacgtga aggttcacta agggagtggc catgattact acaaatttgg   27240
aggacaggtt attatcacaa cctatgtcaa tgggagcatg cttagagggc gctgcactgc   27300
aaaaaatatg gaggaaacat gtaacagggg actaaggtga gacagattct ccagacagag   27360
aggcctcaat ttgcctgggg cctggtgcta ttcgctgaag cacctataga agacttggag   27420
gctaagcaat gcccagttag cccgcccctgg tgtgggccca gtgaaacagc aagagggtaa   27480
gtacaccttc caggcccaga tgccctcagg accagcccta cttttggcaa aggaagcata   27540
agcctgggtt caggcaggga aagagctaca gacagttgtc tttggctggc acagtagttc   27600
acatctataa tctcaccaat ttggaaggtt gagtcaggaa gattacttga gaccaggagt   27660
tcaagaccag cctgggcaac atagaaagac ccccatctct acaaaaaata aatcagccgg   27720
gtgtggtgac accggcctgt agtcccagct actcaggagg ctgaggcagg aggattgctt   27780
gaaccaggag gtcgaggctg cagtgagcca tgatcgcact actgcattcc attctgggtg   27840
acagagagag accctgtctg taaaaacaaa aacagaaaaa aagacaatgg ccttaatctc   27900
cccctgcttt ccctaggcct aaaaggtacc ctgccttttta ggcagggtga atcgggtggg   27960
ggctgcctgc cttcctcaga gagagggaag gaagcaagga gtagggggtc tgactggggc   28020
cctacagctc ccaacctcaa gacctgcctt ttgaggccat agagaagctg cagctttgct   28080
tttgcagctg cagcggcagt gaagaaaagca ggagggcatc ctgaggcggg aaatgcctgt   28140
cagtgtcatc cccagctgct tccggcttcc tccttcaagg attccagggg ctcctctgta   28200
accttgccaa cccctctccc ctgccccagg ttctggcagg cagctgtgcg ccccccctca   28260
gggcccacgt cacaagtcct cagaggggct gtcaactccc cattgttctc ggggcttctg   28320 ggcttctcc ggcattcctt tggctcatga ggggaaatgc ctgaagcttc gtcttcacct   28380
cttcagatgc ttgacctaat agtcacccgg ccctcctggc ccctcaaggg atgctgtggt   28440
gcgtgggaga atctggctag gctagcacta caagtacact tacctcaggt caaagatgaa   28500
atctgagggg gtacctaggc ctctgtgtct tgaactcacc ttgaaggccc cagccaagta   28560
tttccccctc tccctcctga gtattgcaca cagctacccg cagagttaca taaacacagc   28620
catactcctc cattccaaat tctacccatt ccacacagtt ctgtacatgc tctcacatgc   28680
acactcccac ccaacccatc tttccagggg agccatcagg tgtgtcaggg ccagaagcta   28740
cttttgctgt gggtacagga ctgacattct tccaggaagc ctcccctgac tgacaggcaa   28800
aacttcctgg gtagaagctg accccagtcc ccatctacta tttaaaatat ggtgggtagg   28860
gaaggtttta ctggagaagg tgatgtttaa agcaaatact aaaggatgtg aaggagtaaa   28920
caatgctgat attcaaaaga aggacattca gggccaaggg agaaacaaat gcaaaggccc   28980
tgaggtagga atgtgcctag tgtgaataaa gaataacaag gaggccagtg tggggtggag   29040
ggctcgaagg aggaggagta ggaggtgagg ctggggaagt gatggagacc agatcctgtg   29100
gggcctcatt tgcctttgta ataagagaga tgggagggag ttaccagagg gttctgagca   29160
caggtctgat atgatctgac ttagattgta agtgattatt ccagatgttg tgttgagaat   29220
agactgtagg gggacaaggg tggaaacagg gagattggtt gcaataattt cttgatctct   29280
ggcaataatc catgtgaaag gtgatggtgt cttaggccgt ggtggtaatg gtggatgtgg   29340
tgatacgtga gcagaatata gatatattct gaaggtagat ggatttgtca atggattaga   29400
```

-continued

```
tggaggcggg atgtaaagag aacaatcaaa gatgactcaa aatgtttctg cctgacaaga    29460
gaaaggcata aaagtcatcc aaataaaaaa gaggacatcg ggccaggcgc aatggctcac    29520
gcttgtaatc ccagcacttt gggaggccaa ggtgggtgga tcacgaggtc aggagataga    29580
gaccatcctg gctaacacga tgaaaccccg tctccactaa aaaatacaaa aaattagcc    29640 agtcgtggtg gtgggcacct gtagtcccag ctactctgga ggctgaggca ggagaatggc    29700
gggaacccag gaggcggagc ttgcagtgag ctgagatcac gccactgcac tccagcctgg    29760
ctgacagagt gagactctgt ctcaaaacaa aaaagaaca tcgaattatc tctattcatt    29820
gacaatatga ctctacacct agaaaattct aaagatttca cctaaagact gctagatctg    29880
ataaacaacc tcagtaaagt tttaggatac aaaccaatgt acaaaaatca gtaacatttc    29940
tatatgtcaa taacattcaa gctgagaacc aaatggagaa cacaacccca tttataatag    30000
ccaaaaaaag aataaaatac ctaggaacac agctaaccaa agaggtgaaa ggtgtctaca    30060
aggagaacta caaaacactg ctcaatgaaa tcagagaaga cacaaacaaa tgaaaaaaac    30120
attccatgct gatggattga agaaccaat attgtgaaaa cgaccatact gcccaaagca    30180
atctacaaat tcaatgcaat tcctatcaaa atgccaacat catttttcaa ataattagaa    30240
aaaataatct taaattcat atgtgtatta gcctgttctc actctgctaa tgaagacata    30300
cccaaaactg ggtaatttat aaagaaaaag aggtttaatg gacttacagt tccacatgac    30360
tggggaggcc tcacagtcat ggtcgaaggt gaaggaggag caaaggaatg tttcacatgg    30420
tggcaggcaa gagagagcgt gtgtagggaa actcaccgtt ataaaaccat cagatattat    30480
aaaacttact atcatgagaa cagcatggga aaaacccgcc cccatgatta aattacctcc    30540
caccaggtcc ctcccatgac atgtgggat tatgggaact aaaattgaag atgagatttg    30600
ggtgggaaca cagccaaacc gtatcaatat ggaatcaaaa aacggccaga ataaccaaag    30660
caatcctggg caaaaagaac aaagccagag gcgtcacatt acctgacatc aaattatact    30720
acaagggcac agtaaccaaa agagcatggt gctggtacaa aaataaatac agacacatag    30780
accaatggaa cagaatagag accctgaaa taaaactgta cacctacaac caactgatct    30840
tcagcaaagt ggacaaaaat aaacaatggg gaatacccaa taggacaccc tactcaataa    30900
atgctgctgg gaaaactggc taaccatatg cagaagaatg aaattcaacc tctacctgtt    30960
accgcataca aaaattaaca caaggtggaa taaagactta aatgtaagac cataaactat    31020
aaaaatccta gaatcaaact taagaaatac tcttctggcc attggccaag gtaaataatt    31080
tataactaag tcctcaaaag caaatgcaac aaaaccaaaa attgacaagt aggacctgat    31140
taaactaaac agcttctaca catcaaaaga agccatcaac agagtaaaca gacaacccac    31200
agaatgggag aaaatagagg caaactatgc aaacaacaaa ggactaatta atatctggaa    31260
tctattagga acttaaactc atcaacaagg aaaaaacaa acaaccccat taaaactag    31320 acaaaggaca taaacagaca cttctcaaaa gaagacatat gagtggccaa caaacatatg    31380
aaaaaatgct caacatcgct aatcagagaa atgcaaatca aaaccacaat gagataccat    31440
ctcacaccag tcagactggt tcctattaaa aagtcaaaaa taacagatgt tggcgaggtt    31500
gcagagagaa aaaaaacact catacactgt tggtgggatt gtaaattagc tcagctcctg    31560
tagaaagaag tttggagatt tctcaaataa ctgaaaatag aattacaact tgacccagca    31620 atccccattac tgggtatgta tccaaaagaa aataaatcgt tctaccaaaa agacacatgc    31680
actcgcatgt tcatcgcagc actgttcaca acagcaaaga catggaatca catcagcctt    31740
ggtgcccatc agtgtgactg gacaaagaaa atgtggtata tgtacaccat agagtactat    31800
```

-continued

```
gtagccataa aataaatgaa attgtgtcct ttgcagcaac atggatgcag ctagaggcca   31860
ttatcctgag tgaattaaca caaacagaaa accgaatacc acatgttctc acttataaac   31920
agcagctaaa tattgggtaa acacagatat aaggatggga gcaatagaca ctggggactc   31980
caaaaggtgg gagggaagga ggagggcaag ggttgaaaaa ctacctacca ggtgctatgt   32040
tcaccgtttg ggtgatggaa tcaatagaag cccaaacttc agcatcacac aatatatcca   32100
tgtaacaaat ctgcacatat atcccctgaa tctaatgttt tctaaaaaaa ggtttctgcc   32160
tcagccacat gggaattgtc atgtactgcc atttacttca aagggaccag gtatgcagga   32220
ggagaggatc aggcaatcag tgctggtcac attatgtttg agaagcctat tggacatcca   32280
aagggagatg atggataggc agtttagtac atgagtctgg agctcaaggg agatgcctat   32340
aactttccta ttttgttgtt gttattgttt gtttgtttgt tttgttttga cacagagtct   32400
cgctctgttg ccagactgga gtgcagtacc acaatctcag ctcactgcaa tctccgcctc   32460
ctgggtaagt gattctccag cctcagcctc ccgagtagct gggactacag gggtgcgcca   32520
ccacacccag ctaattttg taattttctt agaggtgggg tttcaccatg ttggccagga   32580
tggtctcgat ctcttgacct cgtgatctgc ccacctcggc ctcccaaagt gctgggatta   32640
caggcgtgag ccaccacgcc cagctcctgt gtgttttta tacttgtcca gtgcattgta   32700
tctataaaca atttacagga ttgctttatg agtgttcgaa cttccatca atgacttcct   32760 gtacgtatca ttttgcaact tgctgttttt gctcaacatc aagttttga gattttcac   32820 attgaaacat ctagctcttt ccatttaact ccatagtatt ccattatata aatatgtccc   32880
aatttacgta cttactgccc tattatcagg ataattgggg ttgtttggat ttccgaatgc   32940
ttctttatac tccacagagt gtgatataac gctttgtggt gctgggcaca cagatagtaa   33000
atgattgagt atttctgttc acctgcatct gtgtgcctgg gatcattaat tcccaggcaa   33060
cagggaacac atcatatctg ttgatttcac aaggactat ttactaagct aggaccagct   33120
agatttctcc ccggtgatat ttggttagct gtgttgtcca aggtgctgga aagtaacagc   33180
aatagggcag gtgccatggc tcacacctgt aattccagta ctttgggaag ctgaggtggg   33240
cggatcacat gaggtcagga gttcaagacc agcccggcca tggcaaaacc ccatctctgc   33300
taaaaataca aaaattagcc aggtgtggtg gcgcacacct gtagtcccag ctactcggga   33360
ggctgaggtg gaagaatcgt ttgatcccag gaggcggagg ttacagtgag ctgagattac   33420
atcactgcac tccagcctgg gctacacagc gagactctgt caaaaaaaaa aaagaaaga   33480 aagaagaaa gaaacagcaa tggtttttac tttgctaatt atcgcagacc ttagtggctt   33540
aaaacagtga gtttattatt tcacagtttc tgtgggtcag ggatctgagt acagcttagc   33600
tggaccctcc gcctcgggcc ccctcacaac ctgcagtcaa ggtgttggcc agggctgcag   33660
tcacctcaat gctcaacagg ggaagaatcc atttccaagc tcactcacat ggctgtcaac   33720
aggagccttc aggtgctcac tggctatcag accagagcca cagtttcttg ctggctattg   33780
gctggctcag ttccttgcaa cacagaactc tccagaggac agttcacaac atggcagctg   33840
gcttcctcag agcaagcgag tgagagatgg tgagtgtgtg agaaaggcag gagtcagtct   33900
cacaatttaa tcttggaaat ggcagcccat catctttgcc atattctatt tgttagaagc   33960
gagtcactta gtccagccca tatgcaaggg gacggggtta gacaaaggca ggaataccag   34020
gatgggggat tactgtgggac tatcagagaa gcttccaagc atggaaacca aaggactgag   34080
gtgggggcag gattgattgg ctgaaatgcc tgcagagacc ttgaggagga tgaagagtga   34140
```

```
ggaggggcat agagtgaaag ccagagagca ggagtaggag gatggaaaac gtctggtgta   34200
gaccatttgt ctcagaactt tggtggggaa ggtaaagtgt aagaaatgtc agtggaggga   34260
caggggatct ctgagcacat ttgagggcca aggggaagaa gccaatgcaa atggtggagg   34320
ggaagggaa atgtggacgc caggctccta ggagaagagg aagggcatct tgtcacctac    34380
ccctgaacat ttctacagtg ctctgtaggt aaaaagtac ttttccataa acagtttacc    34440
cttgaacaat gtgggtttga ggtgcactgg tccacttatt tgtggatttc ttttttcaac   34500
caaacacaca ctgaaaatag agtattcgca tattgtgaaa cctgtgtaca tggaggggtg   34560
acttttgtg tatgtgtctc aaagggctga ctgtgggact tgagtataca tggatcttgg    34620
tatatgcggg gtcctggagc taaaccccg tggataccaa aggatgacta tacaggcttg    34680
cttgagcctc ctatcaatcc agtgaggtta gcagaacagg gatcgctttg tccctatttt   34740
agatgaagaa acagatgcag agaggtgaca tggttttttcc taggtcatat aggcaataaa  34800
cggccaagcc aggactagaa ttcaggtatc caatctctaa gtgtttctag tctagtgctg   34860
gcttctcatt aggcctcagc actttcagca tgctgctcct ctgctcaagt cctctccctt   34920
gtgtctgtaa ggtcgagaac tctcttcccc cacagggaac tgaatgagtt tccagttcaa   34980
gcaggccagg caatggctgg aaatgagtga gaattccttg actatcaatc aaggggctgt   35040
aacccaaatt aaggttgaag ttgtgagagt ggtgtgggga agcccctgca tagtgggctg   35100
gtaagatgca cgccacgggt cagtgggact ctaggcccag tgaggagtg ttgtggggag    35160
catccacgtg ggcaagtaa gggccggcat ggaagacagg cgggctggga gcctggctct    35220
cactgcgaat gagctgtccc cattatttcc tcttccagcc actcagtccc gctggctctc   35280
caagcagctg acaagcccag taaaagagtt tccatccagg cctggaaggc cccagtgaga   35340
gctggggagc tgcttttatc cagccttggc aaggcctttc agctggagtc cagcccactt   35400
tgggcaacat ttgaaaactt actgaggaaa tggaggtctc ctttttagga atcctgcccc   35460
acccctgctc ccaccatggg ccttagtttt tccccaggaa acctggagca ccttgagact   35520
ggagactgtg tctaccccag caggcaggaa accaggggct caaacttcca agccctgccc   35580
tttgtgagct cctaggatac acacaattca ttctgaccct gggacaagga gccagtgaac   35640
cagtcatcta taacaacctg agctacacag ggccccagag aaaccttcca gaccctcatt   35700
taccagctaa agaaattgag gtacagaatg gggagggatt tggtccagga tcacagagcc   35760
actgagtggc agaatgggag ggccatagtt tggaggagac tcgatgctca agaaaaaggg   35820
actgtcaaac agttaaggta ggagttcctc taagcagagt ttagagaatc gatccaagaa   35880
acacttgaag cgtgcgagtg gcatagacta ggtgctcaac aaacgcagca taataaaata  35940
aatgaaactg attgttgctg caggggagct gggacggact aggccacgag aataaaaaac  36000
tctgccctgg tctgggtcct gctgggtcca gatcagtgac actagaatag ccagcctggg  36060
ctttttttccc atgggaaagt aggacaactc tgaccagaaa ctggggtaat ggcaatgagc  36120
ggagggagta gattaaaggg agagatgccc caccttact tgggataaag agctcccctc    36180
ttgcttcccc cttcatttt actgattgct tacttggtgc caagcattat cagaaacaca   36240
cacacacaca cacacacaca cacacacaca cacacacaca cacatagcat taacacacat  36300
ggtccctatg aggcaggcac tatcattgcc tccatcttat agataaggaa actggccccg  36360
agaagttcag tgccttgccc ttagtctccc agctgataag aagtaaagct gggatctgaa  36420
ctcaggccat ctgacttcaa tacctatgct tctaaccact aggttatact gccatttcgc  36480
tgagcaaggc agcttgtagt ggagctgatg cccctgcgga ttgaaggccc actcattcac  36540
```

```
acactcacag ccacccctgc ttggaggtgg catagcaggg aacaagttgg agttgccaga    36600
ggccccaagg tctccaccct acctctatct tggagcttaa agtatctcgc tcctggcctc    36660
ttttaggaat ggtagggcca ttagcccaat gaaggctttg ccatgagttt ctcagacctt    36720
tgcagggata gcaggccct aaggagactg aaccagggtg gaaaaatctg aataggagtg    36780
gaagaggagg gtacagggca gcccattatt atctctggtc atttaacact tcttaaacac    36840
ctactatgtg cctgtacagg gggctggaac tacagcaatg gaccagagac ctgtccctgc    36900
aattagagag ctcacagtct agaggggggag agcaactagc aaacagacta cagagaggga    36960
aactgaggcc cagagaggtc aaaggccttg cccaggaata ctcagtgggt gagtcacaga    37020
gctgggccca gagtcagtgc tcagactccc aatccagcat gatccctgct acagcaaaag    37080
caagcaaatg caaacaagct cagatgaaag aggggtgtta tgaactaagg agaggcatga    37140
ggcaggcagg gttaggcaga agggctatct tactggaggt ggagttcaaa ggagggtgct    37200
acagtctgaa tgtgtccccc aaaattcatg tgtcgaaacg taaagcgaat atgacagtat    37260
taagaggcag ggactttcgg aggtgagtca tgagggtgga gcattcatgg atgggattag    37320
ggcccttata aaagggcttg aaggagttgg tttgttggct tctcctcttc tgccatgcga    37380
ggacacagca ttccttccct tttgctcttc tgtccttttcc accacctgag gacacaagtg    37440 ttcctcccctt ccagaggatg cagcaacaag gtgccatctt ggatgcagag agctgccctc    37500
aacagacaac tgaacctgcc agcagcttga tcttggactt cccggcctgc agaactgtga    37560
gaaagagatt tccagttata agtgacttag tctcaggtat gttgttatag cagcacaaac    37620
agactaagac aggggaagga tgccctggtg gaggggtgcg actggagaaa gctcagtgct    37680
cagtgagccc cagtgaagtc ccaggaaagc cactggcagc agcccacacg cttgggcggt    37740
tcctggacag ccaaaggagg aaccacaccc accaggccca ccagccttgg acgtggccca    37800
gcaaggccaa gcgtttagta attggcgaag tgactgtctg ctgccgcccc agtccaaatg    37860
aataattatg gaatgtttac atgatgtggt gttcctgaca ccttctcaag tttccatggc    37920
aactaggaac caccgcccca cccaccccca acccaaccca caagatgttc tgtctgttgt    37980
ggccagcagc tgtgtcatgt tgtgaataaa taacacatgc ctggccttgg agactggagt    38040
taccctacag tcatccctga cagggcagac ttagtgaggg gatggggctg cagcaggcag    38100
taaggcgtct ctaatgcttt gaatgcattc acctgcctca gcccaatgtc accagagata    38160
ggccatgggt cagcgttcat cccagtggtc cctcctggag ctagtaagga gacgtccctg    38220
ctaaagagat gttcaatgtt taatacaccc aagcttcagt ttactcccct tgagcttttg    38280
ttttctcatc tgttgaagat acccatgcct gtctcaataa ctttttataa agaagagata    38340
agatgacaac cagggccagg cactgtggct catgcctaca atcccagcac attgggaggc    38400
tgaggcgggc agatcacctg aggtcaggag ttcgagacca gcctgggcaa catggtgaaa    38460
ccccgtctct actaaaaata aaaaaattag ccaggcgtga tggcacacaa gagaatctct    38520
tgaatccagg aggtggaggt tgcagtgaga tcgcgccatt gtaccccagc ctgggcaaca    38580
gagtgaaacc ctgtctcaaa aaaaaaaaaa aaagaaaag aaaaaagaaa aagatgacaa    38640
ccaaccagca tagaaagcat atcctaccat aatggctagc acttagtagg tgcttaaaaa    38700
tgtcacatct ggaaggttcg ttctaaacat ttgtgcctgc ccccacaacg gaaacttctc    38760
tcctccccag atccccagat ccatgaataa gtggaagggc agaagctcca gtggtcttct    38820
ggaagtcaga gaacccaagt tagaggtcaa taacgtcctg gtggattggg agtaaccta    38880
```

```
caaacgtgag actcttgttt tagctctgac tgtcctaatg gctggcgatg gggccttggg   38940
caagtcactt gcccttttctg gttctcagcc tctctgtctg gactatgaga tggagtggcc   39000
tagaccagag gtttttcaaa ttgtgttcca cagaagcttg ggtgcctcag ggaactctgt   39060
ggtagggaga gggatgagac tgaatgggtg gggctctggg cccctgagcc tgctttgatg   39120
gaatttatat gtgccaaggc tttaaaaaaa cagtttgagg ccaggcacag tggctcacgc   39180
ctgtaatccc aacactttgg gaggccgagt caggtggatc acctgaggtc aggagtttga   39240
gacgggcctg gccaacatgg caaaactccg tctctactaa aaatacaaaa ataaaaataa   39300
aaataaaaat aactgggcgt ggtggcaggc acttgtaatc ccagctacta ctcaggaggc   39360
tgaggcagga gaatcacctg aacctgggag gcggaggttg cagtgagccg aggtcgtgcc   39420
attgcactcc agcctgggca agagagcgag actccatctc aaaaaaaaaa aaaaaaaaag   39480
tttgaaaact ctgaccgcat gcttttggct ttgataggga aagagagctc cttggccact   39540
tcctcaatcc cagagtgcat gagttccctg gcctgggagc agatacacca agagaggcac   39600
tggatcccaa aggtacccca aagctccatt ttctcccaca ccaccatcc tgagctgtct   39660 ttctgtccca gaactcctct ctgacagttc caactgccca aaaccaggct acttccacca   39720
gatgccctga ggaacagtat ggcaaggggc cctgggcagg gaagaggctg aggaggagga   39780
acaggccctg gccacctctt tcctttagga gggtacgaca gttcccagtg gcccaacctc   39840
ccagggcgtt ctcccagagt gtggagggcg ggggcctaat ctgcatttgg gacaaagcct   39900
acccggtgct cgagtgttgt tgtcatgaaa actcaaaagg tgttattagc atcttttcaa   39960
ctcagtggcc ctgtgtggtc cagtccatgc aatcttagca gtagcacacc atcaccctgg   40020
caacccatta gcctagtgtt gttaccatgg aaactccagt aaggtcgatc agtccgggaa   40080
gttcccagag gagataggca ctgggagatc tgcccagcag tgcctactct gagggtctcc   40140
cagctgacag tgacctgctc tgcatacact gacagtagtt taggatcttt tccgagcga   40200 gctaacagtc catgtgacag gaaagaattt ggccctgcag actggcaggt ctatgcctcg   40260
ttaccatgga aatgctgctt gtcaggatct caaagcacag tgcaaaacta actcttccag   40320
gagactgagg ctggcaggaa aggaggctgt gagcctgttc ttcattcaca tgcccattca   40380
ttcattcatt cgttcattca gtatttagtg cacgctcatt aatacagtgg gcactgcgta   40440
tgtccgaggc tctaactgga gcaaacaggt gggctcacca actctcttca attgaaaagt   40500
atattgaggt ggagggggacc atcttacttc ctgtgtcaac ctccactgga ggaaaaggag   40560
ttgacatgcc caaaggaatg gaatcggggg gtctctgtgt gtcgagggt acaggagaa    40620 tacttgcttt ctgtagcctc ctgttttttca cctatccct gcttaagcct tcaggaaaca   40680
gatctttgtg tggtctggat caccaaaggc ttggccagac atgctagaag tttccagcag   40740
ccacagctaa gtgaagttag aacaggctac gttgggaagc aatgagctcc ccatcactgg   40800
agatgtacaa gcagaggcaa aaaatcctgc tcagtgaggg ccatgtagag cccgcagagc   40860
acaatgattc agagctcaga ttctggagcc agatagccag tcttcaaatc ttggctcagt   40920
ttaccagctg tgtgactttg ggcaattcac ttaatcatac tgagccttga tttcctcatt   40980
tgtaaatggg aatgataaga gtttcttcct catgggcttg ttgtggggat gaaatgcgta   41040
taatatataa agcacttaga acagtaccta acatataatt gctcaagaaa tggtagcttg   41100
tattatccct tgatggccca actaaagtcc ctgacaagct tgggattcta tatgactatg   41160
ggtcactaat cttcctgcac acggaaaatc agaaagggac tctggcaagg gtaagattct   41220
gtgctgacca gagagctggc tgagggtagc acctctgagc tttgagctca tcaccacttg   41280
```

```
cgtgcttcca gcaatagttt tcctttccaa gtacttttgg atccatgtct caattgggcc  41340
taaagacaac agcaaagggc acagttacca tcccctgtga tagataatgg gaagtaaagc  41400
taagagcggg agagtggctc acctaccaag tggcacaact gggatggaag ctttctctct  41460
gtcacaccac ctcacagtcc ccagggccgc cataagggga ggacagcagt tgggaaggag  41520
caagtcatgg gctgggcgga ggaggagccc agcatgacaa taacctatga aaatcagctt  41580
tccactgtct gcacttctgc aaggaggagt tgaggccaaa gccagggagc agaaggggt   41640 atttcctaga aatgcggcgg gagtggctgg tgtgctccac ccatgggcaa aggacaaggc  41700
tcggcctgcg tgtgagcact cacttggagc tgaacttgga gcctccagag ctcccatccc  41760
tctgagctca ctcagaaagc tttcccttg ggcaaagtcc aagggggtca ttcaactgtg  41820
atctgacact tctgctttca acttaatagc tcaagtattt aacggatggc tcatggcctc  41880
accaagggat tttgcttgcc gagactagca aggtgggcta tgttttcat gccatttgga  41940 ggagcaatga gaaaggattg tttaaaaaaa aaaaaaactt tgcctgagaa caagagtaac  42000
gccctaactc atggcctcat gaagctccag gttaaaatgc acacgttacc tgggagtatg  42060
ggaattggac agggggcaata gtgaaaaatc tttaatagcc agcaaggtct ggacaccaac  42120
tgattagaat gtttgctggc cagaaacacg ctataggggat gcaccagccc agatagagga  42180
aaacagcagc cctggatgtg ggccttggca ggggccgggt gaagggaggg tttgctccct  42240
gagaggtccc atgagcacac gcaggaatca gatctgccta tggccaccag aaggtatgag  42300
atttcccaca gcagctggtg gtggggggt gggcagggtt ggtgtatctg gtaggggggaa  42360 aactggtggg aacatgggggt tcactgaggg aagagctcct tgggacagct cgagggccag  42420
acagcctagg acagtcctgt aaggatgcaa atggggcctg gcctggcctt ggagacccag  42480
atgctgccct ctgccctcac agacttcacc cctggtgcct ctgggtggca acttctctcc  42540
ctctctcagt gaacatgcat acggactata atatgctaca cagcgtggag caaatatgca  42600
tacccattcg gtgttcacac aagcacatgc atggagccca cgtatgccca tgacctgtag  42660
aggcatcctc tcaagtcagt ggggcacacc cacaaaattg ttcagactca gaatcttgga  42720
gcagaagcaa ttttagagct gcccccatta aaaaagtcgt ctttgatgaa cgccagtcag  42780
ccactcctct acacacactt tggcgtttgc tcgttctcac acctcctgca gaacaggaaa  42840
gaggagatga cctcgggaac tttcttaaaa tggcctgtgc ctagacttga cgcaagcctg  42900
aagaagtccc tgcagttcca ggactcagcc agcaggggc agcctctcat gacacactgg  42960
gtttccccca aagaataagc aggcttgag aagaaagaga ggccgactgc aaagaaaggg  43020
aaacatataa gaagtttcca gagtgtccgg ccatcaagct gacccagatg catgtagcca  43080
gccactcctg tgggtgagga attctcagcc cctcatattc agctggtgaa ttgatagagt  43140
ctggggcaag ttatcagaag aggatgtctt agtgaccata gtacatcctg cttgcccagc  43200
ctagagccac agagggaatc agccagcaca caggagttca gtggaatctc tcattctgca  43260
agtcacagcc tctctcaggg cctgcttcgt tgtctgtgaa atgggtttaa caataaatca  43320
catctgcttc ctcccacctt ggtgctttgg acacaagccc tgtgctccct ctgctgagac  43380
ctcctttctc cagcttaacc cctactcact cctgaggtgt cagctcccac ttcacctcca  43440
ggaagctttc tctgaccccca gatcgtgcac tcagtgataa acttcctaga ggcctgtttt  43500
tcgcctccag ggcccttgcc acagttcctg gttagacatt cggttgtgat ttttgaataa  43560
catctgtttc cctctccagg tattaaggaa tgtggtacaa agtaggccct caataaacat  43620
```

```
tcagcgaatg ctgagaaatg aattcccata gctcttttac agatcaaaaa gcactttcac    43680
atgcaaacag ggtggtcttc atggtacccg ctgagaacga tggggttttt tccccgttac    43740
acacacagca ctctctactg taccaaacat tttaacttca gaaacttcag tcactagaag    43800
cccgagaggg agccagggat tcttacttcc attttagaaa aggtaaagct gaggcctaga    43860
aaggtgaagt gactgaccca ggcttggaac ttggaggagt caggatgttt aagtctccgc    43920
atcccatgct ggaaggtatg atcattacat tccctcatta tcactgtcag catcgtcacc    43980
tccattgtgg ctatggccat gcctagtctg gtgaggaggt gtacagttgg cgagcacaaa    44040
ggcttttgaa ggtggcgggc agaagtctgg gttccaattc tggcctcacc tgcaggtgac    44100
catcggggct aggagagcat ccagggagga ttcatggggg aggggagcct ggctggcag    44160 ttggaggacc cggagaattg gaggaaggtg gagaacctgg gaagggaagt ctgggaaac    44220 tagaagagca ctgaaatggg gttttgggtg acttaggctg aggctttccc tgcttctgct    44280
tcctaaaaga tgggtatgaa gctccctccc tcgcaggtcc tgctgaggcc ggtgcgcagg    44340
ctcagggcca ggagaacatc cctgggggttg cggggagtg gtacagaggg cgctgtggct    44400
acaacagcta atgagggatg tcacaccctc accacacacc tttcgctggt gcctcccaga    44460
ggaaaggtga ggaccaagtc tttctccact gttcctcctc cactgtccct tgcatggtgt    44520
cctgcacaga gtaggcgttt tttttttttc ttttgctgtt gtttgttttg cttgtttgtt    44580
tgagatggag tcttgctctg tcgtccaggc tggagtgtag tggtgcaacc tccgcctccc    44640
aggttcaacg gattctcccg cctcagcctc ctgagtagct gggactacag gtgcccacca    44700
ccacacgcag ctaattttg tattttgtag agacgggttt ttgccatgtt ggccaggata    44760
gtctcgaact cctgacctca gatgatccac ccacttcggc ctcccaaact gctgggatta    44820
caggcatgag ccaccacgcc tggccaaggg taggcatttt ttagctgatt gtttgggt     44880 aggggtaggc caaagagctc tttataggct tgggttctaa aagtttgggc atagattgag    44940 agaagggag ctcctttga aacttacaca aggcatggga cctaaaactt gacaggcaat    45000
ttgggagtgg gaatgggggt ggggcaggct gtggagctga gctagagggt agcccagagt    45060
agagggaagg atgaaagagg ataatcagat cagaaggtct ctgcagtgct ggaggtggaa    45120
ggggctgtgt ggtgagattc cctcctccat cccctgcac tcctcactgg gaccttttttc    45180 ctccctgctt tgtttatcct ctcttatctt tccatatccc tcacatctga ggagttggga    45240
atttccaaag gagagaggaa ctccaggctt ccagaaagct caggagccta gagacatggg    45300
ggatgaaacc ccccataacg tatgccaaag tcaccagcct ctatccctac acctgctggg    45360
gagggagcca gagatgtctc tgcctagatg gaaaaagagg caccctcttt caacaggcc    45420 tctcacagcc cccaaatcac aagcagttct gttgccctgg gactgagggt gccaaagcga    45480
agcccctccc ctacagacga gaggtgactg cagccctgga gggaatgctt ggcatttcag    45540
cagtgccttt gccttccttt aaagcaatgc caccttgttt ctctcagttc gtttgcacat    45600
accacagaag atctttagac taatggctta ccttctcagt gactcagttt cctcagctat    45660
aaaatgggat tgtgatgggg actgactaag tcaggacagg tgaagttcct caaacagtgc    45720
ttggcacatg agaagcgctc tacatgagtt tgctaggact atctagctat gttccttaag    45780
cgttcactta tcctttctga gtcccacttt cttcatttgt aaaaataaca gggcttaggg    45840
tactgaatga tctctcaggc tcatgtcagc tctgcccttc tatgattctg tgtgtttaag    45900
gtagggaaag cagagattgt catcctatga aaatagatga gggagaacca ggaccctga    45960 tagatgaaca gacctgcctg gagtcacaca gccagttact gaccaagctg gggttaggat    46020
```

| | | | | | |
|---|---|---|---|---|---|
| ccagagctca | gaaccccaag | tttcacacca | ccaggctagc | tctgcagcag | tgtgccaatt | 46080 |
| ttttaacatt | cagggaagat | cagaaagcat | ttaatttgtg | caaagggaga | agtatggaat | 46140 |
| ggaggttcca | gcaggccctg | gggttatggg | aagcttgtgc | aacccacgta | acccagcagt | 46200 |
| ggacttcctc | actggcttag | gttcccattt | tcctgccata | tgcctaattc | ttctcccaga | 46260 |
| gctcctccct | acaggtccct | gggtcaggtc | ctgaattgcc | tctggagggc | agcctgaatc | 46320 |
| accccccact | gttagctggg | acccaacaa | atccctagtc | acaagcaggt | gcttcacatc | 46380 |
| tacccaccca | ggtgtcctgg | gcaggtgagg | aggctgagac | ccagaaaggg | ccaaggaaag | 46440 |
| actttgctaa | gctacccagc | aagccctggg | tagaagcaga | ttcaggactg | gaacccacgt | 46500 |
| ttctgagccc | ctggccttgt | gcagaaagga | accccaatgg | ccaagcaggt | gtgctggaac | 46560 |
| aggtgcctgg | ctccacaatt | ccagacagat | caggtgctaa | tggtgagcac | ttaacacctt | 46620 |
| tggagaggcc | tcctgggctg | ctgcccaagc | taagcttcta | caaggaaaaa | tgccgaggac | 46680 |
| gtaatctgtc | cctggggagg | ccctaaaggt | tatctgggag | accggaaatt | tctagtgact | 46740 |
| gaggcacact | catggtggga | aagaggaccc | ttagcagaag | cagggaagct | atcatagttt | 46800 |
| gttttctgta | gccacagact | gggtaactta | taaaaaaaat | agtttattta | gctcacagct | 46860 |
| ctggaggctg | ggaagtccaa | gggcatggca | ctggcgtctg | gtgagggact | ttttgctaaa | 46920 |
| tcatgacgtg | gtagaatggc | atcacatggc | aagagggcaa | gagtgtgcca | gctcaggtct | 46980 |
| ctcttcctct | tcttataaag | ccaccagttc | catcataggg | gcacaaccct | gatgacctta | 47040 |
| tttaatttta | attacctacc | aaaggcacca | cctccaaata | ccatcaacat | atgaatttag | 47100 |
| ggattaaatt | tccaaaacat | gaagttgaag | gatgcattca | aaccatagca | gcagctgacc | 47160 |
| tgagccgggg | acagacccag | gtttgaagct | ctactcaccc | atgagtggct | ctatgaattt | 47220 |
| gaacaagtga | cctcacctcc | atgagcctga | tttttcatct | ataaattggg | gtaatgatgg | 47280 |
| ctgccctgtc | cagttctcag | ggctagaatg | aggcttaaca | gagataataa | tagctcccac | 47340 |
| ttggtaggct | tgtaacatgg | gccgggcact | gtgccaaaca | cttccctgc | atcatcgcgg | 47400 |
| tcaatcctga | ccacagtgct | ataaattggg | cagcagcatc | ctgcctaaag | cagaaacatg | 47460 |
| ggctcatcca | gatcaagacc | cttgctgcaa | ggtcacacag | gtgagtaaat | ggtagtgcca | 47520 |
| ggatttgaac | cctgatctga | ctccagactt | ccccttccac | tggaatcact | tgttagtat | 47580 |
| gattattatc | agaggccatc | tcataaccag | tgtattaaat | cacttaattc | tacaccttgc | 47640 |
| tgcagaatgt | aagtcttccc | cttggactcc | aggcaagggt | tcagggctg | agttgaaggg | 47700 |
| cttgctgatg | cttcatttga | gacagggctg | ggaagccacc | tgcttttata | aagatttttt | 47760 |
| tggaacacag | tcatgtccac | tggtgtatgt | attgtgtatg | gctgcttttg | catgtgccaa | 47820 |
| aaactttacc | tgcatcatca | cagtcaatcc | tgatcacagt | gctaaaaagt | aggcagcagc | 47880 |
| atcaaactca | aagaggtttg | agttgagata | gagaccatat | ggctcaaaaa | gtcaagaaaa | 47940 |
| ctatctggct | ctttacagaa | aaagtctgtt | ggcggctgat | ttgaaacatt | caaggaagtg | 48000 |
| tcctggatgc | ggcttgggcc | tttggctgaa | gtccaagaca | gcggcaaggg | gagtcccttg | 48060 |
| ctgggctcct | tctctgagca | ctggccactg | cataggaaaa | gctggatttt | caaaggagtc | 48120 |
| ctagagaaga | agccttcctt | tcaagagtta | ccaagaaatg | ctggctgagt | cagcggccct | 48180 |
| tctcaagcca | ggagaggaag | atactgagta | aatctctgcc | atctcctttg | gcagttagct | 48240 |
| ggcacaggca | cactctggtc | agaaagaaac | tttggattga | gaaatttcag | ttgagtaacc | 48300 |
| tttaggcttg | gagaatcgaa | ttctataagg | acttcagaat | ggctgctcag | gccaggcctc | 48360 |

-continued

```
atggttccct caatacggag gagcccagcc cctacagggg gtaccaagcc agctaggcct      48420
acagaagagt ctgaaatgtt agatttctaa gcagttatgg ctcattttac accacacctg      48480
gggtcctgaa aagctgtgtg tggtctgagt ctgtttgcct ccctaatctc tgtcatttca      48540
gaggctgcct aattccggat ggatttgaaa gagtgttggt tttcagattc tctgccccca      48600
ctcgtcaacc tctcagttca ggacctccgg tccagaaaca atcagttaag tgaactccta      48660
tttcttttcc taagctctgc attttgaaaa gcaatgccct actctgcttc tgttgtattt      48720
atttggtcta gatatctcca aagggtagta gcaacgcata tcatatgttc agccttcttt      48780
tggtttgagg tctaattatc tttacagaag ccaccaactt tcttttcctt atcccctgcc      48840
ccaaggaggt cacacttgga tccacccaat agtatccagt tgactacgta ggttccatag      48900
accctggtgg ctgctccccc ttccttgtcc ccgccgtctc tgcccatcat cctttcacca      48960
acttaaccaa atgctattgt gccttctagg gcctgttttt atcactcagc ctctattagc      49020
tttccctgat cccaccagtc cacactgtgc cctcttgtac tatgagtttg tattgtactt      49080
actaagaata acaaacatag ctgggcatgg tggctcatgc ttgtaatccc agcactttgg      49140
gaagccaagg caggcggatt acttcgggtc aggagctcaa gactagcctg gctaacctgg      49200
tgaaaccctg tctctactaa aaataataat aataataaaa ataaataaat aaataaaaat      49260
acaaaaaatt acccaggcat ggtgatgggt gcatgtaatc ccagcttctt gggagggtga      49320
ggcaggagaa acatttgaac ccaggaggtg gaggttgcag tgagccgaga ttgcgccact      49380
accttccctc cagcctggga gacagagcaa gactgtgtct cggaaaaaaa aaaaaaaaaa      49440
gaatatcaaa ttgtacctaa ttcttctttc tagttagggg accttctgta gtactgtaga      49500
aagagtttgc attctggaat ttgaagacca gattctagat tcacttatct aattcactgt      49560
acccttatgg gtcagtatta agttgtcctg ccccatgccc cactccttc tccttgcttt      49620 cacgtgaatt tagaactttg gggatgatta ggcaggtaac agactaatca gcataaagcc      49680
agtccacctg aaacctctgc ttaaaaccag ttccacctgt tgcctaaaaa gtcaaactag      49740
taattttaaa ataaggcatt ttgcaccagt tttcctaaga ggcacttcca atgtaacatc      49800 acttttttt ttttttttt tgagatggag tctggctctg tcacccaggc tggagtacag      49860
tggtgtgatc tcggctcact gcaaccttca catcctgtgt tcaagcaatt ctcctgcctc      49920
aacctcccga gtagctggga ttacaggcac ctgccaccat acccagctaa tttttgtatt      49980
ttcagtagag acggagtttc                                                 50000
```

<210> SEQ ID NO 4
<211> LENGTH: 50000
<212> TYPE: DNA
<213> ORGANISM: Homo sapiens

<400> SEQUENCE: 4

```
accatgttgg ccatgctggt ctcaaactcc tgacctcaag tgatctgcct gcctcggcct       60
cccaaagtgc tgggattaca ggtgtgagcc accgctccca gccgtaacat tgcatttta      120 aatcactatc acaacttgca gcattttgtc aataatgaga ttgttttgta tgcttgtggg      180 tgacttttc tattttctc tcctattgat cattttatg acttttagg gagtttgttt         240 gaagacctt tctttaaaat tgtatatttc tagcactaaa tacttgtcaa atctatagga      300
tttcccacga gatttatcaa atgaacccat tttgatccct cctctctgct tctcactgag      360
ttttgctctg tactgtgtat tcctgtgtgc acctaatggg tttattaacc aaattagcat      420
gtacccaatg ttcccttctg ttctgcaaga tattggcatt ttgacaacaa acgtgaagtg      480
```

-continued

```
atgagacaga tggggcagaa ttatattgaa ctctttgcat tttattttc aggctatctc      540 attcatcaag caactctact ttgtgaaaca taaaatgata caaacaaagt cattatcaaa      600
tgtatttatt gctgaaaaca taacatttt caagaaaggc aaactggcta aaaagtcctg      660
aaagtgttca aaagtagata aaatagcaga agacacccac caaggataca aaacaatttt      720
tagtagcgat cctgcattta atcagtatgt tcttaaataa actgctttaa aaaaattctt      780
caaatgacac tgccaaaaaa attaggacac ccaaacagat gccagaaaac ctgtaagtgg      840
gctggatttt atgtgacctg gtcattaagc atagggattc attttgtgag ctcatggcaa      900
atcagtttga ggccagttga cctagaaccg atttgggatg caggcactta cctccctgca      960
cgtgcaatat gtgggcatgg ggacacccat gaccccagg ggaaaggaat gcccctcctg     1020
aacatgacct ccaagagtaa gggcgaactg tcagctttta actgtttatt ataaagacat     1080
atttacacag aacaatcttt acaaacattg aacacagggg aagggaacaa tttcttaatg     1140
aacagggcct taatatcttt gtataaatta gtataagaat cataaacaac cactttaaat     1200
aaggcagccc cctagccca cccactaccc tcttctgttc cctatctccc agctttctta     1260
gccatccccc actttctccc cttccccacg gggctgggct tggctgcagg tcatggcagg     1320
ccgatgaggc aggagacaca gaaaggaagg gggaaagaag gcccaatccc tgatgggggc     1380
gtcagtggca gaagagactt tctgggcacc gaccagtccc cactccaagc atgagccttt     1440
aagcagcagc agcagcagca gcagcgttag cagcagcata ggtaaagggg cttgggggag     1500
gtggataggc aaacattggg gctattgtgg gacttggggg gccctgactc ccccgtcccc     1560
acacacacaa agttgggcat caggctcttg tcttctcttt ctccctcctg ggaaccctgc     1620
tcaagcaaaa ggggagaaag ccccctccaa ggaatggctg gtgatggccc ctcacggaag     1680
ctagggcctc ccggggagag ggtgctattc ctgctgcact tcctcccatc tttctttcct     1740
tccttctgtt cctttgcttt cttttcttcc ctccttcctt ctgcccttcc cttccttctt     1800
ctcccctctc cgcctccccc aaaggaaaag ccctggaagg aaggtccggt caacacgaag     1860
ggaaggccat ggagtccagt gattgaaggc tacctcggac tcctgaaaac caccctgggg     1920
ttgagcggta gtctcagtgc ctgagccgcc cctattagag tacctgggt ctgggaatgc     1980 tgccagttat ggggcagct ggccagttat ggaaccttcc agcccagctg ggggaatggt     2040
gcagcagggg taggtcaggg aggtgggagc agctccagcc ccacaacagg acagttcaca     2100
gccagcttgc ctctcccttc ccttcccctc ccagccaccc ccagcccag cctcgggaaa     2160 aggcacttca tttgctttga aaagacatca tcaagaggga agaggcgtc ataaagtagg     2220 agatgggaga cctggtcccc atcccggctc tgcaatgact ctgagcaggt cactcccctc     2280
tccaggcttc tgttttgcag gcgtttgcct aagaaggcta agtgaccttc aagggtcctg     2340
tcagctctaa cattctgtga ttcttggcaa aaacaacctc ttgcttggct tttactcctg     2400
ggagggtata tagccatgtc aggcccagca ccctcccctc ctgacctgga gcttgggcta     2460
gctggggatg gggtgtgggg gcaggaagaa gggagtattg ggaggcacac taaggcaaga     2520
gaagtgacaa aggacttcac gggcccctct ctacctctcc cttaactgag caaacgctga     2580
tgctccaccc acttcaccag agctcctgaa aaccaccctg gcacttccat gccccaatg     2640 tgccctgtct ggatcccgc agccagcacc tcttaactag agtctctcct tgcttttctc     2700
tgcattcttc cctggaggcc aggtgagggg tccaactgac aggaaaacaa gggatctgct     2760
ggagcccaca gaagggagca cttccacccc gcgctcaggg cagacatgag gaaggaaggc     2820
```

-continued

```
ccaaatgaag gtttggggcg ttagatgaga caggcaggga ctagggcgga ggggacctgg    2880
agaagaaggg aggctttctg gggctaggtc tccaaagtca gtccagggag gggccaggaa    2940
gatggactgg acggattctt gtgagagaac gggaatcatc caaactacag ccaggagcac    3000
gccactgggg gaagcaggca ggtgagaaga gctgggccca ctggtggcta cagcaggtgc    3060
gaggtgagag ctgaatggac gtgaggcctc cagagaagca gaccaatcta tggaggagac    3120
ataaccgccg ggggtgggca cttgggggcc ccttcagtcc taaggagaca aaaatgacaa    3180
gagagaagtc atggacatat cctaggccaa aggaactccc caggaaagga gaggagagag    3240
gagaccgcct tctctttccc ccaaactcca ctcagcccaa acctcaatcc caaggcccct    3300
gagttggtgc ctgcctgtcc ccactgcagt gggacagcca gcagaccagg gaaggggcag    3360
gcttcagctc tcctctctct gctgccacct tggttcttcc ctccttctca cagctccggg    3420
caaccacagc cacaactgtc ctcttgttct ctgcctgaga gcccctagag ctctctgcct    3480
ccttccccaa ctctggcgac aatctacact ggacatctgt aggtttgccc tgggcacccc    3540
tccccagcca ttaaggtcca ccaggatgtc tagaaatctc taagcaggcc agcctcccca    3600
accccaggca gcagggtgga agggagactg gcccccaagta tcaagcccct ctctaggcct    3660
cagacgagga gatcgtctgt aaaataaagg ggctagacag ctgccccata agctctcttg    3720
ccagctctaa gcctctgtga gtgtggcgcc aggactgttt gatggatgtg tctggccagt    3780
gatgagcggc aggatcaccc ggcttctagg ctgtccttct ccctccgctt tagcactgtc    3840
cactgaacag aggctcaagt acctgcttca gaaaggcatg ggtcccttat gggagaggcg    3900
gggccgctgg cggcggaatt tcctccgacc tccctgccag ggccctggcc cattccttga    3960
ccctctgggc tgcaccaggt ggcggacatt gccgtcttcc agcccattcc catcgggaag    4020
cggcatcagg gaccctgcag gaaggagaaa gcctgttagt gaggaaggtt gttggaaacg    4080
ggcaggggct gcagaccaca ggcccgcggg aggggtggtc tgtccatgtg gtggcacttc    4140
tcatagattt tctttgtttc ttttttttcat attgagggaa aatttgccat ttctgcactg    4200
tcctgggaca aacggaacct actactcaca tcttgccatt gatgtagctg actttctgtc    4260
cttttgacag ttatatcatg tttctgacag gcacaagtgg gttctttctt tggaacgtca    4320 ttgggggggtg tgcactttgg gttgtcacgc ctgtacttgg ctgggggggca ggaggcagta    4380 atcaccacgg caccctgca actggtacac ttcaaacatt tcagacatat gacattacaa    4440
tgaccctccc accgccatgg acccatcacc cagattcaac agttatccag atggagtcac    4500
atatgcttta gttatccctt ttctattttc cttgactgca gtattttaaa gcaaatcccg    4560
aacatcacgt cattgtactc ctacatcctt tgatatgcag gatgacccac ttgtgagtac    4620
tagggagctc atatctcgcc cctgggtgtc tcatcggtgg ttaggcatct ctagggcgcc    4680
aagtcctccc agtggatggg gctgggccag gcgggttaag ggggagaggt ctctgactca    4740
gcctgcctca tgctgtgacc agatttagag acctgagacc agatttagag accaataaat    4800
attgcatgaa tatttgagaa tgaataaatg aaacaatggt caccttcagc agcatgtctg    4860
tgcaccagga gggggtggg ctgttgcagt tggtacctcc ccaccaatgc cctacctcct    4920
gaaattccca gatcacaccc tgcatcctgt gtctcatgta aattccttcc atttcaatcc    4980
cagctggctt ctattctgca ctctggggct cctctttaca tctgtccaca tctgtcagga    5040
ggcttagagt agaggcctcc tgacaccaga ctgagccctg acaatggaat ccaagtggtg    5100
cagggtatcc ttgggtgcag tgagggaaaa ggcatgcagg ccgactctcg tgaagcctgc    5160
agtccatgca gggaagctga gctgccaccc ccaagacaag cctggctggt ggtggcaggc    5220
```

-continued

```
agtgtgtgga gatgagatgg tgctggggaa gaggcagcca ggcagggtac ttgtgcaatg      5280
tccagtacag gcctgtgcag atacagcatc tgaggccaga gataatgaat aacagtctct      5340 ctcccccctgc acaccatctg atttgcctgc atctagatcc ctgtccctcg agccccattg     5400
ccatctaccc aggaattccc accacttgct cacagtttcc atagagcctc ccattggctg      5460
ctcacacccc aatcataccc ctggcagctc ccccttcccc tctgcctctg cctccaacat      5520
ccccacgctc tgttccttcc ttggctcctt ggttttttgtg agtcctcctc tgcttgcaca     5580
caatttccaa gtgttcagcc tcctcttggg ccaaaagtgg gtgggtttgg ccttagggcc      5640
ctcttccccc aggcttctga gcctgcagtt ctccccactc acacccagac atacccaccc      5700
cctccacaca cacacacata aacacatatt ctccaagcct gcaccctcct tccctctttc      5760
cccaagaaaa attgccaggc ccatgaggac cccgctgttg acttgggtca tttggttaac     5820
tagccacact tccgtgccaa cttatccctt aaattcataa cctatgagaa ttaaaagaag      5880
aattatctta gcactttgga gcagtaagta tggatggaac aagggggctg cttctgtctg      5940
actgtcatag agctaccctc ttggcgccat ctgtgagggg gctggggctg gagagggaaa     6000
ggaaggaaag accttcacta agctccccac tgcagctgct tcagcctctg ccttgagttc      6060
tggggtcccc acaaggctca ccctgatcac tgagggcgga tctgaatgat gctgataagg     6120
agcaggggaa ggacctaggg gccttgtgaa gtgaaccaag tcaacacttg gctctcacct     6180
ctgcaccttc gactgctggg ggtgcagaag ggatggggca gtggtgcagg ccattgtagc     6240
tcagggtggt ggcagacatg gagaagagaa gcatggtgcc aggaggggga gggcatcatc     6300
tccaggtgct cagattgtga gtgtctggca gtcagaaagg gagggctaga ggccatatgt     6360
caggatgggg agcagggttg gtggctctgg ccaggaagat gtctagactc taggtctgca     6420
gagaagaacc actctgagct gactgaaccc ccagccgggc cctggagagc agccccaggc     6480
ttcttgcatc cctcccattg cgttggggac tcattgtcct cagcatcacc gagatctgct     6540
ggctcctccc gcactctgag cccgtcaccc acctgtttcc tacttttgat tctgagtctg     6600
gctcaccatc agataagctg acatctgaaa ccctggcttt atgctgtcca aaggaacaaa     6660
ttagaggctg ttgattctca tcactgcaga agtcttgact gtaaaaaaga attccccttt     6720
agaaatggag gccagcccta atgcacttaa atattttctt ccagctcatt tgctacgtaa     6780
aaggaggctg gagcaatcct ccaaacaatc tcgagcctag agagattgga gccattgcct     6840
gctgaagtgc catcagccac gaagctacaa catctccacg ctgagaacca cagtcagggg     6900
gaggacagga tttgactttc atgctatctg aactccaacc ctgccaatgc acaaagaggt     6960
acttgcgact tttcaggaac atgccagtct catcaggaat gacgcacctg ttttccctct     7020
ctcagtctgg cctgtcttgt gatgactttta aaagcccaaa cgtatgctcc ggtggggacc    7080
ctgctggcaa tgcccctcca ctgctctgtg gtcctgcatg tgtctctttg tctgcccagc     7140
cccccatccc agtcgccttc tccagggccc tgtgctgtct ccagtgccag ctttgctgcc     7200
ctgggataca tcatgctctg tctggtggcc ctctgcttcc cttgccttag ttcttttgcga    7260 ggagaggcct ggctcaggtt acacggggtgc ttagtgctga ggactgggga tggagtagag    7320
atgcccttcc ctgagcagga ggggtacagt aggctctcct cacactccca ctgtgactgc    7380
aggctttgag ctgggcctgc ggagggggag gagaagggga aaagaggggg tgctcagaga    7440
ccgagggaca cttggccctg gaccaggagt tctcagactc acaagagcaa agtgtatccc     7500
aggtcaggag gcagtggagg agtgtacgtg gtggtagcgg ggtgatgaga ggcagcgtgg    7560
```

-continued

| | | | | | |
|---|---|---|---|---|---|
| agagggtcg | ggggtggaca | tttcaagtca | ggacagactg | tggagaggag | gaagtgtggt | 7620 |
| tttcaggctg | gaactttgac | tggggactct | ggctggggac | agcatgccag | tccgggccaa | 7680 |
| ggacaaagtg | gttctgggat | tcctgcttct | aacccaggac | aggagccagc | gggagcagga | 7740 |
| catgtgtacc | tggacccttg | gctggtggcc | acttccaggg | acatgccctt | ccttggctcc | 7800 |
| aggagaagtc | agggagtaga | gaagtcagtg | agagccctga | aagtttccag | cacgaggctt | 7860 |
| gagcaaaatg | tgagggcaac | gaatttatcc | aaatcacagt | ggacagatga | cctaatgaag | 7920 |
| acggggaat | taaagcacga | agtggcaggc | tctggaccag | ccacatggtg | ttcgggcatc | 7980 |
| ctggctgact | tcccttccct | tgaaaccagc | tctctcccct | ttgctagtac | tgtcccaatg | 8040 |
| gctgggaccc | aggagggtct | gagtggttgt | ctattggcca | ggggtctccc | cacagcctct | 8100 |
| gggggagca | ccaagtgtgc | agatccagga | gccctacctt | cctctggaac | actctctgca | 8160 |
| cccagtcttc | ttcttccctg | aaggcaccac | cctggactat | ttgcctgtgg | tggtattgtg | 8220 |
| caagtgtcat | gccttgccaa | tgacaccaga | tggtaggctc | cctgaggata | ggctggtatg | 8280 |
| gtgtatcatt | cgtatcttac | attcgtatct | tttgctccct | ctgttacctg | cctgacagga | 8340 |
| gtttctgtgg | aaaagccta | cccacttctt | actgtggtgg | tggctcactt | cgtgttcagg | 8400 |
| tcttgaatag | agaaatcacc | ggccagctac | ctggaggcag | gaggtgccag | ccccaaccac | 8460 |
| tgcacctttc | tgagaagcca | ggcagtgttc | ccagagccaa | agcagggcca | aaaagcaaga | 8520 |
| gcagagaaag | gaggtggcct | gcgatgagag | gcaggcagag | ctggctgggc | ccctcggagg | 8580 |
| ctcctgggct | gcatgccatc | ctcctgttct | ggagggtttg | gaaccactta | gggccctgtg | 8640 |
| cccttgcccc | aggaaactca | ctgccctgcc | ttctccttct | ttctgctccc | acctccctgt | 8700 |
| gactccagcc | atggtcctgg | cgttagtcca | cctggtcttg | gccttcccct | tgtgtggtgc | 8760 |
| caggcaggca | gcaatgacag | ccagatcata | ggactgtggc | agctggaggt | gggagctggc | 8820 |
| agccccagga | gacattgaca | cagaggacag | gcagcctggg | atggggctgc | tggggcgtgg | 8880 |
| ttggggacca | ggctaggggc | ggacatgggc | actagtgcca | agtattggca | ggtgagggca | 8940 |
| aaaggactcc | cctttcctga | gctgcaggga | ggggtcgggt | caggtgctgt | gcttcctcct | 9000 |
| ttggtgccta | gcggcaggga | gactaaagtg | aagcatgtcc | gtgcctggga | cagaaaggaa | 9060 |
| ggctggagcc | aggatgtaag | agaaccaagt | ctctgggggt | gggatggagg | ctatggggag | 9120 |
| ggcatcctgt | gcaggggagg | agaccagcca | ggaccttggg | gttagggagg | agaagaccag | 9180 |
| cccagcccgg | ctgggcccgg | ccctgcctgg | gggaggctgc | ctctgctcac | acatgcaggc | 9240 |
| cgaaaggagc | aacagctggg | ctccatgccg | ccacccccctc | cgcgcactcc | tgcctatgca | 9300 |
| acaagtgtca | cgtctgcatg | ttggcacatc | atccccggtt | tcccgcgccc | ctggactggc | 9360 |
| gggaggctcc | cagccttcag | ggaccagaag | acgttcaaca | tgggagccca | gcccactcga | 9420 |
| ctctggtcag | ttccttccat | cgatccacga | gggagcgggc | atgtcccccg | cctccacctc | 9480 |
| taccacgcgg | ggtgcagggc | gtgggacacg | cggcgcacac | ctgtggtcct | gagctcctgg | 9540 |
| gactgcgagc | gacggttagg | agggacaagg | tgacgggcag | gtgatgccaa | aggccgagtt | 9600 |
| gagccccgca | aaagaagcag | tccttgtggc | cagccgcccc | atggctcggg | gcgctctgtc | 9660 |
| aatctgctgc | ctggcgctgg | ccggcgcgtg | gctgctactg | cacggctcgc | gccgggctcc | 9720 |
| ccgggaggcg | gggagagtgc | gaataggggcg | gagggaaagg | agcacgccgg | ctgcagcccg | 9780 |
| ggcgagcggg | agggcgcgca | ctcacctcca | cacaccgcgg | tcaaggagag | ccagagcagc | 9840 |
| aggagcgcct | gcacgcagag | ccgcagattc | atgctgctcc | ttgggccgcc | gcggcccgg | 9900 |
| cgagccggcg | cggggagga | gaggtcgggc | gcccggaggc | caagaaaggc | gcgagccgcg | 9960 |

```
gctggcgcgt gcgggcgcag agctcgggag gctccccggc cgctgagtgt gcgcgctgag    10020
ccccgccgct cccgctggcc gcctccgctc ttctgcagcc tcctctcccg ccgcggggca    10080
gcgccgcgaa gctggcctcg gcggctccgg gagcggcagc ggcgagctct ttcttagcgg    10140
ctggctgctc ggccgcggct gcaactgccc gtgaccccgg ctgccagaga gaatgctccc    10200
cgctcactcc agggctgca ttttgtagct tgtggcttgg ccgcgagccc acttggtcat    10260
gtggtcatcg ggagggctag aggggggca ggaagaggga gagggagcga gcctcccgca    10320 ccgccccct ccaggcacgc actctgcagc cccagcccga gcgtgagcgc gagagggaac    10380
cccgaggtgg ccccacaaca aaggctgcgc ggcctctctg acaacctaca accgctcccc    10440
ggacaatgcc cgcctggccg ggggccagag ggtttgcaga gacctgaagg atttcaaaca    10500
caggaagcat tggggcggt ggagggcac acttaaccct ttctcacctt gcttccttaa    10560
cagctgtcag gaaacctggg cgcttaggga aggactcagt ctgggttgcc ttcactcacg    10620
ccctctacct ctgaccctgg tccttgccct tgccgctggc cagcttcaag ggtttggtca    10680
agacaaccaa acactggccc tcctctctcc tctgcatttt caactggctt tgaattgggg    10740
gtgactgcct aggcttgtgc ccaaggcttg attaattgcc caggcccctc atgttccctg    10800
catcccccag gaggcaccct ctacctggaa tgccccacc ccaccttcc gtgagcaatt    10860 cattctttgc agcagcacct caaatcccat cgcatccaga agccttctca ggataacact    10920
aatccagcag gggccgccca tcagctcctc cccactgttg ggacatggga cagctcctat    10980
ggtctaccct ttcttgttcc ctggagctgt cctcattcta gttccccatc aacgtaagag    11040
gcaggtggtt tacccaactc cacacagtca aggctggatt cattttgcgt gtacttgcga    11100 ttccgctta gaagcgggtc ctgaagttgt ttgccttcc agactcgatt gttagctgct    11160
tctatagctt gggagctccc aaggcatggg gctgcttccc tcattggact gggaacccc    11220 taaggtagga tactgtcttc tcactcttct ggatctctcc aaagtcccca atatcttgct    11280
ctgcacatag gtggcactca acacatatta aaagactgaa tcgaaaggtg tctccacctt    11340
tcagcaagcc aggcagtttg cttgaagtgt taagtccaga tttacacaaa agatacattg    11400
gacagggtgc gtgtgtgcca taaaagacat gagagaccat ggcatattta aaatatcttt    11460
gaaatgttgc aaaaatccta tatatacaca atgtatttat tatcagtctc tctccaccag    11520
aagggttacc tccacaaggg agggatcttt gctttgttca cagctgtgtc cccagaccta    11580
gaacagtacc tgcgacatga ctggtactca atacataatt ttgaatatat aaatgaaatt    11640
ttcaaaaaca tctttactgc ctaaattcag gtagcaggaa gggaataaga taaggttctc    11700
attaatagcc tatggcccat taaccacact caagtaaaaa aaaaaagcat gtgaagcatg    11760 gcaccctct tcatccttga gacccaggat atgagtagca gacatgggta gcaggagacc    11820 attctcctt cactgttccc ctggaaagag tttgcttct ttctctttc ttttcttt    11880 ttttcttttt ctttctttct tcttttttt tttttttttt ttgagaccga gttttgctct    11940
gtcgctcaag ctggagtgca ataccctatc tcagctcact gcaacctccg cctcccaggt    12000
tcaagcgatt ctcctgcctc agcctcctga gtagctggga ttacaggcat gcgccaccat    12060
gcccgactaa ttttgtattt ttagtagaga cggggtttca ccaggttggt caggctggtc    12120
tcgaactcct gacctcagat gatccacccg cctcggcctc ccaaagtgtt gggattacag    12180
gcgttagcca ccacgcctgg atggaaagca ttttctaacc aggaggagaa acacctggct    12240
tctagtctcc accctcattt gctgtagggc cttgccatca tcacctaaac ttactggggt    12300
```

```
tcatggaggt gataatctct gctctaccca cttcaaagtt gttatgggat taagtgagat    12360
aatgtgcctg aaggtaccgt gcaaattaag aataagctct tgcagggttg tttttaggaa    12420
acttggtgct ccaatccttg attgggcaag cccatgcaca cccaaataag tgtcccccat    12480
aactaggtta atagaagcct tcatatttaa ttgcacctttt actagggtgt gtatggcata    12540
ttgctaagtg gttggaacac atagcgcttt ctaatacaat agccactaat catatttcca    12600
atgaagttta aaattcagtt cctcagttcc actggccacg cttcaattgc ctatatgtgg    12660
ctagtggcta ctgtattgga cagcacagaa tagaatcttc aatcactgca gaaagttcta    12720
ttggttagag cattcattca ttcttctttt ttctataatc cattttccca ccctacctag    12780
ccttcaaaat gtacaaggtg aggggaaaaa agcataaaa gcaaaccaat agaaattcaa    12840
gccaagctga aggcatgcgt ttagagtaag atttaaagat ctgacacttg ggagaatcat    12900
tttttaattg aatccttctc ttcatttaac caaattacat ccattttttt ttagaggcag    12960
ggtcttgctc tgttacccta ggctgaagtg cagtagtgca atcacagccc aatgcaggct    13020
caaacttcta ggctcaagtg atcctcccac ctcagcctcc caagtagctg ggactacaga    13080
catgcaccac cataccaggc taattttttaa atttatttat attttttgta gagactgagt    13140
cttactatgt ttctcaggct ggtcttaaac tcctggtctc aagcaatcct cccatctcgg    13200
cctcccaaag tgctgggatt acaagtgtga gtcaccatgc ctggccacat ctgttttcgt    13260
agtcccagat ccaagatttc atctttcttt ctcaggacac ccttgcccac agtgactttg    13320
ccctctccat aacagctatg gctgtacctg tcattggtag gtcctctcac agtgcatcag    13380
gaacactttt gcatctgcac actgtgctct acgggcctgc tgtaattctg cagagaggac    13440
ccatcaccac catatccatt cagggtcaa ggcccatgag gcaaggaacg cagctctgat    13500
tgcccactct gaacccccttg taggctccca gatatcttaa tatcagattg aaatgaccag    13560
ttttcgaata tctgtatcta tttgccagac tttaaggtca ctgctgtgat agcacctagc    13620
acaatgcctg gcacataatt gatacttcat aactgcctgt caggtgagca actgtcggcc    13680
caacactgtg ctgtcttttg ttcaggatac tattgaatga atatcagcag gataaatgtt    13740
ttaaggcata agtctccaat ccctgggcca tggaccacta tggctccctg ttctattagg    13800
aaccaggcct cacagcagga ggtgagcagc agatgggcca gcgaagcatc atctgtattt    13860
acagccgctc tccattgctc ccattaccac ctgagctcca ccttctgtca gatcagcagt    13920
ggcgttacat tgtcatagga gcacgaaccc tattgtaaac tgcatgtgtg agggatctag    13980
gttgcatgtt ctttatgaga atctaatgcc tgatgatctg tcactgtctc tcatcacccc    14040
cagatgggac catctcagttg taggaaaaca aactcagggc tcccactgat tctacattgt    14100
ggtgagttgt agcattattt cattatatat tacaaaaaaa aaatagaaat aaagtgcaca    14160
ataaatataa tgcacttgag tcatcctgaa accatccctc ctaaccctag tccatggaaa    14220
agttgtcttt catgaaacca atccctgatg ccaaaaatgt ggggaccact gtttcaaggt    14280
atttctctgg agatgggaag gaggtacatg aaactgtcca cactctcctg ccctgaggca    14340
gcaagtagct gtaaaatttc tggaaatgtt gctgcatttg gggctcagga cctgtggtca    14400
gcagcaagac tcagttttcca gtcaaggtga gggacaatcc tggggggcaag ggtaggactc    14460 agtgcattgt tggggacaga agtgagatag ctgacctatg tgagttcaaa gtgtgacttg    14520 ccccccctcat cagagctatc cacatgctat tcagttctgc ttattgtcct atgtcaccac    14580
cagccactgc tgttcagttg actcatccac gtctcttgtg ggttaaagtg aacagtgtga    14640
ggcattaaaa agaactcagc ttttggagtt tcacataact gaattcaaat cctgcccctc    14700
```

```
aaccccattc gttagctgtg tgaccttggg caagttattc agcttctctg aggctcagtt   14760
ttttcctctg ttaaatgagg ataataatgg tacctaattt tttaagtgct aaggtttgaa   14820
tgtatgtgtc cctccaaaat tcatatgttt aattttttg tttttgtttt tggagatgga   14880
gtttcactct tgttgcccag gctatagtgc aatggtacga tcttggctca ccgtaacctc   14940
tgcctcccgg gttcaagtga ttcccctgcc tcagcctcca gagtagctgg gattacacgc   15000
atgtgccacc acatccggct aattttttat attttagta gagatggggt ttctccatgt   15060
tggtcaggct ggtctcaaac tcctgacctc aggtgatccc ccgccttgg cctcccaaag   15120 tgctgtgatt acaggcgtga gccaccacgc ctggcctcat atgttgaaat taaaagccca   15180
aggtgatgtg ttaagaggaa gggccttttg agattgatta agtcatgagg gttccaccct   15240
catgaattaa ttagtgctct tataaaagaa gttggaaggg gcaccctagt tccctttttg   15300 ccttctgtc ccttatgtca tatgaggaca cagtgtttga acgctccaga ggaagcagca   15360
ttcaagacac catctagtaa gcacagactg ggccctcatc agacacagaa actgccagca   15420
ccttgatctc agcttccca gcctccagaa ctgtaagaaa taaatttgga ttatttataa   15480
ttatccagtc tcgagtattc tgttatagca acaggaatgg acaaagacat tatggttggg   15540
agattaaatg agataatgtg tgtaaaatac ttagcacagt cccctgctca ttggatgtta   15600
gttttctcct cttcctgacc tgcttctccc cccacctttg ggtctatcct ctggccttct   15660
gaaactgatc aggaagaaag ggctctgata tggtttggat ctgtgtcccc accaaatctc   15720
ctgtagaatt ataatcccaa gtgttggagg tggtgtctgg tgggaggtga ctggatcatg   15780
ggggcagagt tctcatgaga ctgggtaatt tataaagaaa agagttttaa ttgactcacg   15840
gttccacatg gctggggagg cctcaggaga cttgcaatta tggtggaagc caaggggaa   15900 gccaggcaca tcttacaagg cagcaggaga aagagagagg gaggggaac tgccaaacac   15960 ttttaaacca tcagatctta tgagaactca ctcactatca tgagaacagc atgggggaaa   16020
cgaccccatg atcaaatcac ctcccaccag gtccctccct caacatgtgg ggattacaat   16080
tcaagatgag atttgggtgg ggacacagaa ccaaactata tcactgccta acctcaaagc   16140
ccacactctt tcctcactga acatcaagaa gcagtttctc ggggaggctga ggccggggaa   16200 tggcgtgaac ccaggaggcg gagcttgcag tgagccgaga tcgcgccact gcactccaga   16260
ctgggtgaca gagtgagact ctgtctccaa aaaaaaaaaa gaagcagttt ctcactttt   16320 gggtccacct atcactttat ttgaacttct agcacctaac tcatactgtc ttgaattagg   16380
aagccatgaa gtacatagtg gttaagcaca tgggttctag aataaggcag ctctgtctct   16440
tactacatag gtaactttga gcaaattatt aacctttctg agccttaggt gcctcatcag   16500
aaaaaagggc tagcacctag ctcccattgt tactgaaagg attaaaagaa tcaataccta   16560
taaagtactc ggcactgagt ttggttctta tagtaaggga agcattgtgt aaatgttaca   16620
tattcccatg ggtatttgta tatatctctg acttatatga gatagtaaca ctatgtctta   16680
ttcgttttta tattctcacc agcagtgctg ttgcccaaag caaatactca ataaatgttt   16740
gttgaatgaa agaaggaatt gtatattctt gttaataatt gctctaggtt tatgatccat   16800
atcaagtgtc tctatttggg caaaatcatc acaacttgtc caactggttc ttagatgggt   16860
caacactaac agctaacaga catacacaaa gatgtgacca tcttccctct cctcattgtg   16920
tagtagttgt ttttactgga tcaatgcaaa aagtggagtg gggagaggac atctgaagaa   16980
ggatgaccct ggccagcaat cagagagatt tcataacagc aagagcccca accccctcat   17040
```

```
tatgcagatg gagaaactga ggtccagaaa ggaaaagtga cttacccaaa gctacacaga   17100
aagctggtgg caaagtcagg acggagccta ggttcaacta atcccaact cctattttc    17160 cttctgtgtc ttcccagcat agaagtagcg ctcactggcc aagcagtccc ctagctggct   17220
gcataggcac aacaaaatga ctgtggttag gcacaggatt ctcattccat aggccagcgc   17280
ttttggagca tctcagaatg agtcttccca ttgtcactca tctaatttgt tccttaagac   17340
ataagctaaa ttaatgagca aaagaagttc agtagcagca acatcgggaa aaagtattta   17400
agaagaactt caaagcttac cctgcctctg aagctactta acaggaactt ggggggaaaaa  17460 agcatgggcc agctgctagt tgatgcctca ctaactagct tcatgacaaa ttatctttgc   17520
tcagttaacc accacaagag aacatgaatt tttcactctc tcattactga gtatttgtct   17580
ttctgatact aacggctaga gttgagcttt ctaactcatc tataaccacc agagcagcca   17640
gcacaatgct tgccatagag tagtagatgc ttaagccata ttcatgggtt cactttccca   17700
ttctgggtgt gagaccattt aaatcagaga catgatgttc attatgtgaa acttagcctg   17760
gaacttattc tgtgaatcaa aagatcctaa taatcatttt gagggaataa tctcttttgtt  17820 ggactttgct ggggtttctt cttcagctaa ctgtgtgatt cttgtcttga tgtccaatac   17880
ctcttaattc tgatcaccag ctaggtccta agcctggcca cagaccgaga tcttgtcttt   17940
cacacttgcc ctcttcccaa gcacacagag tcaaatacta accatcacac ggtatcaggt   18000
ttgcaaaaat tagagaagta gccattttgc agcataacca cattatctct attcacatct   18060
caagtgttta atactatatt caagtcacta catgctaatt ccttccatgg gacacctttc   18120
agccactgcc acatgggctc caactgccct ggaaatgctt attccatttc tctgtttctt   18180
ccaacttctt tgcaaactac ataccttctc agatcgtctg atatattcaa ggaacaccag   18240
gggttcccac agatacgcct tccttgacac aacacccaag ttcctgaaaa atgttgtcag   18300
tggaattcag ataatcagct atatttcaaa tgtctttgaa gggttcacag tttattagct   18360
gaataagtcc taagagagat tctctgaggt gaagaactgt tcctctgttc ctgccccag    18420 cccagcccag ctcacagaa ttaccccctt ttccctacat cctgcttcat tccttctgat    18480
cctctcccat agccacacag gtccccattc ctcctgtttg tctttcagag cagtttcatt   18540
tcctctgcat atcctctatg acgtctccca ggagcctcca tccttcctct ccctacggt    18600 ctataaatan cctggtctcc caggggaggc atgtgaattc cttccttacg cagcaaggcc   18660
ctgtgagtta ggatagccac tcccaaagga gcaggtttat ctccaaagtc cattgaacct   18720
ttcttcctct tgctttgctg gttaatatta tctgggctta tatcatgtaa gatattatat   18780
gtctcaaatc tggcacctt tgtttgcagag ccagggcaaa gactgttgag gacacggtat   18840
tgagtctatg accagttccg ttatgggctt agagttctgg gataataagg tcaaagtcag   18900
agaganaatg aggtcagctt tgttctatcc caaactcaag tttggattga caccagtcac   18960
tacctgaatc ctaaccatgg ccacagactg agatcttttg aggttcttac tttttgactt   19020
tcatacattt cccatacaca taagagagaa gtcaaatatt gtactaaaat ttaaaaggta   19080
acacttctgg agaaaaaaga aagaaaacta gccatcttac agcaaaactc catgtgttaa   19140
tttctcaggg ctgctatgac agattaccac aaacttcgtg gcttaaaaca acagtttatt   19200
tcttctcact tctggaagcc agaaatctga aatcaagaaa gctctagggt gagaagttta   19260
tgataaatta gtgaagtgat agatgtgtaa attagtttga ttgaatcttt ctacaatgta   19320
tgcatagatc aaaacctcac attgtaccct ataaacatgc acaattatca tttgtcaatt   19380
aaaaataaat aaagataaaa tgaaagtgta agggaggatt cttccttgcc tctttcatcc   19440
```

```
cctggtggct ccaggcattc tttgacttag ggctgcatcc ctccaatctc tgcctccatc   19500
ttcatcttca catgacctga ccctttttgtc tatgtgatat ccttctgcct ctctagggtc   19560
tcactctgtt gcccaggctg gagtgcagtg gtgtgatcat agctcaccat aacctagaac   19620
tcctggcctc aagcaatccc cctggctcag cctcttcagt agctgtagct acaagcacca   19680
ccacaaccag ctgatttttt atttttttatt tttttttgtaa agacgggtct tgccgtgtta   19740
cccaggctgt tctcaaactc ctggcctcaa gtgatcctcc cactttgacc tcccaaagtg   19800
cttggattat aggcgtggct gcctcactct tataaagatt gtcagcaatg gatttagggc   19860
ccacttggat aatccagtat gtctctcttg agatccttaa acttcttaca cctgcaaaga   19920
ccatttttaa atgaggtgtc aaatttacag gttccagggg ttaggacata gacatatctt   19980 ttcggggggct actgttcaac ccattacacc ccactacctc catttacatt tctggcatgc   20040
tggaatcaac acagcatgaa ctttctgcca atttaacctc caaatatctg tcaaatctac   20100
acgtctctat gtttctgctg ccctattctt gttccagccc tgtcattcct cacacatcat   20160
tctccatagc aaccagaatg gttatgccag ttggcttgaa aaccttctgt ggctcatggc   20220
tcttaggaca agaccaaact cttaaccatg gcatgcaagg ccctgcataa tctagcccct   20280
acccacttcg ccagcctctt ctcttgcctc ttatcctctt tctatctgca atgccatgtc   20340
cctcctgtca cagtgccttc ccaatacttt ttcctcctac tgaatgattc tctgctctac   20400
cctgtcttct cctggctaat gcctatcatc aatcagctca tctctaatgt caaatcactc   20460
ctcctcaaga gatgttttcc ttggccctca gactggctga aattcccctg taatcgcttc   20520
tcatagttca caattcagtt tgtgttcagt taatgtctgg ctcacccccat ccaccccctca   20580 ctgtccaact agactgaact ccataagggc aggggccatg gctgtctggt ttcatgactg   20640
tgtcctcagc atctagccag tgtctaactc atagtaggtg ttcaatcatt ttcccaatca   20700
atgcatatat gaatgaatga atgaataggt ctgaacatct gtgctttgct ccctcaagtt   20760
cttctaaaaa atgagaaaac aatgtttcac tcccagggtt gaataagaat caaaacaaga   20820
gaatgaaagg gaaggagctt tataaaccat gaaacgcctt actaatttga ggaatcatta   20880
caatactggc caatgtaacc attcttctgg gggagtggga agtgcactgt gcacgactta   20940
ggggtagcag gaggaacaag ggtggagtg gggaaggata cttgagttct acattcctct   21000
ggataagaag aatttctgtg gctctgctat gtaggataaa attacaagaa cattcaattc   21060
ccctgcttca ggcttgaagc ttataactga tcaccctctg ggatcaagaa gaaaatgcca   21120
ttctgctcag gtgtaaatat tgcccggagt cacctcgggt atttaggatt ttgactgtct   21180
tcctttaaag catctgaccc aggtgcaggc tgaggatagg gtgacagcct cctgggctgg   21240
atccctcttg gctggtgctt cccatgaggt gatccatcag ccgtggcact tgcttaaggc   21300
actgcccagc tgacaaacgg ctttgaagtg tgccttttgg ctttgcattc ttccacttcc   21360
tggccttctt ggctttcact gttagcaggc aggcggaggg gttggcgggg ctgggtgggg   21420
gggcggggga ggtggtatca cctccttcct cttgctcctc tagcacgtcc atctaaaaaa   21480
catcccagga ggcttgacat tccaggtctt tagtttctta catttgattt ccctagaccc   21540
catcaagtca taatctcctt cctgcaggga agggatactt ccacctcttc ctccatatcc   21600
tcttagctcc ttgcatttgg gtcaagagac ctaaaaggc catttcttat ttccatcttg   21660
tcttccattg ttttatcccc tgggatatct ctgcattcat ggccctgaga tgcctcactg   21720
gtctggaatg ctcagggcaa gccgatcctc tgaatcatag acaaagaaac tggaaagagg   21780
```

-continued

```
agtgctcatt aggctgtcat ttccccagtt tcctccactg acctggatgt cttttccactg    21840 gtttggtggt gtgcttcccc actctgtccc actggatttt gaggttcagt ctacacagcc    21900
ccagagaggt gaataacaaa agcatgtcta cgcataatcc aagcaaaatc ctcagttttg    21960
tctcaatgat ttgggcatcc cagtacaaag gactacttca gtagcaggct ttgggataat    22020
tttctctaat agttaccaca gaattgaagc tggaaaggac cttgaagttt atctgttcaa    22080
agacaccctc cttttttgtt tatagcgcta tagaggtata attgacatac aatacctgca    22140
caagtttcat gcagtgtaca aaagtgtaca atttgctaag cttttacata tacatactct    22200
catgaaacca tcaccactat caagttttca tcaatcccta cagtttcctt ctgcctcttt    22260
gtaaactctc catccagccc ctcccctctg ctccatctcc aagcaatcac ttggggataa    22320
tgctttcaag cagtcacctg gggatggagg agaggggagg ggctggaggg agggtttact    22380
tgttaatata tagtttgcat tttctagaat ttttaataaa cagaataaca caatacgtac    22440
tctgtttttg ctggcttctt tcacacagaa aaattatttt gggatttatt cctgctgttg    22500
tatgtattaa cagtgttttg tgtatcagca ggtcattact tttgaatggc tgagtggttt    22560
ccaccatatt ttgtttattc attcatgtgt tgatgcacat ggatggtttt ttttttctag    22620
atgttggcta ttgccaataa aactgctatg aatattcata tacaagtctc tgtatggaca    22680
aagactttca tttcccttgg gaaaatacct aggagtggaa tgctaagcca tatggtagat    22740
gtctgtttaa cttttataac actaccaaac cattttcaa aatggtcata ccatttaaca    22800
ttctcaccag tagtgtatga gaattccagt tcctccatat cctcaccaac acttggtgtg    22860
gtcagtcttt tgtttgtttt ctttattgtg gtgaaaggta tatataacaa aatttaccat    22920 ttagacccttt ttaagaagac ttcatttaca tattttttaa ttgtaggtaa ttacacataa    22980
caaattttaa ctgttgttaa gtttatattt tgtcagcatt aagtatattc acattgctct    23040
gcaaccatta ccaccatcca tctccacacc ttttcacct ttccaaactg aaacactgta    23100
cccattaaac attaactttc catttgcgcc ttccccagcc cctggcaacc accattctac    23160
tttctgtctc tatgactgta actactctac tacctcacat aattggaata gtacttcagt    23220
cagtcttttt aactttagcc attcgaatag atctgtagtg gtatctcact gtggttttaa    23280
tttttatctc cttaatggct aatgaggaaa gcatctttat atgtgtttat ttgccatcca    23340
gatatcttat ttggtgaatt gtctgttcaa atatttagtc cattttttat tggttggttt    23400
tcttagtatt gaattatttt aacaaacttta ttgagatata attcacatac catacaattc    23460
accagtttaa agtgtacaat tcaatggttt ttagtatagt tacagagttg tgcaaccatc    23520
accataatct aatattagaa catttttatt atcccagaag gaaactccat atccattacc    23580
agtcacttcc cattccccta cccttccatc ccctggcaac caataacctt ctttctgtcc    23640
ctatagattt gcctttttctg aacattcgta tgaatggagt catacaatgt tggccttttg    23700
tgtctggctt cttttcactag cataatgctt tcaaggttca tccatgttgt ggcatgtatg    23760
agaaatttat cccctttttac tgccaaatca tatccaattg tttggatatg ccacatttta    23820
tctatccatt tatcagttga tggatatttg ggttgttttt attttgact attatgaata    23880 atgctctatg aacatttgtg tacatattt tgtgtggatg tatgtcttca attctctcag    23940
gaatataact acaaatatgt acttgggcca tatgacaact ccatgtttaa ccatttgaag    24000
aactgctaaa ctgttttcca tagcaacagt accactttcc attcccacca gcaatgtatg    24060
agggttccaa tttctctata tcctacccaa acacttattt ctgtttttgt tttattata    24120 gccattctag tgtgtgtgaa gaggtatttc attgtggttt tgattttcat ttcccttatg    24180
```

```
actaatgatg ttttatgtgc ttgttggtct tttgtgtatc tttggagaaa tgagcctttg    24240 cccactttt  gattgggttg tctttttatt gttgagttgt aagagttcat tacatgtttt    24300
ggatactagg ctcttatcag atatatgatt tgtaatttt tctcttattc catgggttgc    24360
cttttttctt tttcactttc ttaatagtgt tctttgatgc acaaaagttc ttcattttga    24420
tgaagtgaaa tttatctgta ttttccttgg tgcttttggt gttatatcta agaaacaact    24480
aatctaagag cacacagatt tatacctatg ttctaagact tttatagttt gacctcacgt    24540
ttaggtctat gctctatttt gagtacattt ttatgtgtga tgtaggaaag gagatcaact    24600
tcattgtttt gcatgtggat atccacttgt cccagcacca tttgttgaaa agactattct    24660
ttctctcatt gaattgtaaa cagtattgtt ctaaatttc agtttccaat tgtttgttgc     24720
tagcatatag aaataaagtt gacttatata tattaatttt gtacccagaa accttgctaa    24780
tgtcatgtat tagttctagt agatttcttg tagatccttc tagattttct atatacatga    24840
tcatgttatc tacaaataaa gacagttta ctgttttact tcttcctttt ttatctagat     24900
gcctcttatt tcattttctt gcctcattgc actggctaga acttccagta aaatatcgaa    24960
taagggcaga catttttgt ctatctcctg atcttagggg gaaagaattc agtagtcaac     25020
cgttacatgt taactgtggg ttttcataa tacacttcct caagttgaga ttgtttcctt     25080
ctattcctag tttgttgaga gttttctta aaaaggatgt tggattttgt caagtgcttt     25140
ttctgcatct actgagataa tcctatggtt tttttctctc cttttgttta ttaatgtggc    25200
aaattacatt gcttgatttt caaatgttaa gccgactttg ccttgctggg ataaacccca    25260
cttgatcgtg ggtgtatcct cctatttcta tattgttaga tttgatttgc tacaatttta    25320
gcatagatgt ttataaggga tactgctctg tagttttctc ataacatctt tttccttttt    25380
tattatcagg gtaatgctag taataaacat agctaaaatg aaaagggaaa tatttcttcc    25440
ttttcaattt tctgaacag tttgtataaa attggtatta tttctgctta aaatatttg      25500 tagaatttac caataaagtc atctgaccct gaagttatat ttgtagaaag ttttttagcc    25560
acaaagtcat tttttaaata gaaggctatt catagtgcct gttcttcctg agtgagttta    25620
ggtgttttgt gtcttttcaaa aaattttcca tttcatctaa gttgtcaaat ttactggcaa    25680
aaagttgttc ataatattcc cttagtattc tttaatatt tggagaatct gtagttatgt      25740 caccctgtc attcttcaaa ctggtaattt gtgtcttctt tcttctttc ctgattagcc       25800 tggctaaaaa tatatcaatt ttattgatta tctctaagaa cttcagatgt tctctaagaa    25860
ctttcaactc taagcttttg gcttaattcg ttttctctat tgtttgtttc ttttctattt    25920 ctttaattc tgctttgatt tttattattt tctttcttct actttgggtt taatttcttt     25980
atctctttct agtttctttt ttttattatt atactttaag ttctagggta catgtgtaca    26040
caacgtgcag atttgttaca tatgtataca tgtgccatgt tggtgtgctg cacccattaa    26100
ctcgtcattt acattaggta atctcctaat gctatccctc cccctcccc caactccacg     26160 acaggcccca gtgtgtgatg ttccccaccc tgtgtccaag tgttctcatt ggtcaattcc    26220
cacctatgag tgagaacatg tggtgtttgg ttttccgtcc ttgcgatagt ttgctcataa    26280 agatggttc cagcttcatc catgtcccta taaggacat gaactcatca ttttttatgg      26340
ctgcatagta ttccatggtg tatatgtgcc acattttctt aatccagtct atcattgatg    26400
gacatttggg ttggttccaa gtctttgcta ttgtgaatag tgccgcaata aacatacttg    26460
tgcatgtgtc tttatagtag catgattta atcctttgg gtatataccc agtaatggga      26520
```

```
tcgctgggtc aaatggtatt tctagttcta gatccttgag gaatcaccac actgtcttcc   26580
acaatggttg aactagttta cactcccacc aacagtgtaa aaatattcct atttctccac   26640
atcctctcca gcacctgttg tttcctgact ttttaatgat cgccattcta actggtgtga   26700
gatggtatct cattgtggtt ttgatttgca tttctctgat ggccagtgat gatgagcttt   26760
ttttcatgtg tctgctggct gcataaatgt cttcttttga gaagtgtctg ttcatatcct   26820
ttgcccactt tttgatgggg ttgtttgatt ttttcttgta aatttgttta agttctttgt   26880
agattctgga tattagccct ttgtcagatg ggtagattgc aaaaattttc tcccattctg   26940
taggttgcct gttcactctg atggtggttt cttttgctgt gcagaagctc tttagtttaa   27000
ttagatccca tttgtcaatt ttggcttttg ttgccattgc ttttggtgtt ttagacgtga   27060
agtccttgcc catgcctatg tcctgaatgg tattgcctag gttttcttct agggttttta   27120
tggttttagg tctaacattt aagtctttaa tccatcttga attaattttt gtataaggtg   27180
taaggaaggg atccagtttc agctttctat gcatggctag ccgttttttcc cagcaccatt   27240 tattaaatag ggaatgcttt ccccatttct tgttttttgtc aggtttgtca aagatcagat   27300
ggttgtagat gggtgctatt atttctgagg gctctgttct gttccattga tctatatctc   27360
tgttttggta ccagtaccat gctgttttgg ttactgtagc cttgtagtat agtttgaagt   27420
caggtagcat gatgcctcca gctttgttct ttttgcttag gattgtcttg gcaatgcggg   27480
ctcttttttg gttctgaaaa ctaagataat tgatttagga actgtgatgg ttaattttat   27540
gtgtcaactt gactgggtta aggggtgccc agatagctgg taaacattat ttctgggtgt   27600
gtctgtgagg atgtttccag aagagattaa cattggaatt gatagatgga ataaagaaga   27660
ttgccctcac cagcacgagt gggcattatc caatctttta agggcctgaa tagaacaaaa   27720
gggtggagga agagcaaata tgctctctct gcttgagctg gaatattctt cttcacttgc   27780
tctcagacat cagtggtcct ggttcttggg ccctcgaact ggaacttaca ccatcggctc   27840
actcattctc aggcctttgg gtttggactg gaactacatg gctggctttc ctgggcctcc   27900
agcttacaga cagcagatct tgggacttct tagcctccat aatcatgtga gccaatccct   27960
cataatgaac ctctttttat atatctctat atctatctat ctatctatct gtctgtctgt   28020
ctgtctgtct atttatctat ctatctctct gtctatctat ctatctatct atctatctat   28080
ctatctatct atctatctat ctatctatcc tattggttct gtttctctgg agaaccctaa   28140
ctaattcaag agcattattg ctttctaata taggcattta gtggcatcct atgaattcta   28200
ttatcttgta ttttcatttt cattcattta aaaatacatt ctaattatct ttttgacttc   28260
ttctttgact tatggattat ttagaagtgt gttatttagt ttccagatat ctaggcattt   28320
tccagagatc tttctgttat tgatttctaa tttaaattca ttatagtcat agaatatact   28380
ttgtatatac tttactaact tgaattcttt taaatttgtt gaaacttgtt ttatggccca   28440
gaatatggtc tatcttggta aatgtgctgt atgcttttgg aaagaaagta tattcctctc   28500
ttgttgggtg gagtgctcta taaatatcaa ttaggtcaag ttggttgata gtgttattca   28560
tatcttctat attcttgctg atcttctctt tgcttattct atcaattatt gaaagatggg   28620
tcttgaaatc tgcaatttct atttctactt gaagtactgt cagttttttac ttcaggtatt   28680 ttgaagctct gttattgggt acataagcgt ttagaaatgt tatgtcccct tgatgaattg   28740
acccttccat cactatgaaa ttaacttctt tacctctgga aattattttt gctttgaaat   28800
ctactttatc tcatattaat atggacattt cagatttctt ttgattagtg ttagcatggt   28860
ataacttttt tccatacttt taatctattt ctaactttgg agttaaaatg tttttcttat   28920
```

```
aggcagtaca tagttggctg ttgcttttat atccaatctg gaaatctcaa tcctttattt    28980
gggtatttaa gccatttaca tttcatttaa ttattgatac acttaggttt aaatctattg    29040
ttttgttatt tgttttctat ttgtcccatc tattccttgt tacatttttt tttgtcttgg    29100
ggattaactg aatgttttt atgataccat ttcatctcat ttattggctt attagctatg    29160
acttttgtg ctgtttagtg attacttta ggtttattat aaacatcttt aacttacaca    29220
gtctaccttc aagtgatatg taccacatca catatactat aaaaacttta caatagcata    29280
tacccatttc tccccacaac ctctgtgcta ttgtagtcat atattttaca tttacatatg    29340
ttacaaacct cacactacat tgttattatt tttgcctaaa caatccacta tctattaaag    29400
atattcaaat acttttaaa aaatctgacc tatttacctg tgtagttaat tatttccagt    29460
gttcttcttt cctttgtgta gattcatatt ttcatttatt attcttcttc catttcttgt    29520
agcatgggtc tcctagtgat aaattatttg agctttcata taactgaaat gttttttattt    29580
ggccttcatt tttgaaagat attttttgcct gatacacaat ccctggttaa cagttttctt    29640
ttttctttca gtgttgtaaa gattttgctt catcatcttc tcacttatat tgttcacaat    29700
gagaaatctt gtatttgtct ctctgtatat aatgtgtctt ttttctctgg ttgcttttaa    29760
gatattctcc ttatcactgg ttttgagcaa tatgattaca atatgtctcg acataatttt    29820
cttcatgttt cttgcacttg gcatttgttg agtcccctga atctgtgcgt ttataattct    29880
catcaaattt gaaaaaattt tgaccattat ttcttcaaac ttttttctgg tccctttctt    29940
ttcttttct ccatcaggga ttccaattac acatataaga ggccatctga attttttccta   30000
cagtttactg atgctcaatt catttgtaa ttctcttttc tatgtgtgtt tcatttcaaa    30060
tcatttctat ctctgtgtat tcaagttcac taatgttttc ttctgcaatg tctaatcttt    30120
tattaattct atccaatgtg ttttttacct cacatattgt ggttgtcatt accataagtt    30180
tgatttggct attttcaaaa atatcttcca gccaggcacg gtggctcacg cctgtaatcc    30240
cagcactttg ggaggccgag atgggtgaat cacgaggtca ggagatcgag accatccgta    30300
ccgaaaatac aaaaaaatta gccaggcata gtggcgggca cctgtagtcc cagctatttg    30360
ggaggctgaa gcaggagaat ggcgggaacc tgggaggcag agcttgcagt gagccgagat    30420
ggcgccactg cactccagac taggcgactg agcgagactc tgtctcaaaa aaaaaaaaaa    30480
aaacttccat gtctccacct aacttttga acacacagaa tacagttagt tgtaattaac    30540
tttttatca ttgtctgcta attctaacat ctgtgtcagt tctggtttga tttcaattaa    30600
ttgatttatc tccttcttat tagtcacagt ttcctgctct ttccatgcta gggaattttt    30660
tacaggatgc cagacattgt gtattctacc ttgttggttg tttatatgtc taagtttcta    30720
taatcagtgg ttcccatcta aaggcagttt tgtttgtctg aagacattct ttgttgttac    30780
aactggaggg tgctattggt acccaatggg tacaggccag gtatgatggt aaacgtcctg    30840
caatacacaa gacagccccc acaataaaga attatgaagc ccaaatatgt caatcattct    30900
gaggttggga aaccttgctg taattattct tgagttttgt tccgggactc agttaagttt    30960
gttggaaatt gtttgatcct tttggggctt tctgttaagc tttgttaaat gagaccagaa    31020
gagtattaag tttggggcta atcatttcac catactgaag caagaaccttt ctgtgtactc   31080
tacttgtctt agttcaatca ggttgctata acaaaatacc aaaactgggt aacttataaa    31140
caacagaaat ttatttctca cagttctgga agctgggagt ttgaagccag gacaccatca    31200
tcatctagtt cttgtgaggg cccactttct ggtttgcaga ttgctatctt cttgttgtac    31260
```

```
cttcagatga cagagagaga gagaatgaca gagagagaga gaaggaatg aagctctctc    31320
ctatgtctcc ttctaagggc attaatctca taattgggc tccatcgtag tgacctagta    31380
acctcccaaa ggccccactt cctaacactg tcaccttggg ggttaggatt tcaacatatg    31440
aatttggggg gcgaggggta tataaagact cagactgcag cactacccaa tactctaatt    31500
ttagctggtt gagagcaggc actattccca gccctgtgtg aattctgagc actgttcttt    31560
taactatttg ggatagttcc ttttcaaaca ttaaatagtt tcctcacgtg agctagtgaa    31620
tctacattgt gtttgttcca tccccacttc actgctagta cccaacctca gaactttcta    31680
aagatgctta acactcatca tatccactct cacccccacc ccagacccac tcctcctcct    31740
gtatctccag taaatgttgc cagtccctta agttagaaac tcaggagttg ccctccactc    31800
ctccctcctc atcaccccaa tattcaatca gttatcaaat gctgtcaatt tgaacttgcc    31860
aatgtcccct gcaccctgtc cttactttcc agcctcacta tccttgcctt cttagaccat    31920
catcatgtcc tgctttggcc cttcatgtgg caaccccaac ttgcatctcc aacatccccc    31980
tcccctcca ctatacaccc tcacttccag tgctacagaa cctttcattg cttatgaagc    32040
aggccgtgcc gtttcacaac tctatgtctt tgcacatgct attccctttg cctgaaatat    32100
agttttctg ttttctgcct ggcaaattac ttctcatacc ttagatgtca ccttctctgt    32160
caagcccttt ttgatttctc gaggcaccta ttcaccctg ccccttcgtg ctcctgctat    32220
gttctgttca cactgtgtta acaacattgg tcacatctgt ttgcactgct gctttcccca    32280
ttgctatagc tcctagggat ctaacaatcc ctgtaggtgc ttgctatgga ctgacttctg    32340
acaacttcca aaaaactcat atgctgaagc cctaacccc aatatcacta tacctggaga    32400
taggctcttc agcaggtaat taaggtcaaa tgaggtcata agggtggagc cctaagcaga    32460
caggactgca gccttataag aagaagagat ctttctctct cttcctccgc cacgtgaaga    32520
catagcaaga aggcagccat cttacaagcc aggaagagaa ccctcaccag aacttcacca    32580
tgctggcaca ctgatttgg acttccagcc ccaaaaagtg agaaaattaa tttctattgt    32640
tgaagtcaca cagtctctgg tatttttatt atggcagcca ggctgactac tacagtgctt    32700
aatgcatggt gagtgcattt ttaaatgaat ggaaaggaa gaaagaaaca gaagaggaag    32760
aggtggaaca aatgggggaga aagatgaaga aagcagaagt taagaatgag agaaactaag    32820
gaaacaggag gaagaaggta gaggatggga atgagctcat gaaggagcca gtatctcagt    32880
ggagaccatg ccagtgtgag ggaactactg ccaactagga ggcaggtggg tgcaggctcc    32940
agggccagtg ctgagcatcc aggcacaaga cttttaagag agagtgtgtg tgtgtgtgtg    33000
tgtgtgtgtg tgtgtgtgtg tgtgtgtaat tttttcccct agagatagcc tagagggcc    33060
acctttgtgc ttttctcaga ggctatgtgt cctcattggc tgggtaacag ctgggtgccc    33120
ttgcctcccc ggccaaaggc agccgccgtc cacacccagc tgcctgaggg acaaggaggg    33180
tgtttaccca atggcctgtg tccttaaagg actctgctct cagttacaca gcaaacagct    33240
ggcctcgaag gggcctcgtc ctggccgccg cgagcgggcg gcttctgcag cgtttaagct    33300
tctatctacc atgaagatgc ttcccccacc ctcatgcctc ctcccggggg tgggcatgag    33360
gggcacttac gagctgagac ctcacaggcg acatttttta agctgctcat tctgacggaa    33420
cagtccccaa gacaaacaca aggctttctg tctcccaggg cttgtgcgac ttggtttcag    33480
actctgccac ccactgccgc agacagcggc cgtcttccca ggaagaagac atttcctggc    33540
ggggtaccgg gactgacggg cggcggcgca gggcagtgcc agccgggccc aggaagtgaa    33600
cgcgctgggc ccgcgaagga gcgcgtcgcc cgccctgagg ggggcagtgc agcgcccacc    33660
```

```
gcgcgccttc gccagtcccc tggcaccgtt gccctggcca ggggccggga gagggcgtgg  33720
cagcgcggca gtgcgcctac gcaccggggg cactggggat cccgcccca cgctggttcc    33780 cgcgctttca agagcctcag agccccgaga caaggggtg tcggctctac ccacctggcc    33840
cagcccgaaa gaacagggcc aacattttga aaccaaacca ataatagaat tggaatactt  33900
ttgatcactt tttattttcc ttttctggag gagagttgtg gggcggggt ggggagctgg    33960 tagagagaat ctcagggcgc tgtggctttg agggcgggtt ccctgcgcaa gcagcagtgc  34020
tcacagtgcg agcaatcatg gctaggccca gcccgcggtt agttgggtgc agggacgtga  34080
caggaccgcg agggctgatt ctttagtcta ttgttcccac tcctcagaaa ggactcctag  34140
caaatatata ctgctagtcc cagctttccc gatggaatgg aaccccttgc tttgctttgc  34200
tgtcgctatt caggatgggg attttgtcca tgcagaaaga catttacatt atctacactg  34260
gaatgccggc ccactagcct ggcaaaatgc tgagccagct attagatctg gactcgtgga  34320
ggagtggaga tttgcctcca ttcaagcaac cacatacttc cctggaagct gggaggagca  34380
ccactaagtc caccctctcc tgcctggctc cttggtagtg cttctcaaac attatcactt  34440
ggacaaatca cctgaggtcc ttgttaaaag tctgatttag aaaatctggg gaatccggtg  34500
gcacccgaga ctgcattttt aacaagctcc caggtgatgc agctactgct gtgcaccaca  34560
ccttgagaag caagggtac aacattgctc tcaactgcgg ctgcacatta aaattaactt    34620
ggggagcttt aagaactaat taggccagga cccccacccc caagatattc tgatttagtt  34680
ggtctaggta gagtcaggcc tttttttttt tttttgacg gggtctctct ctgtcgcccc    34740
tgctggagtg gcgggatcat ggttcactgc agtttcaaac tcctgggccc aagctatctt  34800
cccacctcag cctcccaagt agctgggaca acaggcgcaa gccaccatgc ccagctaatt  34860 tttttttattt tttgtagaga cagggtctcc ctatgttgcc caggctggtc tcgaactcct  34920
gggctcaaga gagcctcctg cctcaacctc ccaaagttcc gggattacaa gcgtgaggca  34980
gccaccatgc ctgatctggg ctttttttt tttttttttt tttttaatta agcttttgg    35040 gtgattataa tgggcagcag gattgagagc taatggtaca agcagctatg aggaaggact  35100
ttggctgttg ccaggcctat tgatttcata ctgggcccaa ctgtagggtc cagtttatga  35160
ccaagattag gaattcagtt tgtgatcaaa gaacataatt tgtccatctg gcttcaaaca  35220
cttcatctta cctcacattc attcaatcat caaatattta ttgagtcact gtattgggca  35280
ctgtgctagc tactaaggat tcagcagtga gtcagacaga catgggaagg tggtgacatg  35340
tttaagcagg caggtgacat gatcagattt gcattttaaa atgatcagtc tggctgcaga  35400
gtgaacagat tggaggggg ccaagtggct gtgtacagaa gcccttgcat taaaccaggg    35460
gagaaatggc agtgtaggcc agggtggtgg cagggaggag cggaggaact caagggctac  35520
tgaagaggtg aaatcaacag gacttgataa tagatttgac aggggaaat gtgagagagg    35580 gggactgtca aggataactg ctaagtttca gatttaggca actgaatgaa tgggggcacc  35640
gcagagaaaa agaggcctgg aagaggacag tatttggaag gaaggtcata tgtttggtcc  35700
aagtggagct gtcaagtatg cagttggata agctgtctga aacttagagg agagatctga  35760
gctacagatg taaatttggg agccatgagg atagggggtg tgaatcaatc acctggataa  35820
agattgtaga atggcaaaaa caaacaaaca aaaaacaac ttagggtttg aagaactcta   35880
tcatttactg gcttgctctt ccaaggtccc tactattggg caatgctaac ctttccgctt  35940
cctaatcact gtcattttt aaatctcatt cattaaagac ttttggtaaa agagttcatg    36000
```

-continued

```
gttttctcct cttccagaaa ccctgacatt ctcatggatg acttctacat tcatgcagac    36060
atcccttcca atgtcatgtt ctctctattc tttgacttgc tcatctttac ctcctgcact    36120
cctcctcaag ttacactctg cacagtcac accttgggcc ttgacattgc tttcagctgt     36180
gccactttaa aaatcactct ttcaagcctc cccgctctgc taccttctca tcttccagtt    36240
ttcttgtgtg attattcctg tgagaactgt tcttcaactt tattgggatg gccagcccac    36300
tgacccttct acttcttccc actctaccag ctagctctct gctttcctga cttcattatc    36360
tagcctaaag ccttccgttt gtcaattcaa taccaaagat tggcagaggc tgccatgctc    36420
ccaacagatc ctggataaga ggtggggagg ctgaggtctt ctgcgagtgt gcagagggta    36480
ttaaagttgt atgctgtgga ttaaaattta gatgtgggtg ttctgggtga cataggaaga    36540
agaacctcta ttttgttttg aaagtgggcg tacctgcctt tcattcttgc ctggacaggc    36600
cacagcccac ctcaagctac taaagtgcct gggggccaga ggcaacatgt tccttaaaga    36660
agcagctgtg ggtcagctca agtgtttggg caagtgttca gataaagctc cagaatacag    36720
ggtcttggag cataagaaca tgatattagc ctagactgtt ggaagggtag gtgtccctgg    36780
tcatttaccg ttagtgacct tagatctgat gtttgagtag cacggacttg gggctagggc    36840
tgaagctggg cccacattac agccagagga aatagcagag ataaagcaaa ggaggtggga    36900
tgtgtacagc actcccagcc aacagtgaac aatctaattg gctggtacag ggtgtctggg    36960
aaggagtttg agattccatt gcccatccgc atcctacact tggccttttg ccatttgaga    37020
aactaattaa tagacacata ttgtgataga gagtgagatt gttggggatt ggagggtccc    37080
cacccattcc aggaatgact ggaaagggtc tgcactgacc gacttaggct cttcttggaa    37140
gatgtcacgt attctaggag aattgtgacc aattgcaacc agacacactc ttggtcctct    37200
tggtcctttt ttgtgtcatg gacccttag caatctgttg aagcctttgg tccccttttc     37260
agaataatat ttttagatgc ataaaataca aaggatttaa atggaaacca agtatagtga    37320
aatatagcta tcaactttt tttttttttt gagatggggt ctcactctgt ctcccaggct     37380
ggagtgctgt ggcacaatca tagctcactg taacctcaaa ctcctgggct caagtgatcc    37440
tctcacctag gcctcccaaa gtgctgggat tgtaggcatg agccactgca cccggtctcc    37500
aacatatttt ttaaaatttg tgatgtctgt gcttcattat tagcacatta tataactaaa    37560
tctagctgtg agtcttataa ctatcacaat ttcaaagcaa tgatgaacat attgctattt    37620
caagagatgt gcttcattct aatgtgatat gaaaatatgt gtaatttctg ctggtggcca    37680
agtcacaggt cctctaatac tatggtggtt tatcacctgc attcatgatt gaaggaaatg    37740
ctaaaatata gttaaaagat agcagaaaca aagatgtagt tttccccatc taagttcatg    37800
aatcctctga attccagcca cagactactt agaggaacag ggaccccaag ttaaagatcc    37860
acatagcttc ctggtgttcc tttgtggaaa ttcccttat cttagtccat tggggctgct     37920
ataacaaagg cctgcagact ggttggctta taaacagtag acatttattt cttacagttc    37980
tggaggctgg gaagtcgaag atcaaggcac tagcagattt ggtgtccaac aagggcccag    38040
ttccttcgta gatggcacct cctagctgta tcctcacaag gtggaagggc caagggtact    38100
ctcttgggcc tctttataa ggttactaat accattcatg agggctctgc ccccatgacc     38160
taatcaccct ccgaaggccc agcctcctaa tatcatcatg ttagggggtta ggatatcaac   38220 atatgaattt gggaggacac aaaaactcag atcatagcac cttttgtctc aagtctcctt    38280
gctggagggc tctttccag gatcatggtt ggcgatttgg tttttagaaa caggctgagg     38340
cctggccttc cctccactgc actcttagag cctgggttgt ttgggtttct cttgtggcag    38400
```

```
gtagtacttt ccacctcaag tagggttcct ctttcagcta atgtcaactg aacatctgct   38460
aagtacaggg ctctgtgcta agccctgggc ataggaagtt actccataaa gagatagtta   38520
tcagtaataa taactcccat ttaccaaaca cttttttacat gtcagacacc atgttgacac   38580
ttcattcatt cattcagcag agatttacca agtgcctact atgtgccact gttctagaag   38640
ctgtaggtag agcagagact aagacaaact cccagctcac atgaagctta cactctagtg   38700
ggggaagaca gatgatatac aaaataagta agcaagtgag tgtgcaaaaa taggataagt   38760
gctatggaga aaaacaaagc agagaaggag gagaaggaat gcccagagag atgaatgcaa   38820
tgtccgatta gttgaccagg gaaggtctcc cggaggaggt ggacatttca gactaggcct   38880
gaatgatgcc actgaagctt tgcagatatt tgaaggaaga gcattctagg cagagaaaat   38940
agctaggcac ggaccctgag gcaggaatgt gcttagctgt ttgaggcatg tggaggaggc   39000
ccgtggggct ggagaagagt gagtgagaga aggagtggta actacgagag cagagaggaa   39060 atggggtgg gggcggtgac agattgagca ggaccttgga ggtcttatgg tgaccttggc   39120
tcttacccag agggagatgg gaagcccatt gaagggattg aacacagtcc ccacaacaat   39180
gctgttgcgt gatagtatta gtattctcat tttcaaatga ggaaacgaca gctcagaaaa   39240
gttgagtgac ttggctggtg agtggcagag ctgaaactgg accacagacc tttctggagg   39300
tcacatgcct cctccctcca ccagcccgag gctcggagtg gggtcagcat gttctctact   39360
cccttctatt tcctccagac tgttgttcct ttgtcatttc cccaaggacc atacagtgct   39420
ctctgtccac cattcttgct gtatccacca acctctgcta ctggactatg agcccttac    39480 ttactgagca cctgctatgt gccaggtact atgttagatc ctgagcataa aatgatgaat   39540
aagagaagtc agctccttgc tctcctggag cttttattct agtggatggg aaacacaggt   39600
aggtcagaaa attttaaaaa gctttctttt tcttttttttt tttttagaga cagggtctca   39660
ctctgtcaca catgctggag tacagcagcg tgatcgtaac tcactggact caagttattc   39720
tcccgcttca gcctcccagg cgtgtgccac cacacctagc tttgtgtgtg tgtgtgtgtg   39780
tgtgtgtgtg tgtgtgtgtg tgtgtgtgtg tagagagaga cggggtctta ctatgttgcc   39840
cagtctggtc taaaactggg ctcaaatgat cctcctgcct cagcctccca aagcactggg   39900
attataggca tgagccacca caaccgccaa aaatctttag taataagagc catgcagaga   39960
aaagagagta gctattttgt aaagaggtag ggaaggcctc tgtgaggagg tgacatttaa   40020
attgagatct ggatcataag aaggaaccat ctcagaggga gagcattcca ggcaggaggt   40080
atgagagcaa aggctcaaag gtggtcatga gtttggcctg ttagaggaac aggaagaaga   40140
tgcatggcaa gggatgggaa catggcagga gatcaaggta gaaatgcagg ggccagatca   40200
ggcagggcct tctaggtcat gaacatatgg gaatccactg gagtgtttca agcaggagaa   40260
ggaaatgatc tgattggtgt tttaagatca tgctgacttc cttatggaga gtggattggt   40320
gggcagaggg atggtggaga aaagtgtaaa gattaaggat atgtttggtg atgaagtcaa   40380
ccagatagcc tgatagatta gatgtcatgg atgaggtaaa gagaggaatc aaagatggct   40440
tctatgtggg ggttgaacaa ctgcatggat ggtgtctgtt caggctgcta catcaaaata   40500
ccttagattg ggtggctcat aaacaacaga actttttttct tatagttctt gaatgtgagt   40560
caaagatcaa ggcaccagca gattcagtat ctgatgaggg ctcaccctct acttcataga   40620
tggcaccttt tgctgtgtc ttcacatggc agaaggggca aacaagctcc ctgaggcctc   40680
ttctgtatgg gcactaatcc ccttcacctg ggctgtctcc taaagtcccc acccttaat   40740
```

```
accactgcac tagggattag gtttcaacat atgaattttg ggaggagaag ggggccaac   40800 attcagacca taacagatgg ggatgccatt tacagaactg aggaaggcat tgggggagtg   40860
aatttggagg aaacgttgag ttgttttgaa catgtcagtt tgagatacct actaaacatc   40920
cacatagtag tgtcaaatag acagttggat ttatgagtct gcagttctta agagtagtct   40980
aatctaaaga tatagagtca gaaatattgt cattgtgcat acccacctag ccgagcaca    41040 gtgcctggca tatagcagcc agcctaaaat ttgggtgggt tggttgaatg aatgaatgaa   41100
attcttagag cttcagaatg agatagatct tggttcaaat ttaaatcctg gctctgctac   41160
ttactaattt aaccttgaat aaggtattaa acctttcaga gcctcaattt cctcacctgc   41220
aaaatggaga tagtgataat acttatccca tagggtggtt gtaaggatta tactaaataa   41280
accatgtaaa tcacccaagg tgcttagtac agtccctggt gcatagtaag cactcagtaa   41340
attggtggct gttacaatat tcaaaatatg agataggccc caagaaagca agccttggag   41400
agacactcca gagggcagcc ccacaggtg ggacaatgta gctcagctat atgtgtgaag   41460
cagtaatgcc tagtgggtag gtgttgctcc cttgagccaa actgtctggg tttataatcc   41520
tgactcagcc acttagtagc ttacttaacc tctatgtgcc tcagggggt ttagaaatta   41580 ttattattta atctctaaaa tagggataat aatagaccta cctcataggg ctgttgtgaa   41640
ggattaagtg agataatcca tgaaaaaggc tgagaacagt gcctggttca tattaagggc   41700
tcaatcaatg ttaggagcta ttatcacagg gatgtaggag ggaggggat gcaaacaggc   41760 ttcagctgtg cccttgacct ccctccagag aagacagtat tcagccctgc caggcagcag   41820
agcccgtttc atgcagctct tctctcccag cactctcctt cctactcctc cccggctgtg   41880
gcctcccagt ttttgcaact ccctgaatag cttatgaacc tttgccaggg ttggtgtgga   41940
aaaggccaac tcctccagta gagagggctg cagaagctca gcctcccttc acactggggg   42000
aagtgttagc cacaggctac aggcaaaggg aatccagatc cccaagctgc ctgaagttat   42060
ctagaagcag agagaaataa ccaactgaga cagtcccaga gggcccccca agcttctttt   42120
ccatttaaat gctctctttg ttactaagaa gcaaacctag cccatcccca ctggcaccag   42180
cctgcccatt gtttccctaa gagaccatcc caagccaagt gctgggcta cctctcccttt   42240 aaaggaatgg cagcctggag gttgcactgc agtaagagca tcatataacc aaaattctcc   42300
acaactaatg gttctagaac aggacccagg tcaggtgtca tgggcagacc cataaagggc   42360
ccaatcacta gagcatttga cctgcctctt cccccccaggc ttggctacct gtggtgatta   42420
atgctctgag gcctctgaca tctgagcaat ggacacaagg ctagagccta atcccaccta   42480
catttgatca aaatggtagg ccttgtgggt ttgttccgga ggtgagaaag cattaaatat   42540
tccactggaa agacacaatg gagagattgc gtaagtagac ggttctttgg gcagaagaag   42600
atggatggat ctgaagtggg aagtgccaga agaaccctt ctctaaccag gaggggcctc   42660
tggtatcctt gcagctttta gctctcagtg tgatcagtag actgtctgct tgacttaccc   42720
aaactcccac ttcccctcct gtcaggtatt tgcttggggg ctattcatct cctctgtgtt   42780
caccttccat tcagctgaaa agaggaaga ggatttccca gctctgtctt catccatgca   42840
tttttttttt ttgagacaga gtcttgcttt gttgccccgg ctggagtgca gtagcacgat   42900
ctcggctcac tgcaacctcc acctcccagg ttcaagagat tctcctccat ttcaccatgt   42960
tggcctcagg tggtcctccc gccttggcct gccaaagtgg tgggattaca ggtgtgagcc   43020
accgtgccca gcccttattg gagtttttt tgtttggttt tgtttttgt ttttgttttt    43080 ttgtttttgtt ttgtttgaga cggagtctcg ctctgtcacc cgggctggag tgcagtggtg   43140
```

```
ccatctcagc tcactgcaag ctccgcctcc cgggttcacg ccattcttct gcctcagcct   43200
ctcgagtagc tgggactaca ggtgcccacc actgcgcccg gctagttttt tgtattttta   43260
gtagagacgg ggtttcactg tggtctcgat ctcctgacct cgtgatctgc ccgcctcagc   43320
ctcccaaagt gctgggatta caggcatgcc ttattggagt tttatgagca tattctgtga   43380
tgttgaatgt ctagtctata aatgattgcc tagagaagac aggggcttaa ggaacctttt   43440
gaacgccccc actggttttg gagaggtggt gagacttttg gactcaaata atggctactg   43500
tgatgttaac tgtgtttatt gatttacaga agctacgaat ggtgcagtgt acaaatcacc   43560
ccgaaccttg gtggcttaag acatcagcaa tcatgttatt acctctcatg gtttctgtgg   43620
gtaaggaact caggaagggc tcaggtggta gtcctggctc caggtccctc atcaggttgt   43680
aatcagggag tgactggagc taaaacagta tggggtgagg agaatggggc tggagcagct   43740
ggggacaggc cagacacctc tcacttcatg tggtctcgga gatcttcaca tgatctctcc   43800
atgtgagtcg gtttgggctt cctcacagca tggtagcagt caaaccaatc acagggtggc   43860
tcatggcttc aagtgtgatt attccagcaa gcaaagtgga agctgtatcc tcttctacga   43920
cctcgccttg gaagtcatct agcttcactt ctgccatagt cacaaagctg cccagcttca   43980
gggagaagga acatagaccc tacatctcaa tgggggagtg tcaaagtcat actgtaatac   44040
gctcatgcgg aacagacgat actgtcacag caattgtggg aaaatactcc ctactacacc   44100
aatcctactt cctgctcttc cctcagctga acctcagaca agccttttgc tttcttgctt   44160
gcagctgtca gctggtccct cactctgggt gcccttctct cctctccagt gccttcaggc   44220
cccaattgga gtcccacctc ttaaagtttc cctaacggct tccataagca caacaagcag   44280
cagtttttcc ttattcatag caagcagaca cttacatgtt tgataggcca aagagttgct   44340
ccacatttgg tcagggccaa tctgaccagt gggtaggttt ccacatctgg gccctaatac   44400
ctggccaggt ggaacatcta gattctgaaa catcctcctc attcttccag ggtctcagaa   44460
cctcagggtg acatagcttc tggccataaa tgctaggaca gagctatgtt cattgtgcaa   44520
tgtctcttcc aaggtaggca catgggcaga tgaggctctg tgcagaaggc cttggcagtc   44580
agatgagagg tggcagtaaa atgtgttggc aagagccttt ggctgggaat caggaagcca   44640
gggtccccga accagctttc tggctaattt gatgcattca tgatctgaga caaacctccc   44700
aatctccagt tgacctcagt ttccctacct ctgcagtata aaacctagag cttgtccttc   44760
ctacctgtgt ggtgagcaga caagaagaga gacagggctg ggcatggtga ctcacgcctg   44820
taatcccagc actttgggag gccaaggtgg gtggattacc tgaggtcagg agttcaagac   44880
cagcctagcc aacatggcga aaccctctcccc tacaaaaaaa atacaaaaat tagctgggcg   44940
cggtggcaga tgcctgtaat cccagctact ggggaggctg aggcaggaga atcactggaa   45000
cccgggaagc agagattgca gtgagccgag attgcaccat tgcactccag tctatgagac   45060
agagcaggac tccgtctaaa aaagaaaaa agaagagaga caggaagaac ttctcaagag   45120
tagaacatgc taataattct tgtactgtat ttgtttcttc tctcagccgc cacttcctct   45180
ctagcatgta ggctccaagg tagtgggtga gtccgtaggc gcatgattat ggaacaggga   45240
tgggccaaca gcctttccct atacacatac agtaggattc aggcaggggg gtttggcaat   45300
gtggccattc cccagttgct gaagggctta ccctgggtgg atttggtgag gctgagcaaa   45360
tggttaggca cagagctaac aattccaccc tactctgctc caacacacac cccccgcccc   45420
cattagaatg ttctttatta ggctactaat tggctgtgtg gcctcagggg gattccttcc   45480
```

```
cttctctggg cttagtttc cattgaagaa agtgaacata tcaccacccc tgcttctgga    45540
gagaagcttg attatttctt gacccccatc atttctattg tgcaagggtg gcatgtgatc    45600
tctccagggc tgggaagcat taagtcagaa tagctgtcat caaaacaata catgctttcc    45660
tcaaaataaa gggggctccc gtaggcacct tcacctcttg ggacttaaag gctggctgag    45720
gcagagtgtg ggcccagaag ttagcaaatc tggacgtgtg aagtgacctt ggctaagtca    45780
gagaatccca aacgcgcaga gctcaaaggc actgccaaaa acctcaagcc catcagctgt    45840
cagcctccag aataaatgtg tcccagatga cgttcacatg gccacgtcag agtttggggc    45900
aattctccgt cagctgaacc ttcatccctc ttccttccac tctgaaaaac atatcacttc    45960
tctcgacttc tgagaagaac ttgcacatgt gcacaaaggc tggccaccgc agcactattt    46020
gtaatacaga aaactcagaa caacctaaac gtctcccacc aggggctgat tcaatcaat    46080 tatgggacag ccatattaca gaatgctgtg cagatatctt tttatgtatg agacataaat    46140
gtgtggataa agttatccaa gacatatttt tatttatttt taattggcaa ataataattg    46200
tatttgtcta tggagtacaa tgtgatgttt tgatgtacag ctggccctac ttattcgtgg    46260
gttctacatc caaggattca accaagcttg gatgaaaaat atttgggaaa aaataatgga    46320
tgttgtgtct gtactgaaca cgtacaggct tttttcttg tcaggattcc ctgaacaata    46380
taacaactat ttacatgcca cttacattgt attaggtgtt atacacaatc tagagatgat    46440
ttgaaatata aggcaggatg tgcataggtt atatgcgaat actatgccat tttatatcag    46500
ggacttgagc atcctcagat tttggtaccc gcaagcagtc ttgggcccgc tatatgtata    46560
cattgtacaa agattaaata aagttaatta gcatatctat cacctcccat atttatcagt    46620
tttttgtggt gaaaagcata ttgttaagtg gcaaaaaaaa aaaaaaaaaa gctgtggggc    46680
tgggcctggt ggctcacgtc tataatccca gcactttggg aggccgaggc aggcagatca    46740
cctgaggtca ggagttcgag agcagcctga ccaacatggc aaaaccctgt ctctactaaa    46800
aatacaaaaa ttagccagtg tggtggctcg tgcgtgtagt cccagctact cggggaggct    46860
gaggcaggag aatctcttga acccaagagg cagaggttgc agtgagccga gatcacgcca    46920
ctgcactcca gcctgagcga cagagtgaga ctctgtctca aaaacaaaa acaaaaacaa    46980 aaaacaagct gtgggacaat atgtatgata caatatatgt gataaaatgt acacaactat    47040
atatttctat aggtactgta catatacatg taatgtatgc acggtatgca actgcaagga    47100
cagaagtgta ggataccca aaccctaaca gtgttcaccc ccagtaaagg tactaaaatg    47160
agaaacgtgt cttaaggagt tcttccaaa taactaaata ctttggattt tgccaacgt    47220 gagttgattc atcaatttat tttctaatta aaaatgcact ttcacagtaa agcatatgaa    47280
aaggggcaca gaaacagatt agtggctgcc aagggttagg gatggcttgg agggaacagg    47340
tgggcatggg tgggtaggag taacacgagg gagtttattg atggtggtag ttatgcaaaa    47400
ctatacacgc aatgaaactg cataaaactg tgcacacaaa catgcacaca caaatgggcg    47460
catgaaaaag cttgagaaat ctgaatcagg tctggagttc acttagtggc attgtactga    47520
tgttatatcc ctggccttga cattgtacta tagttatgta agatgttacc agcggggaaa    47580
gctgcctgaa gaggacatgg gacctctctg tattattttt gcaacttctc gtgagtagtt    47640 cttttgaaaat aaaaagttta ctaaaagggg ggcacaaaaa gctttttgaa tatttggagg    47700
tgatggaagt gtttcatatc ttgaatgtgg tagtggttac atgactgttt accttgtttt    47760 accttgtta aatctcattg aacttgtaca catcaaaggg tgaaattatg ccttcataaa    47820
cctgacttta aaagtctcca ggccagaact gctctcattt gttaagatga agaaatcatt    47880
```

```
tacaagcttg tgtgctttgt tgtttatttc aaaattacat gcaacacact tcacaatgac    47940
cagtgatgcc tgtgcccagt gggaggtccc cgttagatgc tcagccacct ccagcgatga    48000
ggagcccatc acttaatatt gcagcccata tcattgtcag gagaattgta atagaaagtt    48060
cttgattagg cctgtaatcc cagcactttg ggaggcctag gcggacggat catttgaggt    48120
caagagtttg aaaccagcct gcccaacatg gcaaaacccc ttctctacta aaaatacaaa    48180
aattagcagg gcgtgttggt gcatgcctgt aattccagct actgggggtg ctgaggcacc    48240
agaattgatt gaacccagga ggcggaggtt gcagtgagcc aagatcacac cactgcactc    48300
cagcctgggc aacagagtga gaccctgtct caaaaaaaaa aaaaaaaaaa aagaaaagaa    48360
agaaagaaag aaaagaaaaa ataaagttat ttattaggct actagttagc tgtgtggcct    48420
tgggtagatt acttcctgtc tctgggcctt aatttcctta taagaaaaga tgacctctga    48480
gatcccttct cgctctaaca ttctaagtct ctaaaactgg gaatttaagt tttgacctgg    48540
ttttgccttc tggagtcaca cagaacttaa ccctgtgtgt tgccaacagt cagccagccc    48600
atcgtacact agaagtcagc tagcagctca gctccctagg gcaaacatca tcccctggcc    48660
tttcccattg tcctaccaag aaatggaatt gcaggatctg gtgatggtta ggatcacagg    48720
atcaggagtc aagcagcctg gagtctgact gtggactttg ccacttccca ccgtgtgacc    48780
ttaggcaggt cacttgtgca atcttcagtg tcctatctgt agaaagggaa ttagtagtac    48840
cagcctcctg gggagagggc gtgggcatta aatgaggtaa tgtgtgtaaa tcaggatgtg    48900
tggtaggcag gataatggac tccccaatat ctgcacatcc taatccccac aacctgtgaa    48960
tatattgtgt tacagtggca agaggaaatt aaggctgcta atcagctgac tttaaaatac    49020
ggagatcagc ggggcatggt ggctcatgcc tataatccca gcacttcggg aggccaaggc    49080
aggtggatca cttgaggcca ggagttccag accagcttgg acaacatggc aaaaccttgt    49140
ctctactaaa aatacaaaaa attagtcagg tgtggtggta tgcacctgta atcccagcta    49200
cccgggaggc tgaggcaaga gaattgctcg aacccaggag gcagaggctg aagtgagccg    49260
agatcacacc attgcactcc agcctgggca acagagcgaa tctccatctc aaaataaaat    49320
aaaatagaga gattggggaa taatgatctt ggattatcca gagaggccca atatgatcac    49380
gagggtccct ataagtgaaa gacagaggca ggaaagtcag actcagaatg ctgcaatgtg    49440
agaaagtctc caccagccat tgctggcttt gaagatggaa aggcatcgtg aggcaaagca    49500
tgcaggcagc ctctcgaagc tgaacaaggc agggaaacag atcctcccct tgagcctcta    49560
ggaggaacgc agacttgctg accccttgat tttagcccag tgggactcct gttgaacttc    49620
tggcctacag aactgtaaaa gagtacattt gtggtttggt ttgtttgtgg cgtcttttag    49680
gggattgttt agttttgttc ttgtttttgt agagacaggg tcttgctatg ttgcccagac    49740
ttgtcgcaaa ctcctggcct caagtcatcc ttccacctca gccttccaag tagctaggac    49800
tacaggcaca caccaccacg cctggctaat tgttttttaaa ttgttctgtg gaggtggggc    49860
acagtggctc acagctgtaa tcccagcact ttgggaggcc aaagcgggcg gatcacttga    49920
gcccaggagt tcaagaccag cctggccaac atagcaaaac cctgtctcta ctgaaaaata    49980
caaaaattag ccgggcctgg                                                 50000
```

<210> SEQ ID NO 5
<211> LENGTH: 44453
<212> TYPE: DNA
<213> ORGANISM: Homo sapiens

```
<400> SEQUENCE: 5
tggtgcatgc ctgtagtccc cactgctgag gaggctgagg caggagaatc acttgaaccc      60
aggagtcaga ggttgcagta atctgagatc aggcgactgc actccagcct gggtgacaga     120
gcacgactct gtctcaaaaa aaaaattctt ttgtggagat gaggtccttg ctatgttgcc     180
cagactggtc atgaactcct gggttcgagt gatcctcctg cctcagcgtc caaagctct     240
gggattacag gcatgagcca ccatgcctgg cccatttgcg ttgttttaag ccactaaatg     300
tgaggcaatg tgttgcagtg caataggaa actagtacag atggctgctg ctccctcctg     360
actggtctcc ctgcacccac ccttgcatct ccccagtcca tccccacaa cacagccaaa     420
gcaatgttcc caggacctta gtcaaactaa gtcacatccc ttaatacaac tcgtctccct     480
gtaccttaaa tgtgcctcag ggcctttgaa cctgctgttc tctttgttta aagatgtca     540
tggtcgccta gtaatacct aatctacttt cataaactag ctcaaagatg aaatgctgc     600
ttcctcaagg aaggcttgag gaacccatct gggtcaggtt ctctaggtaa tagcaccctg     660
tcctcctctg tagcacttgt aggtttttaa ataaatccat gtgttgatct gcttcagggc     720
ttattgcctg cctttgctac caggcatgta agcttcccaa gggcagggac agtgtttgtc     780
ttattcacct cccttagccc agtcgctggc acaaggaag cacttaataa atggtagcta     840
ttatcattat tttatttctg aatcctcatc attctgatca cctccccaaa cactccctag     900
tttgaagcgt cctttctgta aagtggtact cctaccttgg cccggtgctc caggggtggt     960
atgaacaaca aaatgtagaa gctgacagtg ctgtccccac ctactgggga cataccactt    1020
ctattcatgc tgcttaaggc taccttcctt tatcaccaac ttcatcatac tctcagctgc    1080
aacagagctg gaggtcactc acacctacac acccacctgc tgcaatcagg acgtctgcca    1140
agccagcttc ccgccatccc gtttctgtat ggttgctttt tgtaacctca gtttcagctt    1200
tactctcgtt cctatggggt cccatcattt tcttgggcca ttgttgtaac ctgtcccaat    1260
ctttccatgt ccctattcag ccagccattc tattaaccaa ccctcctggc ctcgtgtcat    1320
ctacaaaact gagcagtgcg cgtccctgtg cctgcttccg aatcctggcc aacaatatgg    1380
cgcaggacaa aggccaggag caaggctctt gaaagtgcta ctggagagct cctgaggccc    1440
ggtatccatc tcaggggca gcagagggg gtgtttaatc agcaattcaa actgtgccta    1500
ggccaagttc ttacgaggct gtgaaattgg gaatgatatt agtttcctag ggttgccata    1560
agaaaatacc accaactggg tggcttaaaa caacagaaat atatttgcac gtatccctgt    1620
gtaacaaacc tacacattct gcacttgtat cccggaactt aaagtaaaat aagaaaaac    1680
aaaataaaag aagaaaaaa agaaaagaaa tgtatttgct ctgttattag aggctacaag    1740
tccaaaatca aggtatcagc aggaaaatgc tccctccaaa ggctctcaga gagaatcctt    1800
ccttgcccct tccagctcct ggtgactcct ggtgttcttt ggctcgtgca gcatcactcc    1860
aatctctgtc acgtggcctt cctttctgtg cctgtctctc tccgtcttct tataacgaca    1920
cggatcattg aattgagggc ccaccctact ccagggtgac cttatcttac ttaactaatt    1980
acatctgcaa agatcttatg tcccaataag atcacaatgt gaattttggg gtggacatga    2040
atttgggga aaacgctatt caacccacta caaatagcca ttctttctca caggagcttc    2100
atgagggacc agaggataag gtagcacagg gcagggcttc tcaaactata agagccaaga    2160
agcacctggg gatcgcatta aaatgcagat ttggagccag ccagcctggg gtgggtctgc    2220
atttctcaca agctcccagg tgacatcctt gctgcttgtc ctgctttgaa taacgaggat    2280
gtaagtgaaa gaaagtgctt tgaaaacagg tgtcaggtag ggggattaca tttcttttgt    2340
```

```
aatgagtttt tctcacactc ttatttcccc acacctgaat cttgtgtgaa ctgtggaaga    2400
acagaaaaag tgttttcatt tcagtcccct ccaaaagcag acctggagac aaggacttgg    2460
gttcaggtag tttattgggg aggcggaaat agggaaaggg agaaagggga gagaagccaa    2520
tgaagtgcca cattaaagag caggttgccc ttaaggcaac tggagctcca acctgcgggg    2580
gaccactggg aaactgtggg gacactcctc agaactgtcc tgtcaaaggg ctggggcatt    2640
tgcccaccaa ttcccctcct ccatcagttg aaagttacct gggagtgtca actcctccac    2700
actctcccaa gtgctgcaga aaaccctccc tccagcagaa aagttgcagg tgtccgaggt    2760
gggaaatagt ggcatgctgc aaacagccct gtcccacagc taggtgacct cagctaggct    2820
gaagagatgg gggagggagg ggggtcgtca tcatctgcta caaaaagctt ccaggatgtg    2880
cacgtcatct gtgtctctac tattctatt tgagtgcatg agtggctcag gcgagctctt    2940
gcttacagtt gtgattatga ctgtcatcca gcaccagtgg acaccttgct catagggtg    3000 tcatggaaga atccgttgat ggcctgctga aacccacatg tgcccctct ccgctaggcc    3060 tgccttcccg ttggtaaaat agtttatact atgggtgcat gtggaggaga acccacccca    3120
gagtaatgta atcggtgctt cagggtcacc ttaggaagaa gatacttccc tgtctcacag    3180
ttcctacctt cacctagttc agttgatctg ctcttgacat tcagtgttac ctttcatcca    3240
cataacgatc ctatgaggta gtggctatga ttgtccccat tatatagcca aggacactga    3300
aggccagaaa aaccaatgtc acttatcgaa ggtcactctg taagtggcag aagtgggatt    3360
caatcacagt ctttctgatt cactagactc tgtggattcc ataggaaaaa ctaggtggta    3420
ggtctcatga gatttaaatc acaaatctaa ctacacttct agggtgacct gctagatgag    3480
aacagcaaga actgctttta tttgtatgca gcttcttgtc ctattagaac acagtgtgtc    3540
cattagaagc tgattcttta cattaaaaaa gaatttacaa caagtaaaat gtgtgtatga    3600
gtcagtgtgt atttactttt tatgagtcag tgtgtattta ctctgtgttg gtatttactg    3660
ggagggatgg attcattggg atgaatggat ttttcttaga taattggtaa atgaatagat    3720
gccaactcta ataagcaaaa gatgccatgg agaaatgaaa taaattaatt caatgattca    3780
atatcattag ttttcaaaac gtcaccagag gatttcctca actagggact tttcccagca    3840
catcaaaggt aagattccac tcccacaagc atgtcaggaa cacacttatc cacaaaatac    3900
gaaaaatcca tcttcttcta tatttgggc cattttctct cccttactaa gcagtgaact    3960
tcccgaggga aggaagggtg taggttcttt agacttccct acacattgtg tgggcagggc    4020
cacaaggtgt gtacgcaaag aaatttcaac ccctaaattc aggatgccag cacttgaatc    4080
cacaaggctc ttggagggg agggaaagag agttttttcta catttctta attcttgatg    4140 ctttggggga ggacacattt attgctcacc acggagaacc gagaaaagaa gagcccccag    4200
tctccgcctt gaaggagctg acagtccatt ggagaaacaa gtggaacacg ctggaaacaa    4260
cccatgcatg atacaggaga gctggggaag aagcggctct gactgtaagt gctgaagggg    4320 ccaagggct tgggaaaggg agagatcagt gtggcctgag aggagaggag gtggaatgaa    4380
aagagcactg ggctgggagt caggagacct ggcctctaga ccagttcctt gcctaattct    4440
ctgtgtcatc tgatgtgttc acttctctct ctctctctct ctctctctct ctctctctcc    4500
cccccctctc tttagacggg gtctctctct gttgcccagg ctggagtgc agtggcggaa    4560 tcttggctca ctgcaatctc tgccgcctgg gctcaggtga tcctcccacc tcagcctcct    4620
gagacactgg gactataggt gcgcaccgcc acacccagct aattttttgta ttttttagtag    4680
```

-continued

```
accctgggtt tcaccatgtt gcccaggctg gtattgaact cctaaactca aaccatccac    4740
ccgcctcggc ctcccaaagt gctgggatca cgggtgtgag ccaccgcgcc tggccatgtt    4800
cacttctctc ttacagatca ccctcaacta tcttgcagtt tagtaagatg gtcagaactc    4860
ctccagatgc atggcgatcc cccaggagca agaaggtcca tttattcgcc aacatcttc    4920
tgagcaccat atgtgccagc caccatgcca ggcactgaga agcaaaagtc aaacagataa    4980
gctgaaatag ttgcaactcc ccacccagct actgtcactt ttgcatcttt gcttgtgttg    5040
tttcattccc ctgcaccact ctcctcattt tgtccttcta ggaaaactat tgacccttca    5100
aaccccctggc caggaatcac cttgtttgtg aagacttcta tcttaggaca ttcaggttaa    5160
acagaatacc atagactggg tggcttaaac aaatatttat ttctcacagt tctggaggct    5220
ggaagttcaa ggtcagggcg ccatcatggc ctggttcttg gtgaaggcct gcttcctggt    5280
tcacaggtgg ccatcttctt gttgtaccgt cacgtgtctc ttcttctagg gggctctaat    5340
cccataatgg gggctccact ctcacaacct aatcacctcc cagaggcccc accttaatac    5400
catcatcttg ggagtcagga tttcaacata tgaattttgg agagacacaa acattcagac    5460
cacgacaact tccccgagct cccgttctac cctcatgccc agcagagtta cttcattcgt    5520
cctctgtgct cctgtcagtg gacctgcatc agtgtcctta ctgtgctgga ctgagatggt    5580
ctctggaaac ccctggagga cagggaccaa gacatatctt tgtacctagt gctggcaaaa    5640
ggcctggtcc agagcagtgg ctccttcagt aaatgtttgt caaatcacac tgaaccaaat    5700
caaactgaat aggatcttca gctccatcag atttcaattt catttgcttt atggtcacct    5760
ttgggaaaaa gggagcttag aagcatttgc tgactgtgac agagaggatg ccgagagagg    5820
ggctcggagg tgtttgatca aatggaacat tacagaagag tctataaatg gagatcaggg    5880
ctctgctacc accctacct cacgctccag ttgacaaccc aaactccaga ggggcccatt    5940
taataagcca ggaccaggca tcattggtgt ggcaactgca aagtttcact gggctgggga    6000
tgcccatcat gctgcacata gctgtcctcc ctcccccccag agttgtgcaa agcagcagac    6060
ttgtaccaca gatgagcaga ggggtgaggc tgatcagccc atggtgggat ggcccttggc    6120
ctccaccgtg tatctctctt gtacccagcc ccactatggg cagagggaga aggcagagaa    6180
aaataataaa gagtaaatgg cagagtctac acacttacat ccctacttca tccttagtga    6240
ccttgtaaat tggcacacag ggtccagggg agagcatgtg tcacagctca gttccagctc    6300
agctatttcc accctggag cacagaaagc tggggcaaca tcctgggca cagagggcaa    6360
cacagtctcc atgttttggt cctactttc tgtgctgcct tggaaatgaa tcatatgtga    6420
ctcttcccaa ccagagaagt tgtgaacacc acaggtctgc catctgtatt catccagggg    6480
cttgttgggg tcagtgcagc tgggataagg agaaggagca gaggagaaag ccccagtgga    6540
ggcctggcgg caaagaccgc cccttaccat gagacaccat aacactgtgg ccagagccgg    6600
aggccagtgc aagagtggga agaggggtcc agactagacc ctgctgcaca ctgttaatac    6660
tccatccttc catgcagaaa ggcccaggc tgatgagtta aagccgcaa tgaggatggc    6720
aagcaggtga gtgacggagt ggacacctgg acaaacttct aagcaagtgt cttttgcaaga    6780
accttagctt ttttctgggt acaatgttcc atgtccactg ccacctcaga gtttaggccc    6840
cagaggaggc ccatgcatag gattcaggct caatctgaaa caggtctggg ctcagcctca    6900
gtctgtggct ggcagcccag tccagctcac tgggcccgac gtggcctgcg tccatgtgct    6960
tggcttcatt aacaccaagc tctgaccaac cccagtgacc aaccccctggc ccagtctcta    7020
ggaacagctt cagttaaaac tttgtaagat gccagtaaat agcacagtaa tgaaatccac    7080
```

```
agatgagcta aaactggact gttcagaatc agccaaggat gagatggagt ctccagggggg    7140 cccggcaggc tagaaatatg gtgaggaaat aaccatgtga aactcagcct gggaaggggc    7200
cagcaaacgt catgtgcatg ctgccaaatt ctccccacag ttagcaggaa gcgggagggc    7260 tgcgggagc agctgagcta agggagccag agaggcggga tgtggtaggg gctcggagcg    7320
ggtggcccca gtccagtcat ttgggagtga gtctgtagac acagtacagg gaccaaagag    7380
caggcccctg cccatgtggg cccagagaaa ctccaaggca ggccagcagg accaaggagt    7440 tccaggggt gcagagcttt aggcgggacg ggaagggtat tatggatgag tcatgcatgg     7500
gacagctttg tgtcaaggta ccaagatctc tggtgctcac ctgtccgctg tggagccccc    7560
agcaagccca gaaaatacta gaggcagcaa aaacatcagt gatcaagtca gacagaccca    7620
ggtccgactc ctggccctgt tctgaacctt taaactagtt atctaactcc catcagcctc    7680
agtttcttcc ttccttcctt ccttctttct ttctttcctt ccttcctttc tctatctctc    7740
tctctctctc ttcttatttc tttctctctt tctttctttc ttctcactct gtcacccagg    7800
ctggagtgca gtggtgccat ctcaactccc tgcaacctct gcctcccggg ttcaagcgat    7860
tctcctgtct cagcctccca gtagttggg attacagatg cccactacca tgcccagcta    7920
aattttgtat ttttttttt tagtagagat aggatttcgc catgttggcc aggctggtgt     7980
ggacctccta acctcaggcg atccacctcc ctcggcctcc caaagtgctg gaattacagg    8040
catgagccac tgcgcccagc ctagcctcag tttcttcatc tgtaagacaa aatgttagac    8100
tttcttcata tggtgtcctg aggacaaaat aagataatgc ttatgaagca ataagcataa    8160
ttgttagcac acagcatcag ccaagagaag gaggaggagg aaaccaatga cccctggtgc    8220
tgctggagcc ttgtgtcctt ccttgtccct tcccctcaga gcctgacctc cttggggcta    8280
caaaccaacc tatcctctct tcagctggaa ataactgtc ccctcgaaac actactctct     8340
gccaatgcct cattaacgag gcattgccac tttaatagcc aatcatggtc gactctttta    8400
ctccatccat aactcttgca tgagtggaga gagcctttac ctacaacaaa atgttgaac     8460 tttgagcttt tcctcaaaga tttataaaac aagtcctaat gtgttatttg taatagacta    8520
catctcaaca tcgaggctgg ttaactttgg ttgttgtagc ccagtgaggg cccacactat    8580
ggattccatc tgtgtggact actttccttc attctagccc tacccatggc ctcaaccata    8640
attgaaccca aaccttggcc tcagcttgag cccccaagct ctaatctgcc tgcctcagat    8700
gaaatgtgaa aggctcaggc caaactcatc cccaccgtag ggaaaacaac ctaaagacat    8760
ctcatggcaa tgacactggc ttattggttc cttctctctc aattatgagc actcggtgaa    8820
actgaagttg catagaatag actcccccaa ggaatgggag acccttggaa cctgcccttt    8880
aggaatttgt catctcaagt tggtaatgac aacagctagg aatccaaggg caagccacaa    8940
atgatacgat gttctctctt gttggatcaa tactaaagga cctgaggggc ctgctgccat    9000
ggtgaggagg agccttcagg ggtacccagg ctggactgga tgcagggagt aggctgctgc    9060
tctctcatag atccaagaag tgtttgagca ccaagtcttt ctcctccttc aatgcccttg    9120
agttacacca acctccagca agagtttgac ccactggtaa gattcatttc ctgggaactt    9180
ggcccagacc ccagcagaga gcctggcctt catctaggct gttgttttcc atgagcagtt    9240
cttgtctgat actaggaagc gtcctgttgg attttccagg ccagctccac tttcccgcat    9300
cttgtgcctt agtaagacct tgtgtccaga attctggttc agaacatgtg ttctgtataa    9360
ataggaagcc tagaaaggaa atatgtagcc agctcttatc acctccatca tgtcaatgtc    9420
```

```
ccctcaacac aaaggccttc tctggccagc tctagctggc tatgttcttg ctattaactt    9480
tcttttaact gggtccttat gtctagctac ttcacagagt aaatcctagc tccccatctt    9540
ctgcctaagg ggctgtgtct ccccatcagg ctgagagttc tcatgggcag ggcctatcct    9600
ttccgccttt ttgtgttcct gtgaacaagg ctcttgcacc caatggacac tttatttat    9660 tcattcatcc aacacgtatt tgctggccgc ctgctatgtg ccagtctctg agttaggaca    9720
ttgcagtgaa aaatcaaagt tccagccctc acgaacctct cattttagtg gaaggcaaag    9780
gggaaggcct agaagggaaa gccaagagga ggcacttgtt caaccatcaa gtcttgggca    9840
cccactgtgt cccaggcttt agactaggtc ctagaggcac aatgccacag cagagccact    9900
tggtcaggag gagccaccag ccaggccaga gttctggcca ccctcccaga ggaaatgttt    9960 cccccccagga tcctggctga aggtggtgcc actggccctg ccagctgcc tactaccatc    10020 cccatccctt caccctttc tccaccacaa gcagcacagt tggctgtgct gtggagagtc    10080
gttcatcagt acatccacaa ggagccacat tggtgtttcc ttgaaagcca aggagaagag    10140
gtggttccca gctcagcctt ggagagaggc agcagcatcc ttcctttaag ggttattgtt    10200
aacatctcca ttgcctgcac tgaccaactg accagtgggg gagtcaaagc ccttggtccc    10260
tccccagctg ctcccacaac cttcttgctc caagtggaca gtccagcaag gcaggtttct    10320
gggagccagg gccctactgt ggaactggag gaagcccagg aagattgtct ggcctggggt    10380
ttggctgaaa ggagagaaac aattgccttg agaacaaaat accagaactg aggactgatc    10440
ccaagcaaga tggcaagata gtgatcccag gaggctgaag ggatcatgag gtgagcatgg    10500
aattgtgctg ctcagatctc cctccaacag aaacttctgc aggtagcaga attaactgac    10560
agtcccagct gccacacttt tggatctacg gtggtgttca ctataggctg ctcccagcca    10620
atgactaagt ccggcaggga taccagttcc agcccattcc tgcctgacat gggactcctc    10680
caacaggcaa cccttgctcc gggatctccc atcaatctgg ccagactttc tcagagctgc    10740
actgcagccc aagactcttc ctactccagc ctcctccctt gcacctctcc tttctcaagt    10800
gtcagtccca cactgtggtc tgaaggtgct ccctccttgc tcctgcttcc atcttttatc    10860
ctttgcagat ccccaccct tccccaccac ataaaggttt aatcccatct gatgtctact    10920
tctcagagga cccaagctga cctaggaagc aaagatcccg tggatcagga tgagcaggct    10980
aacggatatg tgtgccccct gcagccccaa aggaccacta cccactgcca gagaacattg    11040
ttttcccagg tctgtgggag gagctgagtg tgggctcctt tccagtggcc tagaaggggt    11100
cccagcctca catggctcat atcctgctga gaacctgcac caaccctccc ttcaactcag    11160
gggtctccat tttcctcaag cagaaagcag tcttagaaaa ttctccccca acatttccaa    11220
atatttattc attttaatta aaaaaaaga aatccaaatg tacctcaatt tacccaagaa    11280
ctgtgtcctt gagatgttaa gtgcaaatta aattgggggg aagtagatct tcttgtacat    11340
gctccatggg cctcgcaatt aaagggagct ctgcagcaca tcaaacgtca gttcccatgc    11400
catgtatctg agttgacaat aaaactgatg actatgggta aatgacagta aaactggtta    11460
actgtacaga agtcaagcaa acggcaacca cagcaggtcc ctggccctgg ggatctccca    11520
gcccaccaga gagaccgaca ggatctactt ggagaacaaa ttcaatcaga ccttgatggt    11580
gacagcattg ctcattcact agctctgaga agcaggaaag agtttagaca agaataacca    11640
gggatgccac tgaaggtggg tgcccaggcc tgggctccag gcctccctac cactactaca    11700
cagagctacc ctcttcctgc ctttccctgt ctgtcccagt tgctctaggg tcctcctagt    11760
ctgtgccctg ggcctggcca catggttggc tgcctgggga ggccctggct ttgttcccag    11820
```

```
taccagaggt tggggtgaag acatgcgggc tgactggagt gtggccagcc ctcaggccca    11880
gctgcagggc gcagggccaa gttgacaatg ccagccactg gagacagagt ggcaactact    11940
gctgtcgcct ccaaaatacc agttgaggtt ttctcctact gtggggttta gaaactattt    12000
ccatttctat tatgcctttg ttttgcccta ttttctcttt tcttttttaat agtgttggtg    12060 gttgtgcctg gaggtgagac aggggagggc aggacaagag ccaagagaac gctgaagtca    12120
gcagagtgtg ctctggtgcc tcgcagcttc tcttccagca ctgcccactc ccactgcagg    12180
gcctgggtct caatggcagt ccctctcagg gcctattctc catggacaag aatcagcagg    12240
gctcttactc caccctattt ttccccgatc atgacttcct gtaccgtggc ccactcttag    12300
catccatctg tctgctggta aatgaggata ttcactctgt cctgggccac cttctcctct    12360
cattgcacac tgtcttccta gacagtccca cccacaccca tggcctcagt taccacttac    12420
atgccataaa ctccacattt atttctccag ccccttctcc cctctgattc ttagacctgc    12480
atatccagct gctctctctc ccttagtggc tcacaggcac ctcaaactcc acatggccag    12540
aactgacctc atcatcacca ctctacccag ccaccaaata aacacacccc tcccaaaaga    12600
gaaaagtatc ttctcctgct tcagtcttct ccatctcagt gaatggcagt accatccttc    12660
tagctgttca agacagaaaa ctgggggcga tcctgaactc tgcccttttac ttcacccatc    12720 agctatatcc catctatcag caggtcttgt caatcccatc ttctatagag ctctccatgg    12780
ttttgatagc tccctagtcc cattgtcact cttttaatta agacctccat caactcattc    12840
atagacaact taaattacct cttaatttgt cttttctgcct cagtatttac ctcttgtcca    12900
gttaagagac caccaggtgg ccaccagatt tccttagaa acagatatga tcatgtctct    12960
cccctgttta aaagcctctg ctggaacttc tacttccaac cacattggag taaactgaaa    13020
cagacttttt cttctgccat ttaaaaaaac cctaaaaaac gtaccaaaat acataaaaca    13080
gctatttata gacattggac aataggcagt gcaggactgt gatccctgag agaaggtgag    13140
gtgaagtcta tgatgccctt tggtttctgc ccaaaggcac tttctggacc ataatatggg    13200
atggggaaac cccaaaagag catagtgatc tcctggagtt aatgagtaaa aatattagag    13260
tttgggagac tgaggcagct ggaattttca ggtcagagtt ctagaaagga aagagcaaca    13320
tagaaaaaaa gagttccaga tatctacata gggagcctct tgattgactt gctgaacact    13380
aagctataca tacatagggt gacaccctac aaatccaagc aagaactacc aggaagcgat    13440
aggctgaaat tcccagagtc ctgacaagta taggagacat acaatttcca gctagccaga    13500
gtagagaaac cttatggaaa atccagggta ttcagtcaag gctgccagaa gagtcacacc    13560
tcaccagtaa ggataaacta gacctagaat aaatgatact ctagaccttc cctaatcaac    13620
cttaaaaaca agcagtaaaa ggcccaggcc gatatacaag aaacttaact gctttctaaa    13680
acaaaactca agatttctta aaggaagaca caaaatctag acactcaaca atgaaacatc    13740
cccaatgtct agaatccaat taaaaaatta ctagacatgt aaggaagcag agaaaatgtg    13800
ctgcttccat agccaggaaa gaaaaaaaat cagtcaatag aaacagccag aaatggcaga    13860
gatgatagaa ttaacaaaca aggacttttta aacagctgtt ataaatatgc tcaaggattt    13920
acaagaaaac atggatagag tgaaggaaat ataaatatg tattaaaata gccaaataga    13980
atttttagtg gtaaaaaata caatatttaa aataaaaatt tactagatgg gcgtaacagc    14040
agattagaca ctgcagaaga aaagatcagt gaactagaag aaatagcaat agaaactacc    14100
caaaacgaag cacagaggga aaataaaaag ttattttttct taaataactg atttaataga    14160
```

```
ggctgataaa aagttaacag aatgaatggg taaacaaagt gcagtatatc caaacaatgg      14220
aatattatct gtccataaaa agaaatgaag tactgataca tgctatcaca taagtgagcc      14280
ttacactaag taagaagcca gccacaaaag atcacaattt atatgatttc atttattttc      14340
atttgttgtc cagaataggc aaaaccatac agacaaagta gatccgtggt tccttagggc      14400
tagaggagtc agagggatgg ggaattgcta aaggatatgg ggtttctttg gaggtagtga      14460
aaatgttcta aaattgactg tggtgatggt tgcacatatt atgagtatta taaaagccat      14520
tgaaatgtac tcattaaatg gatgaattgt acagtatgtg gattatatat tagtaaagct      14580
gttatttaaa aaatactaat ggagtttcag tgacctgtgg ttccatatca cacagtctaa      14640
catatgtgta ataagagttc taggaggtgc tggaggcaga aaaacatttg aataaataat      14700
ggctgaaaat ttggcaaatc tgatgaaaac tgtaaactat aataatccaa gaaactcaac      14760
aagcctcaag aagaataaaa atgaagaaaa tcaaaccaaa gcacagtatc agcaaattgc      14820
tgaaaaccac tgataagaga aatgttagt accagcttta gggggaaaaa aatgacacat      14880
tatatactgc ggaaccaaac taagataac cacacgcttc taaaccaaaa cgttgcaagc      14940
cagaagacaa tgaagtgata tctttaaact attcaaagac ttaaactata agaaatgtta      15000
aaggaagctc ttcgggttga gggaaatgat accagttgga aacacagact tacaaaaagg      15060
aatgatgagt gccagaaatg acaaacatgt gggtaaataa gaaaatgctt gcttttctca      15120 atttttaaagt ttttatttaa aagacaatta attgttcaat gccaatgaat tgttcacttg      15180
aaaatggcta attatggcca ggtgcagtgg ctcatgcctg taaccccagc actttgggag      15240
gccgacagga ggatcactcg aggccaggag ttcgagacca gcctggccaa catagcaaaa      15300
cctcttacta aaaaatacaa aaaattagcc agggctgtta gtgcatgcct gtcattccag      15360
ctactcagga ggctgaggca ggagaatcac tggaacctgg gagatggagt ttgcagtgag      15420
ccaagatcat gccactgcac tccagcctgg gtgacagagc cagactctgt ctaaaaaaat      15480
aaaataaaat aaaatggcta attttatatt atgtgaattt caccctcaata cattatttca      15540 aaaaatataa atgactgctt aaagcaaaaa caataacgat ataccttggg tttatatgta      15600
gaagcaaaag gtattacgac aatagcacaa atgatgggag gtacaaaagt atgctgttgt      15660
aaggttctta cttgtccatg aagtcatata atagcatctg aggtagattg tgatggttaa      15720
aaatgcttgt tttaaaccct agatcaactg gaaaaaaaat ttttagctaa taagccaatg      15780
acagagataa agtagaaaag taaaagattt ccgttattcc ttgatactta tctctcaagg      15840
aggtagagct taattcccac ccccttgact gtgggctgaa tttagtgact tgcgtgtaat      15900
gaatataatt tctaaaggga aaagcagtaa ctttacagtg gggaaacgtg gcagacacca      15960
ccttgaccaa gtggtcaagg ttaacatcac cagtaagtca tgtcaatatc atataccct      16020 gatttgatgg gatgacaagg gtacatcacc tcaatggtat tctttccaaa aatgcatatc      16080
cacagaccaa tcaaagaaa atatcagaca aacccaaatt gagagacatt ctacaaaaca      16140
catgaccagt gcttctcaaa actgtccaga tcgtcaaaaa acagaaaaac ctgagaaact      16200
gtcatagcca agaggaacct aagtagacat gatcatgatt aattgaagtg ggatcctgga      16260
atagaaaaag gtgtgaatgg gaaaactggg aaaatccgaa tgaagtctgt agtgtagtag      16320
tattgtacca aggttaattt cttatgtttg agaaatatat tgtgtttatg tcaagtgttt      16380
atgaaaggtt ggatgaaagg tctatgggaa ctctccattt cacaactctt ctataaatct      16440
aaaattattt taaaacaaaa agttttttaag aaaataccag gccgggcgca gtggcttatg      16500
cccgtaatcc caacactttg ggaggctgaa gtgggcagat cgcctgaggt caggagtttg      16560
```

```
agaccagcct ggccaacatg gtgaaatctc atctctacta aaaatacaaa cattagccga   16620
acattgtggt gcacgcctat aatcccagtt actcagaggt tgaggtagga taatcacttg   16680
atcccagaga cggcgattgc agtgagccaa gatcgtgcca ttgcactcca gcctgggcaa   16740
caagagcaaa actgcatctc aacaaaaata aagaaaata ctcaacccaa aagagggcaa    16800
aaatagagga aaaagttgac aaagaataga aaggaagaat agaaacaaa tagagaagtg    16860 gatgacctaa attcaacaat atcaataacg acatcaaatg tgaagggact ctaagcagta   16920
caattaaaag ttagagattg tcctactgca ttaaaagaa aattggactc aacatttgtt    16980
tcaagcatat gttttaagca taaagacaca gatgggttaa aactaaaatg ataaagatgc   17040
accaggagtg gctatgttaa tttcaaagta agctttaaga cacagaatat taccaggaat   17100
agacatgttt aatgataaaa cagtcatcag gacaatataa caatcttaaa tgtgtatgtc   17160
cctaataaca agcttcaaaa tacatgaact caaaactgac agaattgaaa taaatagaca   17220
aatttgcaac tatagttgga gagttcaaca gttctttctc agtaactgat aaaataagta   17280
aacagtaaat cagtaagagt atataagact taacatcttg acaggagtgg tggctcacac   17340
ttgtaatctc agcactttgg gaggccgaag caggcagatc acttgaggtc agaagtttga   17400
gaccagactg gccaatgtgg taaaaccccg tttccactat aataaaaata caaaattag    17460 ccaggcatag tggcaggctc ctaaaatccc agctaccaga gaggctgagg caggagaatc   17520
acttgagcct gggaggtgga tgttgcagta agctgagata gcaccactga actccagcct   17580
gggtgacaga gtgagactca gtctcaaaac aaaacaaaaa caaacaaaca aacaaaaaa    17640 cccacttaaa cagcaccctc aatcaacctg acctaattgg catgaataga acactgcacc   17700
caatatctgc agaatacaca gtcttctcaa gcacatatgg aacattctcc aagatagacc   17760
ataagctgga ccatcaaaca agtctcaata aatttaaaag gactaaaatc atgaatgtat   17820
gttctctgat ctcaacagaa ttaaattcaa aatcaataac aaaaaagata tctatggaat   17880
ccttaaatat ttggaaatta atgacacact tcaaaataat ccatgagtca gagaataaat   17940
caaaagggaa attgaaaagc attttaaat gaatgaaaat gaagacagca tataaaaatt    18000
tgcgggatgt cactaaagca gtatttaggg ggaagcttat ggcactcgat acctatatta   18060
agaaagaaga aaggtcttag atcaatgacc tcagctttgt taaaagaaaa actctagaca   18120
aattaaattt aacagagtta aattcagcaa agaccaattt gcaaatcagg cagcttccta   18180
aaccggaata gatttagagt gactccagca ctgccatgtg gttggagaaa atttatgtac   18240
agaaaaagga aagtgatgta cagaaaacgg gagtgtgggc tgggcagagt ggcttacgcc   18300
tgtaatccca gaaccttggg agatcaaggc tggtggatcg cttgagccca ggagctccag   18360
accagcctga gcaacatggc gaaaccccat ctctaccaaa aatagagaaa tcagctgagt   18420
gtggtgacac acgcccataa tcctagctac tcaggaagct gaggagggag gattgatcgc   18480
ttgagaccca ggaggcagag gttgcagtga gccaaggttg tgccactgca ctccagcctg   18540
ggcgacagag tgagactctg tctcaaaaag aaaaaaaaa aaagaaaaga aaagaaaat    18600 ggaagtgagg tacagaacca gctggattaa ttacagctca atgtttgcct tatttgaaca   18660
caatttgaac agttggccgc ctgtgatttg ccaaaactcg gtgactcgta caagagcagg   18720
ttacagtttg tttacacatc cagttaggtt acagttcact atgcacacag aaacctttag   18780
gccgaactta aaacacgtaa ggaggcaatt tcatgctaaa cttaacagtt tcaagcttaa   18840
aaagctagaa aaggaagaat aaattaagcc caaaataagt agaagaaagg aaataacgaa   18900
```

-continued

```
gataagaaca ggaatcaatg aactagcaaa tagatagaga agatcaatga aaccaaaagt   18960
cagtgctttg aaaatatcaa taaaaacaat aaacttctac ctaggcagta ttagttatat   19020
gattgtatat atttatcaaa ctcattgagc tgtataccta taatgggtgc attttatttt   19080
ctgttaattg tacccaaaaa catggacaaa agatttgaac tgagacttca ctaaggtaga   19140
tgtaaaaatg gccaataaac acatgaaaag atactcaaca tcattagtca tcagtgaaat   19200
agaaattaaa gccatcatga gatgctagta cacattcact tagaatgcct gaaaattttt   19260
taaaaataac tatactaatc ggatataaat caatgaaaac tctacaaagc aatgaaaatt   19320
acatttctgg ctggagtaca aaatggtaca tccattgtgg aaattagtct gatagtgtct   19380
cataaaatta aacgtaagct aatgcttttgg cccagtaatt ccacttgtag gtatttatcc   19440
aagagaaata aaaacatatg cccacaacac acctcataaa agagtattca tagaagcttt   19500
atttatgaaa acccaaaact agaaatagct caggtgtcta gcaatgggtg aatgaataaa   19560
caaattgtga tacatccata gattggatca atggtatacc aatacaatca tacatcgcat   19620
accttataac ttttatggac atacaacata tacaatggca tattaataca atggatattc   19680
agcaattaaa aggaataagc tactgataca tgttacaaca tggagaacct caaaagcatt   19740
atgtaattga gaagccagac acaaaggcta agtaccatat aactctgttt atttgaaatt   19800
ctagaataag taaaactaac ttatagtgac aggaagcaag atagaggtag tcaagggtca   19860
cgagtgggag tgggattgca aaagtcttca aggacatttt tttgccatga tgaaaatgat   19920
gtaaatctca atcatagcag tggcttcaca tacagggcca ctcctaaggt gctcagaacc   19980
taggaaaata tattttgtgc aatccctgtc tacacacaat atttgagtca tccaagacta   20040
gtgtgtcaat accattctgg ttgacccaat ttcatgcact tctgtcaaag atatattgct   20100
ctggctagtg gagcaatcca cttatcatgc tgctctcctg gaaccgggtc tcaaccaaaa   20160
gtaccataga cgatcccata ggtgagaatc gtggagttcc ttgggacatc tggtgggccc   20220
caagcacagg atgggggatg tctagagact cagagtgcct ggaaaaacac agaccaggtc   20280
ctatgtctac gtgggaccca ttctgagcta aggaaagccc aacctgatga caccactgat   20340
tccggggcag cagtctcaag ccgctgagcc tacgtgaata agtcaaggc aactgtagca   20400 tggtgtgctg agacaaaggc tctggtttca gacattggca ggaaaccgaa aattttaagg   20460
aaagtgctgc aaagtgcagt gggttcctcc tgaaatgcag ggcatgggac agaagcccca   20520
tctgcccagt tctaaggtag tgctggttta catgggtgca gacatttatc aaatgaactg   20580
tacactgtat cattgaactg tacacttaca atgagtgcat gttattgcat ataaattata   20640
cctcaataga gaatacttac taccaagaaa gaaaaccctg tagtctcagc tactcaggag   20700
gctgaggcag gagaatcact tgagcccagg agttcaaggc catagtgagc tgtgatcaca   20760
cctgtgaaca gccacttcac tccagcctgg gcaacatagt gagacccat cttgaagaa   20820 agaaagaaag gaaggaagga agagagagtg gggggagg agggagggaa atgaaaggaa   20880
aggaaagaga aagaaagaaa gaaagaaaga agaaagaaaa gaaagaaaga aagaaagaga   20940
gaaagaaaga aagaaagaaa gaaagagaaa gaaagaaaag aaagagaaag aaagaaaaga   21000
gagaaaaaga aggaaagaaa gagaaagaag aaagagagaa agagagaaac agagaaagaa   21060
agagaaagaa gaaagagaaa gagagaaaca gagaagagaaa gaaagaaaag aaaagaaagg   21120
aaagaaagga aggaaggaag gaaggaagga aggaaggaaa aagaagaccg tgtatctcag   21180
attcccaggc cccattccag acaaaatcag aaagtcttct gtctggacac tgagaaattt   21240
tcatctgttg gttctcagtt gcctagagaa ttacatccag ggtgcacttt ccagcccagc   21300
```

```
cctgacgtgc ctcctcatcc tcagttcctg atactccttt tcttaacggg tgctccagac    21360
acgctgaact tagaaccagt ccctaaaagt gctcacaccc cttttgcaaac cagtgcctct    21420 acatattagg tttcccctgc ttgaactcac accttctccc tgcaaggaat tcctacacat    21480
cgttcaaaat ccatctgaaa tgtcactttt tctgtatagc catctccgac cacctaacag    21540
cgttaagatg gatggaggtg ttatcggtgg agggtgtcca tgttctccgt gttttgaaca    21600
aagaattgga caaaacacac aaacaaagca ggaaagaatg aaacaacaaa agcagagatt    21660
tattgaaaac gacagtacac tccaaagcgt gggaacgggc ccgagcagcc actcaagggc    21720
ccagatacag aaacttctcg ggtccaaata cccactagag gtttcccatt ggccacttgg    21780
tgttcacccc atgtaaatga agtggtggtc tgcaaccagt cttattgcaa ccaatcagag    21840
gctgaagtga agttacaaag gtcacacttt tatgcaaaga tctgattggt tgctgtctgc    21900
aaccaatcag aggctcaagt gaagttacaa tgttgcactt ctatgcaaac gaagacttga    21960
cccgcaatca gtctgattgg ttgtggacag cctacagagg ctgaagtgaa gtttcaaagt    22020
tacactccta tgcaaatgtc taacaaccaa tcataggtac tttcaatttc ccatcggcca    22080
cgcagaaaag ctgggagctt gcaaagggag tagcctctgg tccttttgtt acttaggcat    22140
ggaaagttag ggttctcctt tcaatttagt tctaggaact cagcgtgaaa cggccttagg    22200
ttccctgcct ccagaatgta ttctcctgcc tcagagagag gatgatccct cttcagtgac    22260
cccacaaagc ttgggacata cttttttatgg ctatgcacact tgtcaaaagt ggactgttgg    22320
tacctgtctg ggggctttcc ctcatatcta attgcaaatt cctccagggc agggagcata    22380
ccttcttcaa tccagcacct agcacagtgc ctggcaacat aataggctct tgatacaagc    22440
tgttcaatga acgaatgaat cagtgaatga atctcttccc ctttgggac tctttagtgg    22500 gagccttcat tgaagagtgg tttcaccaca gagtgaccta taagcaaaaa atttttaagag    22560 ctgggacagc ctgggttggg gggtgttatt tggtcaggga aatattttaa ccccgaagat    22620
tatgtccctg aggtatttca gcctatccag gacttgtatt tatgagatgg ccagggtcag    22680
ggctcattct gtggccaaaa ttaggtgtta aatacccatt atcatcacca tcatcatgat    22740
tatcctttat ttggcattta tcatgtgtca catgctggta taaacactct tgtatattag    22800
ctcatttaat ctgcacagta actctgggag gaaggcgcta ctgggttgaa ccataagaaa    22860
ttgtcaatat tcaatctttt ttgacccaca aaatagcatt ttcatatagt tcaacctaag    22920
ttaccgaatt cttttaccaa ggttcaagga ggtgagtccc ttgcccagat ttcaatgttc    22980
atctctctgg ctccagagcc ctttttgctat tttctctaca ctgccagctt ctatcagttg    23040
taaaatccct gctataagcc agtccacagg gtctagtaag tcggacagga gcgggactgg    23100
ctagggtttc aaatgctctt ttgcagggaa gatgaactga cttggcctga aaatgttagt    23160
cttttagcgg tcgtgtttcc aattttgttt tagtctctca ctcatccaga atccacctcc    23220
ctcaccacac acacacacac acacacacac acacacatgc acacacacag aagagccaag    23280
cagctgactc acacaccatg ccgcagttgc cttgactttg ttcacgtagg ctcagcagct    23340
tgagactgca gccccagaat cggcagtgtc ctcagttggc acccagagga gctgttgcat    23400
tctccccttt attgtggaga tggctgcagc aggtgctctt gtcctggggg aagacagcca    23460
ttgagattgg cagaggctta agtatgaagt caaaggcaac acctgatatc agaaagggcc    23520
caggcagcag tggggaagtc ctcagctgga tcttttgagcc ttgacggaa tcagcagcag    23580 gtagggcaga ccccaacccc actgatatct ctgctgcttg cttgccaacc ctgtgagctg    23640
```

```
cccactgagg caataggcct ggcagtgctg gaggctggga agggagagac atatagtaca  23700
gtaagcattg accccccagg aaaggctcac agtgacccac cccccttcat agtatgaggg  23760
caatgacaga gcattgtccg gattgggggt gggcaggaaa tagaggccag ggaaatgcac  23820
atactcagag cctcaggcat caggtgggcc tgagaggcct ggctgaggaa tggggggtaa  23880
gtctggacat gcagacagac ttcccatgat attctacctt gagatgaatg tggtcaggag  23940
gagagtccag gctggctggg aggttgatct ggggctacaa gccctgggcc ccaggagaga  24000
ggaactggaa aggcttcctc caagaacccc agaagcctct ggccttttccc ggcataacta  24060 gaaagagaag cagacagccc caggatctta ctcaatgaga gcttaaaggc ttgccttcct  24120
gtttcctctc tcatgaaggg gcagcctgag atgccacgaa gagccctggg ctggaagtta  24180
ggaggccgga gtgctagtcc cattcccgcc tgccagagcc atcctctccc tgggctacag  24240
tgttctccat ctgcagaaat gatgaggcag gatgcgtcaa gtggggaagg cagttggttc  24300
taccagaatc atggttttca aacttttgca gtttggaaca ctttctttaa acaaaatcta  24360
acagggcaac tcaacgtgta aggtggcaga tgaaaataga gctgctctca acccattccc  24420
ctccccagag gttcccctag aacctccatg gtagcccaga gccccttttta aagaccactg  24480 ggttagagct gtgggcttcc aacttgagtg tgcaccagca tcacctggag ggtttgtaag  24540
aatagattgc tgggcccacc cctaaagttt ctgactgtgt atatgggatg gaactgagaa  24600
tttgcatttc taacaagcac ccaggtgatg ctgatgttgc tggtccaggg accacaattt  24660
gagaactact aggttacatt ctacccaagg gccttcctgt gattcatgtc cagtcattca  24720
atatttacat taatccactt cagatagatt ttctgtgata ttaaagcata ggagaacacc  24780
tggtattgtc cctggcacat agcaggcact cggtcaaagc tggtagggtc cgttctaaat  24840
gctctgccta gaagtctgtt taggtgtaca atcatgttag ccactggtca agggattcac  24900
agaagcagaa gctttacttt taataagttt acagtctgcc atggcccctc cacccaccag  24960
gaaataacac ccccactaat tccatcatta gaagttactc catgttaaac attatccttt  25020
ccagatattc tctttttttc caggtaaacc ccctgggaag gggtagttgt tcagtccctg  25080
acccctcagc atttcttaga tgttttcccc atgtgaaggg gacatagctt cgatcctcta  25140
ggagttcttc cagggcaagg accttacctg tatcattctc ccccacatac cccacggctc  25200
ctagcccagt gtctggtaca gagtggacac tcagtacaag tttgcagaat agaataaagg  25260
aagcatggga cccccaactt gacccagccc acgtgagcca ccagcacccc catcatggcc  25320
aaggctgcta actggggaac tttggagggt acatggggag ggcaggtctc cagccacacg  25380
cacctgggat tgctgcccgg gaggttttgc aaactggctc caggaatgtt cggggcctcc  25440
cattccccac atcctccttt tcagcctcac cacgttctta aacaaattgg cactgaccct  25500
ggtgacagac ttgatcattt ccctttgctt cgtgattgtg ttaagtgact gccaaaggcc  25560
tgttcctgaa tagtcagcac attcctcagg acggtgagtg ggagcccatc tgctcctgga  25620
gcgcttcctt tcctttattg tgctatttg gcctcaattt cccatttgga caggagcatc  25680
ttccagccgg tggggaaagg gagagggtgg agagggcgc cacagccttc cttcatttct  25740
cactcatatc cctggtttct ctggaaataa atcaacaaat attatactac gtgcctggcg  25800
ctgctcttag ctctccacat gtgtccatgg agctaatcct tacaacaccc actatgagga  25860
aggcacaaat attaccccca ttttccagat gagggaacag agactgagag aggccaagtg  25920
acttgcccaa ggtcgcacaa tatgtgatag agctgggatt tgaacctaga caggtctggc  25980
tctggagact gagttctcac ccattggctc taccaagggt gtggattctt gaggctgtgg  26040
```

```
atctgggccc aatggtatct gaggccatgg ccctttccct cttcactgtg tgtcagcagg   26100
ttctaaagtc acttagattg aacacagaat tccagcccgg cgcggtggct cacatctata   26160
atcccagcac tttgggaagt tgaagtggga ggatcacttg agaccaggag ttcaagacca   26220
gcctgagcaa catagcaaga ccccattatt acaaaaaaaa ttttaaaccg gccaggtgtg   26280
gtggcgtgtg cctgtagtct catctactcg gcaggctgag gtgagaggat ggcttgagcc   26340
caacactcca ggctggacaa cagagcaaga ccctgtctct taaaaatttt tgaaagaaaa   26400
cagaattcct tgcagatcag aaaaggttat cttcatacct tgccactgac ccactcgttt   26460
aatgcaacat ttgaactcac agatgctaca ccaatgtgga ctctaccttt gggttataaa   26520
gggctgatat agtaatgcta aacagctcat tgtgtgctct tctccatgta ccttgcctca   26580
tttatgtctc acatcaactc taaagtaggt tgtagggaga agctgaggct caaagatccc   26640
ccagccaacc acagacccag catgtgggca attcattact acactagatg ttaaacagcc   26700
aggtagcttt tgctaggtgt caggtgttgt ctaaacactc tccctcattg attcattcaa   26760
gcctcataac aatcccatga agtaggtact attattatcc ctgtctctat ttcgcagatg   26820
aggaagccga ggcacagaga ggtcaagtaa cttgcctgag gtcacacagc cagaaagtgg   26880
gagatctggg atttgaacga agtctgtcag cttagactgt ggggttccta gtgtatgctc   26940
ttaaccactg cactgtgcta cctcttggca ctgaggccac ctctgggcac ttgaggtacc   27000
atgataccat aaccccctcc atctcttctc cttgtcttcc tgctattcca aattgacttg   27060
gtatttccaa taaccataat tctcagaggt tctggagttc aaattacagc actgcactca   27120
ctagcagggt gacctctgtt tctttctgta ccccagtttc ctaatctgta aagtgggagt   27180
aatatggtaa tgagcccata gggtggttgt gagcatgtag gtcaggcaca gtggattccg   27240
ccatcaccac caccacctcc ggttgcatct tctccagccc agcccagca tcctgaaggg    27300 ggaaatggtg cttcacgccc tttcacttat cagtctcacc ctccgtgtct gtctcttcct   27360
gtctcaaatg aaaagcagcc ttcagttaag attccctagc cttttgaaaa cttggtgatt   27420
acaattcctc ccaggaggtc aaagaaacct atttccctag cattctaagc aggaattcta   27480
ttgtcatttg ttaactcaaa catggccaag gtggcccagc ccatctcctt tcgtccacac   27540
ccataggaga catagagaat agataacttg actggaacag atcccaccag cacccatgg   27600 ccagagtccc tgagaaagaa attcacagca aggaaatgca ccaattgcaa ataattattt   27660
ggaatctgat gattccttgc aacgtcagtg actgcgagtg agcctctccc tcttgccgtc   27720
tttacagaaa atgttgaggt actagacagg gaatataaat tttccagtat cttttccctat   27780 gttcctaagt gtccctgtcc tataattcca gtcttgcctc gttgctactg gtgtcttatg   27840
tcctcagctc agtggggtag agcatagcgc tacctataag caggcagtta ggattagaaa   27900
ataaagtccc cttcacttag ctcttcatcc acaaagcaag ctctaaccct ggccactgac   27960
tgagcactaa ccccagccta gaatgttccc taaacctgtt cagagaatga gcctaaacct   28020
tggtaatggg ctgcccttag tctcattcac agactgagta tataattgca gagtgaagaa   28080
actccaacct ggagaggtaa agcaacttgg ccagcatcac acagaaccaa ttctctgtcc   28140
cagccatata ttgaccctga attttagcca ctaagaacaa gattttaagc gtgtgggtgt   28200
atcagtgcaa gtgacctcta ctagtaagat tccaactcag acaggtgagt gggcaccaca   28260
tctttgtctc tgagggagat gccactgttc cagtcttcac ggagtactgg ggttattaaa   28320
aagaattctt gcctagggag agtgatttgt atgatgaaag aaatcaataa attgctgttg   28380
```

```
aatgcagtcc aacctcactt attcaaacta attggaggta gccttcaaa ttagtgaacc    28440 atctgtattg taggttactt gtaaagtaat gaagctttat tgttttgaat aattcacagt    28500
agctccaagt aagctaacaa gttgtagcct aatcgaggtc ttaggagact tgccttaatg    28560
aaatgaaaag aatcctcagc atcaatcatt tgtatgcaaa tggtcctacc aaggaaatga    28620
taaagtttgc tgccttgaag tatagaaact cagtgcacag agtccattta ttcaattcat    28680
ttatgacttt gttgagagtg gacaaagtca agacagacag ggcccaagct atccccattt    28740
ggtactcatg gagtgtcttc taatgaggtt ttactgtaaa aggaaacaat tggagagcag    28800
caggtgcaat ccatccactg ataaaataaa agatggtttt ggaatactgt cacttccttt    28860 cattttttt tcctaagaag acattagaaa aaaagttac caatgtaagt caagtacctc    28920
ggtgctttgt caaacccgg aacaaacatt aaggggaaaa aaatctgaag gtcgaggaag    28980
ggaaataaac aagaagagta agtaaagcat gaatcatcca ttaccacctg atggctcctt    29040
aaaaataaaa ataaaactat ggaaggaaat agagtccatg ccacagtcag gcatgttgat    29100
agggaacctg gcatggactc ttatttcgca gaaagaactg acctttggct tctaatttgg    29160
attgcctttt cctcaaggcc ttgcagagca caaggttaga cgatgctcgc ctagcaccgg    29220
ttcccaattc tttcttgggc actataagtg gagccaagga aacaatttta ttttcatgca    29280
tttaatttaa ttaccccacc ttgtttccca aagactttga ggtggttaat gacaatgaaa    29340
aaataatgac aaaataaaag cagagaatta ggaccaggga aaatattaat agaaagtttt    29400
aaatcaagag ttaaagacct gaaaggtcat ataaagttgc actacaggtt tctaaaaaga    29460
ggcacagttg ggattcaaac cagctcagtc caatggacca ccttcggaag gagcacagga    29520
tccccagatg gacctatcta taagtgtgat cttgggctag atacacaact tccctgagcc    29580
aatttcctca tctgaatgat ggacctaatc aatattgtct atttcacaag ctgttatgag    29640
gactcaacga aatggtttct ttaagccatt gagctccact ggctagcaga aacatgtgc    29700 ttaataaatg gtagctatga aatggatat gaagtctccc atgatgcaat acaaagaatt    29760
tgcccataat ggcatgtcat ttaatcttcg caccagctca ggccttgggc ccaggatcac    29820
agagaaggga gagcagagga aggagggagt ccttgggag gcttcctaca aaggtggta    29880 ccccagtcag agcttctgta ggataggtag gatatgagga gatggaacta aaggtgaaga    29940
atgagctgga agtgtatgag gacagtaaga aaacctacta aagcagatgg ccaggtagga    30000
aatgaggtta tagagaagag gatagggcag gatgggctca tgaacttgct tgaatcgggc    30060
cagatggtga aggaatgtgg atgtcatttg acaggaaatg gggagtcatt gaaggatttt    30120
gagcaggtta agcaggggaa ggatgtgaca tgtttgaagg gatgttttca aaggtggagt    30180
ctgtctgctg ctctctgctg tgtgcaggct gtggtggggg ttgggagaaa cagggactgg    30240
cagaccagct gcagtgatcc aaggaaggga catgataaga gctcaagcta aggcaacggt    30300
gacggagaag atgggcggtt cccaatttca gttagaggca cctgagaggg atgatttgac    30360
tttctttcta gactcaaaat tccatgagga cagggaccat gctctcctgg ttcatcactg    30420 taccccctagg acctagcaaa gtgcttggca catagcaggc gcccagcaag tgttttatga    30480
atgaatgaat aaatgaatga atgcctctat gcagacagac actgaataag aatggttgct    30540
tgctcaataa caagcaatag tacaaggaaa acaaaataga gaattttttt aaagaaaaca    30600
ttactttaac tgactttctt tcaccatccc tggactacag taacaatgtg gtataggaat    30660
gcaactcagg agaaatctag agctgactgg gaaagaagcc ctttaaagca gaacctgtat    30720
cagcagtgac gctctatagg aagcatgcca accatatgtc ccctggacag ttcgcacagt    30780
```

```
gtagaaacat cacaatgcag gtaaattata gataggagaa gaaaaatggc agtatttacc    30840
tcacaaaagg attaactgag cttccattta aagtagcaaa ctgcctttct agtgtactta    30900
atttgagacc aggacttgac gtactgaaac tgggttccat ccaagacaat atagagtaat    30960
tgtctatact ggtaagagcc ttgatttggg agtacagaaa cctaacctttt gacctaggca    31020
agtagcagaa tgtggtggtt acattcacag gccgtggaat tgtgctgcct ggatttgcat    31080
cctggtgcaa cactgactgg ctgtttggcc ttgggcaagt ggcttagcct ttctgtgctt    31140
cagtttcttc ttctgtaaaa tgtgatgata caacacctga tcctggttca tgaggttatt    31200
gtgaggatta agtgaggtaa tgcatggaat gtgttcagca atacctagaa cgtttcagta    31260
aatattggct ttcactctta atcctaacta tatgacctta ggcaagtcac ttcccctctc    31320
tgggccttgg tttcctcatg agcctgaagc ttcttttatt catacctta ggatgtggcc      31380
cctacctgta ctacaaactc atcatctatc acacataaaa gcatctccac cctctggggt    31440
ccccagttga taactctgcc catagaagga ccattgggat tcctagaaat gagcaaaggc    31500
ccaaatagac aagactagga tagattcact tttcttagta tactttgtaa aagttccaac    31560
tcactcactc agctcccact tctaaatctt agcctcctct tttcctccca agcagcctta    31620
cttccttaat catcttcatc ccaggcccta agggaaagga tgctcaagag cactgctatc    31680
ctctggacag ctcctctagc caaaccccca tttggatccc aagttttttcc tttaggtttc    31740
tcctccccaa ccccaactcc aacccaggga actgcaatcg caccaacctc tgctgccctc    31800
tgctgtctag ttccagatgt gctggctcca gttgggccag ttatgtcagc ttccaaggac    31860
ctgtcagttt ttccaggccc tagctgccac tgtgacctca ggaatacaac tcagatgccc    31920
tctgcaatat ctgtgctctc ccttaatctg acaaatgca cagtcttttcc tattcagact     31980
cgacagccaa gccacatctg gtgtagtcca tgagttcaga actgttattt tcagcaaaga    32040
aaggaagctg ctagagccat ccatactctc atctaagccc ccttctcaaa cattctgcaa    32100
tcatttatta cgcatttgct gtgtgccagg cactgtgcaa aatgctgagg atgcattctt    32160
attgaatcct ggcatcaacc ttcccagtag gtaaaattat tattattact tccattttaa    32220
agatgaagaa tctgagactc agaaaagtga atgtcttacg caaggtcaca gagccaatga    32280
atggcagaga tggggcacaa aaacagatct acctagcccc aaagctggtg ttcttaacca    32340
ctggccatag tgtggagggt agcttggagg ggaagagagt gaaagcagac taatcattta    32400
ggatctatgg caatagtcca gggcagaaag cagaggaagt gatgatcttt agatacatgt    32460
aggaggtaga cttgacaaga catggtgtca aggcaagggg gagggagagg tctgcaatga    32520
ccctcagaat tctggcttgg gcaactgggt ggacagggac atgttgggc atgggggaaa      32580
tgaagagatc cattttgcac atatggagaa agagacatcc aggtagggaa ggtcagtagg    32640
caattttttt ttttttaatc ttgctgtgtc gccagtctgg agtgcagtgg tgcgatctcg    32700
gctcactgca atctccgcct cccaggttca agcaattatc ctgcctcagc ctcccgagta    32760
gctgggacta caggcacata tcaccatgcc cagctaattt tttgcgtttt tgtagagacg    32820
gagtttcacc atgttggcca ggatggtctt gatctcctga cctcgtgatc cgcctgcctt    32880
ggcctcccaa agtgctagga ttacaggcat gagccactac gcccagccag caattggttt    32940
tatgagtcta gagctcagga aagagacctg ggccagcacc gacttggaga tgggtgagag    33000
tggagtgtaa ttcatcagaa gaaagagggg ctgaggccag gacatcaata tttaagggga    33060
agggagaata aaagaagtgt aggaaaaaga ctaagaaaaa gtagccacag atgtaggaga    33120
```

```
accaggaaca attgtcaagg aagtcaaaga aaaggagagg ttcaatgagg gaacagttct    33180
gctaagttga ctaccacaga gaagtcatta gccttaaaat ggccctttag atttgggaag    33240
tagaaggctg ttctcgttat ctattgccat gtaaaaacaa aacaacaaac aaacaaacaa    33300
aaaaccttag tggcttaaag caacacaaat catggtatta tcctatcatc tcttatggtt    33360
tctgtgggtt agaaatttgg ggtgggcaag gaatctggct cagggtctca cctattgttg    33420
cagccagaga ggggctggaa gctagaacat tgggtggcgg ggagctgggg gctggcctgg    33480
ggctggctgg ccttctctct ctctcttcct gtggtctcag ggcctttcca tgccacttct    33540
ctgcaggggc tactctgagc ttcctcacag cctggaggtc tccggggagt agacctgctt    33600
gtatggcaac tgaagaccaa gagaaagagt cccatgtgct acagacagaa tgctcgtgtg    33660
cctccgaatt catatgttga aaccctaatc cccaatgtga tggtatttga agatgggaa     33720 gtttgggagg tgattagagg tcatgagggt cgagcccacc tggtgggatt tgtgcactta    33780
taagaagaga ccagagagcc ccatctctgt ctacccccte cctccctctc tctccacctg    33840
tcatatcagg acatagcaag aagatggcca tctgcaaacc aggaagagtg ttctcaccag    33900
acacctgatc tgctagcacc ttgatcttgg actcctcagc ctccagaact gtgaaacata    33960
aatgttcatt gttcaagcca ccccatctat ggcaatgtgt aacagcagcc caaactaact    34020
aatacaccat gtttctgtac atcagcaatg aaaaatccaa aaggaaatga agaaaataat    34080
tccatttaca gtagtacata aaagaataaa atatctatca ataaatttaa cccaggaagt    34140
gaaagacttg tatacagaaa actacaaaac attgcatata gaaattaaag aagacctaaa    34200
taaatgaaaa gttcactttc accacctgcc attggtcaaa atactcataa aaccctgccc    34260
agtttcaagg ggagtggaca aagacatccc cataacctgc catctctcag tagcgaacac    34320
cacaaaggtc attaatgcct ctagcaagag ctccttagt ggagtggtcg gggctcagat    34380
cagaccacta tgggcgagga taggcataga caactttaca gaagggcata caatacctga    34440
atcaatgaaa agataaggta tattccagga tgttttaaa aactcagaca ttttccccag    34500
attaatccaa acatctaatg caatatcaat ttgaatcata acaggaattt ttataggact    34560
tgatgtgctg atcctgagat catctagaga aggaaatatg caatatgaca gagaagtgtt    34620
taaaaaatgg gcaggaagtc ttccactgcc agctatcaaa gcacaacaca agctatagta    34680
attaaagcag tgtaatgttg gcaccgcgac atagatcaat ggaacaaaag agtctagtac    34740
aaccccacgt atatgtgaga ctataatatg cactacataa ggcattgaaa atcaatgaag    34800
aaaagatata ctcgtcaata aatggttacg ggacaattag tgtcaaattg ggggtggggg    34860
gttaaggcac aatattctta aatctgtacc tcatgtcata tccaaataca attcccaaat    34920
ggattaatga gctaaataca cgtgcactca caaaaaaatt atatgaaact gtgagaatat    34980
ataggacagt atttccttgt taagtaagtc acaagtccca gaaattataa gagtatcttg    35040
ataggttttt ggctacacaa aaaaaatttc agtctctaaa attaaaaaca aagttaaaag    35100
ggagaaaata cttgaggtat ataaatattt gtcaaacaga taaatgaaga atgcacataa    35160
tatataaaaa gatctcattt ttaagttaat aagaaaaaaa caaacaaccc aatgagaaca    35220
tgggctaatg aaaggaatgg gtactcaaag atgaagaaaa aaataaaagg caaataaaac    35280
ataaggaagc atagtcaacc tttaccagcc agcaggtaaa cacaaagcag caagagacca    35340
attttcaccc ataaaattgg taaaaccttta aaccattgat gttatccagt gttgaagaca    35400
ttgtggaaac agctattta ttggtagaag tgtgatttgc tacagctttt cttggagggc    35460
agtttggcag aatctattga catgacaaaa ttgtacgctt ttctacttct agatatggat    35520
```

```
cctagagcaa tgcttcatgt gcgtgaattt tcatggcccc tgtttgtaac aatgcaaagt    35580
cagaaacaac ctgaaggtcc atcaatcatg aaatgcaagc agggtaggga tttgaggaca    35640
aggataaagg tctggaatct cccacaaggg caacagaaaa tacagctgac tcaggacagg    35700
gaaaaggatt gccaagcagc accaagaggc ctgccgaggt tggacaccaa aaatttggag    35760
tgatcccaac caacagggtt gggatatatt ctcctgtaga aagacagat ggttcaaatg     35820 ccctggggtt tacttattta ttcaataaaa agttatgaat gcctactaag ctccaggtag    35880
tgttctaggc cctgagatat aacagtggac aaacataaac aaataggtac acaatataat    35940
gtcaggaaaa tactctgaag aggtaataat acagaatagg aaataaagag tgacagaggc    36000
actgtttaaa taatgaggtc agggaagtcc tctctgaaaa ggggacatct gaacagagga    36060
ctgaatgaag cgaaggaatg agccatgttg gcatctgaaa aaagagcat  tcctgttagt    36120 gggaatggta tatgcaatga ccctgggatg ggagcatgct ttacttgggg atggacattg    36180
gcaggataca tggagtggaa gcacaaagga acaggagagt taaatgtgct agcaaaagcg    36240
aggttggagt gatgggttat gtagtttgag ccaaatagag agggaaggga accaagggt     36300 tgctgataag tggagaggaa gagcgcaggg caaggaacag gatgttttgg tgaagtcaaa    36360
aatcaggtgc agtaagagtg aaggagagaa gcacaggagg gtgtgttcgg agaatggggg    36420
gttggagttc agtatgtcaa aggacagtga tcccaagcag tggcaaggcc caagatgcta    36480 cttttggttgt gggaggctga ggaggagtgg aggagaaagg gccttgagct gaggagcttt    36540
ggacttgaag aaggaggaca ttagatgggt cattgacagg aaccttgata tgactcatgg    36600
taatggcaga catgctgcag agaggcagcc atgagctagt tgctgtggtc ctttccacga    36660
ctgaggaagt gttgaaaggc agatgacagg acctgtgaca aaggcagtaa cagaactaat    36720
aggggaagtc aacctcgcca ggaggtcaag gaaagcttcc agaccaaatg acatttgagg    36780
caagactgga aggaagagga gttcacagag taaagagagg aaggaagggt gggtattctg    36840
ggtgaagaga aatgaacaaa gaccctgttg ctagaggaga cactgtaaga gggactcaaa    36900
gaatggcata tggctagagt ggagatggca aggagagggg cataagatgg ctgagaagta    36960
aagagatcag gctcctgaag aggacagaag gttgggagag tgcccaaaga ccaccaaatg    37020
aagggttgag tgaaatcaac tagaaccttg gtgagcccca gtggtgctat cgccatgcat    37080
ccttatgcag tgcaaggccc ctgagagggc agcataggtt tgtgacatgc ctggctgggc    37140
tttggactca gccagggctc aggatctgac ttagtctgtg accactgaag tgaaccaagc    37200
taactggcct acacggggct ctagccagat ccactgggtc tcactagcaa agttcctgaa    37260
ccataatcac tgataatgtt tgaatatatg tctctttcaa atctgatgct gaaatgtaat    37320
ccccagtgtt ggagatgggg cctgggtgga ggtgtttggg tcacggggca gatccctcat    37380
ggtttagtgc tgtcctcatg atagtcagtg agttctcaag tgatcaggtt gtttaaaagt    37440
gtgtggcatc tccttctcca ctctctctgt tgctcctgct cctgccatgt gagatgccta    37500
ttccctcttt gccttctgcc atgattgtaa gtttcctgag gccctcccag aagcagatgc    37560
cagcactatg ctttcctgta cagcccacag aactgtaagc caatcaaacc tcttttcact    37620
ataaattatt cagtctcagg tatttcttta tagcaatcca agattggcct aatacagaaa    37680
attgatgcca agaagtgca gcattgctat aaagatacct gaaaatctgg aagggctttt    37740
ggaactgggt aatgggcaga agttagaaga gtttggaggc ctccaaaaaa agataggaag    37800
atgagggaaa gtttggaact tcttagacac tagttaaatg gttgtgaccc aaatgctgtt    37860
```

```
tgtgatgtag acggtgaagt ccaggctgct gaggtctcag atggaaatga ggaacttatt   37920
gggaactgga acaaaggtca cctgtattat accttagcaa agaacttggc tgtatcacat   37980
ccatgaccta gggatctgtg gagttttgaa cttcagattg atgatttagg gtatctggtg   38040
gaagaaattt ctaagcagca aaacattcaa gaggtactag gctgattcta acaatctatg   38100
ctcaggtgtg ggagtaaagg aatgacttaa tgttggaatt tttatttaaa tgggaagcag   38160
agtgtaaaag tttggaaaat ttgcaccctc actatgtgat agaaagaaa agcccaattt    38220 cagggatga attcaagcag actgtggggt aaccacttgc tagagatatt tgcataacta    38280
aaaaagacat ttcagagatc taagaggcag cccctcccat acaggctct gaggccaagg    38340 tggtttcatg gtccaggcct agggccctgc tgccctgagc agcctctgga cactgcttct   38400
cgcatcctgg ccactccagc tccagccttg gctgaaaggt ccccagatac agctcaggtt   38460
gctgcttcag aaagtgtaag ctgtacgcct tggcagcttc tgtctggcat taagcctgta   38520
ggtgtgcaaa gtgcaagagt gaaggaggct tggcagcctc tgcctagatt tcagaagatg   38580
tataggaaat ctgggtgccc aggcagagcc tgctacaggg gcagagccct catggaaaac   38640
ctctgctagg acagtgcaga ggggaaacgt ggggttggag cccccatgta cagtctccac   38700
tgagggcact gcctagtggg gctgtgggaa ggggccccg gtcctccaaa cctcagaatg    38760
gtagatccac caacagctcg caccctgcac ctggaaaagc cacaggcact caacaactgt   38820
gaaagcagct acaggtgccg aacccagaaa agctacaggg gcagagctgc ccaaggcctt   38880
gggagcccac cccttgtgtc agtgtggcct ggatgtgaga cctggagttg aaggagatta   38940
ttttggagct ttgacattta aagactaccc tgctgggttt caaacttgca tggggcctgt   39000 agcccttat tttgcccaat ttctcccttt tggaatgaaa atgtttactc aatgcctatc    39060 cccccatag catcttggaa gtaaataact tgtttttat tttacaggct cataggttga     39120
aggaactcat ttcagatga actttggac tttggagtta atgctgaaat gagttaagac     39180
tttgggggac tattgagaag agaggactat attttgcaat gtgaaaagga catgacattt   39240
gagggaccaa ggtggaatga cgtgccctg ccaaatctca tgttgaattg taatcctcag    39300
tgttggaatt ggggtctggg gggggatgtt tgagtcatgg gggtggatct ctcatggttt   39360
ggtgctgtct ttgcattatc aagtgagttc tcacaagatc tggttgttag cctgaccaac   39420
atggtgaaac cctatctcaa ctaaaaatac aaaaattagc ggggcatggt ggcatgcgcc   39480
tataatccca gctactcagg aggctgaggc aggagaatcg cttgaaccag ggaggcagag   39540
gttgcagtga gccaagatca cgccattgca ctccagcttg ggtgacagag cgaaactccg   39600
tctcaaaaaa aaaaaaaaag tgtatagcac cttcccttca ctctctctct tgctcccagt   39660
cctgccatat gagatgcctg ttccctcttt gccttcttcc atgattgtaa gcttcctaag   39720
gcctccccaa aagcagatgc cagcactatg cttcctgtac agcctgaaga actgtgaacc   39780 aattaaaccct cttttctta taaattaccc aatctcaagt atttctttat agcaatgcaa   39840
aatggtctaa cacaatcacc aacagatttc acaagaagaa ggaggagcca tgggcagctg   39900
tgagctgctg aaaaggagct gaccactgga tccaccaacc acagcgaagg acgtccaacc   39960
ctcgccctga ggacagaaac tcccttctct gatgcctggc tgtctgggtg aggtcttggg   40020
cctcatagca ccaaagatca aatgccatga aatgagctct tccccctgc tgtgtgacca    40080 caccctacac acacacacac acacacacac acacacacac acacacacac acagaggcag   40140
ggtagctttg tatcaaagca gggcagatgt gatggatgag gcacccaaca gcaccacagc   40200
agccttctgg ggctggaaaa ttgccctcca ttcagagtat tcctttcggg ttaaggatgg   40260
```

```
ggaggctagg ccacacaatg gtggggtttt gcatcaactc cacaaacttg tgctgagccc   40320
actctttgct gggctctgtc ctggatagga cctgttccag gtctaaacat ttataaaaag   40380
caagctcctg cccttgggga tgggtgacct acgacagaag agttgttgag aaagaaaaag   40440
gtcaatgtca gggtttgaaa acagaagctc ccataaaatg ttatgggagt ctccaagatg   40500
aatttgaggt gatgagggct tggtagacaa gatgaatttt gagctggact ttgatggatg   40560
gagagaatgt ggacaagaag agatgaataa tgttagagag gaagaccttg gccactaagc   40620
tgaagagatt gaattctgcc ctgagggcag tgggagccat ggaggatctt cagattgggg   40680
tgactgtgag gtccaaggga cagagcatgg gcttttaagt tccccagacc caggtttgag   40740
tcccagctct gccacaggtc agcttggacc tgggcaaagc cactttttt ctccaagcct    40800 gtcttctctt ctgcttctga gagccctgcc tatctcccag catgagatgc tggaacctga   40860
tgggagggta taacgggaat tcggaagcag caatcacatg ctgtgcccac aaggccaaga   40920
gtccccagtc cctcagcctg tgaggtcaca tgaagagtta gattgggcat gtgctagctc   40980
aaaagcctcc ttcccacctg cagaactgca gaacctcagg tatcatttca tgatttcatc   41040
ctcagtaact tgggacatcc ccaggggatg ctctgcagtg ctcatagccc ccttgggtct   41100
ctgactttcc tattgccacc ggctattcca gtccatggcg ctgtccacct gtgcttcctc   41160
aggctgcttt tcacattatt gccgccagtc tgcccctaga ctgctgtcct tccctgtgac   41220
cacctcctgc aatgccatct ctgcacctct actgccaaga ttcactccac ctctctgatt   41280
cctggccttc ctccaggttc tacccttccc cggggctccc acagcaaagc tgtttgtatc   41340
cctggtgcta gagttccttg cttgctcgtc actttatatg cattttctca ttcacactca   41400
tgacattagt tgttattgtg acctcagctg cgattcagga cacctagtgg ttgtcacctg   41460
gtgggagaac atgtaagtca ggaaggtgta ttctgatgga agtcaaggag gcattggtgc   41520
ccagagaggg caggctcagg ttggaagcct ggggtggcat gagggtgcaa aataagaggc   41580
acagacagga ggtactctag agaagatcac ctctgatttc agaatttggc ctttaggcta   41640
gctttggacc aaaaagtaaa acaagcagaa gtccactgcc tgagtaggcc agagcgagac   41700
tccagtgatg catgcatctt ccaaacaact ttgatgcaaa gactcggcca ttcaaccctc   41760
cccacgttga atcatttctt tccacttcaa gcctgttgcc aacttgggtt gaagtctctc   41820
aactgataag agtaaagaca gtggtttcga gataggagga taaggaagga gctgatgaag   41880
gcaagtgaag ttatctttgc caccagggct aaggctggga cccagaggta tgaaaccaga   41940
gggctgagta ttatgtgggg accatccctg ggcagagtcc ggaagatggg ggtggaatcc   42000
ccgtttagtt tgtttgcttc gggggttggc ccttcagctc agctgatctt tgctctaaca   42060
actgctattt cagcagtgct ggatgccagg gagagaaaga acaaagtaca gatgagactg   42120
gctttattta gttctagtat gtgaattaac aaacatttgt agaacattta ctcttgtctc   42180
tgcgaggcat gttctgagag catcaccaac attagcccat gaatcctca  taacaaccct   42240 aagaagctag tactattatt atgccaactc acaggtgagg acactgggga ctcagggaga   42300
taaagtcact tgcccaagat cacacagcta gtgggtgcca gagctgggat tgaaactcag   42360
gctgattggc tccaagtcca gtgtttcaag gctcagttca ctgacagaaa gacaggacca   42420
tgtttgtcct caaaggctat cttcagggt cttcccctgc aaaatcccat cagctctacc     42480
tgcttgcttg cccttcagga tggctactgc agcaaacaga ggaggcagga gtctttgagg   42540
gggcattttc cagtgctctg gtctctggga ataatttcat taccagtcct ggaagggtg    42600
```

```
ggagagagga gcctgggaa  aaggctgcgg gagcttcagc agttattgaa tgacagcatt   42660
ctcatgttct ccttgtccct ggtctgtcct ctgaggctgt gggctcctgc cctctgcttt   42720
tattcctgag aatgaagttc actgggccac ctcactcatt ttgactctgc cccttcagag   42780
actcccatga aggtccgttt tccctcttca aaatggccta ttttgtcatt cttgaatgga   42840
tggttgaaag ttgctttaca cttgatgtgg acataagcag actgtaaatc cattaaaaat   42900
agaaacaaaa ggaatggtgg ccaggcatgg tgacacgcac ctgtggtctc agctactcag   42960
aaggctgagg ctggagaatc acttgagccc gggaggctga ggttgcagtg aaccgagaac   43020
atgccactgc actccaccct gggcaacaga ataagaccct gtttcaaaaa taaaatagaa   43080
aacaaaagga atgggcagtt tgcctctggg gcctccaggc taggtgagca tccatccccca  43140
ttgggtctgt ttgtctctct aaagcattcc tctctgggaa atcaccttcc tcgaacccaa   43200
agagcaaggg ttctgtagag catttactag gagctgcctt gaagctgccc tctgattcag   43260
ctgggcgtga agacaaggca ggcctcagct tctccatttc cctcattggg agttgtgttg   43320
tttacgagtg actcacactt cagggtaacc aaatccctgt tctagaagct acagcagaaa   43380
cagcatttcc agttcaccaa attagtcttc tcagagcgcc caaactcccc tttctgtgtc   43440
ttcttcccta ttcagtggca tcccccaaac cctccagata ggggcatctt tgggcttca    43500
tttcctccca ggtgtgagtg gctctaacag cctcggttcc ccagagtgca ggttcagaaa   43560
atgcagggga atgggactcc ccagatccca agggaagagc tggcatcact tcttcagagt   43620
gggcactcct gggggactc  atcccagctc aagaaagtaa ctctccagtc acaaccaact   43680
ttcccaaggg gtacagtggg acttgccaag cactacaaga agagaggaca ctggcttttc   43740
cagtcagctt ggaggaagag agggaggaaa aaggagggg  gaggaagagc aaaaaggagg   43800
aggaggagga aatggacaag gaggaaaaaa aaaaaagga  ggaggatgag gagggaaaag   43860
gaggaagaag aagaggaagt ggaggagccc agaaaaggag gggaaggagg aaaaaggagg   43920
aggagaagga aaacgaggag gaagaagagg tggggaggaa aaggagcagc agcaggaggc   43980
aaatctccat ccccacagca aaagcagtgc tggagccaga gcccagagtg tgggagctaa   44040
tgggaatcag cttgctggag ggaagggac  cgaattaagg aatggctggg gctctgccgc   44100
tgagaggggg ctgggaaaag caggctgatt gagaccagct gttgtgcctc tgtctctgag   44160
atctttggac tctgcccagg atagcctcac accctatcct acacgactag gaacttgcac   44220
agtccgcctc gggcagccca aagctcctct gcccaccctg gctcccagag ccctccaaaa   44280
caaaagacca gagaagcact ctccacccag cagccagacg cctccttctt gacgccagcc   44340
cccaccctct gtctgctcga gcccaggaaa ggcctgaagg aagaggccgg ggaaagagcc   44400
ctccctctct cccttgtccc tccatccacc cagcgccggc atctggagac cct           44453
```

<210> SEQ ID NO 6
<211> LENGTH: 45546
<212> TYPE: DNA
<213> ORGANISM: Homo sapiens

<400> SEQUENCE: 6

```
atggcccggg ctcactgggg ctgctgcccc tggctggtcc tcctctgtgg tatgtgcatc     60
ctagcttcca ctggaaggca gctctgacct ctcccctctg agctcagaaa gggttggagt    120
gagggttggg gcccgagtct cttttctgt  tgcttcctct ctctgacttg aggaagagac    180
acctcagggc cagtgttggg ggccctcata acttggatcg agtctggttt ggcacctttc    240
cattcccccc gttatagaaa aaaaatattc tgacactcgt taaaacggta aggaaaactt    300
```

```
aatttaagac taccgcattg caatagagga gagaaatggg gctcaactct gattacagaa    360
aagacttcca gggatctgta gccaaggagc agagtgaggg ggtcagtgga tggaaaagta    420
ttaagaggag atagcaaggg taggggggatt cttgctaaac cgactgaaca gcattcttgc   480
tgacggcagg ccagagtgat cagatatcaa gggtgtctaa actgacttag caagattctt    540
gctaagactg ggtgatgcaa gcctggcaag ggcaggacac acacagaagg ccaaggtcaa    600
ggccaagtgg agaagaggct ttggggggagc ctaactaaac tttggtcagg aagagagtct   660
ttcctctttg tcattcctgc ggcaccctct ctgtcctcaa ctaggtgccc agcccagcgc    720
tcccacccta gccttccttt ctttgttgtc tgtcagcagg gcctgatcag tcactcaatg    780
tccagttcct gagcacctac ccagtgccag gccttgtgcc agggaccaca gagtcattca    840
gctgcagagc ctgctcttgg gagccacagc cctggcctca gagaacagca tattctggtg    900
tccagagaga cataagttgg ctgtgtcctc attcttatgt tagcatatca gtgccaacat    960
tttgccaggg atctgtttct acagaaatgg gtgtttgttt tcttaaatga acagtatggg   1020
tcgcatctga tccttgagtt tatgagacca agataaaatc acacaggacg ttcatggtgt   1080
tgaaccccag ccaccctcct tgcatctgta gctcagccca ctcgaaagtg tggctgggcg   1140
tggtggctca tgcctgtaat cccagctctt gggaggcca tggcaggcgg atcacttgag    1200
gtcaggagtt cgagaccagc ctggccaaca tggtgaaaca ctgtctctat taaaattaca   1260
aaaattagcc aggcatggtg gcgcacgctt gtaatcccag ttcctcaggg ggggctgagg   1320
caggagaatc gcttgaactc aggaggcaga gattgcagtg agccaagatt gtgccactgc   1380
actccagcct gggcaaaaga aggagactcc atctcaaaaa aaaaaaaaat gcgggcgcgg   1440
ggggcgttgg gcgcagtggc tcacgcctgt gatcccaaca ctttgggagg ccggggcggg   1500
tggatcacct gaggtcagga gttcgagacc agcctggcca atatagtgaa accccatct   1560 ctactaaaaa tacaaaaatt agctgggtgt ggtgggtgca tgcctgtagt cccagctact   1620
tgggaggctg aggcaggaga atcgcttgaa cccgggaggc ggaggttgca gtgagctgag   1680
atcgccccac tgcactccag cctgggtgac agagagactc tgtctcaaaa aaaaaaaaa   1740 ggagggggggg cggggggagtg taatgtctcc ccacactcag ggcccccatta ccatctaggg 1800 aaatccctcc ctaaaagaca ggggggttag aggcaaggac tatcagagac cgctttgtct   1860
aattcaagcc cctcctttcc agaggtccag agcctggaga acttagtcca gtgcctggca   1920
cacagtaggc gcttaggaga tggttgctca atgaatattg gggggggggtc actctcgagt  1980 cactctaaat tgggggcaga gcccaaacta gaaactagat ctccatatat tctgtcccctt  2040 ctgtggcatc acctttttca ggcccacctc tcatacttgg cagagtggga ggactgaaag   2100
tgcgctcacc tcttttgtat taagatggcc tgggttcaaa tccctgttct accactgact   2160
cctggtggca caagttagac aagttaccaa atctatctgg gccttgactt cctcctctgc   2220
agaaagtgaa caataatttc cacctcatag tgatgtcaca aatatcaaat gagatactgt   2280
agatgaattg ctgcgttcag tatctggcac ataatagggt gtctttaaat actaattaat   2340
ccatctttcc ccaccatggc agactaggat ttctgtctaa tatattgaaa atgagcctgg   2400
aatgataggc aaagatttgg actgtaagaa acagtgcaag caggccttga attgaagtca   2460
acccaatgta tcatacaatt agatttataa aaggctaaaa tgaaggtggg gtgattattt   2520
agcgtgatct tctagagcat ttcaaagaaa atttgataac aaaaatttaa tttcacacaca   2580 acttttctac ttcactaaac cctgaaaaga cccaattaga ttagaagaaa aattgattta   2640
```

-continued

```
atgagcacta aaacccatcc aaaagtggca atcacttgtc tatgaaacag atttctttga  2700
ttgtgaccca gggtgctatc cagttcagcc tgatttccta tgaaatgtga ttattttttat 2760 cctcaagtag agctggccag cttcgtgcgt ttcaaaggat ggaggcccccg tggggcgggc  2820 tgagaggata ctccttccct ctctaggaac tagctggtcc ccaaatgacc ctggatttt   2880 ctcccggctt ctagcttgtg cctggggcca cacaaagcca gtggaccttg agggcagga   2940 tgtgagaaac tgttccacca accccctgt gagtgcccct tggcccgggg gctgggccct    3000
tgtggcccca caggcacccc cccaccctg ccccacgcac ccctgcaccg cagcaccccc    3060
gccctgctct atcatcttct ctatccctca ttgggtcagt tggtagcccc cctcctacc    3120 aggctttctc ctgatttccg gactcttggg ccccctcccc ctccactccc tcccctccac    3180
atcagtgccc tcccctccct cccattcatt ccccagcag gttatctgct tccgtcctga    3240
tctgggcctg ggaaacccct ctaggaggag ggaggagggc aggaggcccc taactggcct   3300
ttggctgagg ccaggcagag gaaagaaaag acaaattcta gagtgacagc aaaagagaa    3360 gcacagaagg gaagagggag gaagacagag gttagaagag ccaacggagg ccgagcacgg   3420
tggctgacgc ctgtaatccc agcactttgg gagaccgagc caggtggatc acctgaggtc   3480
aggagttcga gaccagcctg gcaacatgg tgaaacccccg tctctactaa aaataaaaaa   3540
attagccagg catggtggcg ggtgcctgta atccccgcta ctcaggaggc taaggcagaa   3600
gaattgcttg aacccaggaa gcagaggttg cagtgagcca agattgtgcc actgcactcc   3660
agtctgggcg acagagcaag actctgtctc aaaaacaaaa caaaacaaaa ccaaaaccaa   3720
agaagagcca acgaaagggc aagagaggga ggcctagggt gtgcagacga ggaaaaggcc   3780
cagcagaagg ggcttgggta gtcagcttcc tagctggaga ccagagtgat tctttctaca   3840
atcagagtag ggctaagggg taggcatgcc agcagcactg taagccatgg gaaaaacgca   3900
gtacatctgc tagcaatatc aactttatgg gaccctgggg gcaggcaggt gggtgggcaa   3960
accacattac ttttatatta aaacaaacat ggatatatcg tggagtagaa agcaaaacag   4020
cacaaacgga aacatgcttt tcgttttaaa gctaaaatga cctgtaaaga aatagagaac   4080
tggtctggaa agggtctttc tgggcaatat ctcaaactgc tgggggcatt cattcactct   4140
cctctgccat ttgggaccag tgggtggcaa cctgaaaaag ccctgccaag ggaaggttgc   4200
cagataaaat acaggacacc cagttacatt tgaattttag ataacaaata agaatttagt   4260
gcaagtatgc cccaaattgt gcatgtttta atataatact tacattaaaa cattacacat   4320
tgtttatttg aaatgcaaac ataactaggt gagtgtcctg tattttttatt tgctaatctg   4380 gcaaccctac ccccaggtag ccaaagaagg actgtctgca tggcctggcc caatgccaga   4440
gctcagaccc ctgcagttct cacccacacc catatcccag actcaggtcc cattactgtc   4500
acaaggggtc cctttccaaa ctctccaaca cctccatctc cacccagccc aggcatctta   4560
atctagacta agcagtaaca tcagttgcca ccccatccct tcccaagcca ggccagccta   4620
acttccccca accgctgctt caggagaggc tgggggctct tctggaggcc aggggcccag   4680
atgtcatttt ctctaagcaa cgtgtgtatc tgtttgtttg tgtctcaatg tcttcttgtc   4740
atctgtcagt accttccagt tactgtggtc aataccacaa tgtcactcac agccctccgc   4800
cagcagatgc agacccagaa tctctcagcc tacatcatcc caggcacaga tgctcacatg   4860
gtaagagaca gcttctctcc cccttgccct ctctgctacc ctgggtcaga gaccacaaac   4920
aggagctgtt aaaactcaga agatgaagac agagaaagga tctgatgggc aaagggaggg   4980
aagtagagag catggacacg gtagttttag ggcaagtgaa agaatgtatc cctctacata   5040
```

```
ggcgggcaga cattgccaaa cctccttaac ctcaagaaat taaactataa acaacttcag    5100
aatcaatttt catcaattcc cagaaggcag atccagaatg aatgtttagg gtatccctgc    5160
cctaggaggt tagaaggtgg gctggaaatt gggctggaag aactccaagc tcccttctgg    5220
cccaggcctt cccatactct gtggaatgga gtagcaaaat aatccaaaat cctgggttaa    5280
gggagcgcgg ggttggttgt ggaggggggc acccatccca ccgtttcccc tcactagctc    5340
caccctccac accatccacc tttccaacac cagcccattt ggaagagagg cattttag     5400 tgtcaatgag cttgtttaaa ttaattttcc cacatgctgg gaagggctaa gaacgttggg    5460
taagtatctg aacttccctg agcctcagtt tcctcttctg caaagagaaa tgggtctgta    5520
atgagatcta tctccaagga ttatgaggat caaaatatga taatgtgtaa agcccttgc    5580 agaagttatg atgttcccag tctactgtgc ttgactcagg agggagaagg attagctgga    5640
ggggaaaacc caaacgagcc aaaagacagg accctagact gcatagaatt tgcagggcag    5700
ggcaacaagt ctcctttgca gaacagtcca gtgttacact gagtccagtg tgaacagtgt    5760
gggggcgggg gagttgaact gcaaaagata cggttgctca aggaaggga agatattgaa    5820 ggctgggaga gttacagagg gcttcctgga agaggcactt ggtgtgcttg ggcttgtagc    5880
tgacaagggg ttgagccga cagacagaaa taactgggat gtggttgggg ccctttcatg    5940
tgggatctga taccacgaaa aaggctaatg atggtgttgt tgatttccta gaacgagtac    6000
atcggccaac atgacgagag gcgtgcgtgg attacaggct ttacagggtc tgcaggtgac    6060
aatcattacc cagccccatt gcttttgttg gtagatccag aggtggtcac agaggaccta    6120
atgtggctag tgtctcagca tctgggaccc cagaacctac tgtagagaaa acccttctac    6180
tctctctgtc tccctccacc accccaaaac catcagattc cccagggcac atatctcata    6240
gcccaccagc cactttctgt gtagaaatga ggcagaggct gccttcctgt gctcattacc    6300
tctgctgcaa ccaggcccag tccagcactc ccaggctccg tttctaaata gttgctactt    6360
ctacctctaa ccgctaagaa cccgctgatt cctttcacat gagggctcat ttggagacaa    6420
agttttcctt tgccggttgt tttacggaca acatcacttc acatggccaa atgagacaca    6480
aacatataag cccttgatga gatcacagtg tctgaagggg cctcgcaccg tgatcctggc    6540
ccattgaatg aaatccaagc ttcctttcct gatcctcaaa cattcctcct tgggcttcaa    6600
actaccctgc ctcgtgcctc gtaggctctt tttccctttg ccaaagtctc tggattattc    6660
ttgcccagca gtcctcagct gagcctctgg tttagcctcc ctatcagcca ccgagtcttt    6720
acgctgagcc ccatctttcc tgagagcgcc tacatgcagc caaaagttga cctcacttct    6780
gctgaaagtc cacaagcagc cctcaacaca aagcagaggt gcctgattca ggacaccttt    6840
ctgccagctc cccccacagc tcttttaag atctccttcc tcacttcttt ccaatggagg    6900
agagaatctc tttccagagg cccttgtgg cattctcaga gccagcactg cattgcacat    6960
ccatcagcta atgccacgtt cctccccttc accctcacct gcaagtttct ctgttctgcc    7020
ccaggaactg cagtggtgac tatgaagaaa gcagctgtct ggaccgacag tcgctactgg    7080
actcaggctg agcggcagat ggactgcaac tgggagctcc ataaggaagg tagaagggcc    7140
gcatggattt gttccccaag tcttgggacc tggactaggt tcaggaaggt ataggtgaga    7200
gcgtgcatgt aagaccatgc tgggcctcta tggggagctt aggaaatttg aggccatcac    7260
tgactttcaa ggctgatctc aaggaagaca cacatggtag gaccatcaga cagaaccct    7320 ggctggagag cctggggctg gccctgaagg tgacctctgc attgcttcct atctttcttt    7380
```

```
cagttggcac cactcctatt gtcacctggc tcctcaccga gattcctgct ggagggcgtg    7440
tgggttttga ccccttcctc ttgtccattg gtatgctctt ccttcagtcc ctgaatttgt    7500
ccatgctaac gagggtgact cagcttccct aggatataaa gaaatggacc ttggtagaag    7560
gaggggcggt gggactataa agatagagca tttgaaattg tagttgcaga atgttttgca    7620
atgaggatgt attcatggat tgtgtaatta aaatacattt aaaagaatca gtacaaatat    7680
tttaaaattc atgagtgcag agacccaacc tagaagactc agtgaatcat taaagagcta    7740
gtggatgaat aggccaggat gtgcttgaac ccagaaccat cctctgtgcc ctggaaccct    7800
gccaatgatg atgctggaat cacatggtaa ccctcttctg gaaggtagct tagaagggtc    7860
aaaagagttg ggagggcttc tgagtttaaa aaaaaaaggg cccctgagaa tacaactccc    7920
ggagttctgg ggcctcagac agctggcaag cccattcccc caaggggag tcctcatgaa    7980 tatgtactga aaggcttgtg ctttagaact ggcttctctg ccagcctgtc caatggcctg    8040
aacatcacca ttccttttga ctgtgacact gaagccctga taaataatt agtgcccaag    8100 agaaggacca cccacagcca ctggcaatga aaaagacaag cttagccaat ttgtggcagt    8160
cagtgttaga gtaggctcag ggcattaggc ttggaaagca gaaagaggat gagaaacata    8220
ccccagcgtg ggcatacatg ccgggggtgg ggggtgggca ggctgctggg gcaggctccg    8280
ggcagctggg ctgcaaaggg aggcaaaggg aaccaggact aactttgcct gaatcacaat    8340
tttttcctgg ggtgtaaatg ggcaagggac aagtgactcc ttcttgtctc tgcagacacc    8400
tgggagagtt atgatctggc cctccaaggc tctaacagac agctggtgtc catcacaacc    8460
aatcttgtgg acctggtatg gggatcagag aggccaccgg ttccaaatca acccatttat    8520
gccctgcagg aggcattcac aggtgattca gtaagcccga tttccttccc aacttgtagc    8580
aacgcaggtc ccggctgcta ttccgtaggt ggcaaacttc atcatcagag gtaccaaagc    8640
agtggtttgc aaaccttagc atgcacctga gtcacctggg atgcttgttt aaaatgcaga    8700
tttcagggcc ccctccccctt gaggagtctg aatcaaaatg tcctccggcc atatttagaa    8760
aatgttgggt taaagaatgt taggatttga acaagatgg agcaggaagg gaggaaagaa    8820
gggaaacaga gaaagatgag agaaaatatc caacccctttt caagagagaa aaaatcatga    8880
tatgatttgc ttgcctggtg gcagagactg atccataatg aatcattcag accctttactt    8940 ctgaccctct tgtgatgaag aatttagatt tgtgagatgg ctggggtcag gtgggccagg    9000
agtggacaga ggaagtaaat aactaagttc agagtcattc tgtagcacag attacagttc    9060
aggttttgct ggaccaatca ggaaggttag aaaaatataa catcaataac cttgaccccg    9120
ttgacactat ctaaatccat cacaaaagaa cagtatgttg taagattcct gtaagtcgta    9180
actaaagtcc tgaccaggac cagcctactg attatgaatc agtgtcttgg ccaccaacca    9240
gtcctatctc cctgggaatt ctgaatgagc caatgaactt ggattcctag taacattgat    9300
caagccaaga gatccctttc cgcatgcaag tccacataat ttctcactta gaaaggagcc    9360
aatacagcag gagggagatt tcaaaatagc agccatgacg aaacaagtga aaattgtgtc    9420 cattttttctt tatctgttct gatgtaactt ccagaatcat tctttctgca tcttgacacc    9480 attttttaaag aaatttgtta tccaagactg ttaaatcata aataaaactc atcttattca    9540
gataaagaaa gtcaaagtta tgtcgggaag gggaagggaa aaaagaaaaa ccttcctggg    9600
gctggaaggg ttttgtcact tcccaaaagt gagggggatgc cgagtcatca cccgctgcca    9660
gtcttcaaga aaaaggcacc tggagcttga gtttggaagc cgaagaacag agttcagctt    9720
caataagctt ataaagacga gagagacttt ccagccactt gcagatttta aaggagaaag    9780
```

```
gagagtgcaa aggcagaac atgaaaagtt cgctactcaa acatacctgt acgcaccaga    9840
ccattgaaat ttgggttcat ttggtttctc agaaaggtat catattcctg aaccttgaaa    9900
acataattgc aagtgaaaga agccagtcag agaaggccac atattgtaca attccatttg    9960
tatgaaatat ccagcactgg caaatccata gagacagaaa atagattagg gatttcctgg   10020
ggctcagggg agggggata gggagtgact ccttagtgag tacagggttt cctttgggga    10080
tgaagaaaat gttctagaat tagatcgtgg cgatggttgc acaacattgt gagtatgctg   10140
aaagccactg aattgtgcac tttaaaaaga ttaaaatgat atgttttatg ttatgtgtaa   10200
aatacacata acataaatta tgtgtaaaat atgtagtaaa ataaacctac aaaaatgtat   10260
tgtacccaaa gctttggtca ttgttgaata gttttacctg ttcacatgaa atattttca    10320
cgacattaag ttatttatgc tcatatctga acccaactag gacccttaat gtttatggcc   10380
ttcggccagc aaactcctag tcctgcctag gggtagactc tttgaatatc ttgcaggggg   10440
cagggataga agatgaaaac taaagtcata gaacccagat ataagcatct gagaaaggac   10500
ggtgctgtga cacagagttt aaggacagat ttggagactg agaatgttat caagacagta   10560
cggtgtctgt acagattaag agcgtgggcc atgcagtcag acagaccaga gttcaaatcc   10620
cagctctacc tcttgcatcc atgaaaccct agacaagtca ctttacctct ctgaagcctc   10680
agtttcctta tctgtaaaat gggatgggta agaattagaa caatgcacat ggagtgctta   10740
gcccagtacc cgtggcttag taaatactgg ggttactgca gagaaagttg aacacggccc   10800
cagccctacc cctttgtcct tcaactagga ctgctctctt gatctcagtc tgcatgatta   10860
tttattaatc agaaagatac aagagttact acatctcaag ataccattct gtgtgcttta   10920
caaatattaa ttcattccat cctcatagca gccctattga ggcagatgct tattatactc   10980
catcccatt ttacaaatgt gcaaaatgga acacagaggg gttaggtaat ttgcccaagg    11040
tcacccatcc agtaatggca aagccaggat ttgagcccca tctgggtcca gggcccatgt   11100
cattaatgag tacacaagta agagtttgtt tgaggaaagg gtttcgctgc ttttaagag    11160
gatgcaaaac tgttacccta aggctgacct tccaggaacc gagtgccaaa ggcaaggtct   11220
gtcacttaca cttttttggg gctcctttgc ttctagggag cacttggcag agaaagtat    11280
ctggcgtccg aagccagatg cagaagcatc aaaaggtccc gactgccgtc cttctgtcgg   11340
cgcttgagga gacggcctgt gagtgtggat ttgcagacat gggtgggcgc ctgggtctcc   11400
ccaatgcccc aagcctcccg ggccctgcag cacagagcta gctcttcccc aaataaccat   11460
gtgcccacca attcttgaga actccatggc cacagcccgt gggaaccaag aagggtaagg   11520
gggcaggagc tcatggcttc agaaaaagga caaaggtag ccctgagcaa gctgggacca    11580
gcccacaggc caccagagga acgaactgac tatggcagca agtgcttct gtcccactaa    11640
ggggaggagg accaggaaat gcctcccaac aacttagcca ctaccccagg gcactcacac   11700
tcccagcttt agcacccagt gggactctac tctttccgac atggctcagg acttcttgtc   11760
tgatccctat ggctgggctt cagatattcc agggacccac tggaactgtg tgctgactgc   11820
taagtatctg cattttctg gggggaaaag atccataact ctcaacagca tctcaaagac    11880
gcccactccc ccacccccc cccccggcaa aagattgag taacatgcag aggtagatga    11940
tacaagcatg ctgttggtaa tcttggagg ccaaaggaaa cagtggggca aaagtgtcag    12000
aaatgcttgc ctctggccgg gtgcggtgac tcacgcctgt aatcccagca ctttgggagg   12060
ccaaggtggg cggatcacct gaagtcagga gttcaagacc agcctgacca acatgttgaa   12120
```

```
acgccgtctc tactaaaaat acaaaaatta gctgggcatg gtggcaggca tctgcaaacc   12180
cagctacctg ggaggctgag gcaggagact tgcttgaacc tgcgaggtgg agattgcagt   12240
gagatcttgc cactgcactc cagcctgggt gacagagcaa gatactgtca aaaagaaag    12300 aaagaaaga aaagaaaga aggaagaaa gaaagaaaga aagaaagaaa gaaagaaaga     12360
aagaaagaaa gaaagaaaga aagaaaggaa ggaaggaagg aaggaaggaa ggaaggaagg   12420
aaggaaggaa gggaggaagg aaagaaggaa ggaaggaaag gaaaaaaaga ggaaaagaaa   12480
agcttgcctc aggcagatca gcattaaata ttccttgtca attctcttcc cagggctctt   12540
caaccttcga gccagtgaca tcccctataa ccccttcttc tattcctaca cgctgctcac   12600
agactcttct attaggtatg gcttttcctt agcttgctgt tgtggacttt ctccaacttc   12660
caccctcttg atgccccacc actgatcccg ccttaatata cagccctctg gctgcccatc   12720
agctcggcgc ctgctgcagc acgaccctt agaaaacccc ctgttgtctt ttcctgactc    12780 tttaacctc tgtccctatt gaatcccaaa tctggcctgc ttggctccct ggggctggct    12840
tcctttgacc tccaggaaca gagggactgt gactgcctct ggtcctttgc atccttagca   12900
gatgctcagg accctccttg tcttcccacc ccacccaggt tgtttgcaaa caagagtcgc   12960
tttagctccg aaaccttgag ctatctgaac tccagttgca caggcccat gtgtgtgcaa    13020 atcgaggatt acagccaagt tcgtgacagc atccaggcct actcattggg agatgtgagg   13080
atctggattg ggaccagcta taccatgtat gggatctatg aaatgatacc caaggtgggt   13140
ttgccaggcc ccagcccaag ccaggcacca atccccactc taggcctgag aagtcttaac   13200
ctaaagtgag gtgaagcccc tcagccattc agtcatctgg tcagccaaca actgtgcagt   13260 gagttcccctt cttggcctaa ctgggaagag ccagaagagg aaacagggat ggccatccag  13320
agagctcata aaattgtcag gaggctggag agtatacggc ctgatctagc agagactttg   13380
gagtcagcca aacttgaaaa tgaattccag ctctgtccct aactagctgt gcagtgactt   13440
tggacaagca acttagccaa tctgggtctt tttcttcacc tataaaatgg caataagagt   13500
cctgacctcg caggagtcgc tcagtggaga tctaaaggag atagtgtata tgactgacac   13560
atggtagtgt ccaataaatg gtagctgtca tgatatgtac aggaaactta cactgtcagg   13620
acagcctgtc gagtgactca ggccagactc tgatccatcc cagagtgctg gtgggatccg   13680
aagacaggga gttcattgcc aagcaaggca gtgtcaatca aggaagcctt cctggaagga   13740 gagggttc agctggacgt ggaaaactag gaaagacaga aagcacacac agagtagaga    13800
gcattgccac gaaatggtgg caaatctcac gtctgctggg tcctcctgcc agtcctctga   13860
aaacacccct gtgccatgga gacctccttt actgtgcccc cagacctgtg cccccagacc   13920 tcctttctc ctccctgccc ccaacaggag aaactcgtga cagacaccta ctccccagtg    13980
atgatgacca aggcagtgaa gaacagcaag agcaggccc tcctcaaggc cagccacgta    14040
agtccacgtt caggcagaca tggcctttg ggagtatcca gcctaatgag ttagaaagga    14100
aaggcctcca gaagagcctg aagaagaccc tcaatgaaac aaagaagcaa gctgggcgcg   14160
gtggctcacg cctgtaatcc tagcacttg ggaggccaag gtgagaggat tgcttgagct    14220
caggagtccg agagcagcct ggccaacatg gtgaagccct gtctctacta aaaatacaaa   14280
aattagccag gcgtggtggc gatcacctgt agtcccagct actcaggagg ctgaggcacg   14340
agaatcgctt gaacctggga gtagaggtt gcaatgagct gagatcatgc cactgcactc    14400
cagcctgggc gagactaggt caaaaaaaaa gaaagaaaga aagaaaaaga aataaagaag   14460
cagacaccaa attattcctg ggcgcccaca tgcacctcat atccttgccc ccaatatagt   14520
```

```
acagtggttt agagcacagg ccctggagct agggtgcctt gagttcaaac cacagctcca    14580
cccaattcct aactgggtga ccttgaccaa gtcattttac ctctctgggc ctcagttacc    14640
ccatctgtaa aatgaggatc ataacagtaa tcttacagca tatggttgtt gtgagaattc    14700
aatgaatatg tatattgctc tgagcaccac ctagcacatt ctaagtgtta aataagtgtt    14760
agctataatg atttcctcac actggcaaga ggatggctca atttttaaaa aagaattctt    14820
gttaaaatta agataaacca cctcatttaa aaaaaacttt gtctcatagg aaattttaaa    14880
cacacacaaa gataaagaaa atagcatcat aatctccagt gtcccttcat ccagcttcaa    14940
taatccttga ctcatggcca ttcttgtctt gtctataacc ccatgttcat taccaccaca    15000
accaccccct ctgctgctgg attcttttaa agtaaatcc tagatagtgt gtcatttctg      15060
ccgtcaacac agaactcttt caaaaacagg aacacactat gatcatatat aaacactaac    15120
aagaattctt tgcatcaaa tagccagtgt tttcaaagct ccacatcctg gagccgctat      15180
ctgatctcca tcatcttgga gcctgtggct gcaaccagac ctcacccggc tcctctgttt    15240
ccctgcttcc ccaactccag gtgcgggacg ctgtggctgt gatccggtac ttggtctggc    15300
tggagaagaa cgtgcccaaa ggcacagtgg atgagttctc gggggcagag atcgtggaca    15360
agttccgagg gtgaagagcc acggccgtcc tttttggctg actgtctttt agtgtggcag    15420
tgggggcagg gagggggaat ttgtcccctt acttagcaga aaggaagatc ctcctcatat    15480
gcgtgctggg tgggggaggg ctctggagaa caaggagtga caggttcttg ggtggtcggg    15540
gagttgagca gggggcgttg atgatatatt cccgccccgc tgaaagcagg acaactcgaa    15600
gggccacaac ccaatagcgt cccctagtgt ctgcttcagg tacggtctga atctccctgg    15660
ggggtgctgt ggctcagacc aggtcagccc ctggaccact tgagaatacc aggtagggag    15720
gaggattccc gaaggcatgc ttggcccagg tcagggccgg attgtaggtt tgaggtacag    15780
gatgctctcc caggactggg ggagttttca gatacagaga gctgggtttc ttcactccta    15840
tccgtaaaat ggaggtggag aggaaataat gtgtgtctac agtgtgtcct ctgatcttcc    15900
tctataaatg acaggtcagg gcttgaggag atggaaccag gaggtgaggg ctgggagagc    15960
caaatggtgt ccagttgaga ggtagaggca gccatgacct tcattggatt tgattagata    16020
tcccgggccc agcctagtcc aggggcccat tcattgacca tgccttgcct tgtactttcc    16080
agagaagaac agttctcctc cggacccagt tttgaaacca tctctgctag tggtctgaat    16140
gctgccctgg cccactacag gtacttgagg aaaaagaatt ttctagggcc ctgttggggc    16200
atcctgttgt gtgtgtagag gaacagggtg aggggagggg gatgttctgg gacctgagtc    16260
cacgttgaag gtccgaggcc cctagccctg tggggctgg gagaggagct cagtgtggag      16320
tagggagttg ccttgtaatg aaaaggcctg agagctggag gctggggac ctggaaggaa      16380 gacaccgatg ccattggatg cttttccctg gcttcccatg tgttgcttat gttagctaat    16440
gcttaaagct cacgagttca catggagaga ggtctgttca ctcagcctga accagccaag    16500
gtgggcccaa gatacaggct agccaggtgt ttggccctat agaaaacaaa ccctgcagg      16560 cctgcctgat gaaaagctga ccagctgcct ccgcctggca tgggcacagc agggagaggt    16620
caatgccctc caagggagtg cctgacatgt cccagaattc cctcccctgg tgtcccctgg    16680
tgtctcccac gccttcggct gccttgcccc agccctcct acccactcgg gctagagtgg      16740
cagggtgggg gctcctcggc tttaccacct cttgctcagc agcccacccc tggaggtatc    16800
ctcccttcct gtgctctgct tcttctcagg gccctctgct ctcggaggca gcaggaagtt    16860
```

```
agagacaaag ggccggaggg agcatctggg tagaggccca gctctttgcc gctttaccgc   16920
gcatcctcgt gcaagcccct tggcctccat aggcctgctt ctccttatgg aaaggagac    16980 agctgagctg gggggtctct agggctctcc cagctctcat attctgggct ttaccctctc   17040
tctcctccct ggggaccagg gcctggctca gccaggtgca ggattaacag acgtgtgctg   17100
aggacagcag caacggaagc tgagttctct tccagggccc tttgggatag aatgacttcc   17160
tccagaggga ctggcctgga agcccaggcc ccagaggtcc tcccaccaag gcctcccacg   17220
tgacccagtg cagggttagg ctgcccttct caacattctc tccccttctc agcccgacca   17280
aggagctgaa ccgcaagctg tcctcagatg agatgtacct gctggactct gggggggcagt 17340 actggtatgt accccgacct caccctagcc tggatgtctc tgctcagacc tcctgagcct   17400
gccaagagtc agccaaagct ttcccttcct gggccacgga ttcttcgtct gaaaaggag   17460 agatctggaa tgagccccga acatcctacc cattttcaca catggggggtc cctgcacagt  17520 gggaaataca cagaggctgg aatagtggca ggacccaggc agcacctctg tgggaattag   17580
gaaaagactc cctttgctta agttgctgtt ttttgtgggt tgtttgtttg tttgtttctt   17640
gacagagtct cactctgtcg cccaggtttg gagtgcagtg gcgcgatctt ggctcactgc   17700
aacctctgca tccgggttc aagtgattct cctgcctcag cctcccaagt agcttggatt    17760
acaggtgtcc accaccatgc ccagctatat atatatatat atatatatat atacacacac   17820
acacacatat atatatacac acacatatat atacacacac atacacacac acacacacac   17880
atatatatat atgtatgtat tagtagagat ggagtttcac catgttggcc aggctgttct   17940
caaactcctg acctcaggtg atccacctgc cccagcctcc caaagtgctg ggattacaga   18000
catgagccac catgcccagc ctcaagtaaa atgttttcta agtccacgta ttattacaca   18060
gtctgagcaa ctatactcaa tgtccctgcc tggccacaca aacacatata ccctactctc   18120
atccactagt gcacaccctg dacaccccccg caccaccaac gtcatgcaga ctcctcagcc  18180
ccctcttccc catggcactg ttcagggtgg aggtgggggc agatgagaga agcaaccctt   18240
ttgatgggct acctttgtac agtgtacaac ctgaatgctc agacatgaca gccgtgcaga   18300
atagactaac ctggccaggc gtggtggctc acacctgtaa tcccagcact tgggaggcc    18360 gaggcgggca gatcacctga ggtcaggagc ttgagaccag cctgggcaac atggtgaaac   18420
cccatctcta ctaaaaatac aaaaattttc cgggtgtggt ggagcatgct cccaaggga    18480 aactgaggca ggagaatcgc ttgaacccgg gaggcggagg ttgcagtgag ccgagatcgt   18540
gacactgcac tccagtctga gcaataagag caagactata aaggaagaa agaaagaaag    18600 aaagaaagaa agaaagaaag aaagaaagaa agaaagaaag aaagaaagag ggagagagag   18660
aaagagagag agagagagag agagaaagaa agaaagaaag aaagaaagaa agaaagaaag   18720
aaagaaagaa agaaagaaag aaagaaagaa aagaatagg ctaaccccat tccttccaaa    18780
cgtgtgactg atcattcaca ccagagttga gctgagctga gctgacctga aagattttcc   18840
cttctcattg aggaaggaag tgtgggaagc gtggggtggg acaaaagaag ggccgtactg   18900
aactgatgga ggagcaagga gtcctgtgga aatggcgaat gtgctaacga cagaggctct   18960
ttgcttgttc ttagcacagc tctagggggat ccagagtagc aggcgctcag cttagcagcc  19020
tttgctggtc aggagttcga tgctgtgtgt acttgagatg gccaatgagc aaaggggaag   19080
tgaatttgtg ggggcgttgc tggaatgggg tgtgctcaga gtagggtgag gccggggaaa   19140
tagtcacctc acttcctctt ctttccttct gaagaagaag gtcaccacac ccatgaccc    19200 aaggagaagc cccagggccc tgggaccatt tctcccctct ccctcaccaa ggcatgatca   19260
```

```
cagggggccat ctgtggcaac tgctgcagct gggagttggg agtcagacct tgggactgag   19320
gcttcaccta actggaactc agcaagtcac tgggtcagat ccgtgtttgc catggagagg   19380
actgtgtgga gaggcagtgc ttgctctagg cctggcttca ctgaggttca gagagggaaa   19440
cagccgcatg gcctcaatgg cctcatctgt gaactgggga taatgaggcc tcttctacca   19500
ttcttcccag ggagcagcaa aagtgtccta taaatggtcg acaactatct gaatatgaga   19560
gtgttatgat aatataatct ctctggacct cagtttcccc agctgtaaaa agggggacatt   19620 cccctttctg cctcccagga agcctggaag aagccttgct ttcataacca gctggaccca   19680
aggaaaccca gacctacaga acagccaaaa tgagtgggat gggggaggag tgtgtagggt   19740
ggggagtcac acttgtcaga caacttagta acttttaact tgataggttt gcagaggcct   19800
ttcacacata ggtgctgaag aggggatttt gattatggta gctgtcttct cctttcgcc   19860 gtccacccat cccatcccag ccctgccact tgtggaaagc acacagaaag cacatggccc   19920
cagtccctag ccccaggcat ttggcatgtt ggttttcctt ctccatagggg acgggaccac   19980 agacatcacc agaacagtcc actggggcac cccctctgcc ttccagaagg taagcatggg   20040
cccagatttc ccctcaccac cttcccccaa gggggcaccc aagcagtcaa gatcccttcc   20100
atttcagagg ctaaaactga agctcagaga ggttaagtag tttgcccaag gtgacaccac   20160
tggtgccgga aaacccagtg ctccctgctg cttccccggg gatatttcag gccactgaca   20220
aggcctcagc ccaagctgag cctcatccta ttctggtaaa tcagtgcaca aatatttttt   20280
tgttgttgcc tgtgtgcctg gccctgtact cagcagaaag gagaaagaaa ggcatcccaa   20340
gtggaggaaa acggcacaag tgaagcctcc gcggtggaaa ggagccagag gtgttcagga   20400
aacatcgagg gctggccagc tggggcagag gcgagggcat tgtctctgtg caccagaggg   20460
ccctgggggt ggagcagcga gctgccgtca tgctgcatgc agcaggccga ctatggggca   20520
gacattgtgc tggaaacaca gagagggaa caaaatgctg tccaggtctc caggagctca   20580
cagtttagcg gcggagtctg ctgcctctgg ctgtcctgcc caaagtgaca agcctgtgaa   20640
cctgtgtggt gatggagatt gaccacatcg cctctggaag tgaccagaag aggccactgt   20700
caggccacct ccctccgctg acagaggaag gctaagctgc caagtcagca aacctcaacc   20760
ctcatgaaag gccttaagaa aactcagcag ccgtcacaac cacaggaatg agtgtgctaa   20820
acttccgtga agcatgcacg ctgttggcag caccttctgt acattagtct gcctgcctct   20880
cccaacaacc ttaggagcta ggtcctgtta tcttcccatc gcagataagg aaactgaggc   20940
acacagcagt taaagtcgcc tgcccaaggt ctcagagtga gtggctaagt caggattcag   21000
cccagggagt cacagcctcg gttcaccgcc accaagtgtc tcctgcagat attgtaatga   21060
tcctcataga ccagccagag ggaagcacgt gatggagccc cagctttggg aaggccctcc   21120
tcagcctctg ctggccatct tccagaaccc gggcagccac acataacgat gagactcccc   21180 ccacccctgcc tacacacacc caggcctggg ccctgcaccg tgtatccata ggccaagcag   21240
ctggatactc ctctggctcc tcctcccgtc ctccatatca cctcttcctc tcccatcag   21300 gaggcataca cccgtgtgct gataggaaat attgacctgt ccaggctcat ctttcccgct   21360
gctacatcag gtgggtttca gaaccagtc tggacacagc ctcaggccct gatttcacag   21420
gactcagacc atcaccctgg gaggctggtg gggcaaggat tttgtcatca tcccatccct   21480
tatgtagatg agaaaatcca gcctagagag agaaagtgac ttgcccaagg tcacacagaa   21540
ggttagcggg agatccaggc cttgaacctg agtttcctgc ctcttaatct aacactgttg   21600
```

```
ctcagaggtg ggagagatca gtgggccaca gcaattatgg gaggattctt agaggaatta     21660
ggtgtcaaag tgcaaagccc tgacagatgg ggagaaatta cagtagaggc atcaattcag     21720
gtaatggata caatgtatgg taagctggag atagtgatgg gctggtctgg cgagggaacc     21780
actaactcca tccatcagcc ctcctccatc ccaacccaac atcattgcat cagtgcatgc     21840
ttagcggcct ctcaggggcc cctcttctta ggcaccactc tgatagtgaa gcaagaaggg     21900
gcaaggtgga cagtcttcgg taaagccatc tgactggggt caatctctct tcccttccag     21960
ggcgaatggt ggaggccttt gcccgcagag ccttgtggga tgctggtctc aattatggtc     22020
atgggacagg ccacggcatt ggcaacttcc tgtgtgtgca tgagtgtagg tgtctcctca     22080
gcactcccca ggccaccccc cttttattat accctctatg aaggtagaga atttcacagg     22140
tatggaaatg acaaagaccc acaaagatgc catgatctac ccaaggttac ccagctccac     22200
agggtaagtg aggaatgcca gcagcaggcc agtcctgctg gctgcttggc attcaagagg     22260
gcaccagaaa gagggtcaag ccctagtgac taacttatat agaccccaga gaaataaaag     22320
ccagagccag ctgcatgtgg tgactcacac ccatagtccc actgctttgg gaggccaagg     22380
tgggaggatc acttgaggcc aggagtttga gatcagcctg ggaaacacag caagaccccg     22440
tctctacaaa agaaatgttt taagtatcca ggtatggtgg catgtgcctg tagtcctggc     22500
tactcgggag gctgaggtgg gaggatccca ggaggtcaag gctgcagtga gccatgatgg     22560
cgccactgca ctccagcctg gcaacacag caagacccct ctcaatacct aaataaataa     22620
taaaagccag agccaatctg gtgtgtgcca ggcccaggca gacaatgatg tgatggacct     22680
gtgctcatag agatgctctg ggatcctcac ttatctgctc ttcctcggaa gctgctcact     22740
tccaagctgg tgagtatagg agaactgata ccatgtttat gtcttccttt ctagggccag     22800
tgggattcca gtccaacaac atcgctatgg ccaagggcat gttcacttcc attggtatgg     22860
ccctcaggcc cctctacctc accacccat cccagagcag gactagccca ggactgcagt     22920
ctagagtgta ccagacttca gaggagcaca gcaggcacta gtacagctcg ggactcacct     22980
ccccattccc accgctacgc ccagcccaa atggcttgtc ccaccctaat tccagctccc     23040
ctcagcccag accctcttt tgctcttggg agttgtttcc cagctgtata ttcagacgag     23100
atcaggtgcg ttcagggtgg tatggccgta gacccagctg tatattcaga ctctggagtt     23160
gccaaatgct ggagtaacag gacagtggca tccagggaga tgggagtacc ttcaggaccc     23220
aagtgggttt ttagggcttc cctgctgggc tacagggaag agagagtgag tcagagatgc     23280
ccctgtgggg gatctgaggc ctgacaggga tgagttgcct ctgcttagcc aacaaacatc     23340
taaccagttg tggggctgcc agagtcaaca gccaggggac agccagacag ccagtccctc     23400
cagccactca tcagtaggta caggaagcct gggcttgggc cctctcccag cttaatgcca     23460
ccagcatctc tgtgtctccc agaacctggt tactataagg atggagaatt tgggatccgt     23520
ctcgaagatg tggctctcgt ggtagaagca aagaccaagg taaactgcca ccaggatggg     23580
ctggaggtgt gggcagcatg tcagtgactt tgggctgcat ggggaggaaag tggggaggaa     23640 gatcaaagga gaagggcatt tagtgtgcag gcatgaattt atctggagtc ttccttagga     23700
attccataag tcagacttttt caaactcgct tgcacatttg aatcacccag agagctttct     23760
ggtgctttaa atgcccatgc ccaggcccca ttccagacca agtgaatcag tatccctgcc     23820
ctatatcatt ggttctcaat gcacataata atcgccaggg gagcttgtta gaaataaaga     23880
ttctgtataa tagcagccaa caagataaaa tacctagatg taaacttaaa aaggcttaca     23940
tggagaaact ctctactaag ggacataaaa aagatttaag taaatggtgc tctctggaga     24000
```

```
gaagcctcaa tattatgaag atatcattac tctctaaatt aatctataaa ttcaagataa    24060
cctcaattcc agtgctaact ggatactttt gtaacttcac aaaatgatag taaagtttat    24120
ttgtaaaaat aaacatgcga agatagctag gaaaattctg aaaaagaaga gcagggccag    24180
gtgcagtgcc tcatgcctgt aatcccagca ctctgggagg ccaaggcagg aggatcgctt    24240
gagctcagga gtttgagagc agcctgggca acatggcaag accccatctc aacaaaaaat    24300
acaaaaaaaa attagctgca catggtgtca tgcacctgca gtcccagcta ctcgggaggc    24360
tgaagtggga ggatggtcta agcctaggga ggttgaggct gcagtgagct gtgaccacgc    24420
cactgcactc tagcctcggt aacagagcaa acccaatct aaaaaaaaag caataagaaa    24480
agccagtcct ctcaaatttg aacacaaact accataacta aaacagtatg acactggaga    24540
tgaaatagat agctgtaaca atgaaacaga acaatcagtc cagaagtaaa ccctcttatt    24600
cccataaaca acatgggaat ttagtttaca agaaagctga ttttgcaaaa aagtaagaaa    24660
aaaatgatta ttcagcaaat ggacaggggg aacaaatggc taatcatttg ggggattaa     24720 actgaataac ctccaaaata aaattccaga tggaccaaag ttttaaggtg agcaatgaga    24780
ccacaaaaga tgtagaggaa aacctatatc aattcattta taatctcagg gtggaaaaga    24840
gtctttctgt gcaagaccag aagccatgaa ggaaaagatt aataactctg actaaataga    24900
aaatggaaac aatgtttatg gaaacaatgc cataaacaaa gccaagagat gtgtgacaaa    24960
tatctcttgg ctttgtttat ggcattgtga gagggtgagt tttcttattt taccatgagc    25020
tttttacaaa tccgtaagac aaaaatagac aaaacaggaa aaaataggc aaaggacatg     25080 aaaaggcaat tcactaaaat taacaccaaa tggtccacat gcatgtggaa agatgctcaa    25140
gttcatcctt aaagaaatac aagaccgggc gtggtggctt atgcctgtaa tcccagcact    25200
ttggaaggcc gaggctggtg gatcacctga ggtcaggagt tcgagaccag cctgaccaac    25260
acggagaaac cccatatcta ctaaaaatac aaaattagcc gggtgtggtg gtgcatgcct    25320
gtaatcccag ctactcatgg ggctgaggca ggagaatcac ttgaacctgg gaggcggagg    25380
ttgcggtgag ccaagatcat gccattgtac tccaacctgg gcaacaagag caaaactctg    25440
tctcaaaaaa aaaaaaaaaa tacaaatcag ggccaggcat ggtggctcac acctgtaatc    25500
ccaacacttt gggaggcaga agtcagcgga tcacttgagg tcaggagttc aagaccagcc    25560
tggccaacat ggtgaagccc catttctact aaaaatacaa aaattagcca ggcgtggtag    25620
tgtgtgcctg taatctcagc tactcaggag gctgaggcaa gagaatcgct tgaacccggg    25680
aggtggaggt tgcggtgagc caagatcaca ccactgcact ccagcctggg cgacagagcg    25740
agaatctgtc tctaaaaaaa gaagaaggaa aagaagaaa agagaaggga aaaaaagtc     25800 tctttcttgc tcagtttcct tcctgagaac atttcaggca cacacagcgt atgtatctat    25860
ctatgtatat attttgaaaa tacaaacaaa atggattcta ctgtacatac ttttctgcac    25920
cttccttccc tgccccgctg ccccttactt aatagtaaac ctaggagagt ggtctgcaat    25980
agcgcaggga gatctacctc attcttttga agggttgtcg aagagcctat agtatgtgga    26040
tgtcccatga tttatttaac caaccgtgga tattgaggct gttccaaat ttttactata     26100 tttgccatca atgctacaaa tcactgtata aacatcttgg tgagcttttg ggactatatc    26160
cagaaggtac atatctggcg tagggatttc caagacaaaa agtacaagca ttttaatag     26220 gtaatttgat agatattgtc aaactgccct ccagaaaggt tgcaccaatt gtactttctc    26280
caacagtgtg tgagagtgcc catttcctca catactcact agcactgaga atcatcgaag    26340
```

```
tcactaattt ttccaatctg ataggtgaaa catggtattc tattgttgtt ttgacttgta   26400
tttctttttt tctttctttc tttcttttt ttttttttt tttttttgatg gagtctccct   26460 ctttctccca ggctggagtg cagtggcgag atcttggctc actgcaacct ccgcctccca   26520
ggttcaagtg attctcttgc cttagtctct tgagtagctg gaattacagg cacacaccac   26580
cacgactggc taattttgt attttagta gaaacagggt ttcaccgtgt tggccaggct   26640
ggtcttgaac tcctgacctc aggtgatgca cctgccttgg cctcccaaag ttctggatta   26700
caggcgtgag ccaccacacc cagccttgaa tttctttaag gatgaacttg agcatctttc   26760
cacatgtatg tgaaccattt ggtgttaaat tttagtgaat tgcttttca tgtcctttgc   26820 cttatttttt cctgttttgc ctattttgt cttatggatt tgtaaaagct catggtaaat   26880
atgaaaattc accctctctc tgtgatatgt gctatatttg tcacacaact cttggctttg   26940
tttatggcat tgtttccata acattgttt ccattttctg tttagtttag tcagagttat   27000
taatcttttc cttcatagct tctggtcttg cacagaaaga ctcttttcca ccctgagatt   27060
ataaatgaat tgatataggt tttcctctac atcttttgtg gtttcagcct cccgagtagc   27120
tgggactaca ggcgcccacc accatgccca actaattttt gtgttttag tagagagtag   27180 agacggggtt tcaccatgtt ggtaatgctg gtcttgaact cctgacctca aatgatccac   27240
ccacctcagc ctcccaaagt gctgggatta caggcgtaag ccatccattg cacctggcct   27300
cttttttttt ttttagagac agggtctcac tctgttgctg aggctggagt gcagtggcac   27360
gatcacagcc cgctgcagct tcaacctcct gggctcaggt gatgctccca ccttccacc   27420 tcagactccc aaataactag gactatagat ggacaccacc atgctcagct aattttgtg   27480 ttttttgta gagactggtg tattagtctg ttctcacatt gctataaaga tactacccaa   27540
gactgggtaa ttttaaagg aaagaggttt aattggctca cagttcccac atgcctgggg   27600
aggccttggg aaacttataa tcatggcaga aggcgaaggg gaagcaagga tctcgacatg   27660
gtggcaggaa agagagagct aacaagagca gggaaaactg tcttataaaa ccatcagatc   27720
agccaggcgt ggtgggtcat gcctgtaatc ccagcacttt gggaagctga ggtgggtggt   27780
tcacctgagc ttaggagttc gagaccagcc tagccaacat ggtgaaacct catctctaca   27840
aaaaatacaa aaagtatctg ggtgtggtgg tgcccatcaa taatcccagc tacttggaag   27900
gctgaggtag aaggatcacc tgagcccagg aggtagaggc tgcagagggc cgtcatcgtg   27960
tcactgctct ccagcttggg taacagaggg agatcctatc tcaaaaaaaa taaaataaa   28020 taattgaaat ttagatttct gggccctgcc ctaaggattc tgcctccagt aggtttggga   28080 ggtgggcct ggaatctgca tatttatcat gctccctaag tgctgttgat gtgcgtactt   28140
tgaaaaacac aaacctaagt ctaaatttcc agaatcagga gggaagcacc aaaggtggag   28200
cactaagtgg cagacaaggg ggctggccaa gagaagggac tctagaaggc tcaggcctag   28260
ccagggtgtc cagggttgat gaggcccagc tccttgtgtc ctccgggtgg agtgctcctt   28320
ccttcccttc agcccagttc ctcctcctcc ctcactgtcc tgcttacccg gcttctattc   28380
tgggctccca gtacccaggg agctacctga cctttgaagt ggtatcattt gtgccctatg   28440
accggaacct catcgatgtc agcctgctgt ctcccgagca tgtgagtgcc cctcagcatt   28500
gccttctccc tgaccctggg cctttcctgc ctctgctacc tgccaccaca tcctctgtcc   28560
ctgcccctcc tccaggaggg tccacactgg tggcacctgc agacacacac tgggcattc   28620 ctccccagct catcagagac cccagagctt ctagaacttt ccagtcagac cagcctgccc   28680
aaccccaggt agtgaataac tggaggaatc tgagattggg cctctgagct cggccactac   28740
```

```
aaggcctgga actataagtg atcccttcta ttcttttgcc tcagtctcct cttttgtaag    28800
ctgaggataa gaatgcctgc ccagcttact cccattcccg ggcctgaaat ctacccaccc    28860
caccgcccat gaacatcacc atgacatgaa acagccagcc aggggaactg cctctgaaaa    28920
gccccagaga attcctgaag cctgatgatg gtgggggacc tgtggccatc tggactatgg    28980
tgacagctgg agtaccacaa caggggactg ggcgtcacca agacttcacc tcttggcagc    29040
ttggcttaga gaggctgtca cccottctat ccttcgcagc tccagtacct gaatcgctac    29100
taccagacca tccgggagaa ggtgggtcca gagctgcaga ggcgccagct actagaggag    29160
ttcgagtggc ttcaacagca cacagagccc ctggccgcca gggccccaga caccgcctcc    29220
tgggcctctg tgttagtggt ctccaccctt gccatccttg gctggagtgt ctagaggctc    29280
cagactctcc tgttaaccct ccatctagat gggggctcc cttgcttagc tcccctcacc    29340
ctgcactgaa cataccccaa gagccoctgc tgcccattg cctagaaacc tttgcattca    29400
tcctccttct ccaagaccta tggagaaggt cccaggcccc aggaacacag ggcttcttgg    29460
ccccagatgg cacctccctg caccccgggg ttgtatacca caccctgggc ccctaatccc    29520
aggccccgag ataggaaagc cagctagtct cttctcttct gtgatctcag taggcctaac    29580
ctataaccta gcacagactg ctacagctgc tccoctcccg ccaaacaaaa ccccaagaga    29640
gcaatgcccc taccacccaa gggtgccatg gtcccgggag agcccaaacc tatcaccacc    29700
tgttgggcat agccagagct gttcccaccc agccagggca tgaaacatca acccccacca    29760
tgtgaaccca tcattcctaa accctgggta ggctccatgc caagtaacag cagagggagt    29820
taagccatag gaatttggct gtggagtaag agggaatgcg gtgaggcact ctggaatatg    29880
accctaccag aggttggaga caaacttgg gcagccggaa cccgtcacta ttctagactt    29940
ccctggcatt cgaggagccc tttgaacttt ccaaagtgca gccacagcta caatgctgtt    30000
aaatcctccc acattcttgg atgcccttc accttgtgtg gacagtgtct ggtttctcca    30060
ttttacagac aggaaaactg agcttcagac agggggtggg cttgcctaa ggacacacaa    30120 atttggttgg gagttgatgg ggccagatga gccagcattc cagctctttc acccttcagc    30180
aacatgcaga gtccctgagc ccacctccca gccctctcct cattctctga acccactgtg    30240
gtgagaagaa tttgctccgg ccaaattggc cgttagccac ctgggtccac atcctgctaa    30300
gacgtttaaa acagcctaac aaagacactt gcctctgggt tttgcattgt gtctgctgtg    30360
ttgccggaga ctgctgtcac ctgtggcttt tgtggtgggg gaggaagaag agagggtgag    30420 gtggggggtgg ggacatgagg ctcctagaag ctcagtgggg gagcacgtgg gcttgagagt    30480
atgtgtgtga gcatgcatat gaatatgtgt gcgcatgtgc acagatgcac gtgcacacca    30540
cgcccaacca gccaacctcc agcctgtcta aaaaggtatt gtaaccttgt ggaagggaca    30600
gaaaggagcc ctacactggg gaacttgtca aatgtaatcc agaaaagttg gggctggcac    30660
ctttgccaag cagcgcacag ttggtggaag gaaagaacca aggtgcaggg tgccaggcaa    30720
aggcaccagg cagagaagtc tcctggcctg aaaccatcag gcctagtctg ctgagtgtga    30780
gggtgacctg tgatggttac catcaccagt gcttgcatcc agaggctcca gccctgacca    30840
agccttactg agtatccaaa gatgggcctc tgtttgctaa ataatttgct ccctcacctg    30900
ctcaccccac aaagacaggt actactaata aaattaaagt catcatcacc ctcatcatca    30960
tcaccatcat catcatcatg gctgccattt actgagtgtt tatgtgccac cgtgcaagaa    31020
gctttacatg cattttctca tttaatcctc acaacctctg agaaggccct tttcttattc    31080
```

```
ccattttaca agtgcaggaa ctcagtgagg cccatagaga tttatcaagt gactcaaagt    31140
cacttttttc attgggtaaa tgaaaaaaag ccagatttaa accagtcaga ggactctaga    31200
atccactctc aagaaagggc aagtcctggc cgggtgtggt ggctcacccc tgtaatcaca    31260
gcactttggg aggccgaggt gggaggatca catgaggcca ggatttcaag agcagcctgg    31320
gcaacatggt gaaaccccat ctctactgaa aatacaaaaa ttagctgggt gtggtggcgc    31380
acacctatag tcccagctac tcgggaggct gatgcaggag aatcgtttga acccaggagg    31440
cggaggttgc agtgagctga gatcgtgcca ctgcactcca gcctgggcaa cagagcgaga    31500
ctccatctca aaaataata ataataataa aataaagaaa aataaagggc aagtggtatg    31560
gctttcatca ttttactgac aagaaaactg aggctcaagc aggagaagca gatccacacc    31620
atagtgcctc cccagaccct gccagacctt tgcctttgca ccctgacact tgctcctggg    31680
gttctggcag gtcatgggtg gcaagaccag gcacctgacc aacaccctca cacaggcctt    31740
tcggaccgag gcagctcgtg cttttttcct cagtgcgaga cccaggactc cacctcatct    31800
ctgaatcccc ttaactgccc cttccagcct accattctgg gaggaagaac ccagccctgg    31860
aacgtggctg gaacgagggc tcacagtcac cccagctctt ccctcccctg gacccagat    31920 ggccagactt gaccattcct gctttaaggg attaactctg ggtcaggcag ggaaacaggg    31980
cacatacacc agggctgata cacagggact cttgtgacat cgttaggaat gaaagattgt    32040
taggaactgt cccctgggc tctagtactt tgttttaatg ttggaggatg gggcttagca    32100
aacctctcct cgcctgctga ttgcctgggg agccggccat gtggaaaagc cccttttcct    32160
aggagttaag attctggggt ttgagtccca tttgtgccag ctgtgtggcc ttgggcaagt    32220
cacttctccc tggtcttcag ttatcctttc tggaatctcc catgctgcct tcttggtgag    32280
gttacagcga gaggctcatg agacccggat gtggcagcac tctaaaccag gaagccacac    32340
agacaagaaa tgatattgct gttatttgcc cagcacaagt tcaattcagc ttcacctttg    32400
caggtaggta agaaaaaggt ctggaaccca agttttatat ataaatagcc aaaattagaa    32460
aggctctaga gcaaacatct aatttacgtc tttccaacta tgctcccggg agcctgagat    32520
gcctcagaaa caccacaggg gctgtcgagg aaaacagagc tgctgcacga agtagccctg    32580
acgggcttcc cgtaaaattg tacttgaagt agttgcaggg ccagcttcac gggtgtagga    32640
cctgtgcagt ccctcaagac tttgtgctta caagggcccc atgcttggtt taatgctcgc    32700
ctgtcactgt ctcaaaattc ttgataattt ttaagcaaga ggcaccgggc attttcattt    32760
tgcacaaggc ccgcaaaatt caagagccaa tcctgaatag gagctccatg accaaacaca    32820
cacacacaca cacacacaca cacacacaca cacacacaca cacaaaacct ggtgcagtcc    32880
tttcagtgta cagatgggaa aacttcaaca gcaacccagg aagaggaagg gacttgtcca    32940
aggtcacaca gtccagtggg gccagagcaa ggactaaatc cgcagcatac tgactcagct    33000
ccacaatggc tccgctctcg ctttcagtgt gtgcttctgt cactccctta ctgcctctaa    33060
tgacccactg aggcccaagg agacctgttg aaggtcacac agctgtgaca acaatggtga    33120
cggcggtgtt gagccacgtt ccttcaagct tcaaatctga atagaaaagg gcataggtaa    33180
gatgataggt agataggtac atacacaaat catctaaata gctccttttg tttttttgttt    33240 tttttttag agagagggtc ttgctctgtc acccaggctg gagagcaatg gcaccatcat    33300
agctcaccgt aaccttgaaa tcctgggctc aagtgcttct cccgcctcag cctcctgatt    33360
agctaggact acaggcatgc accgccatgc ccgattaatt ttttttttaa tttttatttt    33420
atagagatga tgtctatgtt gcctaggctg gtctcaaatt tctggcctca agcaatcctc    33480
```

```
ctgccttggc ctcccaaagt gctgggatta caggtgtgag acaatagttc atttttaaa    33540
atgataacta actcagcctt tgctggtttg ccagtcagct ggttccagct gtgtgtgagt   33600
tgggacctca gaaggggctg ggctggctac tcttcagcca gctaaaccac gtcagcagtg   33660
aattttacca actcactggg tgcttcctca aatcagtggt tgggcactct tggcaccaaa   33720
aaatatatat atatagaagt gcgaaagatt cagtagcaac cgtttcctcc ctgtccgtcc   33780
ctgctcctca tggctcgtca cagccaggag ggggaggtgc tccccaaacc ccaagccagc   33840
tagcctttgc ccagaggccg gcccatctct tcacttcctt gtttctttgt gaaacaggaa   33900
ctgagcaagc agcttaagtc gggtaggatg ggtggttgag aaagcccag tggtccgtgg    33960
caagtccacg aagctgaaaa gctggtttct ctcccagcgg gtcccaggca gcttcaggcc   34020
ctcttgtttg tcacacctct tgtgttctag aacaacttgg ggtgagggat gcactcttga   34080
caaggtggag acataggata tgggccacag ggtcacgtag cagagattca gatgcggacc   34140
tcaagagaca tagaagcagg tgccaggccg ggcatggtgg ctcacgccta taatcccagc   34200
tctttaggag gccaaggtgg gtggatcacc tgaggtcagg ggttcgagac cagcctggtt   34260
tggcaacatg gtcggcaaca tggtgaaacc ctgtctctac taaaaataca aaaaattagc   34320
tgggtgtggt ggcaggcgcc tgtaatccca gctactcggg aggctgagac aggagaatct   34380
gggaggcgaa ggctgcagtg agccgagatc ttgccactgc actccagcct gggccacaga   34440
gtgagactct gtctcaaaaa aaaaaaaag aagaagaaga agattccaag gggacactaa    34500
gggagaaagc ggcagctcct aacggtcacc aaggccttcc tggatttagc aagggagaa    34560
actccaggtg gagtctgaag tgaactgatg tggagtcact caccaggtac ccagcacttt   34620
ccactagctg gggcactggg ctgagagcac tccctctatg catgtcacct gagtagtaac   34680
cctagtcaca cacacccaca agaaaggccc acattatcac tgttaccatc ttcactaagg   34740
ctcattgcag gtgaggtcac ttgcccaagg ttatgcagcc agtaggtgac catacaacaa   34800
tctgaatcca atcaggacaa cctgactcca tttctgagag gtgttctgtt cctcctcttc   34860
cctggagccc tggacaattg tccccatggg gagagggcc cactgatcag agaggtttgt    34920
ccttgtaacc ttgggacaga gatttatgca gagtagccca gccctactt gtcccccata    34980
gaaagtgcac ccccccacca gtgagtcatg agtgtgtttt aatctgagca ccaaagtcca   35040
gcctcctctt ctgatggtaa ttgacagagc taccagcagg tgtttttgt tttgttttgt    35100
tttaaaacca agaccttatc acgagttcag agttccaaag atcactgtct ttccctcccc   35160
tcccatcagc ccctgccacc agatgcccac tctgtgtgtg ttgtatgtgg gcatgaggaa   35220
tgggcgcaag agtcacctgc ccttgtctcc ttgctttcct ctgcccgcct tctccctcct   35280
gcaattttgc tctttctgcc ctccctgcct aaaatgacca ccattaaatt tgctaatggg   35340
ccgggctact aaagtgggct tcaccttgga aatgtccagg tattttcaag aaactatgtg   35400
gcctctgctt ggatatttct ttttcttttc ttttttcttt tctttttttt tttttggttg   35460
ttttgttttg ttttgttttg ttttgtttga gacagagttt cactcttgtt gcccagcctg   35520
gagtgcagtg gcgtgatctt ggctcacagc aacctccacc tctcaggttc aagcgattct   35580
cctgcctcag cctcccaagt agctgggatt acaggcatgt gccaccatgc ccgcctaatt   35640
tttgtatttt tagtagagac gggtttcacc atgttagtca ggcgggtctc aaactcctga   35700
cctctggtga tccactcacc tggcttccc aaagtgctga gattacaggt gtcagccacc    35760
gtgcccggcc tacttgaata tttcaagaga tggggagatc attacttacc agagctgaac   35820
```

-continued

```
tagtgccatc tgaatagcca aaatttgttc cttggaatat actaaaacct tccatttatc    35880
tgttccccat cattcatacc acttgcttcc ccaccccaat cacctaggct aaatgtgaca    35940
ggagtttagt acttcacacg ttgacgactt ccctatactt caccccgct taatcgaccc    36000 tagctattgc agctttgcag atgtgatgcg acttccagat gtcctcccca tcctgttcac    36060
tcccctctgg gcctgcttca aggtggctct gtggcaccta gtgtggcacc caaaccagca    36120
tcaggtgcca agagaaggct gcaagccgag ggctccataa ttctctcacc tccccgttca    36180
ggaactccgc atcagaggca cttcagctga gtggttagtt gtgtgggccc tggccaagac    36240
cagacctgca tttaacgctg ggctccactg cttactagct gtgtgggcaa ttcacttaac    36300
tcctctgggc ctcagcttcc tccctggaaa atggggataa caatagtgcc tgacttacca    36360
ggttgttgta aagcccactg cctgccatga agtataataa ttttcagcta gatgtgggga    36420
ctggggggaa tggaaataag aatctttggg ggccgggtgc agtggcttac acctgtaatt    36480
gcagcacttt gggaggtaga ggcaggagga tcacttgagg ccaggagttc aagatcagcc    36540
tggacaacat aggcaaaaaa aaaaaaaaaa aattagccag gaatggtggc acgtgcctgt    36600
agtcccaact acccgggagg ctgaggtggg aggatcatga gccccaggag tttgaagctg    36660
cagcgagctg tgaccacacc actgcattcc agcctgggca acagaggag accctgtctc    36720 aaattaatta attaattaat taattaatta attaaaactt aaagaatctt ttgggaggtt    36780
tttccagata taagtatctc tcactatcca aactcttact atctcaaatt agaaatatat    36840
ccattcagag agtgagagat gcttttgtac atggtctgga tcttacctgc cccaaatatc    36900
ccactcatga tcatctacta aataagaatt tcttggctga gtgcagtggc tcacacctgt    36960
aatcccagca ctttgggagg ccaaggtggg cagatcacga ggtcaggaga tcaagaccat    37020
cctggctaac atggtgaaac cccgtctcta ctaaaaacac aaaaaataag ccaggcatgg    37080
tggcatgcgc ctgtagtccc agctacccag gaggctgagg caggagaata gcttgaaccc    37140
aggaggtgaa ggttgcagtg agccgagatc gcgtcactgc actccagcct aggcaacaga    37200
gtaagactca aaaaaaaatt aaattaaatt aaatttaaaa aaatacttgg agtgtgctgg    37260
tgtgggagct gctttatctg aatgtggcct acgatgacct ttgtgtcttt ggtagtccta    37320
catccaccct ctgagggttc aggttgattt cactatcagt ggaaccccaa aacacacaca    37380
cacacacaca cacatacaca ccctgcaatc ctgcagtatt ggcgctaaat caaggttctt    37440
ctgccccaaa tctatacttc tggatacgtc tttatattaa actactcgcc tccagggggtt    37500 gtggtgggat taaacatctg tcaagtgctt aatgtagtgc ttggtaaaga caagtgctg    37560 ggtaaatgta agcttgccac tccacctagg atgtcagctc ccaggtacaa ggggccctga    37620
tggctattta ttttgtacct cctcccgagg cctagcacaa ggctgtgccc acagcaagtt    37680
cctaggttct gcctgccggc ccattatcaa gtttaaggtg accttgttcc ctgaactact    37740
gactcgtatc acttccttag ctgagagctc tgcgtacctc aaacaacata acctgtaaaa    37800
tgcaaatatg ttacccagaa gggaaaatct attaaaacaca tgtttaaggg tcattagcca    37860
gcaaggacct ggcctattgg gattcagcca gggcaatctg ttggaagaga aaagctgggg    37920
gaaggcaagt cccgatgggg ggtcctggac acccgcctc cactggcccc ggtccccagg    37980
tggcggggag gaggtgttcc tgaacagagg agacagatct gaaaaggaga acgaaggaag    38040
ccgttgaaaa cacttgctcc cttctgtcct gggagctggt cacctctcca tatttctctc    38100
caaggcaccc tcacctcccct ctcgctgcct tttcccaagc ctcgccagcc ctgtgccctg    38160
gtttgctggc cgccttttgaa ggttctgcgg ttagtgtgtg atcttctgtc gctgccggcg    38220
```

-continued

```
ctgagcaaac aggaagcggg cacatcctgc gaggcggcca gggacgcagc cgctgcgcag    38280
gcccggaaga ttctgcgacc tgcttcctcc ctcacggctc tggctccagg tgccccaggc    38340
cactacagcg gcgtcCccaa tcccagaacc ctctggggct gccctcctgc tcctggtcac    38400
gcagagcccc aaaggcccga tgggtcccct acacggctgc caggctactg tatatgccga    38460
aaagccttaa ccagttaccg cgcttgctag tgaccctggg ccgcctggga gggactttca    38520
gggtggaaaa cacaggccag tgggaaggag atctggggtg tggaatcttt tcatgagtct    38580
gcctggccga ctgagtaggc caaagaatgt atggtttcag cttagggaag aaagatctta    38640
tcttccctga gctcaccctg aaggttggat ggtcagaggg cataaagcag aatcggagag    38700
gaagtcacga aacatcttg ggaacagggg tggacaagcc tagtatttca caagtaccac    38760
agaattgaaa gccttaaaaa tgtgcatacc tttgacccca gcaattcctc ttctggatat    38820
ttcccctaca gaaaaaaaac tatggatgtg aatatttacc ataagtatgt tcaatgaata    38880
atttaaaaat ttaagccaac ccaagttcat cagcaagggc ttggtgaaat aagcacggca    38940
catccacaca atgggatgtt ccacagccgt tataaattac gtagttgaag actatttcat    39000
agcatgagac aatcttgata ctgtgttcag ctggacgtag tggctcacgc ctgtaatccc    39060
agcactttgg gaggatgagg caagaggtc acttgagacc aggagttcaa gaccagcctg    39120
ggcaacatgg tgaaaccctg tctctacaaa aaatacaaaa attaaccagg gtggtggtac    39180
gcacctatag tcccagctac ttgggaggca gaggcacaag aattgcttga actcaggagg    39240
tggaggttgc agtgagccga gatcacgcca ctgcactcca gcctgggaga cagagtgaga    39300
gactccatct cgaaaaaaaa acaaaaaaga tactgtgttt agtgtgaaaa gcagacacca    39360
atagtgtgaa ttatgacctt ttttaattaa aaaattttaa acagctttat tgaggtataa    39420
tggagctaca ataaactgca catatttgaa gtatacaatt tgatacgttt tgacatgtgt    39480
attcccccat gaaatcatca ccacagtcaa gatagtgaac atattcatca ctcctaaaag    39540
cttcctgtta ccctgtgtga tgtctcccct cccttctctc cctccccttt ctccccaaac    39600
caattatctg ttttctgagc agtatgattt ttgtaaaaag aaaaaaaatg tttatagaca    39660
gagagtagat agatgcttaa aacagtgtag aggacaatga tgggaaattt tgaaatttt    39720 tttgtttatg tgtttgtgaa attgtatgac aaatacaagt tgcttttgta ataccaagaa    39780
gttattaaag ttattaaaat ctgccacaga caacccacaa attgaatata ctgcataggt    39840
gtttgataaa tgcctgttgg atacttgcta gaggtgtgga gttggctgta agtgcttttc    39900
agctgtggtg gtgataaata tactcatgat ggctgagggg tactgactgg aggggtgact    39960
gctctagtga tgatggcttt aggtgtactg atggctgtag gagtgatggc tgcagggctg    40020
atggctgcac ggatgtgatg atggttgtag gagagatgac tgtagggacg atggttatag    40080
gggtgagagg gtcatgagtg cggttggctg taatgtccag aagggtgaca gctgtaagga    40140
tgatggctgg aagggtgata gcagcaatgg tgatgactgt agaggtgatg gctgaaggat    40200
gtcaactgta gaggtgatta ccatagtgac aatggctata ggtgtgctga tggcagcggg    40260
gatggctgca ggcctgatgg ctgtaggggt gatggctgta tggtgatggc tattgatagg    40320
agtgatggta gcagtggtga tggtcacagg ggtgatggta gtggtagtga tggcagtgac    40380
gaccttgaag acgtgagttg accgggagca ttgatccaac aggcagccag atggtccaac    40440
ttctggtttc tggattctgg tcagtgagat aaagggcttg ggtacgccat ataatgtcga    40500
gctgattgtc cacctctagg aagatggagc agaaggactg atgatgatcg acatgagaca    40560
```

-continued

```
acaaggtagg gactttctct gactgttcaa cccaagagcc gtctgcatca gaatctctgg    40620
agactgaagc ttggacttcc ttcctcccta ggggccggca ggggctgcga ttgctgtaag    40680
agtaggtcac gtggcagggc ttcctgtatg ctgctgctgc cgggtgtcca tggcccgcac    40740
ccccaagctg ccactgcagc agtcagagtg gcagctgaag gctcggttca tgccgtgccc    40800
ccgggcagtt ctggtgaggc taagcaagag gcctctgcat cttgacacct aggagagcag    40860
ggacggagtc tcccagggtg gaggaccatg ctgcgccgca agccctccaa tgccagtgag    40920
aaggagccca ctcagaagaa aaaggtgagg agcattttgg gaactcacat cttcctttcc    40980
tctgcttgct cgacccatcc cttccaagac tcttggaagt gggaagagcc aaaggccata    41040
tgttgagtct gtaggtgagg ccactcacc tagaaggcaa cgggacaggg acccaaaggt    41100
taacagaagt acagaagaga tgtttaaaat tctggagcaa cagagttaca gaatagatcc    41160
ttagaaatct agagtcatgc aattcaaccc tagaagaatg ggaaaaaaga tctaaaatta    41220
ggggccagaa tcttagacta gaatttgaga ataacaaaat acaatgctta agctgaaccc    41280
taagcttgta cttaactatc tctcctctac gctggtcctg ctgccacttc tgccccggcc    41340
acggcctctc aggagccatc tcactcaaag ggccctgctg ggctgccag cttggagcca    41400
tgatgctcac aggactgcca ccccctcctc cactttggcc atggcccaga ccctgcccac    41460
ttggctcagc tctgtggtag ctcccaggcc ctacccgaga tggagccaac ctggagatgg    41520
gggcctgagg ccattccagt cttgggggaa aaggcatccg gaagtgcagt gggatgcagg    41580
gggcatacag gttcttcctg ggtggggaat gagaaattaa gttgaggtgg tgagtaggag    41640
tgaaggctga ggagggagga ttttaaaggc caggaggaaa aacagctgtc atggatggct    41700
gaggtgttca tccccctggg gcagagaccg gactggaaga atccttgaag gctgtgccag    41760
atctaggatt tgtggttga atttgaggat ttccagattt cttggttgg gtttgaggat    41820
ttctagacct aattctttaa ttcaattgaa ggattctccc agacaatcag caagtatatc    41880
ctacacatcc aatgggatgc taggacagtc ccaaagcagg cctgaactag gtccaagagg    41940
cccaggctat cccccgccaa ttttccctgg aactcagccc aggtgcccta tggtggatcc    42000
cccttgtcag gggagtagct cagagatgga ggccaaggca gctgaaagac tgagactcgg    42060
ggcagtgggg tgtgcatcct gccccagctc tcaggtcctg gggtggctgc cacttccggc    42120
tgtattctcc ccaccccagc tgcttctcta aggttgcagt ggtggtgggc ggggagggg    42180
ggaggttcat gaatcttcac acgggctctg tcatccccgt ccaaaccctg cagggtgcta    42240
ggcccagcag gactgccatt ggctgccact cctaagagag cagggccact tccccttgct    42300
ctctggctgg tgggggtggg aaacagagat tgctctatag acactgctag gcctcaaacc    42360
acagggcgc tgagctggag gaaagtgtga gaaagagctg acactttgac actgggaccc    42420
tgtgccacat caggaagacg tacctagggg cacacagaag ccagaagtcc ccttttctt    42480
tcccagcttc aattacccag attctgtgtt cggcaggcaa gtgggcccct gggatttccc    42540
caggtctctc ccaggagaag gggtcctttc gggagagta gtccaggcaa accccacccc    42600
aacccctgcc agagccggtg ccagcctcca gagctgggat gagcttgcct ccacacactc    42660
tgctagcccc agactatgga aatgtccccc agaagccaag cttccagaag gtacagagca    42720
tcttccccag gcccagaggc agcgggctgg ctgaatcact gctagtccct tcttctcaga    42780
ggctgagatg acgtggtgga gaggaaagca caaaggcaag agaggcctct ttctcctgcc    42840
cctgcttctc ctcttgggcc tgccaatgga gaatgtgcca gacaggggc aagaaagctg    42900
agctggaatc ctaccacgct ctagctgtag gaccttggac agctcattga ctttcttgg    42960
```

-continued

```
gcctcagttt cctcgcctct gaaaaggagg ataactccta atctgccccc ctcaagaggt   43020
tgtacagatc acccaaaaga atagatgtga gagtaccctg tcacaagtgt gcacgtgcat   43080
accacacaag ggggtgcctg ctgtaggcat gggtggggat agggagacac tgcaaagaag   43140
aatgagccat gccccagtg ctggcacaga gaacacaaga cttaatagta ctaagagcca   43200
ccacagagtg agagctcatg ggatgccagg cacggtgctg tgcatctctt accttgttca   43260
ctccccacga caacctggtg aggtaggggc agatattgtc attatcccta tttgacactt   43320
gaggctcaca gaggtgaagc aacttgctga aggtcacaca gctgggaagc tgccgagcag   43380
ggatccaagc caagatttgt ctgactccag aatcttgacc ccttctctct ccactctctt   43440
gtccccttgt tgatctcaaa ggcgctagaa gagtctgatg agcataaaag attcaaccca   43500
tcagcaggag agctccgtgg ggcagaccca gatagctgtg aatgagtga ccttccagcc   43560 agcagagcag aggagggtgc gggccctcta gaatggtagg gctaggacat ggcgcctccc   43620
atggatcgtg aaggattgga gaggcccag ggttgggaga cagacctctt agctgccctt   43680
tggagacttt cacttccttc aagttcttgc tctgcaagcc ctttgatctg atttcaccca   43740
aaggccagtg ttggggtata ggaagtggag agggattttt cctggacttg gttcccctaa   43800
ggatgctcct actctaccac atccccactt tctccatggc tcccttccta cagcacacct   43860
ctagtatgac ccccacaccc tgccagcatg cactttgtat tttcagtggc tcctcactgc   43920
ccacaggata catgcccttg gcctggcggg caagagcctt ccatagcctt ttctactccc   43980
ccacccacca tcccatcatc aggctctcaa cgtctctaac tttcattctt gttcaaaccc   44040
ttccgagctc cacctggaga aatcctgcct ccctgcatg gccagctca gatatacctc   44100 ctccacaaag ccccgccaga gcccttcccc ctctgcactc ccacctgctt tcctaggagc   44160
tctgttcaaa aacccctgc atgccatcac cactacactc aatccactgc taacttctac   44220
actggtgggg cggggcaaca gcatgagctc tgaggtagca cgagcacagc aacatacttg   44280
ggtttccaga gtcatagacc tgggtttgga ggcttgctct tcctaagacc agctgcgcca   44340
ccctgcctag ggcacttcat ttcgcatctt ggtctcctct gcttcgaggt gcgaatatga   44400
tgcggggctg cgatgaggct ggagtgagct ggcacacagg aagtgcttgg caggacacgg   44460
gcatgcggga ggagtttaga ccctcattgc tggattctca cacacacaga ggtagggcct   44520
agagctcaca gggtgctcag tatatgcctg ataccctgaa ggagcagagg gggtagctca   44580
ggagaccact ggggaaagcc aagtttgctc aggaagtaag ggaagaggat gctggctggg   44640
gcagtgtgga cctctgagag attgatcagg gcatggtttc tgcatggatg ctgccttta   44700 agctggaatt gaaaaatctt tccatagaag tataatatcc atacagagaa gtggataaat   44760
cataattgcg ccaccgaatg agtttctata atgtgaacat cccatgtag acagcactta   44820 gatcaagaaa caacactctc agaagtctag aagcttccct catgcccctg ccagttacta   44880 caccccccc ttccccagg gcaaccgcta tcctgacttc aacagcaca ggtgagctct   44940 gccaggcttt gaacttacag ggggaaccat atcgtgtata tatactcttt ggtggccagc   45000 cccttactc aaccatatgt ttgtgacact catccatact gttgggaaca gttgtactgt   45060
ctcctacctg ggtactattc ttttgtgtga ctctgccaca attaatttat ccattctaca   45120 gatgatggc atttgcgggt tttccactta aattggaagg gtgagaaact acggctgaca   45180
gagagaaggg cagagtattc cagtgggga aatgcccagg gtaagaggct ggaggtgggg   45240
tgtaggaaag agtaagcata aacctacatt ccacaaggga ctgccgtgtc agacaatgtt   45300
```

-continued

| | |
|---|---|
| ccaagcactg taggcgtact cgctcatttc atcctcacaa cagccagatg aggtcggtgc | 45360 |
| ttttgtcttc attccactaa tgaggaaaca gaaacctaga gaagttaaga aacatacccca | 45420 |
| gtttacacaa tcagtggcag aaccaagatg ggaacacttg ccctgatgtg aagtgggctt | 45480 |
| cagagaggtt cgataacttg ccggaggtca caaatccaga gttgaacttc tgagaaagct | 45540 |
| tccctc | 45546 |

<210> SEQ ID NO 7
<211> LENGTH: 16595
<212> TYPE: DNA
<213> ORGANISM: Homo sapiens

<400> SEQUENCE: 7

| | |
|---|---|
| atgcccctgc ctgtcactac atgcccccctt tctcccacag taaccactat cctgacttac | 60 |
| aatagcatag gtgagttctg ccaggctttg aactataatt atacaggggg aaccatatgg | 120 |
| tgtatatata ctctttggtg gccctacatt tcaaatgtat tgtatattac atttgaaata | 180 |
| tatattgaaa tatatattgt tgagtatact caatgtatat ttcaaatgta atatacaata | 240 |
| caatacatat atacaataca atacatatat actcaacaat atatatttca atatatattt | 300 |
| caaatgtaat atacaataca tatatactca acaatatatt tagtatattt caaatgtaat | 360 |
| atacatttga aatgtagctc tttccaagag gcccacacat tcccctgagc catgaagtga | 420 |
| aaaggggggcc aacagtgtat ggtaccacct ccccgtcag gcacgactcc caggaagtcc | 480 |
| tcactccaaa gggaagccag cagaaaagcc agccaggctc aagaatttca actcaaccct | 540 |
| gaatgggggt cacctctctc tgaaaggcgg tcaagatact tggggctgtc cctgaggttg | 600 |
| gaggtaggct tggcaaaatg ccaccctgga gggccctgaa actcgatcac ccaaagaaca | 660 |
| tgtgttttgtc ctttccatct ccctgggctg agagtagcca actgggccca agacccagca | 720 |
| ccatctctat agtcctttgt gattatctcc tcccactttg gactaaaact gagacagagg | 780 |
| gaccctcgca caagggtctg ggagccaaag gcctttcctc ccagccccca gactgcagat | 840 |
| taatgacagg aaaaggcctt gggaaagagc tgcaattaga gggcaggcag gcagtgaatt | 900 |
| tactcttccc caacaaagcc gacttccggc cccatgcctg ccctcctgct tgctttccag | 960 |
| cctcaccagt ccccagggtt tcaggggcga ctcttagcct cctggtctgc agatcaggct | 1020 |
| gagggttggt ggagagaagg ccacaatagg ccccatcggc ctataaatag cagcccagcc | 1080 |
| tgccctcctt gggccaggc cagcccgatg cccacccctct ctccgttccc tcttttccat | 1140 |
| gcaataagag gaggaagtta ccaggcagc tgcatcctag ccatacaaga ggaggaaata | 1200 |
| aatggaaggt ggaggagaga agggaaaga aaggagaaa aagaggaaag aatagtggga | 1260 |
| ggggacaacc aagaaaggaa gatggaggag atgcaggtga accagagtgg tcaccctgtg | 1320 |
| gtcatgcttc ccctccccca cacccaccta tggcccccctt ttcagctccc cagggcaaca | 1380 |
| cagaggaggc tttctgacag aggctgcagg caccccaccc atcaggcccc aatcgtgcta | 1440 |
| gcgtctgctt ggcctgacca ctgacctagt ttctcatcaa ctaccttgct gtgactttta | 1500 |
| ggaatgtgtg acccctgacc cccaattgct gacttggctt tggtcaagac ccatcaagag | 1560 |
| tactaaactg ctacactgca gtccccagga gttgggccca attatttgtg tgtgtgttgg | 1620 |
| tgggggacag gtgatattgc ccctgccctg ggagtttgtc actggacaca cacaaccccct | 1680 |
| ttagtaggaa agaggatgtg aaaccttcaa cgttgtgtgg gtttgggct tcagttcctc | 1740 |
| aagcccttat ctcgggtgtc tgcagtctat cccactctat ctgtctggcc atctgtgaac | 1800 |
| cctggttcct gtgtgtatct tctggtcttg actgtttatc ttgatacagg ctcagcctta | 1860 |

-continued

```
acttcttgtg tcgagggcct gtcccccttc cctgccttgc cctggtttct ggctgctacc    1920
ttgcatgtgc atgcatatat atttaagaaa gctcactaga ctgggctcgg tggctcacgc    1980
ctgtaatccc agcactttgg gaggctgagg cggcagatcg cgaggtcagg agatcaaggc    2040
catcctggct aacatggtga agcctcgtct ctactgaaaa tacaaaaaat tagccgggcc    2100
tggtggcagg cacctgtagt cccagctact caggaggctg aggcaggaga atggcatgaa    2160
cctgggaggc agagcttgca gtgagcgaga atctcgccac tgcactccag cctgggtgac    2220
agggcgagac tccatctcag aaaaaaaaaa aaaaggcaag ctcagccggg catggtggct    2280
cacacctgta atcccagcac tttgggaggc cgaggtgggc agatcacctg aggtcaggag    2340
ttcgagacca gcctgaccaa catggtgaaa ccccgtctcc actaaaaata caaaaataa    2400 taataataaa ataaagctca tatcctgaaa acatctcat caacacagac cacaaacaat    2460
aataggtcat gcctaaaagt ccaaacactg gcaaacgtca ctattgccag ctcatcacat    2520
tagtggctaa gattaaaagc tgagaagaaa agaaaatgg tgtctttctt ctaccaaatt    2580
agccccaatc acgtatgtcc taaatctgtg gccccttct gtgaataagc ctctactgtg    2640
cttttccaga aagtgtcatg ccaggtcttg ctggcttcta gtcagattgt cttgctcttc    2700
ttgggacaca aattcatcag gctggagacc ccagtgtgtt tgttcctatc actgtgactg    2760
gggacctggc tcagagtaca cccaggacat ggaggccaga gccacgggtt ttgggaggga    2820
tttgctcagt tacacactgg gcgatgtgct catggatgct gaggtatgtc tctagtagta    2880
gatacacatt tactctgact catgtagtct ttcactccag gattctgggg accaaacttg    2940
aggaactggt ggaatttcag gctaagtctg aggcccgatt gaggtgtgaa gctcttgagg    3000
tcaggaactt ggtctgtggc cagggctggg gtgaagaatg aatgaaacc aggtagcccc    3060 aagaacatcg aggtgcgtca cccattagcc tggggctccc atggcaatgt ggctctgtca    3120
gctctgggct gtgggtattg tgtggtgggg ggaggcgagt atgtgggccc tcgggcagcc    3180
atttagccca ctgattgcaa cacccaccct ttttccagct ctcccttcag cgctccagca    3240
gcttcaagga ttttgccaaa tccaaaccca gctccccgt ggtgagcgag aaggagttta    3300
atctggatga taacgtgagt ttcagggcat ccttgtggga tctggctgca ggccctgggc    3360
aggggggtgg gggtgggagg gaagagggtg aagaggagat agaattgttg gggcgaagcc    3420
ccctttaaca cagagggtcc acctctcccc acaccaagca ctcccctgca ttcctttcaa    3480
ttatacatta aatagcaaac tatttataaa tttatagggc taaggacatg gctggggtta    3540
agaggggagg ggatgggggc ctctcagttc caccccctcc agcttctgct gtgaccccaa    3600
ggcctctttt gcctcaagtc ccggacctag gcaggaccac caggtccct ggatcgcctc    3660 ttttgttgtc acagattcca gaagatgact caggtgtccc cacccagaa gatgctggga    3720 agagtggcaa aaagctgggg aagaagtgga gggcagtgat ttcccgaacc atgaacagga    3780
agatgggcaa gatgatggtg aaggccctgt cagaagagat ggtgaggcct gcagatatag    3840
gggatggggt gtccaggggg cctggggacc gctctggcga aatgtgagca tgaccacctc    3900
aatagccact actcaggccg gaaggcccta tttgatgcaa gaaggaaggt cacatgggag    3960
gggaaactca cttgcagcca cggacaggca gccaggcaat cttgacgggg caggaggctg    4020 gcggggaag gggtggagtt tgagaaggga tgaaagtctg gcaacaggg ctggacatgg    4080 tggctcctgc ctataatccc agcactttgg gagactgggg ccgatcactt gaggtcagga    4140
gtttgagacc agcctggcca acatggcaaa acccatctc tactaaaaat acaaaaatta    4200
```

```
gccaggcgtg gtggcacatg cctgtaattc cagctactca gagactgagg caggagaatt    4260
gcttgaactt aggagacaga ggttacagtg tgccaagatc gtgccactgc actccagcct    4320
gggcaacaga gcaagactct gtctcaaaaa aaaaagaaa gaaagaaaga aagaaagaaa     4380
gaaagaaaga aagaaagaaa gaaagaaaga gaaaaaaaa aaaagaaaa gtctgggcaa      4440 gggatgcttc ttgaggaggc gggcctggga caggggcagc ttgagaaaga tgaaatggcc    4500
tgaggcaatc catccacctc aaagctttgc tttggaactt ccccgggatt gggaaggcct    4560
attttctctc atagaatccc tatgagagaa acagattgg gcacagtggc tcacacctgt     4620
aatcccagca ctttgagagg ccaaggcagg tggatcacct gaggtcagga gttcgagacc    4680
agcctggcca acatggcaaa atcccgtctc tactaaaaat accaaaacaa attagccagg    4740
cgtggtggca ggtgcctgta atcccagata ctcgggaggc taaggcagga gaattgcttg    4800
aacccgggag gtggaggttt cagtgagcca agatcacacc actgcactct ggtctgggtg    4860
acaagagcaa aactccgtct caaaaaaaag aaaaaaaag agagaaaaca gagaaggctg     4920
gcttcagccc aggaggaaa gttggcacag gcagctgtgg ggcaggcatg acccaagaag    4980
cttaaatcac acagtgggtt tgggttgcca tggctctaaa aggagccact gaggcagtgg    5040
tgtgctggag ttggctcgta ctgggcttat accagctcac aagagcagtt ggtcaaactg    5100
tcaaaaattg tgcaagccag ttgttaaaca caaccattat taaaaatcaa attaaagaaa    5160
cttacaattc agttaattat attttttaa aaagtaaac tgggcatggt ggtgtacacc      5220
tataatccca gctactcagg aggacgaggc aagatgattg cttgagccca gtaagagtcc    5280
agcctgggca acatagggag actctgtctc taaataaata aatttaaaaa ataaaattt     5340 tgtaaaaacg aacaaaggta atacagtaaa tcttcaaaac tcatcacttc ctaattcttg    5400
tactaccttt tactcttatc aatgctgctg aggttacgtg catccatagc atcttcatgg    5460
tggcaatagc ctcaccctca tttcagacaa cacgtccagt gatgtcaaaa tggtagcttg    5520
acattggccg tggaggggag tgtttacaac acaggaattg caactcatc agggccagct     5580 gttaaacagt tatcacctca ctgaggtgtg gtgaggtagg gggagctctg gagtctggct    5640
tggttgtggg ttgccttggg acttgaacct gaattcccctt ggcctgagtt tacagatgag   5700
gagtaagtaa cccttgggcc ttactcctca tttgtaaact caggccaaca ataccactta    5760
ccttcaagtg tcactgtaag gattcagtga atggcaggc aggcctggca cacagaaaca     5820
caggcaaaag tagtttcctc tctagcgaca ttgtctgccc agttgtgcgg tagcaatggt    5880
tgagtccagg ttgtgccacc gtggtctttt ctgtatgtac atcggcactt gaggctgaca    5940
aaagcacatc cacatggtgc cctggttgaa cctgtttctg tgaggtaacc agggcaagga    6000
ctgtcactct cattttaca aagggggaag aaactagggc tcagagagtg ccattcagcc     6060
tataagtggt agagttgggg tttgagccag cccctagctc ttcactaagc ccaggcccat    6120
ttcttcagct tcatgcacac cccagcaagg ctccttaaag cttcccgcct accctccctg    6180
caggcagaca ctctggagga gggctctgcc tccccgacat ctccagacta cagcctggac    6240
agccctggcc ctgagaagat ggcgctggcc ttttctgagc aagaggagca tgaacttccg    6300
gtgctcagcc gccaggcatc aacaggtgag taggggatgc ggggggacacc tgccgaatct   6360 ggaggaaagg actgggttac agccgtgctg gtggcacact gtctgggcgg ggggtaagag   6420
aaatgaatgc ttactctttg cctgctggga acattctcag tcctcttcac attaaatctt    6480
ctcaacaacc tcatggggcc agtactgtta tccttgcttt attgatgtgg aaacagggtc    6540
ttagggaggt taagtgactt gcccaagatg acccagtctt gaactcagat gtaccgtaga    6600
```

```
ggaacttcca cttgctatcc tcaggccccg gagaggccca cgggcagagg aagagtctca   6660
gtcaccctct tggaccagcc cgtccccacc tttccaaggg gagctagagg ctacagatcc   6720
ctgggcctct gatgcccag tcggggtgg gcgtatgagg tctccagctg tgaagagtca    6780
gcctcttgac cctagaccat agttgctggg ctcagggcat cacctggcat cttctagaag   6840
tccatgggac aggacaagag gtgccagcag ggaactcgtc caggcagggg ctttgggttc   6900
tgcagcccca ttcagcaccg cctttcttgc ccctcaagtc cactccaagt ttcctgcttt   6960
ctctgcctcc acagacactt ccctgccccc gactgaaaat cattcaaaat gcccactact   7020
ctgtacttcc cagggagaag gagcccaact gagtttctat gtgacattgt aactacacat   7080
tgagttaagc agggaaagtc aaatatgaat gcagggcata gcttcctggg tggagggagc   7140
gttggagtgg gtatcaggga acatggagtc taatggactg actcagtgct gccagttata   7200
aaatgagaag ccttgagcag ttcacttggt ctgtgtgacc tcagatttcc gcatctgttc   7260
attggagtgt tggcccagtt gttctctaga ggccctccta atttgcccat tctttggtca   7320
gtgagccatt tctcctccca ttgccaactc ttttcatgtc caagggccca gaggtgaagc   7380
cgtgctcctg gtcggtagcc aaggggtgg ttcagaatcc cttctgcagt gtaaagcttg    7440
ccagagccca gctgccttcc cggtgtatac ccttgggatt tctaggcagg tccctggaa    7500 ggcacctgct aggcactgtc tcagctgttc taggacaaag gtgagcctcc tcctgcccc    7560 atctcctgca ggcagtgagc tctgcagccc cagcccaggt tctggcagct tcggggagga   7620
accacctgcc ccccagtaca cagggccttt ctgtggccgg gcacgagtcc acaccgactt   7680
cactcccagc ccctatgacc acgactcgct gaaactgcag gtaagatcag catccgggct   7740
tctctggagc ctggcaggct gtgcccaaaa aggaagctgg actgaaccag gctatgacag   7800
tgtcagtgga ggccaaggcc ccccatatcc tctctccctt gctcccttct cctctcctct   7860
cccccaacag aaaggagatg tgatccagat cattgaaaag ccacctgtgg gcacgtggct   7920
gggcctactc aatggcaagg tgggctcttt caaattcatc tatgtggatg tgctgcccga   7980
ggaggccgtg gggcatgccc gccccagccg ccgacagagc aagggcaaga ggcccaagcc   8040
taagaccctg catgagctgc tggagcgcat cggcctggag gtttgagctt ggtcctcact   8100
agtatctagt atcagggagg cacaactgcc ccagggatgg ggaccaggaa atgacagcta   8160
tgcgtagttg gggaggacct aggcaggggt ggctggtaag cagctgtgcc gatggcctgc   8220
ctctgcctac aggagcacac atccaccctc ctgctcaatg ctaccagac actggaagac    8280 ttcaaagagc tgcgagaaac acacctcaat gagctgaaca tcatggatcc acagcaccgg   8340
gccaagctgc tcacggccgc cgagctgctg ctggactatg acagtgagtg gctttaggag   8400
cggcctggtg agggtgtgtg cccaccggca ttccagggag gggaggcttg ccctggcctt   8460
gccttctgtc cacgctctgc ctaggactg ctctgcagtg gaaaggtact ttccacttga    8520
attagaattt caggggaaagt gtacgggaga aaggagttgt agggatgatt gggcccaacc   8580
tcctttggat caaaggggac ccttaaggcc aagaaggca aagccttact tgaggcctca    8640
aagctgagta ataacagagc caggattcaa gcccactgcc tggctccagc ttagtgctaa   8700
agaagtgtga gctcctggac tgcagagctg gcctggaaac aactcctacc agcttctaag   8760
ctggaagcag tgaggagagg ggcagggcgg tggcaggtgc ccagaaggag agactgccta   8820
tggtgtattt cccaaggtcc ctacctccac ccccatattc tgtctccctc tctcgtccct   8880
ggcagctggc agtgaggagg ctgaagaggg cgccgagagc agccaggagc cagtggcaca   8940
```

-continued

```
cacagtgtcg gaacccaagg tggacatccc gcgcgactca ggctgctttg agggctcgga    9000
gagcgggcgc gatgacgcag agctggcagg cactgaggag cagctgcaag gcctctccct    9060
ggccggggca ccttgaggtg gcggtggcaa taggccaagg ctgggaccca gctgcaaagg    9120
ctgtaggagt gggcccagcc tcccgtggtg gcccaggtcc tgaggactgg cactgagcct    9180
ggccctgctt cccagggac acttaggcc acagaggcca ggccagggcc ctacaggttc       9240
caggctcagc tggagtggtt ggggagtcgc ccaagggcac atcccacctg cctgagcccc    9300
gccctccacc agcgactgac agcgcagccc tcctggcac caactgctcc cctgccatgg     9360
ccacggccac agcaagtggg gcactgggaa accctgccca tgtccctcac caacaaggcc    9420
tccaaatcct cctcacccc acaccaccta ccctgtcgc actgctcctg aaaggggc         9480
caagtcaatg tttcaggtca gtctaaaaac cctagggaag ctggccattt aaaagaaccc    9540
aaactgacca tgggtaaatc cagttcccct aaataaggcc tgaagaaatc cacaggtacc    9600
attcccactt tccttctccc tagctttctt agaggtttgg ccactaaatc ttatgagact    9660
tgaaccaagt ggcttcctct ttctaggctt aggacgggtt ggggttagaa aggtgatca    9720
ctgaaggcct tgcctgctct gacattctgt gacattaaat gtctattctc ctgttacctg    9780
tggcctggga caccagtggg gtttatcgag gggaccagag gggcctcagg ctttcagatg    9840
aaatggctcc tcctactcac ccactttatt cctctccatg taattcagga caagctgcaa    9900
cttcccccag cttaacacaa tgcccatacc tcatacgata tgcgccctcc cgttccatcc    9960
ctggccccct caaacgagac ttctcacaag gctgattaca gatggtcaaa cctggcttcc   10020
aaggacagaa ttgcctctcg gaagccagct gtggatctga gtccagagtt ggccacttgt   10080
gtgggtcctc acaagcaaag agagcactaa acttgacatt ggggtccac cactccaact    10140
ttgctttctg aaggttttgg tgtacattga gccccagaag gaaaggagag tatctgtgag   10200
tgggggcctc ccttgacccc agtacgaagt ctatgccctg aatccccaga gtagcccttc    10260
ctggtgccca actggcctgg ggacaaacag cgtccactac atctaggact gccggctaag   10320
tggacacact tcttgacctc ctaccaggaa ctttggtaaa agctagcttt ggggaagggg    10380
ttgggtgtaa atatgagagg gtggagggag accagctggt agcaataaac atgggtagaa   10440
ctaaattacc gtctccagtt atcttttcta tggagagagt gttgtgggga ggggcagacc   10500
ggtctccttc aaagctggcc tcagcaaagt gtccctcact gtcctttcag gtccatcttt   10560
cccttcccct aaatgttcag tgcccttgac tctgctgacc taaagctcca gtctgaagcc   10620
ctagctggct ctgccctccc ctctaaccag ccctcctcag aacaaggctc aagctcccat   10680
gaccacgggc tttgctgggg tccaagaggt gtagggggga atggctattt ccctcatcca   10740
ataactgttc attttaacag ggcccttaaa gaccttcacc cgtgtgaaga aaggcctgca   10800
ctgaggagct gtccaggatc taagaggggg agatttgggg tcagcatggc ctttcctctg   10860
aagtcacctt ttcctggccc ccaccctgta cccactaaag cagtgccatc tcctgggagg   10920
taggatggag atgaagacct ctagcttcct ttctgttttct gccagaatta actgcattgg   10980
gcattgggaa gggggttact ggagagagag ctgccaccag agtgaggacg aggccacttg   11040
acttccaggc cttgttctca gttgcattca tcccaccacc cttagtgact gggggtgcca    11100
ggaaactgca agcatgatcc tcaccaaaga tataagagcc ctaacagcct caaagcccca    11160
agggtactga ataattgcag tcatttaagg agcacctcca cttgtgccag cactgagcca    11220
ctttacatat agcatctcct gtaatcctca cagtgtcccc ctgaggtggg tgccctcatc    11280
atcccagttt acagaggagg aaactgaggg ttggggaggt tgaagaagtt gactagaaag    11340
```

```
taacagagca ggagtcttcc tgactgcaga acccatgttc ttaactccta tgctacaatg   11400
cttctccaaa ggcctcatcc aacaagcatt caaaagtcct gggcactttg gagggcaagc   11460
tgactctctg acccagccat ttcccttcta gaatttaatc agccacataa gtgcagaaac   11520
agccacataa gtgcacaaat acctatggac aaagatatct acaacagctc tgtctgtaat   11580
agtaaaaaat tgaaaacaat gcaaatgggg aattaaatgc tttatggttt gttcatatac   11640
cacgcagcca tgcacatga tgttgtagaa aaatatttaa taacatgagg aaaatctttg   11700 tgtttttta ttctttgatt ctatttattt ttctagagac agggtttcgc tctgttgccc    11760
aggctggagt gatgtggcac aatcatagct cactgcagcc tcgaattccc aggttcaggt   11820
gatcctccca cctcagtttc ctgagttagc tgggactaga ggcatgcgcc accacaccca   11880
gctaattttt gtttagtttt tgtagagatg aagtgtagtt atgttgccca gttgcccagg   11940
ctggtctcaa actcctgggc tcaagcaatc cgcccgcctc agcctcccaa agtgctggga   12000
ttacaggcgt gagctaccac acccagcctt caatttcaaa tttgaaaatt acacaaataa   12060
tgtataaaca ttttagttgt aaaataaatt tgtgttatag caaggggaaa agcaaatcct   12120
aaaacattat aataggatg attccatttt tattttagaa aaggagaaca tatacataga    12180
ataaagacta tgaagatctg caccaaatga ctactactgg tgatcttgtg aggcgtgtgg   12240
ggtgggacta ggggagtgag ggagaaaaat gctcactttc tacattcttc ttttatttgc   12300
acttcaaaag tattatttt atatctatga agaaaaggaa actgcatttc aattttgaa    12360 aaaaaaaata aaactaaatt aacaaataaa tagggcccac gcctctggcc tccaatacgg   12420
gacagtagca gcaaaatcat tatcctgctg ccttttggta cacggttctg gaaagatgag   12480
aggtgaataa tggccaaagt gcttaaaatc catgcatgcc agggtgcacc tatcagagga   12540
gattcctaaa cctttaaaa cccctgtgta ataggtattg ctctaagctg gggaaaggaa    12600
aagatcagaa ggagatgaat gcctgggaac atgatgtttg gaaatcctct cctaccctgg   12660
ggaggcagct caggggtggt gtgtctcaga tatcaggccc agtttggcat ataggatgat   12720
tacaggctgg aggtaggtag ctgtgcaagg acccaagga tcacagtagt ttgggagggg    12780
caggtaaggc ggggcatcaa gggaatgtag aacaggccag ggcccaaggg gcaagaaagg   12840
cagtgctgag gagggccaca gggcccaaag ctcctcctcc aggcagggct gctgacacct   12900
attgtcctgc cccatgtact tctagaagat gccaagtggt gccctgaatc cagcaaccaa   12960
ggtctagggt gcaaagagct gattcttcac agctggagac cttacacgcc caccccagcc   13020
tgggatgtca gcagcccaga gagctgtagc ctctagctga ctcccctttcg aagggtgggg   13080 acaggctggt ctaaagggt gatgaggcaa gctcttcttc tgcccgtggg cctctccagg    13140
gcctggggag agcaagcaga agcttctcta gggtagttga ggcctagcac ttaggagctc   13200
aggcccacct gagttcaagt cttggctgtg tcacttccta gctgggtcac cttagacaag   13260
tcatttaacc tccttgagcc tccgtttcca cgacaataat gtaggaatac tagcactagc   13320
cccatggggc tgttatgaag atttaatgta ctagcataaa gtcctttgca cagtgtccag   13380
cacaaaataa atgctcaagg agtgatagtg tgtctggctg cctcgatttg ctccatcctg   13440
ctacctccat ttcactcctt tcaaggccca tctgacctttt gactcccagt tagtatagtg   13500
aagtgaccaa aagcaaaagg ccttggagtt caaataaagt gttttcaaac tcttgctaca   13560
ccacttacta gttatatgac attgggtaaa gtacatacat atacatttct tttcgtggaa   13620
acaggaataa tgatctaata atacctacct cttggggggtc atgagagaaa tcaatcagat   13680
```

```
aactcgtaca aagttcctgg cacataggac attaaatggc ggctattcga cttttttgta    13740
aactccaagg cactgagctc aagactgggc acaaaggcca tgtcggtaca tgcttgtctg    13800
aggactgact gatgttcaga cctgtcatat cccagacacc actgatgtcc aggtccccag    13860
gaggtgttgg gattcagggg taaagggtgc caactctggt acccagagag gctggtgatg    13920
aaagaaaacc cacttgagga gcctggggca gccctggctc tgcccagtcc acagcaagtt    13980
gatcagccct gggcattaga cttactttag gcaactctct tggacttcca ggagctgcta    14040
gaaagaagag aataaagacc agatttcaga agaaagagtt gagtctagcc agctcctcac    14100
cagttcagag ttagagccac cttctgtgtc tccttcctat caggagaagc agctggaggc    14160
accagcacag cccaactgaa ccatgtcctc tctcacttgc ttcctctgta tctcacaacc    14220
tgaccttaga ctaccccagc aggttctgat ccgccccccca aaggcctctg caaattccct    14280
ctcctaaacc ccaaacccta tggcactgtg atctgataca tggcactgag gccccagccc    14340
ctatgagtca gtttctcatt tcctactcac agagctcccc gcccacagtt gggccatgag    14400
agacctaggc attaaaacaa aggctaaacg aggtgtttta cgggaaaaat aggcactgat    14460
caccatcgtc tcaacaaggc ccaacaaggc ccttcccccc tcccaagtca ggaaattcag    14520
gatgaggtat gaggtttccc actgggaaaa agaagtggct ctcccacctc tccttcacaa    14580
tagaggctac catagcttct cacacaacat tggccatatt acatattatt cagccaacaa    14640
cacaatcaag tgggaaggaa ctgcctcccc tctagactca gccaagactc ctcctccagg    14700
aaggacctaa ataaatggaa ttctatagca cttgatatgt aggcttcacc ttttcctata    14760
acttcacagt aaccaatata gcatttgtat accattgcct ctgggacctg ccagggatag    14820
cgtcagaaag agcccagagc aatggccctc acaaagggac agccaacttg actgtgggaa    14880
cttagcaagg caatttcctg actttctgtg ctaagaaac cacatcatca gttcaaccta    14940
aatgcagggg tctggagaga gacttaagag agttaagttg aaaacaaaaa tccaacaacc    15000
agcctcatat cagcccgact atatataagt cctctgtatg cctaaaatgg agagcttatc    15060
agtaatattc atcccaaatg gcaaataatc ctaaaaatca ttgctgtttc tcaacttacg    15120
agggttggta ctgcaatttc tcctaaagtt aaccctagca tgcagtcaat cttcaacaag    15180
tatttattga atgttaaata aatgaaagct tcatttcatt caagtgtcat ttgcagttat    15240
tctaactctt ttatccatct acacctgctt gacagaggac cagtcggtta tgccagaaag    15300
ctctctagac tgggagccag tacatctggg ttctggtctt ggctctgaca gtaactctct    15360
atgtgaccct aagttacagt atttaatttg agggagaaag agagagagag agagaagcat    15420
agactacatg atcaatatgt tcctttaagc tatgtcgttc aacagaatct gtgttttatg    15480
acgaataatc atcatgtctc gtatttgggc agaaaacccc aaccctttta accaagttgg    15540
aacagctaaa cagctggaga tgggcagggg ctggcagaaa aagcagtgag aaggcaagtg    15600
ggggagtgaa gaaagtgaag ggcttggaat gtcagggagg taattctact ctagattcta    15660
aagttgtaaa gccacttcta aatcaagggc cccttcattt cctggcccgt ggtgaagtgt    15720
gagctctaag ttcaatttta ttaatcaatc agaaaacccc ttaatgcctg aagaaaaata    15780
gacaaaagat taggacagac aatttacaga agaaatacaa atggtaataa acataaggca    15840
gaggagaggt gcagaaagtg tttaacttca ctattaatca aataaatata aactaacact    15900
gagatataag tttacaacta tcaaattacc ataggtttag gtcgggcacg gtggctcacg    15960
cctgtaatcc cagcactttg ggaggccgag gcgggcagat cacttgaagt caggagttgg    16020
agaccagcct ggctgacatg gcaaaacccc gtctccaata aaatataaaa aattagccag    16080
```

```
gtgtggtggc gcacacctgt agtcccagct aatgaggagg ctgaggcagg agaatcactt    16140
gaacccggga gggagagaat gcagtgagcc aagatcgtgc cactgcactc cagcctggat    16200
gacaaagcga gactctgtct caaaaaagct aaaataaaaa ttcgaaaggt ttaaatgaca    16260
tgggttgatt agagtcttct ctgatacact gctggcaaaa caaacaggga cggcctttca    16320
ataaagcaat ttggccacat ttatcaagag cctttaaaag agcattccct ttgactcaat    16380
aattccactt ctaggaatct atcctaaaga aatactcaca gacacaccca tatttaagga    16440
agttcatcac agcattattt gtaataatga aaaattagaa actcttaaat gcctgacatg    16500
tacacattac aaagtcatta agaagtattt ttgagccagg cgcggtggct cacgcctgta    16560
atcccagcac tttgggagtc cgaggcaggt ggatc                              16595
```